(12) United States Patent
Sun et al.

(10) Patent No.: US 12,286,630 B2
(45) Date of Patent: Apr. 29, 2025

(54) TREATMENT METHODS FOR MUSCULAR DYSTROPHY

(71) Applicant: Sarepta Therapeutics, Inc., Cambridge, MA (US)

(72) Inventors: Huadong Sun, Cambridge, MA (US); Lilly East, Cambridge, MA (US); Jon Tinsley, Cambridge, MA (US); Jake Elkins, Cambridge, MA (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 133 days.

(21) Appl. No.: 17/732,757

(22) Filed: Apr. 29, 2022

(65) Prior Publication Data
US 2023/0193282 A1     Jun. 22, 2023

Related U.S. Application Data

(60) Provisional application No. 63/182,327, filed on Apr. 30, 2021, provisional application No. 63/249,721, filed on Sep. 29, 2021.

(51) Int. Cl.
| | | |
|---|---|---|
| C12N 15/11 | (2006.01) | |
| A61P 21/00 | (2006.01) | |
| C12N 15/113 | (2010.01) | |

(52) U.S. Cl.
CPC .......... *C12N 15/1138* (2013.01); *A61P 21/00* (2018.01); *C12N 15/113* (2013.01); *C12N 2310/11* (2013.01); *C12N 2310/3233* (2013.01)

(58) Field of Classification Search
CPC ................... C12N 2310/11; C12N 2310/3233
See application file for complete search history.

(56) References Cited

U.S. PATENT DOCUMENTS

| | | |
|---|---|---|
| 5,034,506 A | 7/1991 | Summerton et al. |
| 5,142,047 A | 8/1992 | Summerton et al. |
| 5,166,315 A | 11/1992 | Summerton et al. |
| 5,217,866 A | 6/1993 | Summerton et al. |
| 5,506,337 A | 4/1996 | Summerton et al. |
| 5,521,063 A | 5/1996 | Summerton et al. |
| 5,698,685 A | 12/1997 | Summerton et al. |
| 6,683,173 B2 | 1/2004 | Dempcy et al. |
| 6,692,911 B2 | 2/2004 | Pack et al. |
| 7,070,807 B2 | 7/2006 | Mixson et al. |
| 7,163,695 B2 | 1/2007 | Mixson et al. |
| 8,076,476 B2 | 12/2011 | Reeves et al. |
| 8,299,206 B2 | 10/2012 | Fox et al. |
| 8,969,551 B2 | 3/2015 | Ueda |
| 9,161,948 B2 | 10/2015 | Hanson |
| 9,840,706 B2 | 12/2017 | Watanabe et al. |
| 9,988,629 B2 | 6/2018 | Wakayama et al. |
| 10,683,322 B2 | 6/2020 | Watanabe et al. |
| 10,781,448 B2 | 9/2020 | Watanabe et al. |
| 10,851,373 B2 | 12/2020 | Enya et al. |
| 10,888,578 B2 | 1/2021 | Passini et al. |
| 11,000,600 B2 | 5/2021 | Passini et al. |
| 11,382,981 B2 | 7/2022 | Passini et al. |
| 2012/0289457 A1 | 11/2012 | Hanson |
| 2013/0090465 A1 | 4/2013 | Matsuo et al. |
| 2021/0261963 A1 | 8/2021 | Uno et al. |
| 2022/0127606 A1 | 4/2022 | Okada et al. |

FOREIGN PATENT DOCUMENTS

| | | | |
|---|---|---|---|
| WO | WO-9402595 A1 | 2/1994 | |
| WO | WO-9610390 A1 | 4/1996 | |
| WO | WO-9610391 A1 | 4/1996 | |
| WO | WO-9610392 A1 | 4/1996 | |
| WO | WO-2004048570 A1 | 6/2004 | |
| WO | WO-2004097017 A2 | 11/2004 | |
| WO | WO-2009005793 A2 | 1/2009 | |
| WO | WO-2009127230 A1 | 10/2009 | |
| WO | WO-2012150960 A1 | 11/2012 | |
| WO | WO-2017062862 A2 | 4/2017 | |
| WO | WO-2018007475 A1 | 1/2018 | |
| WO | WO-2018091544 A1 | 5/2018 | |
| WO | WO-2018118627 A1 * | 6/2018 | ......... A61K 31/7088 |
| WO | WO-2018129384 A1 | 7/2018 | |
| WO | WO-2019060775 A1 | 3/2019 | |
| WO | WO-2020004675 A1 | 1/2020 | |
| WO | WO-2020028832 A1 | 2/2020 | |
| WO | WO-2020089325 A1 | 5/2020 | |
| WO | WO-2020158792 A1 | 8/2020 | |
| WO | WO-2020214763 A1 * | 10/2020 | ........... A61K 47/645 |
| WO | WO-2020219820 A1 | 10/2020 | |

OTHER PUBLICATIONS

Clinical Trial NCT03375255 , printed from ClinicalTrials.gov, NCT03375255, version 19, Mar. 26, 2020, pp. 1-13 (Year: 2020).*

Aartsma-Rus, et al., "Theoretic applicability of antisense-mediated exon skipping for Duchenne muscular dystrophy mutations," Hum. Mutat. 30(3):293-299, Wiley, United States (Mar. 2009).

Akhtar, S., et al., "Cellular uptake and intracellular fate of antisense oligonucleotides," Trends Cell Biol 2(5):139-144, Cell Press, United States (May 1992).

Benner, S.A., and Sismour, A., "Synthetic biology," Nat. Rev. Genet. 6(7):533-543, Nature Publishing Group, Germany (Jul. 2005).

Berge, S.M., et al., "Pharmaceutical Salts," J. Pharm. Sci. 66(1):1-19, Elsevier, Netherlands (Jan. 1977).

(Continued)

*Primary Examiner* — Ekaterina Poliakova-Georgantas

(74) *Attorney, Agent, or Firm* — Sterne, Kessler, Goldstein & Fox P.L.L.C.

(57) ABSTRACT

New dosing regimens for treating muscular dystrophy in a patient suffering from Duchenne muscular dystrophy (DMD) with an antisense oligonucleotide conjugate that causes skipping of an exon in the human dystrophin gene are described. Also described is a method of treating a patient with an antisense oligomer CPP conjugate and a magnesium supplement.

22 Claims, 3 Drawing Sheets

Specification includes a Sequence Listing.

(56) References Cited

OTHER PUBLICATIONS

Chiu, Y.L. and Rana, T.M., "siRNA function in RNAi: a chemical modification analysis," RNA 9(9):1034-1048, Cold Spring Harbor Laboratory Press, United States (Sep. 2003).
Fletcher, S., et al., "Dystrophin isoform induction in vivo by antisense-mediated alternative splicing," Mol. Ther. 18(6):1218-1223, Cell Press, United States (Jun. 2010).
Gurvich, O.L., et al., "DMD exon 1 truncating point mutations: amelioration of phenotype by alternative translation initiation in exon 6," Hum. Mutat. 30(4):633-640, Wiley, United States (Apr. 2009).
Henricson, E., et al., "Percent-predicted 6-minute walk distance in duchenne muscular dystrophy to account for maturational influences," PLOS Curr. 4:RRN122297, PLOS, United States (Jan. 2012).
Henry, A.A., and Romesberg, F.E., "Beyond A, C, G and T: augmenting nature's alphabet," Curr. Opin. Chem. Biol. 7(6):727-733, Elsevier, Netherlands (Dec. 2003).
Hirao, I., "Unnatural base pair systems for DNA/RNA-based biotechnology," Curr. Opin. Chem. Biol. 10(6):622-627, Elsevier, Netherlands (Dec. 2006).
Hong, Y., et al., "Model-based approach for optimization of atazanavir dose recommendations for HIV-infected pediatric patients," Antimicrob. Agents Chemother. 55(12):5746-5752, Oxford University Press, United Kingdom (Dec. 2011).
Ishiwata, H., et al., "Physical-chemistry characteristics and biodistribution of poly(ethylene glycol)-coated liposomes using poly(oxyethylene) cholesteryl ether," Chem. Pharm. Bull. 43:1005-1011, Pharmaceutical Society of Japan, Japan (Jun. 1995).
Kool, E.T., "Replacing the nucleobases in DNA with designer molecules," Acc. Chem. Res. 35(11):936-943, American Chemical Society, United States (Nov. 2002).
Krueger, A.T., et al., "Synthesis and properties of size-expanded DNAs: toward designed, functional genetic systems," Acc. Chem. Res. 40(2):141-150, American Chemical Society, United States (Feb. 2007).
Lasic, D.D., et al., "The "Stealth" Liposome: A Prototypical Biomaterial," Chem. Rev. 95(8):2601-2627, American Chemical Society, United States (1995).
Lasic, D.D., et al., "Liposomes revisited," Science 267(5202):1275-1276, American Association for the Advancement of Science, United States (1995).
Limbach, P.A., et al., "Summary: the modified nucleosides of RNA," Nucleic Acids Res. 22(12):2183-2196, Oxford University Press, United Kingdom (Jun. 1994).
Liu, Y., et al., "Cationic liposome-mediated intravenous gene delivery," J. Biol. Chem. 270(42):24864-24870, Elsevier, Netherlands (Oct. 1995).
Mann, C.J., et al., "Improved antisense oligonucleotide induced exon skipping in the mdx mouse model of muscular dystrophy," J. Gene. Med. 4(6):644-654, Wiley, United States (Dec. 2002).
McDonald, C.M., et al., "The 6-minute walk test in Duchenne/Becker muscular dystrophy: Longitudinal observations," Muscle Nerve 42(6):966-974, Wiley, United States (Dec. 2010).
Monaco, A.P., et al., "An explanation for the phenotypic differences between patients bearing partial deletions of the DMD locus," Genomics 2(1):90-95, Elsevier, Netherlands (Jan. 1988).
Oku, N., et al., "Real-time analysis of liposomal trafficking in tumor-bearing mice by use of positron emission tomography," Biochim. Biophys. Acta. 1238:86-90, Elsevier, Netherlands (Aug. 1995).
Peacock, H., et al., "Nucleobase and ribose modifications control immunostimulation by a microRNA-122-mimetic RNA," J. Am. Chem. Soc. 133(24):9200-9203, American Chemical Society, United States (Jun. 2011).
Revankar, T. and Rao, S., "DNA with Altered Bases," in *Comprehensive Natural Products Chemistry*, Kool, E.T., ed., pp. 313-339, Pergamon Press, United Kingdom (1999).
Schroeder, U., et al., "Diffusion enhancement of drugs by loaded nanoparticles in vitro," Prog. Neuropsychopharmacol. Biol. Psychiatry 23(5):941-949, Elsevier, Netherlands (Jul. 1999).
Summerton, J., et al., "Morpholino antisense oligomers: design, preparation, and properties," Antisense Nucleic Acid Drug Dev. 7(3):185-195, Mary Ann Liebert, Inc., United States (Jun. 1997).
"The Glen Research Catalog," www.glenresearch.com, accessed at https://www.glenresearch.com/site-content, accessed on Aug. 22, 2022.
International Search Report and Written Opinion for International Application No. PCT/US2022/026887, European Patent Office, Netherlands, mailed on Jul. 21, 2022, 12 pages.
Mukashyaka, M., et al., "Pharmacokinetic/Pharmacodynamic Modeling of a Cell-Penetrating Peptide Phosphorodiamidate Morpholino Oligomer in mdx Mice," Pharm Res 38(10:1731-1745, Springer New York, United States (Oct. 2021).
Shabashvili, A., "Sarepta and Solid: the future of DMD therapy—Life Sciences Finance," lifescifin.com, accessed at https://lifescifin.com/2021/05/20/sarepta-and-solid-the-future-of-dmd-therapy/, 11 pages.
Sarepta Therapeutics, Inc.: "Sarepta Therapeutics Reports Positive Clinical Results from Phase 2 Momentum Study of SRP-5051 in Patients with Duchenne Muscular Dystrophy Amenable to Skipping Exon 51," accessed at https://investorrelations.sarepta.com/node/20641/pdf, 3 pages.
Amantana, A., et al., "Pharmacokinetics, biodistribution, stability and toxicity of a cell-penetrating peptide-morpholino oligomer conjugate," Bioconjug Chem 18(4):1325-1331. American Chemical Society, United States (Aug. 2007).[KC2].
Greene, T.W., et al., "Protective Groups in Organic Synthesis, Second Edition, John Wiley and Sons, United States (1991).
Dellorusso, C., et al., "Functional correction of adult mdx mouse muscle using gutted adenoviral vectors expressing full-length dystrophin," Proc Natl Acad Sci USA 99(20):12979-12984, National Academy of Sciences, United States (Sep. 2002).
Akhtar, S., Delivery Strategies for Antisense Oligonucleotide Therapeutics, First Edition, CRC Press, Boca Raton, Florida, United States (1995).
Emerich, D.F., et al., "Biocompatibility of poly (DL-lactide-co-glycolide) microspheres implanted into the brain," Cell Transplant 8(1):47-58, Sage Publications, Inc., United States (Feb. 1999).

\* cited by examiner

```
                        SEQUENCE LISTING

<160> NUMBER OF SEQ ID NOS: 738

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000
```

```
<210> SEQ ID NO 9
<400> SEQUENCE: 9
000

<210> SEQ ID NO 10
<400> SEQUENCE: 10
000

<210> SEQ ID NO 11
<400> SEQUENCE: 11
000

<210> SEQ ID NO 12
<400> SEQUENCE: 12
000

<210> SEQ ID NO 13
<400> SEQUENCE: 13
000

<210> SEQ ID NO 14
<400> SEQUENCE: 14
000

<210> SEQ ID NO 15
<400> SEQUENCE: 15
000

<210> SEQ ID NO 16
<400> SEQUENCE: 16
000

<210> SEQ ID NO 17
<400> SEQUENCE: 17
000

<210> SEQ ID NO 18
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(12)
<223> OTHER INFORMATION: Wherein Xaa is 6-aminohexanoic acid

<400> SEQUENCE: 18

Arg Xaa Arg Arg Xaa Arg Arg Xaa Arg Arg Xaa Arg
1               5                   10
```

```
<210> SEQ ID NO 19
<211> LENGTH: 10
<212> TYPE: PRT
<213> ORGANISM: Artificial Sequence
<220> FEATURE:
<223> OTHER INFORMATION: Synthetic sequence

<400> SEQUENCE: 19

Arg Phe Phe Arg Phe Phe Arg Phe Phe Arg
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(13)
<223> OTHER INFORMATION: Wherein Xaa is 6-aminohexanoic acid
<220> FEATURE:
<221> NAME/KEY: MISC_FEATURE
<222> LOCATION: (14)..(14)
<223> OTHER INFORMATION: Wherein Xaa is beta-alanine

<400> SEQUENCE: 20

Arg Xaa Arg Arg Xaa Arg Arg Xaa Arg Xaa Arg Xaa Xaa
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic sequence

<400> SEQUENCE: 21

Arg Phe Phe Arg Phe Phe Arg Phe Phe Arg Gly
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic sequence

<400> SEQUENCE: 22

Arg Arg Arg Arg Arg Arg Gly
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic sequence

<400> SEQUENCE: 23

Arg Arg Arg Arg Arg Arg
1               5

<210> SEQ ID NO 24
<211> LENGTH: 6
<212> TYPE: PRT
<213> ORGANISM: Artificial Sequence
```

```
<220> FEATURE:
<223> OTHER INFORMATION: Synthetic sequence

<400> SEQUENCE: 24

Arg Arg Arg Arg Arg Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic sequence

<400> SEQUENCE: 25

Arg Arg Arg Arg Arg
1               5

<210> SEQ ID NO 26
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (11)..(11)
<223> OTHER INFORMATION: Wherein Xaa is 6-aminohexanoic acid
<220> FEATURE:
<221> NAME/KEY: MISC_FEATURE
<222> LOCATION: (12)..(12)
<223> OTHER INFORMATION: Wherein Xaa is beta-alanine

<400> SEQUENCE: 26

Arg Phe Phe Arg Phe Phe Arg Phe Phe Arg Xaa Xaa
1               5                   10

<210> SEQ ID NO 27
<211> LENGTH: 22
<212> TYPE: DNA
<213> ORGANISM: Artificial Sequence
<220> FEATURE:
<223> OTHER INFORMATION: Synthetic sequence

<400> SEQUENCE: 27
caatgccatc ctggagttcc tg                                            22

<210> SEQ ID NO 28
<211> LENGTH: 22
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(22)
<223> OTHER INFORMATION: Wherein each thymine (T) is optionally uracil
      (U)

<400> SEQUENCE: 28
caatgccatc ctggagttcc tg                                            22

<210> SEQ ID NO 29
<211> LENGTH: 25
<212> TYPE: DNA
<213> ORGANISM: Artificial Sequence
<220> FEATURE:
<223> OTHER INFORMATION: Synthetic sequence
```

<400> SEQUENCE: 29
gttgcctccg gttctgaagg tgttc					25

<210> SEQ ID NO 30
<211> LENGTH: 25
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(25)
<223> OTHER INFORMATION: Wherein each thymine (T) is optionally uracil
      (U)

<400> SEQUENCE: 30
gttgcctccg gttctgaagg tgttc					25

<210> SEQ ID NO 31
<211> LENGTH: 30
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: Wherein each thymine (T) is optionally uracil
      (U)

<400> SEQUENCE: 31
ctccaacatc aaggaagatg gcatttctag					30

<210> SEQ ID NO 32
<211> LENGTH: 30
<212> TYPE: DNA
<213> ORGANISM: Artificial Sequence
<220> FEATURE:
<223> OTHER INFORMATION: Antisense oligomer

<400> SEQUENCE: 32
ctccaacatc aaggaagatg gcatttctag					30

<210> SEQ ID NO 33
<211> LENGTH: 26
<212> TYPE: DNA
<213> ORGANISM: Artificial Sequence
<220> FEATURE:
<223> OTHER INFORMATION: Antisense oligomer

<400> SEQUENCE: 33
gagcaggtac ctccaacatc aaggaa					26

<210> SEQ ID NO 34
<211> LENGTH: 25
<212> TYPE: DNA
<213> ORGANISM: Artificial Sequence
<220> FEATURE:
<223> OTHER INFORMATION: Antisense oligomer

<400> SEQUENCE: 34
ctgaaggtgt tcttgtactt catcc					25

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

-continued

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

```
<400> SEQUENCE: 58
000

<210> SEQ ID NO 59
<400> SEQUENCE: 59
000

<210> SEQ ID NO 60
<400> SEQUENCE: 60
000

<210> SEQ ID NO 61
<400> SEQUENCE: 61
000

<210> SEQ ID NO 62
<400> SEQUENCE: 62
000

<210> SEQ ID NO 63
<400> SEQUENCE: 63
000

<210> SEQ ID NO 64
<400> SEQUENCE: 64
000

<210> SEQ ID NO 65
<400> SEQUENCE: 65
000

<210> SEQ ID NO 66
<400> SEQUENCE: 66
000

<210> SEQ ID NO 67
<400> SEQUENCE: 67
000

<210> SEQ ID NO 68
<400> SEQUENCE: 68
000

<210> SEQ ID NO 69
<400> SEQUENCE: 69
```

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)..(10)
<223> OTHER INFORMATION: Xaa = glycine or proline

<400> SEQUENCE: 89

Arg Phe Phe Arg Phe Phe Arg Phe Phe Xaa
1               5                   10

<210> SEQ ID NO 90
<211> LENGTH: 11
<212> TYPE: PRT
<213> ORGANISM: Artificial Sequence

```
<220> FEATURE:
<223> OTHER INFORMATION: cell penetrating peptide
<220> FEATURE:
<221> NAME/KEY: MOD_RES
<222> LOCATION: (11)..(11)
<223> OTHER INFORMATION: Xaa = glycine or proline

<400> SEQUENCE: 90

Arg Thr Arg Thr Arg Phe Leu Arg Arg Thr Xaa
1               5                   10

<210> SEQ ID NO 91
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)..(11)
<223> OTHER INFORMATION: Xaa = glycine or proline

<400> SEQUENCE: 91

Arg Phe Phe Arg Phe Phe Arg Phe Phe Arg Xaa
1               5                   10

<210> SEQ ID NO 92
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)..(11)
<223> OTHER INFORMATION: Xaa = glycine or proline

<400> SEQUENCE: 92

Lys Thr Arg Thr Lys Phe Leu Lys Lys Thr Xaa
1               5                   10

<210> SEQ ID NO 93
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)..(10)
<223> OTHER INFORMATION: Xaa = glycine or proline

<400> SEQUENCE: 93

Lys Phe Phe Lys Phe Phe Lys Phe Phe Xaa
1               5                   10

<210> SEQ ID NO 94
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)..(11)
<223> OTHER INFORMATION: Xaa = glycine or proline

<400> SEQUENCE: 94

Lys Phe Phe Lys Phe Phe Lys Phe Phe Lys Xaa
1               5                   10
```

```
<210> SEQ ID NO 95
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (7)..(7)
<223> OTHER INFORMATION: Xaa = glycine or proline

<400> SEQUENCE: 95

Arg Phe Phe Arg Phe Phe Xaa
1               5

<210> SEQ ID NO 96
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 96

Arg Phe Phe Arg Phe Phe Arg Xaa
1               5

<210> SEQ ID NO 97
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(3)
<223> OTHER INFORMATION: Xaa = 6-aminohexanoic acid
<220> FEATURE:
<221> NAME/KEY: MOD_RES
<222> LOCATION: (5)..(6)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = glycine or proline

<400> SEQUENCE: 97

Arg Xaa Xaa Arg Xaa Xaa Arg Xaa
1               5

<210> SEQ ID NO 98
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = 6-aminohexanoic acid
```

```
<220> FEATURE:
<221> NAME/KEY: MOD_RES
<222> LOCATION: (11)..(11)
<223> OTHER INFORMATION: Xaa = 6-aminohexanoic acid
<220> FEATURE:
<221> NAME/KEY: MOD_RES
<222> LOCATION: (13)..(13)
<223> OTHER INFORMATION: Xaa = glycine or proline

<400> SEQUENCE: 98

Arg Xaa Arg Arg Xaa Arg Arg Xaa Arg Arg Xaa Arg Xaa
1               5                   10

<210> SEQ ID NO 99
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)..(12)
<223> OTHER INFORMATION: Xaa = glycine or proline

<400> SEQUENCE: 99

Tyr Gly Arg Lys Lys Arg Arg Gln Arg Arg Arg Xaa
1               5                   10

<210> SEQ ID NO 100
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)..(11)
<223> OTHER INFORMATION: Xaa = glycine or proline

<400> SEQUENCE: 100

Gly Arg Lys Lys Arg Arg Gln Arg Arg Arg Xaa
1               5                   10

<210> SEQ ID NO 101
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)..(10)
<223> OTHER INFORMATION: Xaa = glycine or proline

<400> SEQUENCE: 101

Arg Lys Lys Arg Arg Gln Arg Arg Arg Xaa
1               5                   10

<210> SEQ ID NO 102
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (19)..(19)
<223> OTHER INFORMATION: Xaa = glycine or proline

<400> SEQUENCE: 102
```

```
Arg Gln Ile Lys Ile Trp Phe Gln Asn Arg Arg Met Lys Trp Lys Lys
1               5                   10                  15

Gly Gly Xaa
```

<210> SEQ ID NO 103
<211> LENGTH: 28
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (28)..(28)
<223> OTHER INFORMATION: Xaa = glycine or proline

<400> SEQUENCE: 103

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu Xaa
            20                  25
```

<210> SEQ ID NO 104
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (23)..(23)
<223> OTHER INFORMATION: Xaa = glycine or proline

<400> SEQUENCE: 104

```
Tyr Ala Arg Val Arg Arg Arg Gly Pro Arg Gly Tyr Ala Arg Val Arg
1               5                   10                  15

Arg Arg Gly Pro Arg Arg Xaa
            20
```

<210> SEQ ID NO 105
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)..(12)
<223> OTHER INFORMATION: Xaa = glycine or proline

<400> SEQUENCE: 105

```
Tyr Ala Arg Val Arg Arg Arg Gly Pro Arg Arg Xaa
1               5                   10
```

<210> SEQ ID NO 106
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)..(10)
<223> OTHER INFORMATION: Xaa = glycine or proline

<400> SEQUENCE: 106

```
Ala Lys Ala Ala Arg Gln Ala Ala Arg Xaa
1               5                   10
```

```
<210> SEQ ID NO 107
<211> LENGTH: 35
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (35)..(35)
<223> OTHER INFORMATION: Xaa = glycine or proline

<400> SEQUENCE: 107

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu Xaa
        35

<210> SEQ ID NO 108
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (22)..(22)
<223> OTHER INFORMATION: Xaa = glycine or proline

<400> SEQUENCE: 108

Lys Glu Thr Trp Trp Glu Thr Trp Trp Thr Glu Trp Ser Gln Pro Lys
1               5                   10                  15

Lys Lys Arg Lys Val Xaa
            20

<210> SEQ ID NO 109
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (22)..(22)
<223> OTHER INFORMATION: Xaa = glycine or proline

<400> SEQUENCE: 109

Lys Glu Thr Trp Phe Glu Thr Trp Phe Thr Glu Trp Ser Gln Pro Lys
1               5                   10                  15

Lys Lys Arg Lys Val Xaa
            20

<210> SEQ ID NO 110
<211> LENGTH: 17
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (17)..(17)
<223> OTHER INFORMATION: Xaa = glycine or proline

<400> SEQUENCE: 110

Arg Gln Ile Lys Ile Trp Phe Gln Asn Arg Arg Met Lys Trp Lys Lys
1               5                   10                  15
```

Xaa

<210> SEQ ID NO 111
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (25)..(25)
<223> OTHER INFORMATION: Xaa = glycine or proline

<400> SEQUENCE: 111

Arg Arg Arg Arg Arg Arg Arg Gln Ile Lys Ile Trp Phe Gln Asn Arg
1               5                   10                  15

Arg Met Lys Trp Lys Lys Gly Gly Xaa
            20                  25

<210> SEQ ID NO 112
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)..(11)
<223> OTHER INFORMATION: Xaa = glycine or proline

<400> SEQUENCE: 112

Arg Arg Arg Gln Arg Arg Lys Lys Arg Cys Xaa
1               5                   10

<210> SEQ ID NO 113
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 113

Cys Tyr Gly Arg Lys Lys Arg Arg Gln Arg Arg Arg Xaa
1               5                   10

<210> SEQ ID NO 114
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 114

Arg Arg Arg Arg Arg Arg Arg Arg Arg Phe Phe Cys Xaa
1               5                   10

<210> SEQ ID NO 115
<211> LENGTH: 13
<212> TYPE: PRT
<213> ORGANISM: Artificial Sequence

```
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 115

Arg Arg Arg Arg Arg Arg Arg Arg Arg Cys Phe Phe Xaa
1               5                   10

<210> SEQ ID NO 116
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 116

Arg Arg Arg Arg Arg Arg Arg Cys Phe Phe Arg Xaa
1               5                   10

<210> SEQ ID NO 117
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 117

Arg Arg Arg Arg Arg Arg Cys Phe Phe Arg Arg Xaa
1               5                   10

<210> SEQ ID NO 118
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 118

Arg Arg Arg Arg Arg Phe Cys Phe Arg Arg Arg Xaa
1               5                   10

<210> SEQ ID NO 119
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)..(12)
<223> OTHER INFORMATION: Xaa = glycine or proline

<400> SEQUENCE: 119

Arg Arg Arg Arg Arg Phe Phe Arg Arg Arg Xaa
1               5                   10
```

```
<210> SEQ ID NO 120
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 120

Arg Arg Arg Arg Cys Phe Phe Arg Arg Arg Arg Arg Xaa
1               5                   10

<210> SEQ ID NO 121
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 121

Arg Arg Cys Phe Phe Arg Arg Arg Arg Arg Arg Arg Xaa
1               5                   10

<210> SEQ ID NO 122
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 122

Cys Phe Phe Arg Arg Arg Arg Arg Arg Arg Arg Arg Xaa
1               5                   10

<210> SEQ ID NO 123
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 123

Cys Arg Arg Arg Arg Arg Arg Arg Arg Arg Phe Phe Xaa
1               5                   10

<210> SEQ ID NO 124
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)..(12)
```

```
<223> OTHER INFORMATION: Xaa = glycine or proline

<400> SEQUENCE: 124

Phe Phe Arg Arg Arg Arg Arg Arg Arg Arg Xaa
1               5                   10

<210> SEQ ID NO 125
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (15)..(15)
<223> OTHER INFORMATION: Xaa = glycine or proline

<400> SEQUENCE: 125

Arg Arg Arg Arg Arg Phe Phe Cys Phe Phe Arg Arg Arg Arg Xaa
1               5                   10                  15

<210> SEQ ID NO 126
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)..(12)
<223> OTHER INFORMATION: Xaa = glycine or proline

<400> SEQUENCE: 126

Arg Arg Arg Arg Arg Arg Arg Arg Arg Ile Ile Xaa
1               5                   10

<210> SEQ ID NO 127
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)..(12)
<223> OTHER INFORMATION: Xaa = glycine or proline

<400> SEQUENCE: 127

Arg Arg Arg Arg Arg Arg Arg Arg Phe Phe Phe Xaa
1               5                   10

<210> SEQ ID NO 128
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (14)..(14)
<223> OTHER INFORMATION: Xaa = glycine or proline

<400> SEQUENCE: 128

Arg Arg Arg Arg Arg Arg Arg Arg Arg Phe Phe Phe Phe Xaa
1               5                   10

<210> SEQ ID NO 129
<211> LENGTH: 11
<212> TYPE: PRT
```

```
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)..(11)
<223> OTHER INFORMATION: Xaa = glycine or proline

<400> SEQUENCE: 129

Arg Arg Arg Arg Arg Arg Arg Arg Phe Phe Xaa
1               5                   10

<210> SEQ ID NO 130
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (9)..(9)
<223> OTHER INFORMATION: Xaa = glycine or proline

<400> SEQUENCE: 130

Arg Arg Arg Arg Arg Arg Phe Phe Xaa
1               5

<210> SEQ ID NO 131
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 131

Arg Arg Arg Arg Arg Phe Phe Xaa
1               5

<210> SEQ ID NO 132
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (3)..(3)
<223> OTHER INFORMATION: Xaa = 6-aminohexanoic acid
<220> FEATURE:
<221> NAME/KEY: MOD_RES
<222> LOCATION: (6)..(6)
<223> OTHER INFORMATION: Xaa = 6-aminohexanoic acid
<220> FEATURE:
<221> NAME/KEY: MOD_RES
<222> LOCATION: (9)..(9)
<223> OTHER INFORMATION: Xaa = 6-aminohexanoic acid
<220> FEATURE:
<221> NAME/KEY: MOD_RES
<222> LOCATION: (12)..(12)
<223> OTHER INFORMATION: Xaa = glycine or proline

<400> SEQUENCE: 132

Arg Arg Xaa Arg Arg Xaa Arg Arg Xaa Arg Arg Xaa
1               5                   10

<210> SEQ ID NO 133
```

<400> SEQUENCE: 133

000

<210> SEQ ID NO 134
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = 6-aminohexanoic acid
<220> FEATURE:
<221> NAME/KEY: MOD_RES
<222> LOCATION: (7)..(7)
<223> OTHER INFORMATION: Xaa = 6-aminohexanoic acid
<220> FEATURE:
<221> NAME/KEY: MOD_RES
<222> LOCATION: (10)..(10)
<223> OTHER INFORMATION: Xaa = 6-aminohexanoic acid
<220> FEATURE:
<221> NAME/KEY: MOD_RES
<222> LOCATION: (13)..(13)
<223> OTHER INFORMATION: Xaa = glycine or proline

<400> SEQUENCE: 134

Xaa Arg Arg Xaa Arg Arg Xaa Arg Arg Xaa Arg Arg Xaa
 1               5                  10

<210> SEQ ID NO 135
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = 6-aminohexanoic acid
<220> FEATURE:
<221> NAME/KEY: MOD_RES
<222> LOCATION: (6)..(6)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (10)..(10)
<223> OTHER INFORMATION: Xaa = 6-aminohexanoic acid
<220> FEATURE:
<221> NAME/KEY: MOD_RES
<222> LOCATION: (12)..(12)
<223> OTHER INFORMATION: Xaa = glycine or proline

<400> SEQUENCE: 135

Arg Xaa Arg Xaa Arg Xaa Arg Xaa Arg Xaa Arg Xaa
 1               5                  10

<210> SEQ ID NO 136
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (10)..(10)
<223> OTHER INFORMATION: Xaa = glycine or proline

<400> SEQUENCE: 136

Arg Xaa Arg Arg Xaa Arg Arg Xaa Arg Xaa
1               5                   10

<210> SEQ ID NO 137
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = glycine or proline

<400> SEQUENCE: 137

Arg Xaa Arg Arg Xaa Arg Arg Xaa
1               5

<210> SEQ ID NO 138
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = 6-aminohexanoic acid
<220> FEATURE:
<221> NAME/KEY: MOD_RES
<222> LOCATION: (7)..(7)
<223> OTHER INFORMATION: Xaa = glycine or proline

<400> SEQUENCE: 138

Arg Xaa Arg Arg Xaa Arg Xaa
1               5

<210> SEQ ID NO 139
<211> LENGTH: 12
<212> TYPE: PRT
<213> ORGANISM: Artificial Sequence

```
<220> FEATURE:
<223> OTHER INFORMATION: cell penetrating peptide
<220> FEATURE:
<221> NAME/KEY: MOD_RES
<222> LOCATION: (3)..(3)
<223> OTHER INFORMATION: Xaa = 6-aminohexanoic acid
<220> FEATURE:
<221> NAME/KEY: MOD_RES
<222> LOCATION: (6)..(6)
<223> OTHER INFORMATION: Xaa = 6-aminohexanoic acid
<220> FEATURE:
<221> NAME/KEY: MOD_RES
<222> LOCATION: (9)..(9)
<223> OTHER INFORMATION: Xaa = 6-aminohexanoic acid
<220> FEATURE:
<221> NAME/KEY: MOD_RES
<222> LOCATION: (12)..(12)
<223> OTHER INFORMATION: Xaa = glycine or proline

<400> SEQUENCE: 139

Arg Lys Xaa Arg Lys Xaa Arg Lys Xaa Arg Lys Xaa
1               5                   10

<210> SEQ ID NO 140
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (3)..(3)
<223> OTHER INFORMATION: Xaa = 6-aminohexanoic acid
<220> FEATURE:
<221> NAME/KEY: MOD_RES
<222> LOCATION: (6)..(6)
<223> OTHER INFORMATION: Xaa = 6-aminohexanoic acid
<220> FEATURE:
<221> NAME/KEY: MOD_RES
<222> LOCATION: (9)..(9)
<223> OTHER INFORMATION: Xaa = 6-aminohexanoic acid
<220> FEATURE:
<221> NAME/KEY: MOD_RES
<222> LOCATION: (12)..(12)
<223> OTHER INFORMATION: Xaa = glycine or proline

<400> SEQUENCE: 140

Arg His Xaa Arg His Xaa Arg His Xaa Arg His Xaa
1               5                   10

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144
```

```
000

<210> SEQ ID NO 145

<400> SEQUENCE: 145

000

<210> SEQ ID NO 146
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(12)
<223> OTHER INFORMATION: Xaa = 6-aminohexanoic acid
<220> FEATURE:
<221> NAME/KEY: MOD_RES
<222> LOCATION: (14)..(14)
<223> OTHER INFORMATION: Xaa = glycine or proline

<400> SEQUENCE: 146

Arg Xaa Arg Xaa Arg Xaa Arg Xaa Arg Xaa Arg Xaa Arg Xaa
1               5                   10

<210> SEQ ID NO 147
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(14)
<223> OTHER INFORMATION: Xaa = 6-aminohexanoic acid
<220> FEATURE:
<221> NAME/KEY: MOD_RES
<222> LOCATION: (16)..(16)
<223> OTHER INFORMATION: Xaa = glycine or proline

<400> SEQUENCE: 147

Arg Xaa Arg Arg Xaa Arg Arg Xaa Arg Arg Xaa Arg Arg Xaa Arg Xaa
1               5                   10                  15

<210> SEQ ID NO 148
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (11)..(11)
<223> OTHER INFORMATION: Xaa = beta-alanine
<220> FEATURE:
<221> NAME/KEY: MOD_RES
<222> LOCATION: (13)..(13)
<223> OTHER INFORMATION: Xaa = glycine or proline
```

```
<400> SEQUENCE: 148

Arg Xaa Arg Arg Xaa Arg Arg Xaa Arg Arg Xaa Arg Xaa
1               5                   10

<210> SEQ ID NO 149
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (11)..(11)
<223> OTHER INFORMATION: Xaa = beta-alanine
<220> FEATURE:
<221> NAME/KEY: MOD_RES
<222> LOCATION: (13)..(13)
<223> OTHER INFORMATION: Xaa = glycine or proline

<400> SEQUENCE: 149

Arg Xaa Arg Arg Xaa Arg Arg Xaa Arg Arg Xaa Arg Xaa
1               5                   10

<210> SEQ ID NO 150
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(11)
<223> OTHER INFORMATION: Xaa = beta-alanine
<220> FEATURE:
<221> NAME/KEY: MOD_RES
<222> LOCATION: (12)..(12)
<223> OTHER INFORMATION: Xaa = 6-aminohexanoic acid
<220> FEATURE:
<221> NAME/KEY: MOD_RES
<222> LOCATION: (14)..(14)
<223> OTHER INFORMATION: Xaa = beta-alanine
<220> FEATURE:
<221> NAME/KEY: MOD_RES
<222> LOCATION: (16)..(16)
<223> OTHER INFORMATION: Xaa = glycine or proline

<400> SEQUENCE: 150

Arg Xaa Arg Xaa Arg Xaa Arg Xaa Arg Xaa Arg Xaa Arg Xaa Arg Xaa
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(7)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (10)..(14)
<223> OTHER INFORMATION: Xaa = beta-alanine
<220> FEATURE:
```

```
<221> NAME/KEY: MOD_RES
<222> LOCATION: (16)..(16)
<223> OTHER INFORMATION: Xaa = glycine or proline

<400> SEQUENCE: 151

Arg Xaa Arg Xaa Arg Xaa Arg Xaa Arg Xaa Arg Xaa Arg Xaa Arg Xaa
1               5                   10                  15

<210> SEQ ID NO 152
<211> LENGTH: 17
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Xaa = 6-aminohexanoic acid
<220> FEATURE:
<221> NAME/KEY: MOD_RES
<222> LOCATION: (3)..(7)
<223> OTHER INFORMATION: Xaa = beta-alanine
<220> FEATURE:
<221> NAME/KEY: MOD_RES
<222> LOCATION: (9)..(9)
<223> OTHER INFORMATION: Xaa = 6-aminohexanoic acid
<220> FEATURE:
<221> NAME/KEY: MOD_RES
<222> LOCATION: (11)..(15)
<223> OTHER INFORMATION: Xaa = beta-alanine
<220> FEATURE:
<221> NAME/KEY: MOD_RES
<222> LOCATION: (17)..(17)
<223> OTHER INFORMATION: Xaa = glycine or proline

<400> SEQUENCE: 152

Xaa Arg Xaa Arg Xaa Arg Xaa Arg Xaa Arg Xaa Arg Xaa Arg Xaa Arg
1               5                   10                  15

Xaa

<210> SEQ ID NO 153
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa = 6-aminohexanoic acid
<220> FEATURE:
<221> NAME/KEY: MOD_RES
<222> LOCATION: (6)..(6)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (10)..(10)
<223> OTHER INFORMATION: Xaa = beta-alanine
<220> FEATURE:
<221> NAME/KEY: MOD_RES
<222> LOCATION: (12)..(12)
<223> OTHER INFORMATION: Xaa = 6-aminohexanoic acid
<220> FEATURE:
<221> NAME/KEY: MOD_RES
<222> LOCATION: (14)..(14)
<223> OTHER INFORMATION: Xaa = beta-alanine
```

```
<220> FEATURE:
<221> NAME/KEY: MOD_RES
<222> LOCATION: (16)..(16)
<223> OTHER INFORMATION: Xaa = glycine or proline

<400> SEQUENCE: 153

Arg Xaa Arg Xaa Arg Xaa Arg Xaa Arg Xaa Arg Xaa Arg Xaa Arg Xaa
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(9)
<223> OTHER INFORMATION: Xaa = beta-alanine
<220> FEATURE:
<221> NAME/KEY: MOD_RES
<222> LOCATION: (10)..(14)
<223> OTHER INFORMATION: Xaa = 6-aminohexanoic acid
<220> FEATURE:
<221> NAME/KEY: MOD_RES
<222> LOCATION: (16)..(16)
<223> OTHER INFORMATION: Xaa = glycine or proline

<400> SEQUENCE: 154

Arg Xaa Arg Xaa Arg Xaa Arg Xaa Arg Xaa Arg Xaa Arg Xaa Arg Xaa
1               5                   10                  15

<210> SEQ ID NO 155
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = beta-alanine
<220> FEATURE:
<221> NAME/KEY: MOD_RES
<222> LOCATION: (6)..(6)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (10)..(14)
<223> OTHER INFORMATION: Xaa = beta-alanine
<220> FEATURE:
<221> NAME/KEY: MOD_RES
<222> LOCATION: (16)..(16)
<223> OTHER INFORMATION: Xaa = glycine or proline

<400> SEQUENCE: 155

Arg Xaa Arg Xaa Arg Xaa Arg Xaa Arg Xaa Arg Xaa Arg Xaa Arg Xaa
1               5                   10                  15

<210> SEQ ID NO 156
<211> LENGTH: 16
<212> TYPE: PRT
<213> ORGANISM: Artificial Sequence
<220> FEATURE:
<223> OTHER INFORMATION: cell penetrating peptide
```

```
<220> FEATURE:
<221> NAME/KEY: MOD_RES
<222> LOCATION: (1)..(14)
<223> OTHER INFORMATION: Xaa = beta-alanine
<220> FEATURE:
<221> NAME/KEY: MOD_RES
<222> LOCATION: (16)..(16)
<223> OTHER INFORMATION: Xaa = glycine or proline

<400> SEQUENCE: 156

Arg Xaa Arg Xaa Arg Xaa Arg Xaa Arg Xaa Arg Xaa Arg Xaa Arg Xaa
1               5                   10                  15

<210> SEQ ID NO 157
<211> LENGTH: 6
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Xaa = unmodified amino terminus, or the amino
      terminal capped with an acetyl, benzoyl or stearoyl group (i.e.,
      an acetyl amide, benzoyl amide or stearoyl amide)
<220> FEATURE:
<221> NAME/KEY: MOD_RES
<222> LOCATION: (6)..(6)
<223> OTHER INFORMATION: Xaa = glycine or proline

<400> SEQUENCE: 157

Xaa Arg Arg Arg Arg Xaa
1               5

<210> SEQ ID NO 158
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Xaa = unmodified amino terminus, or the amino
      terminal capped with an acetyl, benzoyl or stearoyl group (i.e.,
      an acetyl amide, benzoyl amide or stearoyl amide)
<220> FEATURE:
<221> NAME/KEY: MOD_RES
<222> LOCATION: (7)..(7)
<223> OTHER INFORMATION: Xaa = glycine or proline

<400> SEQUENCE: 158

Xaa Arg Arg Arg Arg Arg Xaa
1               5

<210> SEQ ID NO 159
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Xaa = unmodified amino terminus, or the amino
      terminal capped with an acetyl, benzoyl or stearoyl group (i.e.,
      an acetyl amide, benzoyl amide or stearoyl amide)
<220> FEATURE:
<221> NAME/KEY: MOD_RES
<222> LOCATION: (8)..(8)
<223> OTHER INFORMATION: Xaa = glycine or proline

<400> SEQUENCE: 159
```

```
Xaa Arg Arg Arg Arg Arg Arg Xaa
1               5

<210> SEQ ID NO 160
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Xaa = unmodified amino terminus, or the amino
      terminal capped with an acetyl, benzoyl or stearoyl group (i.e.,
      an acetyl amide, benzoyl amide or stearoyl amide)
<220> FEATURE:
<221> NAME/KEY: MOD_RES
<222> LOCATION: (9)..(9)
<223> OTHER INFORMATION: Xaa = glycine or proline

<400> SEQUENCE: 160

Xaa Arg Arg Arg Arg Arg Arg Arg Xaa
1               5

<210> SEQ ID NO 161
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Xaa = unmodified amino terminus, or the amino
      terminal capped with an acetyl, benzoyl or stearoyl group (i.e.,
      an acetyl amide, benzoyl amide or stearoyl amide)
<220> FEATURE:
<221> NAME/KEY: MOD_RES
<222> LOCATION: (10)..(10)
<223> OTHER INFORMATION: Xaa = glycine or proline

<400> SEQUENCE: 161

Xaa Arg Arg Arg Arg Arg Arg Arg Arg Xaa
1               5                   10

<210> SEQ ID NO 162
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Xaa = unmodified amino terminus, or the amino
      terminal capped with an acetyl, benzoyl or stearoyl group (i.e.,
      an acetyl amide, benzoyl amide or stearoyl amide)
<220> FEATURE:
<221> NAME/KEY: MOD_RES
<222> LOCATION: (12)..(12)
<223> OTHER INFORMATION: Xaa = glycine or proline

<400> SEQUENCE: 162

Xaa Arg Arg Arg Arg Arg Gly Arg Arg Arg Arg Xaa
1               5                   10

<210> SEQ ID NO 163
<211> LENGTH: 13
<212> TYPE: PRT
<213> ORGANISM: Artificial Sequence
<220> FEATURE:
```

```
<223> OTHER INFORMATION: cell penetrating peptide
<220> FEATURE:
<221> NAME/KEY: MOD_RES
<222> LOCATION: (1)..(1)
<223> OTHER INFORMATION: Xaa = unmodified amino terminus, or the amino
      terminal capped with an acetyl, benzoyl or stearoyl group (i.e.,
      an acetyl amide, benzoyl amide or stearoyl amide)
<220> FEATURE:
<221> NAME/KEY: MOD_RES
<222> LOCATION: (13)..(13)
<223> OTHER INFORMATION: Xaa = glycine or proline

<400> SEQUENCE: 163

Xaa Arg Arg Arg Arg Arg Phe Phe Arg Arg Arg Arg Xaa
1               5                   10

<210> SEQ ID NO 164
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Xaa = unmodified amino terminus, or the amino
      terminal capped with an acetyl, benzoyl or stearoyl group (i.e.,
      an acetyl amide, benzoyl amide or stearoyl amide)
<220> FEATURE:
<221> NAME/KEY: MOD_RES
<222> LOCATION: (11)..(11)
<223> OTHER INFORMATION: Xaa = glycine or proline

<400> SEQUENCE: 164

Xaa Arg Lys Lys Arg Arg Gln Arg Arg Arg Xaa
1               5                   10

<210> SEQ ID NO 165
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Xaa = unmodified amino terminus, or the amino
      terminal capped with an acetyl, benzoyl or stearoyl group (i.e.,
      an acetyl amide, benzoyl amide or stearoyl amide)
<220> FEATURE:
<221> NAME/KEY: MOD_RES
<222> LOCATION: (11)..(11)
<223> OTHER INFORMATION: Xaa = glycine or proline

<400> SEQUENCE: 165

Xaa Arg Arg Arg Gln Arg Arg Lys Lys Arg Xaa
1               5                   10

<210> SEQ ID NO 166

<400> SEQUENCE: 166

000

<210> SEQ ID NO 167
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
```

```
<222> LOCATION: (2)..(5)
<223> OTHER INFORMATION: Xaa = beta-alanine
<220> FEATURE:
<221> NAME/KEY: MOD_RES
<222> LOCATION: (7)..(7)
<223> OTHER INFORMATION: Xaa = glycine or proline

<400> SEQUENCE: 167

Arg Xaa Arg Arg Xaa Arg Xaa
1               5

<210> SEQ ID NO 168
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = beta-alanine
<220> FEATURE:
<221> NAME/KEY: MOD_RES
<222> LOCATION: (7)..(7)
<223> OTHER INFORMATION: Xaa = glycine or proline

<400> SEQUENCE: 168

Arg Xaa Arg Arg Xaa Arg Xaa
1               5

<210> SEQ ID NO 169
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (5)..(5)
<223> OTHER INFORMATION: Xaa = 6-aminohexanoic acid
<220> FEATURE:
<221> NAME/KEY: MOD_RES
<222> LOCATION: (7)..(7)
<223> OTHER INFORMATION: Xaa = glycine or proline

<400> SEQUENCE: 169

Arg Xaa Arg Arg Xaa Arg Xaa
1               5

<210> SEQ ID NO 170
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
```

```
<221> NAME/KEY: MOD_RES
<222> LOCATION: (6)..(6)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa - glycine or proline

<400> SEQUENCE: 170

Arg Xaa Arg Xaa Arg Xaa Arg Xaa
1               5

<210> SEQ ID NO 171
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = glycine or proline

<400> SEQUENCE: 171

Arg Xaa Arg Xaa Arg Xaa Arg Xaa
1               5

<210> SEQ ID NO 172
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = glycine or proline

<400> SEQUENCE: 172

Arg Xaa Arg Xaa Arg Xaa Arg Xaa
1               5

<210> SEQ ID NO 173
<211> LENGTH: 8
<212> TYPE: PRT
<213> ORGANISM: Artificial Sequence
<220> FEATURE:
```

```
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = glycine or proline

<400> SEQUENCE: 173

Arg Xaa Arg Xaa Arg Xaa Arg Xaa
1               5

<210> SEQ ID NO 174
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(10)
<223> OTHER INFORMATION: Xaa = 6-aminohexanoic acid
<220> FEATURE:
<221> NAME/KEY: MOD_RES
<222> LOCATION: (12)..(12)
<223> OTHER INFORMATION: Xaa = glycine or proline

<400> SEQUENCE: 174

Arg Xaa Arg Ile Leu Phe Gln Tyr Arg Xaa Arg Xaa
1               5                   10

<210> SEQ ID NO 175
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(10)
<223> OTHER INFORMATION: Xaa = beta-alanine
<220> FEATURE:
<221> NAME/KEY: MOD_RES
<222> LOCATION: (12)..(12)
<223> OTHER INFORMATION: Xaa = glycine or proline

<400> SEQUENCE: 175

Arg Xaa Arg Ile Leu Phe Gln Tyr Arg Xaa Arg Xaa
1               5                   10

<210> SEQ ID NO 176
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
```

```
<222> LOCATION: (10)..(10)
<223> OTHER INFORMATION: Xaa = beta-alanine
<220> FEATURE:
<221> NAME/KEY: MOD_RES
<222> LOCATION: (12)..(12)
<223> OTHER INFORMATION: Xaa = glycine or proline

<400> SEQUENCE: 176

Arg Xaa Arg Ile Leu Phe Gln Tyr Arg Xaa Arg Xaa
1               5                   10

<210> SEQ ID NO 177
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (10)..(10)
<223> OTHER INFORMATION: Xaa = 6-aminohexanoic acid
<220> FEATURE:
<221> NAME/KEY: MOD_RES
<222> LOCATION: (12)..(12)
<223> OTHER INFORMATION: Xaa = glycine or proline

<400> SEQUENCE: 177

Arg Xaa Arg Ile Leu Phe Gln Tyr Arg Xaa Arg Xaa
1               5                   10

<210> SEQ ID NO 178

<400> SEQUENCE: 178

000

<210> SEQ ID NO 179
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = beta-alanine
<220> FEATURE:
<221> NAME/KEY: MOD_RES
<222> LOCATION: (10)..(10)
<223> OTHER INFORMATION: Xaa = glycine or proline

<400> SEQUENCE: 179

Arg Xaa Arg Arg Xaa Arg Arg Xaa Arg Xaa
1               5                   10

<210> SEQ ID NO 180
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
```

```
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (10)..(10)
<223> OTHER INFORMATION: Xaa = glycine or proline

<400> SEQUENCE: 180

Arg Xaa Arg Arg Xaa Arg Arg Xaa Arg Xaa
1               5                   10

<210> SEQ ID NO 181
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(8)
<223> OTHER INFORMATION: Xaa = beta-alanine
<220> FEATURE:
<221> NAME/KEY: MOD_RES
<222> LOCATION: (10)..(10)
<223> OTHER INFORMATION: Xaa = glycine or proline

<400> SEQUENCE: 181

Arg Xaa Arg Arg Xaa Arg Arg Xaa Arg Xaa
1               5                   10

<210> SEQ ID NO 182
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(5)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = beta-alanine
<220> FEATURE:
<221> NAME/KEY: MOD_RES
<222> LOCATION: (10)..(10)
<223> OTHER INFORMATION: Xaa = glycine or proline

<400> SEQUENCE: 182

Arg Xaa Arg Arg Xaa Arg Arg Xaa Arg Xaa
1               5                   10

<210> SEQ ID NO 183
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (5)..(5)
```

```
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = beta-alanine
<220> FEATURE:
<221> NAME/KEY: MOD_RES
<222> LOCATION: (10)..(10)
<223> OTHER INFORMATION: Xaa = glycine or proline

<400> SEQUENCE: 183

Arg Xaa Arg Arg Xaa Arg Arg Xaa Arg Xaa
1               5                   10

<210> SEQ ID NO 184
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (5)..(8)
<223> OTHER INFORMATION: Xaa = 6-aminohexanoic acid
<220> FEATURE:
<221> NAME/KEY: MOD_RES
<222> LOCATION: (10)..(10)
<223> OTHER INFORMATION: Xaa = glycine or proline

<400> SEQUENCE: 184

Arg Xaa Arg Arg Xaa Arg Arg Xaa Arg Xaa
1               5                   10

<210> SEQ ID NO 185
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(5)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (10)..(10)
<223> OTHER INFORMATION: Xaa = glycine or proline

<400> SEQUENCE: 185

Arg Xaa Arg Arg Xaa Arg Arg Xaa Arg Xaa
1               5                   10

<210> SEQ ID NO 186
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
```

```
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(9)
<223> OTHER INFORMATION: Xaa = 6-aminohexanoic acid
<220> FEATURE:
<221> NAME/KEY: MOD_RES
<222> LOCATION: (11)..(11)
<223> OTHER INFORMATION: Xaa = glycine or proline

<400> SEQUENCE: 186

Arg Xaa Arg Xaa Arg Xaa Arg Xaa Arg Xaa
1               5                   10

<210> SEQ ID NO 187
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(5)
<223> OTHER INFORMATION: Xaa = 6-aminohexanoic acid
<220> FEATURE:
<221> NAME/KEY: MOD_RES
<222> LOCATION: (7)..(7)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (9)..(9)
<223> OTHER INFORMATION: Xaa = 6-aminohexanoic acid
<220> FEATURE:
<221> NAME/KEY: MOD_RES
<222> LOCATION: (11)..(11)
<223> OTHER INFORMATION: Xaa = glycine or proline

<400> SEQUENCE: 187

Arg Xaa Arg Arg Xaa Arg Xaa Arg Xaa Arg Xaa
1               5                   10

<210> SEQ ID NO 188
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(13)
<223> OTHER INFORMATION: Xaa = 6-aminohexanoic acid
<220> FEATURE:
<221> NAME/KEY: MOD_RES
<222> LOCATION: (15)..(15)
<223> OTHER INFORMATION: Xaa = glycine or proline

<400> SEQUENCE: 188

Arg Xaa Arg Ile Leu Phe Gln Tyr Arg Xaa Arg Arg Xaa Arg Xaa
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(13)
<223> OTHER INFORMATION: Xaa = 6-aminohexanoic acid
<220> FEATURE:
```

```
<221> NAME/KEY: MOD_RES
<222> LOCATION: (15)..(15)
<223> OTHER INFORMATION: Xaa = glycine or proline

<400> SEQUENCE: 189

Arg Xaa Arg Arg Xaa Arg Ile Leu Phe Gln Tyr Arg Xaa Arg Xaa
1               5                   10                  15

<210> SEQ ID NO 190
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (10)..(10)
<223> OTHER INFORMATION: Xaa = 6-aminohexanoic acid
<220> FEATURE:
<221> NAME/KEY: MOD_RES
<222> LOCATION: (12)..(12)
<223> OTHER INFORMATION: Xaa = glycine or proline

<400> SEQUENCE: 190

Arg Xaa Arg Xaa Arg Xaa Arg Xaa Arg Xaa Arg Xaa
1               5                   10

<210> SEQ ID NO 191
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(18)
<223> OTHER INFORMATION: Xaa = 6-aminohexanoic acid
<220> FEATURE:
<221> NAME/KEY: MOD_RES
<222> LOCATION: (20)..(20)
<223> OTHER INFORMATION: Xaa = glycine or proline

<400> SEQUENCE: 191

Arg Xaa Arg Ile Leu Phe Gln Tyr Arg Xaa Arg Ile Leu Phe Gln Tyr
1               5                   10                  15

Arg Xaa Arg Xaa
            20

<210> SEQ ID NO 192
<211> LENGTH: 16
<212> TYPE: PRT
<213> ORGANISM: Artificial Sequence
<220> FEATURE:
<223> OTHER INFORMATION: cell penetrating peptide
```

```
<220> FEATURE:
<221> NAME/KEY: MOD_RES
<222> LOCATION: (2)..(10)
<223> OTHER INFORMATION: Xaa = 6-aminohexanoic acid
<220> FEATURE:
<221> NAME/KEY: MOD_RES
<222> LOCATION: (12)..(12)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (14)..(14)
<223> OTHER INFORMATION: Xaa = 6-aminohexanoic acid
<220> FEATURE:
<221> NAME/KEY: MOD_RES
<222> LOCATION: (16)..(16)
<223> OTHER INFORMATION: Xaa = glycine or proline

<400> SEQUENCE: 192

Arg Xaa Arg Ile Leu Phe Gln Tyr Arg Xaa Arg Xaa Arg Xaa Arg Xaa
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(14)
<223> OTHER INFORMATION: Xaa = 6-aminohexanoic acid
<220> FEATURE:
<221> NAME/KEY: MOD_RES
<222> LOCATION: (16)..(16)
<223> OTHER INFORMATION: Xaa = glycine or proline

<400> SEQUENCE: 193

Arg Xaa Arg Xaa Arg Xaa Arg Ile Leu Phe Gln Tyr Arg Xaa Arg Xaa
1               5                   10                  15

<210> SEQ ID NO 194
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = beta-alanine
<220> FEATURE:
<221> NAME/KEY: MOD_RES
<222> LOCATION: (9)..(9)
<223> OTHER INFORMATION: Xaa = beta-alanine
<220> FEATURE:
<221> NAME/KEY: MOD_RES
```

```
<222> LOCATION: (11)..(11)
<223> OTHER INFORMATION: Xaa = glycine or proline

<400> SEQUENCE: 194

Arg Xaa Arg Xaa Arg Xaa Arg Xaa Arg Xaa
1               5                   10

<210> SEQ ID NO 195
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(5)
<223> OTHER INFORMATION: Xaa = beta-alanine
<220> FEATURE:
<221> NAME/KEY: MOD_RES
<222> LOCATION: (7)..(7)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (9)..(9)
<223> OTHER INFORMATION: Xaa = beta-alanine
<220> FEATURE:
<221> NAME/KEY: MOD_RES
<222> LOCATION: (11)..(11)
<223> OTHER INFORMATION: Xaa = glycine or proline

<400> SEQUENCE: 195

Arg Xaa Arg Arg Xaa Arg Xaa Arg Xaa Arg Xaa
1               5                   10

<210> SEQ ID NO 196
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(13)
<223> OTHER INFORMATION: Xaa = beta-alanine
<220> FEATURE:
<221> NAME/KEY: MOD_RES
<222> LOCATION: (15)..(15)
<223> OTHER INFORMATION: Xaa = glycine or proline

<400> SEQUENCE: 196

Arg Xaa Arg Ile Leu Phe Gln Tyr Arg Xaa Arg Xaa Arg Xaa
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(13)
<223> OTHER INFORMATION: Xaa = beta-alanine
<220> FEATURE:
<221> NAME/KEY: MOD_RES
<222> LOCATION: (15)..(15)
<223> OTHER INFORMATION: Xaa = glycine or proline

<400> SEQUENCE: 197

Arg Xaa Arg Arg Asx Arg Ile Leu Phe Gln Tyr Arg Xaa Arg Xaa
1               5                   10                  15
```

<210> SEQ ID NO 198
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(6)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (10)..(10)
<223> OTHER INFORMATION: Xaa = beta-alanine
<220> FEATURE:
<221> NAME/KEY: MOD_RES
<222> LOCATION: (12)..(12)
<223> OTHER INFORMATION: Xaa = glycine or proline

<400> SEQUENCE: 198

Arg Xaa Arg Tyr Arg Xaa Arg Xaa Arg Xaa Arg Xaa
1               5                   10

<210> SEQ ID NO 199
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(18)
<223> OTHER INFORMATION: Xaa = beta-alanine
<220> FEATURE:
<221> NAME/KEY: MOD_RES
<222> LOCATION: (20)..(20)
<223> OTHER INFORMATION: Xaa = glycine or proline

<400> SEQUENCE: 199

Arg Xaa Arg Ile Leu Phe Gln Tyr Arg Xaa Arg Ile Leu Phe Gln Tyr
1               5                   10                  15

Arg Xaa Arg Xaa
            20

<210> SEQ ID NO 200
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(14)
<223> OTHER INFORMATION: Xaa = beta-alanine
<220> FEATURE:
<221> NAME/KEY: MOD_RES
<222> LOCATION: (16)..(16)
<223> OTHER INFORMATION: Xaa = glycine or alanine -continued

```
<400> SEQUENCE: 200

Arg Xaa Arg Xaa Arg Xaa Arg Ile Leu Phe Gln Tyr Arg Xaa Arg Xaa
1               5                   10                  15

<210> SEQ ID NO 201
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(10)
<223> OTHER INFORMATION: Xaa = beta-alanine
<220> FEATURE:
<221> NAME/KEY: MOD_RES
<222> LOCATION: (12)..(12)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (14)..(14)
<223> OTHER INFORMATION: Xaa = beta-alanine
<220> FEATURE:
<221> NAME/KEY: MOD_RES
<222> LOCATION: (16)..(16)
<223> OTHER INFORMATION: Xaa = glycine or proline

<400> SEQUENCE: 201

Arg Xaa Arg Ile Leu Phe Gln Tyr Arg Xaa Arg Xaa Arg Xaa Arg Xaa
1               5                   10                  15

<210> SEQ ID NO 202
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = beta-alanine
<220> FEATURE:
<221> NAME/KEY: MOD_RES
<222> LOCATION: (9)..(9)
<223> OTHER INFORMATION: Xaa = 6-aminohexanoic acid
<220> FEATURE:
<221> NAME/KEY: MOD_RES
<222> LOCATION: (11)..(11)
<223> OTHER INFORMATION: Xaa = glycine or proline

<400> SEQUENCE: 202

Arg Xaa Arg Xaa Arg Xaa Arg Arg Xaa Arg Xaa
1               5                   10

<210> SEQ ID NO 203
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
```

```
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = beta-alanine
<220> FEATURE:
<221> NAME/KEY: MOD_RES
<222> LOCATION: (7)..(7)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (9)..(9)
<223> OTHER INFORMATION: Xaa = 6-aminohexanoic acid
<220> FEATURE:
<221> NAME/KEY: MOD_RES
<222> LOCATION: (11)..(11)
<223> OTHER INFORMATION: Xaa = glycine or proline

<400> SEQUENCE: 203

Arg Xaa Arg Arg Xaa Arg Xaa Arg Xaa Arg Xaa
1               5                   10

<210> SEQ ID NO 204
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (10)..(10)
<223> OTHER INFORMATION: Xaa = beta-alanine
<220> FEATURE:
<221> NAME/KEY: MOD_RES
<222> LOCATION: (13)..(13)
<223> OTHER INFORMATION: Xaa = 6-aminohexanoic acid
<220> FEATURE:
<221> NAME/KEY: MOD_RES
<222> LOCATION: (15)..(15)
<223> OTHER INFORMATION: Xaa = glycine or proline

<400> SEQUENCE: 204

Arg Xaa Arg Ile Leu Phe Gln Tyr Arg Xaa Arg Arg Xaa Arg Xaa
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = beta-alanine
<220> FEATURE:
<221> NAME/KEY: MOD_RES
<222> LOCATION: (13)..(13)
<223> OTHER INFORMATION: Xaa = 6-aminohexanoic acid
<220> FEATURE:
<221> NAME/KEY: MOD_RES
<222> LOCATION: (15)..(15)
<223> OTHER INFORMATION: Xaa = glycine or proline

<400> SEQUENCE: 205
```

Arg Xaa Arg Arg Xaa Arg Ile Leu Phe Gln Tyr Arg Xaa Arg Xaa
1               5                   10                  15

<210> SEQ ID NO 206
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (10)..(10)
<223> OTHER INFORMATION: Xaa = 6-aminohexanoic acid
<220> FEATURE:
<221> NAME/KEY: MOD_RES
<222> LOCATION: (12)..(12)
<223> OTHER INFORMATION: Xaa = glycine or proline

<400> SEQUENCE: 206

Arg Xaa Arg Xaa Arg Xaa Arg Xaa Arg Xaa Arg Xaa
1               5                   10

<210> SEQ ID NO 207
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (10)..(10)
<223> OTHER INFORMATION: Xaa = beta-alanine
<220> FEATURE:
<221> NAME/KEY: MOD_RES
<222> LOCATION: (18)..(18)
<223> OTHER INFORMATION: Xaa = 6-aminohexanoic acid
<220> FEATURE:
<221> NAME/KEY: MOD_RES
<222> LOCATION: (20)..(20)
<223> OTHER INFORMATION: Xaa = glycine or proline

<400> SEQUENCE: 207

Arg Xaa Arg Ile Leu Phe Gln Tyr Arg Xaa Arg Ile Leu Phe Gln Tyr
1               5                   10                  15

Arg Xaa Arg Xaa
            20

<210> SEQ ID NO 208
<211> LENGTH: 16
<212> TYPE: PRT

```
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = beta-alanine
<220> FEATURE:
<221> NAME/KEY: MOD_RES
<222> LOCATION: (14)..(14)
<223> OTHER INFORMATION: Xaa = 6-aminohexanoic acid
<220> FEATURE:
<221> NAME/KEY: MOD_RES
<222> LOCATION: (16)..(16)
<223> OTHER INFORMATION: Xaa = glycine or proline

<400> SEQUENCE: 208

Arg Xaa Arg Xaa Arg Xaa Arg Ile Leu Phe Gln Tyr Arg Xaa Arg Xaa
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (10)..(10)
<223> OTHER INFORMATION: Xaa = beta-alanine
<220> FEATURE:
<221> NAME/KEY: MOD_RES
<222> LOCATION: (12)..(12)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (14)..(14)
<223> OTHER INFORMATION: Xaa = 6-aminohexanoic acid
<220> FEATURE:
<221> NAME/KEY: MOD_RES
<222> LOCATION: (16)..(16)
<223> OTHER INFORMATION: Xaa = glycine or proline

<400> SEQUENCE: 209

Arg Xaa Arg Ile Leu Phe Gln Tyr Arg Xaa Arg Xaa Arg Xaa Arg Xaa
1               5                   10                  15

<210> SEQ ID NO 210
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
```

```
        each R is independently, at each occurrence, hydrogen or methyl
<220> FEATURE:
<221> NAME/KEY: MOD_RES
<222> LOCATION: (6)..(9)
<223> OTHER INFORMATION: Xaa = beta-alanine
<220> FEATURE:
<221> NAME/KEY: MOD_RES
<222> LOCATION: (11)..(11)
<223> OTHER INFORMATION: Xaa = glycine or proline

<400> SEQUENCE: 210

Arg Xaa Arg Xaa Arg Xaa Arg Arg Xaa Arg Xaa
1               5                   10

<210> SEQ ID NO 211
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = beta-alanine
<220> FEATURE:
<221> NAME/KEY: MOD_RES
<222> LOCATION: (7)..(7)
<223> OTHER INFORMATION: Xaa = NH- (CHR)-C(O) - wherein n is 2 to 7 and
        each R is independently, at each occurrence, hydrogen or methyl
<220> FEATURE:
<221> NAME/KEY: MOD_RES
<222> LOCATION: (9)..(9)
<223> OTHER INFORMATION: Xaa = beta-alanine
<220> FEATURE:
<221> NAME/KEY: MOD_RES
<222> LOCATION: (11)..(11)
<223> OTHER INFORMATION: Xaa = glycine or proline

<400> SEQUENCE: 211

Arg Xaa Arg Arg Xaa Arg Xaa Arg Xaa Arg Xaa
1               5                   10

<210> SEQ ID NO 212
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (10)..(13)
<223> OTHER INFORMATION: Xaa = beta-alanine
<220> FEATURE:
<221> NAME/KEY: MOD_RES
<222> LOCATION: (15)..(15)
<223> OTHER INFORMATION: Xaa = glycine or proline

<400> SEQUENCE: 212

Arg Xaa Arg Ile Leu Phe Gln Tyr Arg Xaa Arg Xaa Arg Xaa
1               5                   10                  15

<210> SEQ ID NO 213
<211> LENGTH: 15
<212> TYPE: PRT
<213> ORGANISM: Artificial Sequence
```

```
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(13)
<223> OTHER INFORMATION: Xaa = beta-alanine
<220> FEATURE:
<221> NAME/KEY: MOD_RES
<222> LOCATION: (15)..(15)
<223> OTHER INFORMATION: Xaa = glycine or proline

<400> SEQUENCE: 213

Arg Xaa Arg Arg Xaa Arg Ile Leu Phe Gln Tyr Arg Xaa Arg Xaa
1               5                   10                  15

<210> SEQ ID NO 214
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = NH-(CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = NH-(CHR)-C(O) - wherein n is 2 to 7 and
      each R is independently, at each occurrence, hydrogen or methyl
<220> FEATURE:
<221> NAME/KEY: MOD_RES
<222> LOCATION: (10)..(10)
<223> OTHER INFORMATION: Xaa = beta-alanine
<220> FEATURE:
<221> NAME/KEY: MOD_RES
<222> LOCATION: (12)..(12)
<223> OTHER INFORMATION: Xaa = glycine or proline

<400> SEQUENCE: 214

Arg Xaa Arg Xaa Arg Xaa Arg Xaa Arg Xaa Arg Xaa
1               5                   10

<210> SEQ ID NO 215
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (10)..(18)
<223> OTHER INFORMATION: Xaa = beta-alanine
<220> FEATURE:
<221> NAME/KEY: MOD_RES
<222> LOCATION: (20)..(20)
<223> OTHER INFORMATION: Xaa = glycine or proline
```

-continued

```
<400> SEQUENCE: 215

Arg Xaa Arg Ile Leu Phe Gln Tyr Arg Xaa Arg Ile Leu Phe Gln Tyr
1               5                   10                  15

Arg Xaa Arg Xaa
            20

<210> SEQ ID NO 216
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(14)
<223> OTHER INFORMATION: Xaa = beta-alanine
<220> FEATURE:
<221> NAME/KEY: MOD_RES
<222> LOCATION: (16)..(16)
<223> OTHER INFORMATION: Xaa = glycine or proline

<400> SEQUENCE: 216

Arg Xaa Arg Xaa Arg Xaa Arg Ile Leu Phe Gln Tyr Arg Xaa Arg Xaa
1               5                   10                  15

<210> SEQ ID NO 217
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (10)..(10)
<223> OTHER INFORMATION: Xaa = beta-alanine
<220> FEATURE:
<221> NAME/KEY: MOD_RES
<222> LOCATION: (12)..(12)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (14)..(14)
<223> OTHER INFORMATION: Xaa = beta-alanine
<220> FEATURE:
<221> NAME/KEY: MOD_RES
<222> LOCATION: (16)..(16)
<223> OTHER INFORMATION: Xaa = glycine or proline

<400> SEQUENCE: 217

Arg Xaa Arg Ile Leu Phe Gln Tyr Arg Xaa Arg Xaa Arg Xaa Arg Xaa
1               5                   10                  15

<210> SEQ ID NO 218
<211> LENGTH: 11
<212> TYPE: PRT
<213> ORGANISM: Artificial Sequence
<220> FEATURE:
<223> OTHER INFORMATION: cell penetrating peptide
```

```
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = 6-aminohexanoic acid
<220> FEATURE:
<221> NAME/KEY: MOD_RES
<222> LOCATION: (9)..(9)
<223> OTHER INFORMATION: Xaa = beta-alanine
<220> FEATURE:
<221> NAME/KEY: MOD_RES
<222> LOCATION: (11)..(11)
<223> OTHER INFORMATION: Xaa = glycine or proline

<400> SEQUENCE: 218

Arg Xaa Arg Xaa Arg Xaa Arg Arg Xaa Arg Xaa
1               5                   10

<210> SEQ ID NO 219
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(5)
<223> OTHER INFORMATION: Xaa = 6-aminohexanoic acid
<220> FEATURE:
<221> NAME/KEY: MOD_RES
<222> LOCATION: (7)..(7)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (9)..(9)
<223> OTHER INFORMATION: Xaa = beta-alanine
<220> FEATURE:
<221> NAME/KEY: MOD_RES
<222> LOCATION: (11)..(11)
<223> OTHER INFORMATION: Xaa = glycine or proline

<400> SEQUENCE: 219

Arg Xaa Arg Arg Xaa Arg Xaa Arg Xaa Arg Xaa
1               5                   10

<210> SEQ ID NO 220
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(10)
<223> OTHER INFORMATION: Xaa = 6-aminohexanoic acid
<220> FEATURE:
<221> NAME/KEY: MOD_RES
<222> LOCATION: (13)..(13)
<223> OTHER INFORMATION: Xaa = beta-alanine
<220> FEATURE:
<221> NAME/KEY: MOD_RES
<222> LOCATION: (15)..(15)
<223> OTHER INFORMATION: Xaa = glycine or alanine

<400> SEQUENCE: 220
```

Arg Xaa Arg Ile Leu Phe Gln Tyr Arg Xaa Arg Arg Xaa Arg Xaa
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(5)
<223> OTHER INFORMATION: Xaa = 6-aminohexanoic acid
<220> FEATURE:
<221> NAME/KEY: MOD_RES
<222> LOCATION: (13)..(13)
<223> OTHER INFORMATION: Xaa = beta-alanine
<220> FEATURE:
<221> NAME/KEY: MOD_RES
<222> LOCATION: (15)..(15)
<223> OTHER INFORMATION: Xaa = glycine or proline

<400> SEQUENCE: 221

Arg Xaa Arg Arg Xaa Arg Leu Leu Phe Gln Tyr Arg Xaa Arg Xaa
1               5                   10                  15

<210> SEQ ID NO 222
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (4)..(4)
<223> OTHER INFORMATION: Xaa = NH-(CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = NH-(CHR)-C(O) - wherein n is 2 to 7 and
      each R is independently, at each occurrence, hydrogen or methyl
<220> FEATURE:
<221> NAME/KEY: MOD_RES
<222> LOCATION: (10)..(10)
<223> OTHER INFORMATION: Xaa = beta-alanine
<220> FEATURE:
<221> NAME/KEY: MOD_RES
<222> LOCATION: (12)..(12)
<223> OTHER INFORMATION: Xaa = glycine or proline

<400> SEQUENCE: 222

Arg Xaa Arg Xaa Arg Xaa Arg Xaa Arg Xaa Arg Xaa
1               5                   10

<210> SEQ ID NO 223
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(10)
<223> OTHER INFORMATION: Xaa = 6-aminohexanoic acid
<220> FEATURE:

```
<221> NAME/KEY: MOD_RES
<222> LOCATION: (18)..(18)
<223> OTHER INFORMATION: Xaa = beta-alanine
<220> FEATURE:
<221> NAME/KEY: MOD_RES
<222> LOCATION: (20)..(20)
<223> OTHER INFORMATION: Xaa = glycine or proline

<400> SEQUENCE: 223

Arg Xaa Arg Ile Leu Phe Gln Tyr Arg Xaa Arg Ile Leu Phe Gln Tyr
1               5                   10                  15

Arg Xaa Arg Xaa
            20

<210> SEQ ID NO 224
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Wherein Xaa is 6-aminohexanoic acid
<220> FEATURE:
<221> NAME/KEY: MOD_RES
<222> LOCATION: (4)..(4)
<223> OTHER INFORMATION: Wherein Xaa is NH- (CHR)-C(O) - wherein n is 2
      to 7 and each R is independently, at each occurrence, hydrogen or
      methyl
<220> FEATURE:
<221> NAME/KEY: MOD_RES
<222> LOCATION: (6)..(6)
<223> OTHER INFORMATION: Wherein Xaa is 6-aminohexanoic acid
<220> FEATURE:
<221> NAME/KEY: MOD_RES
<222> LOCATION: (12)..(12)
<223> OTHER INFORMATION: Wherein Xaa is NH- (CHR)-C(O) - wherein n is 2
      to 7 and each R is independently, at each occurrence, hydrogen or
      methyl
<220> FEATURE:
<221> NAME/KEY: MOD_RES
<222> LOCATION: (14)..(14)
<223> OTHER INFORMATION: Wherein Xaa is 3-alanine
<220> FEATURE:
<221> NAME/KEY: MOD_RES
<222> LOCATION: (16)..(16)
<223> OTHER INFORMATION: Wherein Xaa is 6-aminohexanoic acid
<220> FEATURE:
<221> NAME/KEY: MOD_RES
<222> LOCATION: (16)..(16)
<223> OTHER INFORMATION: Xaa = glycine or proline

<400> SEQUENCE: 224

Arg Xaa Arg Xaa Arg Xaa Arg Ile Leu Phe Gln Tyr Arg Xaa Arg Xaa
1               5                   10                  15

<210> SEQ ID NO 225
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(10)
<223> OTHER INFORMATION: Xaa = 6-aminohexanoic acid
<220> FEATURE:
<221> NAME/KEY: MOD_RES
<222> LOCATION: (12)..(12)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
```

```
<222> LOCATION: (14)..(14)
<223> OTHER INFORMATION: Xaa = beta-alanine
<220> FEATURE:
<221> NAME/KEY: MOD_RES
<222> LOCATION: (16)..(16)
<223> OTHER INFORMATION: Xaa = glycine or proline

<400> SEQUENCE: 225

Arg Xaa Arg Ile Leu Phe Gln Tyr Arg Xaa Arg Xaa Arg Xaa Arg Xaa
1               5                   10                  15

<210> SEQ ID NO 226
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = 6-aminohexanoic acid
<220> FEATURE:
<221> NAME/KEY: MOD_RES
<222> LOCATION: (9)..(9)
<223> OTHER INFORMATION: Xaa = beta-alanine
<220> FEATURE:
<221> NAME/KEY: MOD_RES
<222> LOCATION: (11)..(11)
<223> OTHER INFORMATION: Xaa = glycine or proline

<400> SEQUENCE: 226

Arg Xaa Arg Xaa Arg Xaa Arg Arg Xaa Arg Xaa
1               5                   10

<210> SEQ ID NO 227
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (5)..(5)
<223> OTHER INFORMATION: Xaa = 6-aminohexanoic acid
<220> FEATURE:
<221> NAME/KEY: MOD_RES
<222> LOCATION: (7)..(7)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (9)..(9)
<223> OTHER INFORMATION: Xaa = beta-alanine
<220> FEATURE:
<221> NAME/KEY: MOD_RES
<222> LOCATION: (11)..(11)
<223> OTHER INFORMATION: Xaa = glycine or proline

<400> SEQUENCE: 227

Arg Xaa Arg Arg Xaa Arg Xaa Arg Xaa Arg Xaa
1               5                   10
```

```
<210> SEQ ID NO 228
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (10)..(10)
<223> OTHER INFORMATION: Xaa = 6-aminohexanoic acid
<220> FEATURE:
<221> NAME/KEY: MOD_RES
<222> LOCATION: (13)..(13)
<223> OTHER INFORMATION: Xaa = beta-alanine
<220> FEATURE:
<221> NAME/KEY: MOD_RES
<222> LOCATION: (15)..(15)
<223> OTHER INFORMATION: Xaa - glycine or proline

<400> SEQUENCE: 228

Arg Xaa Arg Ile Leu Phe Gln Tyr Arg Xaa Arg Arg Xaa Arg Xaa
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (5)..(5)
<223> OTHER INFORMATION: Xaa = 6-aminohexanoic acid
<220> FEATURE:
<221> NAME/KEY: MOD_RES
<222> LOCATION: (13)..(13)
<223> OTHER INFORMATION: Xaa = beta-alanine
<220> FEATURE:
<221> NAME/KEY: MOD_RES
<222> LOCATION: (15)..(15)
<223> OTHER INFORMATION: Xaa = glycine or proline

<400> SEQUENCE: 229

Arg Xaa Arg Arg Xaa Arg Ile Leu Phe Gln Tyr Arg Xaa Arg Xaa
1               5                   10                  15

<210> SEQ ID NO 230
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = 6-aminohexanoic acid
```

```
<220> FEATURE:
<221> NAME/KEY: MOD_RES
<222> LOCATION: (8)..(8)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (10)..(10)
<223> OTHER INFORMATION: Xaa = beta-alanine
<220> FEATURE:
<221> NAME/KEY: MOD_RES
<222> LOCATION: (12)..(12)
<223> OTHER INFORMATION: Xaa = glycine or proline

<400> SEQUENCE: 230

Arg Xaa Arg Xaa Arg Xaa Arg Xaa Arg Xaa Arg Xaa
1               5                   10

<210> SEQ ID NO 231
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (10)..(10)
<223> OTHER INFORMATION: Xaa = 6-aminohexanoic acid
<220> FEATURE:
<221> NAME/KEY: MOD_RES
<222> LOCATION: (18)..(18)
<223> OTHER INFORMATION: Xaa = beta-alanine
<220> FEATURE:
<221> NAME/KEY: MOD_RES
<222> LOCATION: (20)..(20)
<223> OTHER INFORMATION: Xaa = glycine or proline

<400> SEQUENCE: 231

Arg Xaa Arg Ile Leu Phe Gln Tyr Arg Xaa Arg Ile Leu Phe Gln Tyr
1               5                   10                  15

Arg Xaa Arg Xaa
            20

<210> SEQ ID NO 232
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = 6-aminihexanoic acid
<220> FEATURE:
<221> NAME/KEY: MOD_RES
<222> LOCATION: (14)..(14)
<223> OTHER INFORMATION: Xaa = beta-alanine
<220> FEATURE:
<221> NAME/KEY: MOD_RES
<222> LOCATION: (16)..(16)
<223> OTHER INFORMATION: Xaa = glycine or proline
```

```
<400> SEQUENCE: 232

Arg Xaa Arg Xaa Arg Xaa Arg Ile Leu Phe Gln Tyr Arg Xaa Arg Xaa
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (10)..(10)
<223> OTHER INFORMATION: Xaa = 6-aminohexanoic acid
<220> FEATURE:
<221> NAME/KEY: MOD_RES
<222> LOCATION: (12)..(12)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (14)..(14)
<223> OTHER INFORMATION: Xaa = beta-alanine
<220> FEATURE:
<221> NAME/KEY: MOD_RES
<222> LOCATION: (16)..(16)
<223> OTHER INFORMATION: Xaa = glycine or proline

<400> SEQUENCE: 233

Arg Xaa Arg Ile Leu Phe Gln Tyr Arg Xaa Arg Xaa Arg Xaa Arg Xaa
1               5                   10                  15

<210> SEQ ID NO 234
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(9)
<223> OTHER INFORMATION: Xaa = 6-aminohexanoic acid
<220> FEATURE:
<221> NAME/KEY: MOD_RES
<222> LOCATION: (11)..(11)
<223> OTHER INFORMATION: Xaa = glycine or proline

<400> SEQUENCE: 234

Arg Xaa Arg Xaa Arg Xaa Arg Arg Xaa Arg Xaa
1               5                   10

<210> SEQ ID NO 235
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
```

```
<222> LOCATION: (2)..(2)
<223> OTHER INFORMATION: Xaa = beta-alanine
<220> FEATURE:
<221> NAME/KEY: MOD_RES
<222> LOCATION: (5)..(5)
<223> OTHER INFORMATION: Xaa = 6-aminohexanoic acid
<220> FEATURE:
<221> NAME/KEY: MOD_RES
<222> LOCATION: (7)..(7)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (9)..(9)
<223> OTHER INFORMATION: Xaa = 6-aminohexanoic acid
<220> FEATURE:
<221> NAME/KEY: MOD_RES
<222> LOCATION: (11)..(11)
<223> OTHER INFORMATION: Xaa = glycine or proline

<400> SEQUENCE: 235

Arg Xaa Arg Arg Xaa Arg Xaa Arg Xaa Arg Xaa
1               5                   10

<210> SEQ ID NO 236
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (10)..(13)
<223> OTHER INFORMATION: Xaa = 6-aminohexanoic acid
<220> FEATURE:
<221> NAME/KEY: MOD_RES
<222> LOCATION: (15)..(15)
<223> OTHER INFORMATION: Xaa = glycine or proline

<400> SEQUENCE: 236

Arg Xaa Arg Ile Leu Phe Gln Tyr Arg Xaa Arg Arg Xaa Arg Xaa
1               5                   10                  15

<210> SEQ ID NO 237
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (5)..(13)
<223> OTHER INFORMATION: Xaa = 6-aminohexanoic acid
<220> FEATURE:
<221> NAME/KEY: MOD_RES
<222> LOCATION: (15)..(15)
<223> OTHER INFORMATION: Xaa = glycine or proline

<400> SEQUENCE: 237

Arg Xaa Arg Arg Xaa Arg Ile Leu Phe Gln Tyr Arg Xaa Arg Xaa
1               5                   10                  15

<210> SEQ ID NO 238
<211> LENGTH: 12
<212> TYPE: PRT
```

```
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (10)..(10)
<223> OTHER INFORMATION: Xaa = 6-aminohexanoic acid
<220> FEATURE:
<221> NAME/KEY: MOD_RES
<222> LOCATION: (12)..(12)
<223> OTHER INFORMATION: Xaa = glycine or proline

<400> SEQUENCE: 238

Arg Xaa Arg Xaa Arg Xaa Arg Xaa Arg Xaa Arg Xaa
1               5                   10

<210> SEQ ID NO 239
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (10)..(18)
<223> OTHER INFORMATION: Xaa = 6-aminohexanoic acid
<220> FEATURE:
<221> NAME/KEY: MOD_RES
<222> LOCATION: (20)..(20)
<223> OTHER INFORMATION: Xaa = glycine or proline

<400> SEQUENCE: 239

Arg Xaa Arg Ile Leu Phe Gln Tyr Arg Xaa Arg Ile Leu Phe Gln Tyr
1               5                   10                  15

Arg Xaa Arg Xaa
            20

<210> SEQ ID NO 240
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
```

```
<220> FEATURE:
<221> NAME/KEY: MOD_RES
<222> LOCATION: (6)..(14)
<223> OTHER INFORMATION: Xaa = 6-aminohexanoic acid
<220> FEATURE:
<221> NAME/KEY: MOD_RES
<222> LOCATION: (16)..(16)
<223> OTHER INFORMATION: Xaa = glycine or proline

<400> SEQUENCE: 240

Arg Xaa Arg Xaa Arg Xaa Arg Ile Leu Phe Gln Tyr Arg Xaa Arg Xaa
1               5                   10                  15

<210> SEQ ID NO 241
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (10)..(10)
<223> OTHER INFORMATION: Xaa = 6-aminohexanoic acid
<220> FEATURE:
<221> NAME/KEY: MOD_RES
<222> LOCATION: (12)..(12)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (14)..(14)
<223> OTHER INFORMATION: Xaa = 6-aminohexanoic acid
<220> FEATURE:
<221> NAME/KEY: MOD_RES
<222> LOCATION: (16)..(16)
<223> OTHER INFORMATION: Xaa = glycine or proline

<400> SEQUENCE: 241

Arg Xaa Arg Ile Leu Phe Gln Tyr Arg Xaa Arg Xaa Arg Xaa Arg Xaa
1               5                   10                  15

<210> SEQ ID NO 242
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = beta-alanine
<220> FEATURE:
<221> NAME/KEY: MOD_RES
<222> LOCATION: (9)..(9)
<223> OTHER INFORMATION: Xaa = 6-aminohexanoic acid
<220> FEATURE:
<221> NAME/KEY: MOD_RES
<222> LOCATION: (11)..(11)
<223> OTHER INFORMATION: Xaa = glycine or proline

<400> SEQUENCE: 242
```

```
Arg Xaa Arg Xaa Arg Xaa Arg Arg Xaa Arg Xaa
1               5                   10
```

<210> SEQ ID NO 243
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(5)
<223> OTHER INFORMATION: Xaa = beta-alanine
<220> FEATURE:
<221> NAME/KEY: MOD_RES
<222> LOCATION: (7)..(7)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (9)..(9)
<223> OTHER INFORMATION: Xaa = 6-aminohexanoic acid
<220> FEATURE:
<221> NAME/KEY: MOD_RES
<222> LOCATION: (11)..(11)
<223> OTHER INFORMATION: Xaa = glycine or proline

<400> SEQUENCE: 243

```
Arg Xaa Arg Arg Xaa Arg Xaa Arg Xaa Arg Xaa
1               5                   10
```

<210> SEQ ID NO 244
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(10)
<223> OTHER INFORMATION: Xaa = beta-alanine
<220> FEATURE:
<221> NAME/KEY: MOD_RES
<222> LOCATION: (13)..(13)
<223> OTHER INFORMATION: Xaa = 6-aminohexanoic acid
<220> FEATURE:
<221> NAME/KEY: MOD_RES
<222> LOCATION: (15)..(15)
<223> OTHER INFORMATION: Xaa = glycine or proline

<400> SEQUENCE: 244

```
Arg Xaa Arg Ile Leu Phe Gln Tyr Arg Xaa Arg Arg Xaa Arg Xaa
1               5                   10                  15
```

<210> SEQ ID NO 245
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(5)
<223> OTHER INFORMATION: Xaa = beta-alanine
<220> FEATURE:
<221> NAME/KEY: MOD_RES
<222> LOCATION: (13)..(13)
<223> OTHER INFORMATION: Xaa = 6-aminohexanoic acid
<220> FEATURE:
<221> NAME/KEY: MOD_RES
<222> LOCATION: (15)..(15)
<223> OTHER INFORMATION: Xaa = glycine or proline

<400> SEQUENCE: 245

```
Arg Xaa Arg Arg Xaa Arg Ile Leu Phe Gln Tyr Arg Xaa Arg Xaa
1               5                   10                  15
```

<210> SEQ ID NO 246
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (10)..(10)
<223> OTHER INFORMATION: Xaa = 6-aminohexanoic acid
<220> FEATURE:
<221> NAME/KEY: MOD_RES
<222> LOCATION: (12)..(12)
<223> OTHER INFORMATION: Xaa = glycine or proline

<400> SEQUENCE: 246

```
Arg Xaa Arg Xaa Arg Xaa Arg Xaa Arg Xaa Arg Xaa
1               5                   10
```

<210> SEQ ID NO 247
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(10)
<223> OTHER INFORMATION: Xaa = beta-alanine
<220> FEATURE:
<221> NAME/KEY: MOD_RES
<222> LOCATION: (18)..(18)
<223> OTHER INFORMATION: Xaa = 6-aminohexanoic acid
<220> FEATURE:
<221> NAME/KEY: MOD_RES
<222> LOCATION: (20)..(20)
<223> OTHER INFORMATION: Xaa = glycine or proline

<400> SEQUENCE: 247

```
Arg Xaa Arg Ile Leu Phe Gln Tyr Arg Xaa Arg Ile Leu Phe Gln Tyr
1               5                   10                  15

Arg Xaa Arg Xaa
            20
```

<210> SEQ ID NO 248
<211> LENGTH: 16
<212> TYPE: PRT
<213> ORGANISM: Artificial Sequence
<220> FEATURE:
<223> OTHER INFORMATION: cell penetrating peptide
<220> FEATURE:

```
<221> NAME/KEY: MOD_RES
<222> LOCATION: (2)..(2)
<223> OTHER INFORMATION: Xaa = beta-alanine
<220> FEATURE:
<221> NAME/KEY: MOD_RES
<222> LOCATION: (4)..(4)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (6)..(6)
<223> OTHER INFORMATION: Xaa = beta-alanine
<220> FEATURE:
<221> NAME/KEY: MOD_RES
<222> LOCATION: (14)..(14)
<223> OTHER INFORMATION: Xaa = 6-aminohexanoic acid
<220> FEATURE:
<221> NAME/KEY: MOD_RES
<222> LOCATION: (16)..(16)
<223> OTHER INFORMATION: Xaa = glycine or proline

<400> SEQUENCE: 248

Arg Xaa Arg Xaa Arg Xaa Arg Ile Leu Phe Gln Tyr Arg Xaa Arg Xaa
1               5                   10                  15

<210> SEQ ID NO 249
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(10)
<223> OTHER INFORMATION: Xaa = beta-alanine
<220> FEATURE:
<221> NAME/KEY: MOD_RES
<222> LOCATION: (12)..(12)
<223> OTHER INFORMATION: Xaa = NH- (CHR)-C(O) - wherein n is 2 to 7 and
      each R is independently, at each occurrence, hydrogen or methyl
<220> FEATURE:
<221> NAME/KEY: MOD_RES
<222> LOCATION: (14)..(14)
<223> OTHER INFORMATION: Xaa = 6-aminohexanoic acid
<220> FEATURE:
<221> NAME/KEY: MOD_RES
<222> LOCATION: (16)..(16)
<223> OTHER INFORMATION: Xaa = glycine or proline

<400> SEQUENCE: 249

Arg Xaa Arg Ile Leu Phe Gln Tyr Arg Xaa Arg Xaa Arg Xaa Arg Xaa
1               5                   10                  15

<210> SEQ ID NO 250

<400> SEQUENCE: 250

000

<210> SEQ ID NO 251
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = beta-alanine
<220> FEATURE:
```

```
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (16)..(16)
<223> OTHER INFORMATION: Xaa = 6-aminohexanoic acid
<220> FEATURE:
<221> NAME/KEY: MOD_RES
<222> LOCATION: (18)..(18)
<223> OTHER INFORMATION: Xaa = beta-alanine
<220> FEATURE:
<221> NAME/KEY: MOD_RES
<222> LOCATION: (20)..(20)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 251

Arg Xaa Arg Arg Xaa Arg Arg Xaa Arg Ile Leu Phe Gln Tyr Arg Xaa
1               5                   10                  15

Arg Xaa Arg Xaa Arg Xaa
            20

<210> SEQ ID NO 252

<400> SEQUENCE: 252

000

<210> SEQ ID NO 253
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 253

Tyr Gly Arg Lys Lys Arg Arg Gln Arg Arg Pro Xaa
1               5                   10

<210> SEQ ID NO 254
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(13)
<223> OTHER INFORMATION: Xaa = 6-aminohexanoic acid
<220> FEATURE:
<221> NAME/KEY: MOD_RES
<222> LOCATION: (14)..(14)
<223> OTHER INFORMATION: Xaa = beta-alanine
<220> FEATURE:
<221> NAME/KEY: MOD_RES
<222> LOCATION: (22)..(22)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 254

Arg Xaa Arg Arg Xaa Arg Arg Xaa Arg Arg Xaa Arg Xaa Xaa Ala Ser
```

```
1               5                   10                  15
Ser Leu Asn Ile Ala Xaa Cys Xaa
                20

<210> SEQ ID NO 255
<211> LENGTH: 32
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (16)..(16)
<223> OTHER INFORMATION: Xaa = 6-aminohexanoic acid
<220> FEATURE:
<221> NAME/KEY: MOD_RES
<222> LOCATION: (18)..(18)
<223> OTHER INFORMATION: Xaa = beta-alanine
<220> FEATURE:
<221> NAME/KEY: MOD_RES
<222> LOCATION: (20)..(20)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = beta-alanine
<220> FEATURE:
<221> NAME/KEY: MOD_RES
<222> LOCATION: (30)..(30)
<223> OTHER INFORMATION: Xaa = 6-aminohexanoic acid
<220> FEATURE:
<221> NAME/KEY: MOD_RES
<222> LOCATION: (32)..(32)
<223> OTHER INFORMATION: Xaa = glycine or proline

<400> SEQUENCE: 255

Arg Xaa Arg Arg Xaa Arg Xaa Arg Ile Leu Phe Gln Tyr Arg Xaa
1               5                   10                  15

Arg Xaa Arg Xaa Arg Xaa Ala Ser Ser Leu Asn Ile Ala Xaa Cys Xaa
                20                  25                  30

<210> SEQ ID NO 256
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (18)..(18)
```

```
<223> OTHER INFORMATION: Xaa = 6-aminohexanoic acid
<220> FEATURE:
<221> NAME/KEY: MOD_RES
<222> LOCATION: (20)..(20)
<223> OTHER INFORMATION: Xaa = beta-alanine
<220> FEATURE:
<221> NAME/KEY: MOD_RES
<222> LOCATION: (22)..(22)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = beta-alanine
<220> FEATURE:
<221> NAME/KEY: MOD_RES
<222> LOCATION: (26)..(26)
<223> OTHER INFORMATION: Xaa = glycine or proline

<400> SEQUENCE: 256

Arg Xaa Arg Arg Xaa Arg Arg Xaa Arg Ala Ser Ser Leu Asn Ile Ala
1               5                   10                  15

Arg Xaa Arg Xaa Arg Xaa Arg Xaa Cys Xaa
            20                  25

<210> SEQ ID NO 257
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (11)..(11)
<223> OTHER INFORMATION: Xaa = beta-alanine
<220> FEATURE:
<221> NAME/KEY: MOD_RES
<222> LOCATION: (13)..(13)
<223> OTHER INFORMATION: Xaa = 6-aminohexanoic acid
<220> FEATURE:
<221> NAME/KEY: MOD_RES
<222> LOCATION: (14)..(14)
<223> OTHER INFORMATION: Xaa = beta-alanine
<220> FEATURE:
<221> NAME/KEY: MOD_RES
<222> LOCATION: (22)..(22)
<223> OTHER INFORMATION: Xaa = glycine or proline

<400> SEQUENCE: 257

Arg Xaa Arg Arg Xaa Arg Arg Xaa Arg Arg Xaa Arg Xaa Xaa Ala Ser
1               5                   10                  15

Ser Leu Asn Ile Ala Xaa
            20

<210> SEQ ID NO 258
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
```

<222> LOCATION: (13)..(13)
<223> OTHER INFORMATION: Xaa = glycine or proline

<400> SEQUENCE: 258

Thr His Arg Pro Pro Met Trp Ser Pro Val Trp Pro Xaa
1               5                   10

<210> SEQ ID NO 259
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)..(12)
<223> OTHER INFORMATION: Xaa = glycine or proline

<400> SEQUENCE: 259

His Arg Pro Pro Met Trp Ser Pro Val Trp Pro Xaa
1               5                   10

<210> SEQ ID NO 260
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)..(11)
<223> OTHER INFORMATION: Xaa = glycine or proline

<400> SEQUENCE: 260

Thr His Arg Pro Pro Met Trp Ser Pro Val Xaa
1               5                   10

<210> SEQ ID NO 261
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)..(10)
<223> OTHER INFORMATION: Xaa = glycine or proline

<400> SEQUENCE: 261

Thr His Arg Pro Pro Met Trp Ser Pro Xaa
1               5                   10

<210> SEQ ID NO 262
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 262

Thr His Arg Pro Pro Met Trp Ser Pro Val Phe Pro Xaa
1               5                   10

<210> SEQ ID NO 263
<211> LENGTH: 13

```
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 263

Thr His Arg Pro Pro Met Trp Ser Pro Val Tyr Pro Xaa
1               5                   10

<210> SEQ ID NO 264
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 264

Thr His Arg Pro Pro Met Trp Ser Pro Ala Trp Pro Xaa
1               5                   10

<210> SEQ ID NO 265
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 265

Thr His Arg Pro Pro Met Trp Ser Pro Leu Trp Pro Xaa
1               5                   10

<210> SEQ ID NO 266
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 266

Thr His Arg Pro Pro Met Trp Ser Pro Ile Trp Pro Xaa
1               5                   10

<210> SEQ ID NO 267
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (14)..(14)
<223> OTHER INFORMATION: Xaa = glycine or proline

<400> SEQUENCE: 267
```

```
Thr His Arg Pro Pro Met Trp Thr Pro Val Val Trp Pro Xaa
1               5                   10
```

<210> SEQ ID NO 268
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 268

```
Thr His Arg Pro Pro Met Phe Ser Pro Val Trp Pro Xaa
1               5                   10
```

<210> SEQ ID NO 269
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (9)..(9)
<223> OTHER INFORMATION: Xaa = glycine or proline

<400> SEQUENCE: 269

```
Thr His Arg Pro Pro Met Trp Ser Xaa
1               5
```

<210> SEQ ID NO 270
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)..(11)
<223> OTHER INFORMATION: Xaa = glycine or proline

<400> SEQUENCE: 270

```
His Arg Pro Pro Met Trp Ser Pro Val Trp Xaa
1               5                   10
```

<210> SEQ ID NO 271
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 271

```
Thr His Arg Pro Pro Met Tyr Ser Pro Val Trp Pro Xaa
1               5                   10
```

<210> SEQ ID NO 272
<211> LENGTH: 13
<212> TYPE: PRT
<213> ORGANISM: Artificial Sequence
<220> FEATURE:
<223> OTHER INFORMATION: cell penetrating peptide
<220> FEATURE:

```
<221> NAME/KEY: MOD_RES
<222> LOCATION: (6)..(6)
<223> OTHER INFORMATION: Xaa = norleucine
<220> FEATURE:
<221> NAME/KEY: MOD_RES
<222> LOCATION: (13)..(13)
<223> OTHER INFORMATION: Xaa = glycine or proline

<400> SEQUENCE: 272

Thr His Arg Pro Pro Xaa Trp Ser Pro Val Trp Pro Xaa
1               5                   10

<210> SEQ ID NO 273
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 273

Thr His Lys Pro Pro Met Trp Ser Pro Val Trp Pro Xaa
1               5                   10

<210> SEQ ID NO 274
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 274

Ser His Arg Pro Pro Met Trp Ser Pro Val Trp Pro Xaa
1               5                   10

<210> SEQ ID NO 275
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 275

Ser Thr Phe Thr His Pro Arg Xaa
1               5

<210> SEQ ID NO 276
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 276

Tyr Asp Ile Asp Asn Arg Arg Xaa
```

```
1               5

<210> SEQ ID NO 277
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 277

Ala Tyr Lys Pro Val Gly Arg Xaa
1               5

<210> SEQ ID NO 278
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 278

His Ala Ile Tyr Pro Arg His Xaa
1               5

<210> SEQ ID NO 279
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 279

His Thr Pro Asn Ser Thr His Xaa
1               5

<210> SEQ ID NO 280
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 280

Ala Ser Ser Pro Val His Arg Xaa
1               5

<210> SEQ ID NO 281
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
```

```
<222> LOCATION: (8)..(8)
<223> OTHER INFORMATION: Xaa = glycine or proline

<400> SEQUENCE: 281

Ser Ser Leu Pro Leu Arg Lys Xaa
1               5

<210> SEQ ID NO 282
<211> LENGTH: 5
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(5)
<223> OTHER INFORMATION: Xaa = glycine or proline

<400> SEQUENCE: 282

Lys Lys Arg Ser Xaa
1               5

<210> SEQ ID NO 283
<211> LENGTH: 5
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(5)
<223> OTHER INFORMATION: Xaa = glycine or proline

<400> SEQUENCE: 283

Lys Arg Ser Lys Xaa
1               5

<210> SEQ ID NO 284
<211> LENGTH: 6
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (6)..(6)
<223> OTHER INFORMATION: Xaa = glycine or proline

<400> SEQUENCE: 284

Lys Lys Arg Ser Lys Xaa
1               5

<210> SEQ ID NO 285
<211> LENGTH: 5
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(5)
<223> OTHER INFORMATION: Xaa = glycine or proline

<400> SEQUENCE: 285

Lys Ser Arg Lys Xaa
1               5

<210> SEQ ID NO 286
<211> LENGTH: 5
```

```
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(5)
<223> OTHER INFORMATION: Xaa = glycine or proline

<400> SEQUENCE: 286

Ser Arg Lys Arg Xaa
1               5

<210> SEQ ID NO 287
<211> LENGTH: 5
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(5)
<223> OTHER INFORMATION: Xaa = glycine or proline

<400> SEQUENCE: 287

Arg Lys Arg Lys Xaa
1               5

<210> SEQ ID NO 288
<211> LENGTH: 6
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (6)..(6)
<223> OTHER INFORMATION: Xaa = glycine or proline

<400> SEQUENCE: 288

Lys Ser Arg Lys Arg Xaa
1               5

<210> SEQ ID NO 289
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 289

Gln His Pro Pro Trp Arg Val Xaa
1               5

<210> SEQ ID NO 290
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 290
```

```
Thr His Pro Pro Thr Thr His Xaa
1               5
```

<210> SEQ ID NO 291
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 291

```
Tyr Lys His Thr Pro Thr Thr Xaa
1               5
```

<210> SEQ ID NO 292
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 292

```
Gln Gly Met His Arg Gly Thr Xaa
1               5
```

<210> SEQ ID NO 293
<211> LENGTH: 6
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (6)..(6)
<223> OTHER INFORMATION: Xaa = glycine or proline

<400> SEQUENCE: 293

```
Ser Arg Lys Arg Lys Xaa
1               5
```

<210> SEQ ID NO 294
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (7)..(7)
<223> OTHER INFORMATION: Xaa = glycine or proline

<400> SEQUENCE: 294

```
Lys Ser Arg Lys Arg Lys Xaa
1               5
```

<210> SEQ ID NO 295
<211> LENGTH: 8
<212> TYPE: PRT
<213> ORGANISM: Artificial Sequence
<220> FEATURE:
<223> OTHER INFORMATION: cell penetrating peptide
<220> FEATURE:

```
<221> NAME/KEY: MOD_RES
<222> LOCATION: (8)..(8)
<223> OTHER INFORMATION: Xaa = glycine or proline

<400> SEQUENCE: 295

Pro Lys Lys Lys Arg Lys Val Xaa
1               5

<210> SEQ ID NO 296
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 296

Gly Lys Lys Arg Ser Lys Val Xaa
1               5

<210> SEQ ID NO 297
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 297

Lys Ser Arg Lys Arg Lys Leu Xaa
1               5

<210> SEQ ID NO 298
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 298

His Ser Pro Ser Lys Ile Pro Xaa
1               5

<210> SEQ ID NO 299
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 299

His Met Ala Thr Phe His Tyr Xaa
1               5

<210> SEQ ID NO 300
```

```
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 300

Ala Gln Pro Asn Lys Phe Lys Xaa
1               5

<210> SEQ ID NO 301
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 301

Asn Leu Thr Arg Leu His Thr Xaa
1               5

<210> SEQ ID NO 302
<211> LENGTH: 5
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(5)
<223> OTHER INFORMATION: Xaa = glycine or proline

<400> SEQUENCE: 302

Lys Lys Lys Arg Xaa
1               5

<210> SEQ ID NO 303
<211> LENGTH: 5
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(5)
<223> OTHER INFORMATION: Xaa = glycine or proline

<400> SEQUENCE: 303

Lys Lys Arg Lys Xaa
1               5

<210> SEQ ID NO 304
<211> LENGTH: 6
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (6)..(6)
<223> OTHER INFORMATION: Xaa = glycine or proline

<400> SEQUENCE: 304
```

```
Lys Lys Lys Arg Lys Xaa
1               5

<210> SEQ ID NO 305
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (25)..(25)
<223> OTHER INFORMATION: Xaa = glycine or proline

<400> SEQUENCE: 305

Arg Arg Arg Arg Arg Arg Gln Ile Lys Ile Trp Phe Gln Asn Arg Arg
1               5                   10                  15

Met Lys Trp Lys Lys Gly Gly Cys Xaa
            20                  25

<210> SEQ ID NO 306
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (26)..(26)
<223> OTHER INFORMATION: Xaa = glycine or proline

<400> SEQUENCE: 306

Arg Arg Arg Arg Arg Arg Arg Gln Ile Lys Ile Trp Phe Gln Asn Arg
1               5                   10                  15

Arg Met Lys Trp Lys Lys Gly Gly Cys Xaa
            20                  25

<210> SEQ ID NO 307
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (20)..(20)
<223> OTHER INFORMATION: Xaa = glycine or proline

<400> SEQUENCE: 307

Arg Gln Ile Lys Ile Trp Phe Gln Asn Arg Arg Met Lys Trp Lys Lys
1               5                   10                  15

Gly Gly Cys Xaa
            20

<210> SEQ ID NO 308
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (24)..(24)
<223> OTHER INFORMATION: Xaa = glycine or proline

<400> SEQUENCE: 308

Arg Arg Arg Arg Arg Arg Arg Gln Ile Lys Ile Trp Phe Gln Asn Arg
```

```
1               5                   10                  15
Arg Met Lys Trp Lys Lys Cys Xaa
                20

<210> SEQ ID NO 309
<211> LENGTH: 29
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (29)..(29)
<223> OTHER INFORMATION: Xaa = glycine or proline

<400> SEQUENCE: 309

Arg Xaa Arg Arg Xaa Arg Arg Xaa Arg Arg Gln Ile Lys Ile Trp Phe
1               5                   10                  15

Gln Asn Arg Arg Met Lys Trp Lys Lys Gly Gly Cys Xaa
                20                  25

<210> SEQ ID NO 310
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (17)..(23)
<223> OTHER INFORMATION: Xaa = 6-aminohexanoic acid
<220> FEATURE:
<221> NAME/KEY: MOD_RES
<222> LOCATION: (25)..(25)
<223> OTHER INFORMATION: Xaa = glycine or proline

<400> SEQUENCE: 310

Arg Arg Arg Arg Arg Arg Arg Gln Ile Lys Ile Leu Phe Gln Asn Arg
1               5                   10                  15

Xaa Arg Xaa Arg Xaa Arg Xaa Cys Xaa
                20                  25

<210> SEQ ID NO 311
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(11)
<223> OTHER INFORMATION: Xaa = 6-aminohexanoic acid
<220> FEATURE:
<221> NAME/KEY: MOD_RES
<222> LOCATION: (14)..(14)
<223> OTHER INFORMATION: Xaa = glycine or proline

<400> SEQUENCE: 311

Arg Xaa Arg Arg Xaa Arg Arg Xaa Arg Arg Xaa Arg Cys Xaa
1               5                   10

<210> SEQ ID NO 312
<211> LENGTH: 15
<212> TYPE: PRT
<213> ORGANISM: Artificial Sequence
```

```
<220> FEATURE:
<223> OTHER INFORMATION: cell penetrating peptide
<220> FEATURE:
<221> NAME/KEY: MOD_RES
<222> LOCATION: (2)..(13)
<223> OTHER INFORMATION: Xaa = 6-aminohexanoic acid
<220> FEATURE:
<221> NAME/KEY: MOD_RES
<222> LOCATION: (15)..(15)
<223> OTHER INFORMATION: Xaa = glycine or proline

<400> SEQUENCE: 312

Arg Xaa Arg Arg Xaa Arg Arg Xaa Arg Arg Xaa Arg Xaa Cys Xaa
1               5                   10                  15

<210> SEQ ID NO 313
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 313

Arg Xaa Arg Arg Xaa Arg Arg Xaa Arg Ile Lys Ile Leu Phe Gln Asn
1               5                   10                  15

Arg Arg Met Lys Trp Lys Lys Gly Gly Cys Xaa
            20                  25

<210> SEQ ID NO 314
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (25)..(25)
<223> OTHER INFORMATION: Xaa = glycine or proline

<400> SEQUENCE: 314

Arg Xaa Arg Arg Xaa Arg Arg Xaa Arg Ile Lys Ile Leu Phe Gln Asn
1               5                   10                  15

Arg Arg Met Lys Trp Lys Lys Cys Xaa
            20                  25

<210> SEQ ID NO 315
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline
```

```
<400> SEQUENCE: 315

Arg Xaa Arg Arg Xaa Arg Arg Xaa Arg Ile Lys Ile Leu Phe Gln Asn
1               5                   10                  15

Arg Met Lys Trp Lys Lys Cys Xaa
            20

<210> SEQ ID NO 316
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (25)..(25)
<223> OTHER INFORMATION: Xaa = glycine or proline

<400> SEQUENCE: 316

Arg Xaa Arg Arg Xaa Arg Arg Xaa Arg Ile Lys Ile Leu Phe Gln Asn
1               5                   10                  15

Xaa Arg Met Lys Trp Lys Lys Cys Xaa
            20                  25

<210> SEQ ID NO 317
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (25)..(25)
<223> OTHER INFORMATION: Xaa = glycine or proline

<400> SEQUENCE: 317

Arg Xaa Arg Arg Xaa Arg Arg Xaa Arg Ile Lys Ile Leu Phe Gln Asn
1               5                   10                  15

His Arg Met Lys Trp Lys Lys Cys Xaa
            20                  25

<210> SEQ ID NO 318

<400> SEQUENCE: 318

000

<210> SEQ ID NO 319

<400> SEQUENCE: 319

000

<210> SEQ ID NO 320
<211> LENGTH: 25
<212> TYPE: PRT
<213> ORGANISM: Artificial Sequence
<220> FEATURE:
<223> OTHER INFORMATION: cell penetrating peptide
<220> FEATURE:
```

<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (25)..(25)
<223> OTHER INFORMATION: Xaa = glycine or proline

<400> SEQUENCE: 320

Arg Xaa Arg Arg Xaa Arg Arg Xaa Arg Ile Lys Ile Leu Phe Gln Asn
1               5                   10                  15

Xaa Arg Met Lys Trp Lys Ala Cys Xaa
            20                  25

<210> SEQ ID NO 321
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (26)..(26)
<223> OTHER INFORMATION: Xaa = glycine or proline

<400> SEQUENCE: 321

Arg Xaa Arg Arg Xaa Arg Arg Xaa Arg Ile Lys Ile Leu Phe Gln Asn
1               5                   10                  15

Xaa Arg Met Lys Trp His Lys Ala Cys Xaa
            20                  25

<210> SEQ ID NO 322
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (25)..(25)
<223> OTHER INFORMATION: Xaa = glycine or proline

<400> SEQUENCE: 322

Arg Xaa Arg Arg Xaa Arg Arg Xaa Arg Ile Lys Ile Leu Phe Gln Asn
1               5                   10                  15

Xaa Arg Met Lys Trp His Arg Cys Xaa
            20                  25

<210> SEQ ID NO 323
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (25)..(25)
<223> OTHER INFORMATION: Xaa = glycine or proline

<400> SEQUENCE: 323

Arg Xaa Arg Xaa Arg Xaa Arg Xaa Arg Ile Lys Ile Leu Phe Gln Asn
1               5                   10                  15

Arg Arg Met Lys Trp Lys Lys Cys Xaa
            20                  25

<210> SEQ ID NO 324
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (25)..(25)
<223> OTHER INFORMATION: Xaa = glycine or proline

<400> SEQUENCE: 324

Arg Ala Arg Ala Arg Ala Arg Ala Arg Ile Lys Ile Leu Phe Gln Asn
1               5                   10                  15

Arg Arg Met Lys Trp Lys Lys Cys Xaa
            20                  25

<210> SEQ ID NO 325
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (26)..(26)
<223> OTHER INFORMATION: Xaa = glycine or proline

<400> SEQUENCE: 325

Arg Xaa Arg Arg Xaa Arg Arg Xaa Arg Ile Xaa Ile Leu Phe Gln Asn
1               5                   10                  15

Xaa Arg Met Lys Trp His Lys Ala Cys Xaa
            20                  25

<210> SEQ ID NO 326
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (26)..(26)
<223> OTHER INFORMATION: Xaa = glycine or proline

<400> SEQUENCE: 326

Arg Xaa Arg Arg Xaa Arg Arg Xaa Arg Ile His Ile Leu Phe Gln Asn
1               5                   10                  15

Xaa Arg Met Lys Trp His Lys Ala Cys Xaa
            20                  25

<210> SEQ ID NO 327

```
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (26)..(26)
<223> OTHER INFORMATION: Xaa = glycine or proline

<400> SEQUENCE: 327

Arg Xaa Arg Arg Xaa Arg Arg Xaa Arg Ile Arg Ile Leu Phe Gln Asn
1               5                   10                  15

Xaa Arg Met Lys Trp His Lys Ala Cys Xaa
            20                  25

<210> SEQ ID NO 328
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (26)..(26)
<223> OTHER INFORMATION: Xaa = glycine or proline

<400> SEQUENCE: 328

Arg Xaa Arg Arg Xaa Arg Arg Xaa Arg Ile Xaa Ile Leu Phe Gln Tyr
1               5                   10                  15

Xaa Arg Met Lys Trp His Lys Ala Cys Xaa
            20                  25

<210> SEQ ID NO 329
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(18)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 329

Arg Xaa Arg Arg Xaa Arg Arg Xaa Arg Leu Tyr Ser Pro Leu Ser Phe
1               5                   10                  15

Gln Xaa Arg Met Lys Trp His Lys Ala Cys Xaa
            20                  25

<210> SEQ ID NO 330
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
```

```
<222> LOCATION: (2)..(17)
<223> OTHER INFORMATION: Xaa = 6-aminohexanoic acid
<220> FEATURE:
<221> NAME/KEY: MOD_RES
<222> LOCATION: (26)..(26)
<223> OTHER INFORMATION: Xaa = glycine or proline

<400> SEQUENCE: 330

Arg Xaa Arg Arg Xaa Arg Arg Xaa Arg Ile Ser Ile Leu Phe Gln Tyr
1               5                   10                  15

Xaa Arg Met Lys Trp His Lys Ala Cys Xaa
            20                  25

<210> SEQ ID NO 331
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 331

Arg Xaa Arg Arg Xaa Arg Arg Xaa Arg Ile Leu Phe Gln Tyr Xaa Arg
1               5                   10                  15

Met Lys Trp His Lys Ala Cys Xaa
            20

<210> SEQ ID NO 332
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(14)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 332

Arg Xaa Arg Arg Xaa Arg Ile Xaa Ile Leu Phe Gln Tyr Xaa Arg Met
1               5                   10                  15

Lys Trp His Lys Ala Cys Xaa
            20

<210> SEQ ID NO 333
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (26)..(26)
<223> OTHER INFORMATION: Xaa = glycine or proline
```

```
<400> SEQUENCE: 333

Arg Xaa Arg Arg Ala Arg Arg Xaa Arg Ile His Ile Leu Phe Gln Tyr
1               5                   10                  15

Xaa Arg Met Lys Trp His Lys Ala Cys Xaa
            20                  25

<210> SEQ ID NO 334
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(17)
<223> OTHER INFORMATION: Xaa = 6-aminohexanoic acid
<220> FEATURE:
<221> NAME/KEY: MOD_RES
<222> LOCATION: (26)..(26)
<223> OTHER INFORMATION: Xaa = glycine or proline

<400> SEQUENCE: 334

Arg Ala Arg Arg Xaa Arg Arg Ala Arg Ile His Ile Leu Phe Gln Tyr
1               5                   10                  15

Xaa Arg Met Lys Trp His Lys Ala Cys Xaa
            20                  25

<210> SEQ ID NO 335
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (26)..(26)
<223> OTHER INFORMATION: Xaa = glycine or proline

<400> SEQUENCE: 335

Arg Xaa Arg Arg Xaa Arg Arg Xaa Arg Ile His Ile Leu Phe Gln Tyr
1               5                   10                  15

Xaa Arg Met Lys Trp His Lys Ala Cys Xaa
            20                  25

<210> SEQ ID NO 336

<400> SEQUENCE: 336

000

<210> SEQ ID NO 337

<400> SEQUENCE: 337

000

<210> SEQ ID NO 338
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
```

```
<222> LOCATION: (2)..(8)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 338

Arg Xaa Arg Arg Xaa Arg Arg Xaa Arg Ile Lys Ile Leu Phe Gln Asn
1               5                   10                  15

Arg Arg Met Lys Trp His Lys Xaa
            20

<210> SEQ ID NO 339
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 339

Arg Xaa Arg Arg Xaa Arg Arg Xaa Arg Ile Lys Ile Leu Phe Gln Asn
1               5                   10                  15

Xaa Arg Met Lys Trp His Lys Xaa
            20

<210> SEQ ID NO 340
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(11)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 340

Arg Xaa Arg Arg Xaa Arg Arg Xaa Arg Ile Xaa Ile Leu Phe Gln Asn
1               5                   10                  15

Arg Arg Met Lys Trp His Lys Xaa
            20

<210> SEQ ID NO 341
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline
```

```
<400> SEQUENCE: 341

Arg Xaa Arg Arg Xaa Arg Arg Xaa Arg Ile Xaa Ile Leu Phe Gln Asn
1               5                   10                  15

Xaa Arg Met Lys Trp His Lys Xaa
            20

<210> SEQ ID NO 342
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 342

Arg Xaa Arg Arg Xaa Arg Arg Xaa Arg Ile His Ile Leu Phe Gln Asn
1               5                   10                  15

Arg Arg Met Lys Trp His Lys Xaa
            20

<210> SEQ ID NO 343
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 343

Arg Xaa Arg Arg Xaa Arg Arg Xaa Arg Ile His Ile Leu Phe Gln Asn
1               5                   10                  15

Xaa Arg Met Lys Trp His Lys Xaa
            20

<210> SEQ ID NO 344
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 344

Arg Xaa Arg Arg Xaa Arg Arg Xaa Arg Ile Arg Ile Leu Phe Gln Asn
1               5                   10                  15

Arg Arg Met Lys Trp His Lys Xaa
            20
```

<210> SEQ ID NO 345
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 345

Arg Xaa Arg Arg Xaa Arg Arg Xaa Arg Ile Arg Ile Leu Phe Gln Asn
1               5                   10                  15

Xaa Arg Met Lys Trp His Lys Xaa
            20

<210> SEQ ID NO 346
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 346

Arg Xaa Arg Arg Xaa Arg Arg Xaa Arg Ile Ile Leu Phe Gln Asn Arg
1               5                   10                  15

Arg Met Lys Trp His Lys Xaa
            20

<210> SEQ ID NO 347
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 347

Arg Xaa Arg Arg Xaa Arg Arg Xaa Arg Ile Ile Leu Phe Gln Asn Xaa
1               5                   10                  15

Arg Met Lys Trp His Lys Xaa
            20

<210> SEQ ID NO 348
<211> LENGTH: 23
<212> TYPE: PRT
<213> ORGANISM: Artificial Sequence
<220> FEATURE:

```
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 348

Arg Xaa Arg Arg Xaa Arg Arg Xaa Arg Lys Ile Leu Phe Gln Asn Arg
1               5                   10                  15

Arg Met Lys Trp His Lys Xaa
            20

<210> SEQ ID NO 349
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 349

Arg Xaa Arg Arg Xaa Arg Arg Xaa Arg Lys Ile Leu Phe Gln Asn Xaa
1               5                   10                  15

Arg Met Lys Trp His Lys Xaa
            20

<210> SEQ ID NO 350
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(10)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 350

Arg Xaa Arg Arg Xaa Arg Arg Xaa Arg Xaa Ile Leu Phe Gln Asn Arg
1               5                   10                  15

Arg Met Lys Trp His Lys Xaa
            20

<210> SEQ ID NO 351
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
```

```
<222> LOCATION: (23)..(23)
<223> OTHER INFORMATION: Xaa = glycine or proline

<400> SEQUENCE: 351

Arg Xaa Arg Arg Xaa Arg Arg Xaa Arg Xaa Ile Leu Phe Gln Asn Xaa
1               5                   10                  15

Arg Met Lys Trp His Lys Xaa
            20

<210> SEQ ID NO 352
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 352

Arg Xaa Arg Arg Xaa Arg Arg Xaa Arg His Ile Leu Phe Gln Asn Arg
1               5                   10                  15

Arg Met Lys Trp His Lys Xaa
            20

<210> SEQ ID NO 353
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 353

Arg Xaa Arg Arg Xaa Arg Arg Xaa Arg His Ile Leu Phe Gln Asn Xaa
1               5                   10                  15

Arg Met Lys Trp His Lys Xaa
            20

<210> SEQ ID NO 354
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 354

Arg Xaa Arg Arg Xaa Arg Arg Xaa Arg Arg Ile Leu Phe Gln Asn Arg
1               5                   10                  15
```

```
Arg Met Lys Trp His Lys Xaa
            20

<210> SEQ ID NO 355
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 355

Arg Xaa Arg Arg Xaa Arg Arg Xaa Arg Arg Ile Leu Phe Gln Asn Xaa
1               5                   10                  15

Arg Met Lys Trp His Lys Xaa
            20

<210> SEQ ID NO 356
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 356

Arg Xaa Arg Arg Xaa Arg Arg Xaa Arg Ile Leu Phe Gln Asn Arg Arg
1               5                   10                  15

Met Lys Trp His Lys Xaa
            20

<210> SEQ ID NO 357
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 357

Arg Xaa Arg Arg Xaa Arg Arg Xaa Arg Ile Leu Phe Gln Asn Xaa Arg
1               5                   10                  15

Met Lys Trp His Lys Xaa
            20

<210> SEQ ID NO 358
<211> LENGTH: 24
```

```
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 358

Arg Xaa Arg Arg Xaa Arg Arg Xaa Arg Ile Lys Ile Leu Phe Gln Tyr
1               5                   10                  15

Arg Arg Met Lys Trp His Lys Xaa
            20

<210> SEQ ID NO 359
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 359

Arg Xaa Arg Arg Xaa Arg Arg Xaa Arg Ile Lys Ile Leu Phe Gln Tyr
1               5                   10                  15

Xaa Arg Met Lys Trp His Lys Xaa
            20

<210> SEQ ID NO 360
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(11)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 360

Arg Xaa Arg Arg Xaa Arg Arg Xaa Arg Ile Xaa Ile Leu Phe Gln Tyr
1               5                   10                  15

Arg Arg Met Lys Trp His Lys Xaa
            20

<210> SEQ ID NO 361
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
```

<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 361

Arg Xaa Arg Arg Xaa Arg Arg Xaa Arg Ile Xaa Ile Leu Phe Gln Tyr
1               5                   10                  15

Xaa Arg Met Lys Trp His Lys Xaa
            20

<210> SEQ ID NO 362
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 362

Arg Xaa Arg Arg Xaa Arg Arg Xaa Arg Ile His Ile Leu Phe Gln Tyr
1               5                   10                  15

Arg Arg Met Lys Trp His Lys Xaa
            20

<210> SEQ ID NO 363
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 363

Arg Xaa Arg Arg Xaa Arg Arg Xaa Arg Ile His Ile Leu Phe Gln Tyr
1               5                   10                  15

Xaa Arg Met Lys Trp His Lys Xaa
            20

<210> SEQ ID NO 364
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 364

```
Arg Xaa Arg Arg Xaa Arg Arg Xaa Arg Ile Arg Ile Leu Phe Gln Tyr
1               5                   10                  15

Arg Arg Met Lys Trp His Lys Xaa
            20
```

<210> SEQ ID NO 365
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 365

```
Arg Xaa Arg Arg Xaa Arg Arg Xaa Arg Ile Arg Ile Leu Phe Gln Tyr
1               5                   10                  15

Xaa Arg Met Lys Trp His Lys Xaa
            20
```

<210> SEQ ID NO 366
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa - glycine or proline

<400> SEQUENCE: 366

```
Arg Xaa Arg Arg Xaa Arg Arg Xaa Arg Ile Ile Leu Phe Gln Tyr Arg
1               5                   10                  15

Arg Met Lys Trp His Lys Xaa
            20
```

<210> SEQ ID NO 367
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 367

```
Arg Xaa Arg Arg Xaa Arg Arg Xaa Arg Ile Ile Leu Phe Gln Tyr Xaa
1               5                   10                  15

Arg Met Lys Trp His Lys Xaa
            20
```

<210> SEQ ID NO 368
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 368

Arg Xaa Arg Arg Xaa Arg Arg Xaa Arg Lys Ile Leu Phe Gln Tyr Arg
1               5                   10                  15

Arg Met Lys Trp His Lys Xaa
            20

<210> SEQ ID NO 369
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 369

Arg Xaa Arg Arg Xaa Arg Arg Xaa Arg Lys Ile Leu Phe Gln Tyr Xaa
1               5                   10                  15

Arg Met Lys Trp His Lys Xaa
            20

<210> SEQ ID NO 370
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(10)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 370

Arg Xaa Arg Arg Xaa Arg Arg Xaa Arg Xaa Ile Leu Phe Gln Tyr Arg
1               5                   10                  15

Arg Met Lys Trp His Lys Xaa
            20

<210> SEQ ID NO 371
<211> LENGTH: 23
<212> TYPE: PRT
<213> ORGANISM: Artificial Sequence
<220> FEATURE:
<223> OTHER INFORMATION: cell penetrating peptide

```
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 371

Arg Xaa Arg Arg Xaa Arg Arg Xaa Arg Xaa Ile Leu Phe Gln Tyr Xaa
1               5                   10                  15

Arg Met Lys Trp His Lys Xaa
            20

<210> SEQ ID NO 372
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 372

Arg Xaa Arg Arg Xaa Arg Arg Xaa Arg His Ile Leu Phe Gln Tyr Arg
1               5                   10                  15

Arg Met Lys Trp His Lys Xaa
            20

<210> SEQ ID NO 373
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 373

Arg Xaa Arg Arg Xaa Arg Arg Xaa Arg His Ile Leu Phe Gln Tyr Xaa
1               5                   10                  15

Arg Met Lys Trp His Lys Xaa
            20

<210> SEQ ID NO 374
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (23)..(23)
```

```
<223> OTHER INFORMATION: Xaa = glycine or proline

<400> SEQUENCE: 374

Arg Xaa Arg Arg Xaa Arg Arg Xaa Arg Arg Ile Leu Phe Gln Tyr Arg
1               5                   10                  15

Arg Met Lys Trp His Lys Xaa
            20

<210> SEQ ID NO 375
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 375

Arg Xaa Arg Arg Xaa Arg Arg Xaa Arg Arg Ile Leu Phe Gln Tyr Xaa
1               5                   10                  15

Arg Met Lys Trp His Lys Xaa
            20

<210> SEQ ID NO 376
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 376

Arg Xaa Arg Arg Xaa Arg Arg Xaa Arg Ile Leu Phe Gln Tyr Arg Arg
1               5                   10                  15

Met Lys Trp His Lys Xaa
            20

<210> SEQ ID NO 377
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 377

Arg Xaa Arg Arg Xaa Arg Arg Xaa Arg Ile Leu Phe Gln Tyr Xaa Arg
1               5                   10                  15
```

Met Lys Trp His Lys Xaa
            20

<210> SEQ ID NO 378

<400> SEQUENCE: 378

000

<210> SEQ ID NO 379

<400> SEQUENCE: 379

000

<210> SEQ ID NO 380
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (7)..(7)
<223> OTHER INFORMATION: Xaa = glycine or proline

<400> SEQUENCE: 380

Arg Ala Arg Arg Ala Arg Xaa
1               5

<210> SEQ ID NO 381
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)..(10)
<223> OTHER INFORMATION: Xaa = glycine or proline

<400> SEQUENCE: 381

Arg Ala Arg Arg Ala Arg Arg Ala Arg Xaa
1               5                   10

<210> SEQ ID NO 382
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)..(13)
<223> OTHER INFORMATION: Xaa = glycine or proline

<400> SEQUENCE: 382

Arg Ala Arg Arg Ala Arg Arg Ala Arg Arg Ala Arg Xaa
1               5                   10

<210> SEQ ID NO 383
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid

```
<220> FEATURE:
<221> NAME/KEY: MOD_RES
<222> LOCATION: (9)..(9)
<223> OTHER INFORMATION: Xaa = glycine or proline

<400> SEQUENCE: 383

Arg Xaa Arg Arg Xaa Arg Ile Xaa Xaa
1               5

<210> SEQ ID NO 384
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(8)
<223> OTHER INFORMATION: Xaa = 6-aminohexanoic acid
<220> FEATURE:
<221> NAME/KEY: MOD_RES
<222> LOCATION: (10)..(10)
<223> OTHER INFORMATION: Xaa = glycine or proline

<400> SEQUENCE: 384

Arg Xaa Arg Arg Ala Arg Arg Xaa Arg Xaa
1               5                   10

<210> SEQ ID NO 385
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(5)
<223> OTHER INFORMATION: Xaa = 6-aminohexanoic acid
<220> FEATURE:
<221> NAME/KEY: MOD_RES
<222> LOCATION: (10)..(10)
<223> OTHER INFORMATION: Xaa = glycine or proline

<400> SEQUENCE: 385

Arg Ala Arg Arg Xaa Arg Arg Ala Arg Xaa
1               5                   10

<210> SEQ ID NO 386
<211> LENGTH: 6
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (6)..(6)
<223> OTHER INFORMATION: Xaa = glycine or proline

<400> SEQUENCE: 386

Arg Arg Arg Arg Arg Xaa
1               5

<210> SEQ ID NO 387
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (7)..(7)
```

<223> OTHER INFORMATION: Xaa = glycine or proline

<400> SEQUENCE: 387

Arg Arg Arg Arg Arg Arg Xaa
1               5

<210> SEQ ID NO 388
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 388

Arg Arg Arg Arg Arg Arg Arg Xaa
1               5

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

```
<210> SEQ ID NO 408
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 408

Arg Arg Met Lys Trp His Lys Xaa
1               5

<210> SEQ ID NO 409
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = glycine or proline

<400> SEQUENCE: 409

Xaa Arg Met Lys Trp His Lys Xaa
1               5

<210> SEQ ID NO 410
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(20)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 410

Xaa Xaa Xaa Xaa Xaa Xaa Xaa Xaa Xaa Xaa Xaa Xaa Xaa Xaa Ile Leu
1               5                   10                  15

Phe Gln Xaa Xaa Arg Met Lys Trp His Lys Xaa
            20                  25

<210> SEQ ID NO 411

<400> SEQUENCE: 411

000

<210> SEQ ID NO 412
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (26)..(26)
<223> OTHER INFORMATION: Xaa = glycine or proline
```

<400> SEQUENCE: 412

Arg Arg Arg Arg Arg Arg Arg Gln Ile Lys Ile Leu Phe Gln Asn Pro
1               5                   10                  15

Lys Lys Lys Arg Lys Val Gly Gly Cys Xaa
            20                  25

<210> SEQ ID NO 413
<211> LENGTH: 17
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (17)..(17)
<223> OTHER INFORMATION: Xaa = glycine or proline

<400> SEQUENCE: 413

His His Phe Phe Arg Arg Arg Arg Arg Arg Arg Arg Phe Phe Cys
1               5                   10                  15

Xaa

<210> SEQ ID NO 414
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (19)..(19)
<223> OTHER INFORMATION: Xaa = glycine or proline

<400> SEQUENCE: 414

His His His His His His Arg Arg Arg Arg Arg Arg Arg Arg Phe
1               5                   10                  15

Phe Cys Xaa

<210> SEQ ID NO 415
<211> LENGTH: 21
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (21)..(21)
<223> OTHER INFORMATION: Xaa = glycine or proline

<400> SEQUENCE: 415

His His His His His His Phe Phe Arg Arg Arg Arg Arg Arg Arg
1               5                   10                  15

Arg Phe Phe Cys Xaa
            20

<210> SEQ ID NO 416
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (6)..(7)
<223> OTHER INFORMATION: Xaa = 6-aminohexanoic acid
<220> FEATURE:

```
<221> NAME/KEY: MOD_RES
<222> LOCATION: (20)..(20)
<223> OTHER INFORMATION: Xaa = glycine or proline

<400> SEQUENCE: 416

His His His His His Xaa Xaa Arg Arg Arg Arg Arg Arg Arg Arg
1               5                   10                  15

Phe Phe Cys Xaa
            20

<210> SEQ ID NO 417
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (7)..(8)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 417

His His His His His His Xaa Xaa Phe Phe Arg Arg Arg Arg Arg
1               5                   10                  15

Arg Arg Arg Phe Phe Cys Xaa
            20

<210> SEQ ID NO 418
<211> LENGTH: 21
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (4)..(16)
<223> OTHER INFORMATION: Xaa = 6-aminohexanoic acid
<220> FEATURE:
<221> NAME/KEY: MOD_RES
<222> LOCATION: (21)..(21)
<223> OTHER INFORMATION: Xaa = glycine or proline

<400> SEQUENCE: 418

His His His Xaa Arg Arg Arg Arg Arg Arg Arg Arg Arg Phe Phe Xaa
1               5                   10                  15

His His His Cys Xaa
            20

<210> SEQ ID NO 419

<400> SEQUENCE: 419

000

<210> SEQ ID NO 420
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(1)
<223> OTHER INFORMATION: Xaa = 6-aminohexanoic acid
<220> FEATURE:
```

```
<221> NAME/KEY: MOD_RES
<222> LOCATION: (8)..(8)
<223> OTHER INFORMATION: Xaa = glycine or proline

<400> SEQUENCE: 420

Xaa Arg Trp Lys Trp His Lys Xaa
1               5

<210> SEQ ID NO 421
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(6)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = glycine or proline

<400> SEQUENCE: 421

Arg Xaa Arg Ala Arg Xaa Arg Xaa
1               5

<210> SEQ ID NO 422
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(6)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = glycine or proline

<400> SEQUENCE: 422

Arg Xaa Arg Xaa Arg Xaa Arg Xaa
1               5

<210> SEQ ID NO 423
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (4)..(4)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = glycine or proline

<400> SEQUENCE: 423

Arg Ala Arg Xaa Arg Ala Arg Xaa
1               5

<210> SEQ ID NO 424
<211> LENGTH: 6
<212> TYPE: PRT
<213> ORGANISM: Artificial Sequence
<220> FEATURE:
<223> OTHER INFORMATION: cell penetrating peptide
```

```
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (6)..(6)
<223> OTHER INFORMATION: Xaa = glycine or proline

<400> SEQUENCE: 424

Arg Xaa Arg Ala Arg Xaa
1               5

<210> SEQ ID NO 425
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(20)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 425

Xaa Xaa Xaa Xaa Xaa Xaa Xaa Xaa Xaa Xaa Xaa Xaa Xaa Xaa Ile Leu
1               5                   10                  15

Phe Gln Xaa Xaa His Met Lys Trp His Lys Xaa
            20                  25

<210> SEQ ID NO 426
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(20)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 426

Xaa Xaa Xaa Xaa Xaa Xaa Xaa Xaa Xaa Xaa Xaa Xaa Xaa Xaa Ile Leu
1               5                   10                  15

Phe Gln Xaa Xaa Arg Trp Lys Trp His Lys Xaa
            20                  25

<210> SEQ ID NO 427
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(20)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 427
```

```
Xaa Xaa Xaa Xaa Xaa Xaa Xaa Xaa Xaa Xaa Xaa Xaa Xaa Xaa Ile Leu
1               5                   10                  15

Phe Gln Xaa Xaa His Trp Lys Trp His Lys Xaa
            20                  25

<210> SEQ ID NO 428
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(25)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 428

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Ala Arg Xaa Arg Xaa
            20                  25

<210> SEQ ID NO 429
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(25)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 429

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Xaa Arg Xaa Arg Xaa
            20                  25

<210> SEQ ID NO 430
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(24)
<223> OTHER INFORMATION: Xaa = 6-aminohexanoic acid
<220> FEATURE:
<221> NAME/KEY: MOD_RES
<222> LOCATION: (26)..(26)
<223> OTHER INFORMATION: Xaa = glycine or proline

<400> SEQUENCE: 430

Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Arg Xaa Arg Xaa
            20                  25
```

```
<210> SEQ ID NO 431
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(23)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 431

Xaa Xaa Xaa Xaa Xaa Xaa Xaa Xaa Xaa Xaa Xaa Xaa Xaa Xaa Ile Leu
1               5                   10                  15
Phe Gln Xaa Arg Ala Arg Xaa Arg Ala Arg Xaa
            20                  25

<210> SEQ ID NO 432

<400> SEQUENCE: 432

000

<210> SEQ ID NO 433
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(21)
<223> OTHER INFORMATION: Xaa = 6-aminohexanoic acid
<220> FEATURE:
<221> NAME/KEY: MOD_RES
<222> LOCATION: (25)..(25)
<223> OTHER INFORMATION: Xaa = glycine or proline

<400> SEQUENCE: 433

Xaa Xaa Xaa Xaa Xaa Xaa Xaa Xaa Xaa Xaa Xaa Xaa Xaa Xaa Ile Leu
1               5                   10                  15
Phe Gln Xaa Arg Xaa Arg Ala Arg Xaa
            20                  25

<210> SEQ ID NO 434
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(20)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 434

Xaa Xaa Xaa Xaa Xaa Xaa Xaa Xaa Xaa Xaa Xaa Xaa Xaa Xaa Ile Leu
1               5                   10                  15
Ile Gln Xaa Xaa Arg Met Lys Trp His Lys Xaa
            20                  25
```

<210> SEQ ID NO 435
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(20)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 435

Xaa Xaa Xaa Xaa Xaa Xaa Xaa Xaa Xaa Xaa Xaa Xaa Xaa Xaa Ile Leu
1               5                   10                  15

Ile Gln Xaa Xaa His Met Lys Trp His Lys Xaa
            20                  25

<210> SEQ ID NO 436
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(20)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 436

Xaa Xaa Xaa Xaa Xaa Xaa Xaa Xaa Xaa Xaa Xaa Xaa Xaa Xaa Ile Leu
1               5                   10                  15

Ile Gln Xaa Xaa Arg Trp Lys Trp His Lys Xaa
            20                  25

<210> SEQ ID NO 437
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(20)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 437

Xaa Xaa Xaa Xaa Xaa Xaa Xaa Xaa Xaa Xaa Xaa Xaa Xaa Xaa Ile Leu
1               5                   10                  15

Ile Gln Xaa Xaa His Trp Lys Trp His Lys Xaa
            20                  25

<210> SEQ ID NO 438
<211> LENGTH: 27
<212> TYPE: PRT
<213> ORGANISM: Artificial Sequence
<220> FEATURE:
<223> OTHER INFORMATION: cell penetrating peptide

```
<220> FEATURE:
<221> NAME/KEY: MOD_RES
<222> LOCATION: (1)..(25)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 438

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Ala Arg Xaa Arg Xaa
            20                  25

<210> SEQ ID NO 439
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(25)
<223> OTHER INFORMATION: Xaa = 6-aminohexanoic acid
<220> FEATURE:
<221> NAME/KEY: MOD_RES
<222> LOCATION: (27)..(27)
<223> OTHER INFORMATION: Xaa = glycine or proline

<400> SEQUENCE: 439

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Xaa Arg Xaa Arg Xaa
            20                  25

<210> SEQ ID NO 440
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(24)
<223> OTHER INFORMATION: Xaa = 6-aminohexanoic acid
<220> FEATURE:
<221> NAME/KEY: MOD_RES
<222> LOCATION: (26)..(26)
<223> OTHER INFORMATION: Xaa = glycine or proline

<400> SEQUENCE: 440

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Arg Xaa Arg Xaa
            20                  25

<210> SEQ ID NO 441
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(23)
<223> OTHER INFORMATION: Xaa = 6-aminohexanoic acid
<220> FEATURE:
<221> NAME/KEY: MOD_RES
<222> LOCATION: (27)..(27)
```

<223> OTHER INFORMATION: Xaa = glycine or proline

<400> SEQUENCE: 441

Xaa Xaa Xaa Xaa Xaa Xaa Xaa Xaa Xaa Xaa Xaa Xaa Xaa Xaa Ile Leu
1               5                   10                  15

Ile Gln Xaa Arg Ala Arg Xaa Arg Ala Arg Xaa
            20                  25

<210> SEQ ID NO 442

<400> SEQUENCE: 442

000

<210> SEQ ID NO 443
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)..(21)
<223> OTHER INFORMATION: Xaa = 6-aminohexanoic acid
<220> FEATURE:
<221> NAME/KEY: MOD_RES
<222> LOCATION: (25)..(25)
<223> OTHER INFORMATION: Xaa = glycine or proline

<400> SEQUENCE: 443

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Ala Arg Xaa
            20                  25

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

```
<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460
```

000

<210> SEQ ID NO 461

<400> SEQUENCE: 461

000

<210> SEQ ID NO 462

<400> SEQUENCE: 462

000

<210> SEQ ID NO 463
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(13)
<223> OTHER INFORMATION: Xaa = 6-aminohexanoic acid
<220> FEATURE:
<221> NAME/KEY: MOD_RES
<222> LOCATION: (15)..(15)
<223> OTHER INFORMATION: Xaa = glycine or proline

<400> SEQUENCE: 463

Arg Xaa Arg Arg Ala Arg Arg Xaa Arg Arg Ala Arg Xaa Ala Xaa
1               5                   10                  15

<210> SEQ ID NO 464
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 464

Arg Xaa Arg Arg Ala Arg Arg Xaa Arg Ile Leu Phe Gln Tyr Xaa His
1               5                   10                  15

Met Lys Trp His Lys Ala Cys Xaa
            20

<210> SEQ ID NO 465
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 465

```
Arg Xaa Arg Arg Ala Arg Arg Xaa Arg Ile Leu Phe Gln Tyr Xaa Arg
1               5                   10                  15

Met Lys Trp His Lys Ala Cys Xaa
            20
```

<210> SEQ ID NO 466
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 466

```
Arg Xaa Arg Arg Ala Arg Arg Xaa Arg Ile Leu Phe Gln Tyr Xaa Arg
1               5                   10                  15

Trp Lys Trp His Lys Ala Cys Xaa
            20
```

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

```
<210> SEQ ID NO 474
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(15)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 474

Arg Ala Arg Arg Xaa Arg Arg Ala Arg Ile Leu Phe Gln Tyr Xaa Arg
1               5                   10                  15

Met Lys Trp His Lys Ala Cys Xaa
            20

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
```

```
<222> LOCATION: (24)..(24)
<223> OTHER INFORMATION: Xaa = glycine or proline

<400> SEQUENCE: 481

Arg Xaa Arg Arg Ala Arg Arg Xaa Arg Ile Leu Phe Gln Tyr Xaa His
1               5                   10                  15

Trp Lys Trp His Lys Ala Cys Xaa
            20

<210> SEQ ID NO 482
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(20)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 482

Arg Xaa Arg Arg Ala Arg Arg Xaa Arg Ile Leu Phe Gln Tyr Arg Xaa
1               5                   10                  15

Arg Ala Arg Xaa Arg Ala Cys Xaa
            20

<210> SEQ ID NO 483
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(20)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 483

Arg Xaa Arg Arg Ala Arg Arg Xaa Arg Ile Leu Phe Gln Tyr Arg Xaa
1               5                   10                  15

Arg Xaa Arg Xaa Arg Ala Cys Xaa
            20

<210> SEQ ID NO 484
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 484

Arg Xaa Arg Arg Ala Arg Arg Xaa Arg Ile Leu Ile Gln Tyr Xaa Arg
1               5                   10                  15
```

Met Lys Trp His Lys Ala Cys Xaa
            20

<210> SEQ ID NO 485
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (19)..(19)
<223> OTHER INFORMATION: Xaa = glycine or proline

<400> SEQUENCE: 485

Arg Xaa Arg Arg Xaa Arg Ile Leu Phe Gln Tyr Arg Xaa Arg Arg Xaa
1               5                   10                  15

Arg Cys Xaa

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489
<211> LENGTH: 21
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (21)..(21)
<223> OTHER INFORMATION: Xaa = glycine or proline

<400> SEQUENCE: 489

Arg Xaa Arg Arg Xaa Arg Ile Leu Phe Gln Tyr Arg Xaa Arg Arg Xaa
1               5                   10                  15

Arg Cys Tyr Ser Xaa
            20

<210> SEQ ID NO 490
<211> LENGTH: 24
<212> TYPE: PRT
<213> ORGANISM: Artificial Sequence
<220> FEATURE:
<223> OTHER INFORMATION: cell penetrating peptide

```
<220> FEATURE:
<221> NAME/KEY: MOD_RES
<222> LOCATION: (5)..(18)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 490

Arg Ala Arg Arg Xaa Arg Arg Ala Arg Ile Leu Phe Gln Tyr Arg Ala
1               5                   10                  15

Arg Xaa Arg Ala Arg Ala Cys Xaa
            20

<210> SEQ ID NO 491
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(20)
<223> OTHER INFORMATION: Xaa = 6-aminohexanoic acid
<220> FEATURE:
<221> NAME/KEY: MOD_RES
<222> LOCATION: (24)..(24)
<223> OTHER INFORMATION: Xaa = glycine or proline

<400> SEQUENCE: 491

Arg Ala Arg Arg Xaa Arg Arg Ala Arg Ile Leu Phe Gln Tyr Arg Xaa
1               5                   10                  15

Arg Ala Arg Xaa Arg Ala Cys Xaa
            20

<210> SEQ ID NO 492
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(19)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 492

Arg Ala Arg Arg Xaa Arg Arg Ala Arg Ile Leu Phe Gln Tyr Arg Xaa
1               5                   10                  15

Arg Arg Xaa Arg Ala Cys Xaa
            20

<210> SEQ ID NO 493
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(20)
<223> OTHER INFORMATION: Xaa = 6-aminohexanoic acid
<220> FEATURE:
<221> NAME/KEY: MOD_RES
<222> LOCATION: (23)..(23)
```

```
<223> OTHER INFORMATION: Xaa = glycine or proline

<400> SEQUENCE: 493

Arg Ala Arg Arg Xaa Arg Arg Ala Arg Ile Leu Phe Gln Tyr Arg Xaa
1               5                   10                  15

Arg Ala Arg Xaa Ala Cys Xaa
            20

<210> SEQ ID NO 494
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(19)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 494

Arg Xaa Arg Arg Ala Arg Arg Xaa Arg Ile Leu Phe Gln Tyr Arg Xaa
1               5                   10                  15

Arg Arg Xaa Arg Ala Cys Xaa
            20

<210> SEQ ID NO 495
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(20)
<223> OTHER INFORMATION: Xaa = 6-aminohexanoic acid
<220> FEATURE:
<221> NAME/KEY: MOD_RES
<222> LOCATION: (23)..(23)
<223> OTHER INFORMATION: Xaa = glycine or proline

<400> SEQUENCE: 495

Arg Xaa Arg Arg Ala Arg Arg Xaa Arg Ile Leu Phe Gln Tyr Arg Xaa
1               5                   10                  15

Arg Ala Arg Xaa Ala Cys Xaa
            20

<210> SEQ ID NO 496
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (26)..(26)
<223> OTHER INFORMATION: Xaa = glycine or proline

<400> SEQUENCE: 496

Arg Xaa Arg Arg Ala Arg Arg Xaa Arg Ile His Ile Leu Phe Gln Asn
1               5                   10                  15
```

```
Xaa Arg Met Lys Trp His Lys Ala Cys Xaa
            20                  25

<210> SEQ ID NO 497
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(13)
<223> OTHER INFORMATION: Xaa = 6-aminohexanoic acid
<220> FEATURE:
<221> NAME/KEY: MOD_RES
<222> LOCATION: (16)..(16)
<223> OTHER INFORMATION: Xaa = glycine or proline

<400> SEQUENCE: 497

Arg Xaa Arg Arg Ala Arg Arg Xaa Arg Ala Arg Xaa Ala Cys Xaa
1               5                   10                  15

<210> SEQ ID NO 498
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 498

Arg Xaa Arg Arg Ala Arg Arg Xaa Arg Ile Leu Phe Gln Tyr Xaa His
1               5                   10                  15

Met Lys Trp His Lys Xaa
            20

<210> SEQ ID NO 499
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 499

Arg Xaa Arg Arg Ala Arg Arg Xaa Arg Ile Leu Phe Gln Tyr Xaa Arg
1               5                   10                  15

Met Lys Trp His Lys Xaa
            20

<210> SEQ ID NO 500
<211> LENGTH: 22
<212> TYPE: PRT
<213> ORGANISM: Artificial Sequence
<220> FEATURE:
<223> OTHER INFORMATION: cell penetrating peptide
```

```
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 500

Arg Xaa Arg Arg Ala Arg Arg Xaa Arg Ile Leu Phe Gln Tyr Xaa Arg
1               5                   10                  15

Trp Lys Trp His Lys Xaa
            20

<210> SEQ ID NO 501

<400> SEQUENCE: 501

000

<210> SEQ ID NO 502
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(20)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 502

Arg Xaa Arg Arg Ala Arg Arg Xaa Arg Ile Leu Phe Gln Tyr Arg Xaa
1               5                   10                  15

Arg Ala Arg Xaa Arg Xaa
            20

<210> SEQ ID NO 503
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(20)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 503

Arg Xaa Arg Arg Ala Arg Arg Xaa Arg Ile Leu Phe Gln Tyr Arg Xaa
1               5                   10                  15

Arg Xaa Arg Xaa Arg Xaa
            20

<210> SEQ ID NO 504
<211> LENGTH: 21
<212> TYPE: PRT
<213> ORGANISM: Artificial Sequence
<220> FEATURE:
<223> OTHER INFORMATION: cell penetrating peptide
```

```
<220> FEATURE:
<221> NAME/KEY: MOD_RES
<222> LOCATION: (2)..(19)
<223> OTHER INFORMATION: Xaa = 6-aminohexanoic acid
<220> FEATURE:
<221> NAME/KEY: MOD_RES
<222> LOCATION: (21)..(21)
<223> OTHER INFORMATION: Xaa = glycine or proline

<400> SEQUENCE: 504

Arg Xaa Arg Arg Ala Arg Arg Xaa Arg Ile Leu Phe Gln Tyr Arg Xaa
1               5                   10                  15

Arg Arg Xaa Arg Xaa
            20

<210> SEQ ID NO 505
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(18)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 505

Arg Xaa Arg Arg Ala Arg Arg Xaa Arg Ile Leu Phe Gln Tyr Arg Ala
1               5                   10                  15

Arg Xaa Arg Ala Arg Xaa
            20

<210> SEQ ID NO 506
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (20)..(20)
<223> OTHER INFORMATION: Xaa = glycine or proline

<400> SEQUENCE: 506

Arg Xaa Arg Arg Ala Arg Arg Xaa Arg Ile Leu Phe Gln Tyr Arg Xaa
1               5                   10                  15

Arg Ala Arg Xaa
            20

<210> SEQ ID NO 507
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (22)..(22)
```

<223> OTHER INFORMATION: Xaa = glycine or proline

<400> SEQUENCE: 507

Arg Xaa Arg Arg Ala Arg Arg Xaa Arg Ile Leu Ile Gln Tyr Xaa His
1               5                   10                  15

Met Lys Trp His Lys Xaa
            20

<210> SEQ ID NO 508
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 508

Arg Xaa Arg Arg Ala Arg Arg Xaa Arg Ile Leu Ile Gln Tyr Xaa Arg
1               5                   10                  15

Met Lys Trp His Lys Xaa
            20

<210> SEQ ID NO 509
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 509

Arg Xaa Arg Arg Ala Arg Arg Xaa Arg Ile Leu Ile Gln Tyr Xaa Arg
1               5                   10                  15

Trp Lys Trp His Lys Xaa
            20

<210> SEQ ID NO 510

<400> SEQUENCE: 510

000

<210> SEQ ID NO 511
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(20)
<223> OTHER INFORMATION: Xaa = 6-aminohexanoic acid
<220> FEATURE:
<221> NAME/KEY: MOD_RES
<222> LOCATION: (22)..(22)

<223> OTHER INFORMATION: Xaa = glycine or proline

<400> SEQUENCE: 511

Arg Xaa Arg Arg Ala Arg Arg Xaa Arg Ile Leu Ile Gln Tyr Arg Xaa
1               5                   10                  15

Arg Ala Arg Xaa Arg Xaa
            20

<210> SEQ ID NO 512
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(20)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 512

Arg Xaa Arg Arg Ala Arg Arg Xaa Arg Ile Leu Ile Gln Tyr Arg Xaa
1               5                   10                  15

Arg Xaa Arg Xaa Arg Xaa
            20

<210> SEQ ID NO 513
<211> LENGTH: 21
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(19)
<223> OTHER INFORMATION: Xaa = 6-aminohexanoic acid
<220> FEATURE:
<221> NAME/KEY: MOD_RES
<222> LOCATION: (21)..(21)
<223> OTHER INFORMATION: Xaa = glycine or proline

<400> SEQUENCE: 513

Arg Xaa Arg Arg Ala Arg Arg Xaa Arg Ile Leu Ile Gln Tyr Arg Xaa
1               5                   10                  15

Arg Arg Xaa Arg Xaa
            20

<210> SEQ ID NO 514
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(18)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 514

Arg Xaa Arg Arg Ala Arg Arg Xaa Arg Ile Leu Ile Gln Tyr Arg Ala
1               5                   10                  15

Arg Xaa Arg Ala Arg Xaa
        20

<210> SEQ ID NO 515
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (20)..(20)
<223> OTHER INFORMATION: Xaa = glycine or proline

<400> SEQUENCE: 515

Arg Xaa Arg Arg Ala Arg Arg Xaa Arg Ile Leu Ile Gln Tyr Arg Xaa
1               5                   10                  15

Arg Ala Arg Xaa
        20

<210> SEQ ID NO 516
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(15)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 516

Arg Ala Arg Arg Xaa Arg Arg Ala Arg Ile Leu Phe Gln Tyr Xaa His
1               5                   10                  15

Met Lys Trp His Lys Xaa
        20

<210> SEQ ID NO 517
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(15)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 517

Arg Ala Arg Arg Xaa Arg Arg Ala Arg Ile Leu Phe Gln Tyr Xaa Arg
1               5                   10                  15

Met Lys Trp His Lys Xaa
        20

<210> SEQ ID NO 518
<211> LENGTH: 22
<212> TYPE: PRT

<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(15)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 518

Arg Ala Arg Arg Xaa Arg Arg Ala Arg Ile Leu Phe Gln Tyr Xaa Arg
1               5                   10                  15

Trp Lys Trp His Lys Xaa
            20

<210> SEQ ID NO 519

<400> SEQUENCE: 519

000

<210> SEQ ID NO 520
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(20)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 520

Arg Ala Arg Arg Xaa Arg Arg Ala Arg Ile Leu Phe Gln Tyr Arg Xaa
1               5                   10                  15

Arg Ala Arg Xaa Arg Xaa
            20

<210> SEQ ID NO 521
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(20)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 521

Arg Ala Arg Arg Xaa Arg Arg Ala Arg Ile Leu Phe Gln Tyr Arg Xaa
1               5                   10                  15

Arg Xaa Arg Xaa Arg Xaa
            20

<210> SEQ ID NO 522
<211> LENGTH: 21
<212> TYPE: PRT

<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(19)
<223> OTHER INFORMATION: Xaa = 6-aminohexanoic acid
<220> FEATURE:
<221> NAME/KEY: MOD_RES
<222> LOCATION: (21)..(21)
<223> OTHER INFORMATION: Xaa = glycine or proline

<400> SEQUENCE: 522

Arg Ala Arg Arg Xaa Arg Arg Ala Arg Ile Leu Phe Gln Tyr Arg Xaa
1               5                   10                  15

Arg Arg Xaa Arg Xaa
            20

<210> SEQ ID NO 523
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(18)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 523

Arg Ala Arg Arg Xaa Arg Arg Ala Arg Ile Leu Phe Gln Tyr Arg Ala
1               5                   10                  15

Arg Xaa Arg Ala Arg Xaa
            20

<210> SEQ ID NO 524
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(16)
<223> OTHER INFORMATION: Xaa = 6-aminohexanoic acid
<220> FEATURE:
<221> NAME/KEY: MOD_RES
<222> LOCATION: (20)..(20)
<223> OTHER INFORMATION: Xaa = glycine or proline

<400> SEQUENCE: 524

Arg Ala Arg Arg Xaa Arg Arg Ala Arg Ile Leu Phe Gln Tyr Arg Xaa
1               5                   10                  15

Arg Ala Arg Xaa
            20

<210> SEQ ID NO 525
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(15)
<223> OTHER INFORMATION: Xaa = 6-aminohexanoic acid

```
<220> FEATURE:
<221> NAME/KEY: MOD_RES
<222> LOCATION: (22)..(22)
<223> OTHER INFORMATION: Xaa = glycine or proline

<400> SEQUENCE: 525

Arg Ala Arg Arg Xaa Arg Arg Ala Arg Ile Leu Ile Gln Tyr Xaa His
1               5                   10                  15

Met Lys Trp His Lys Xaa
            20

<210> SEQ ID NO 526
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(15)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 526

Arg Ala Arg Arg Xaa Arg Arg Ala Arg Ile Leu Ile Gln Tyr Xaa Arg
1               5                   10                  15

Met Lys Trp His Lys Xaa
            20

<210> SEQ ID NO 527
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(15)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 527

Arg Ala Arg Arg Xaa Arg Arg Ala Arg Ile Leu Ile Gln Tyr Xaa Arg
1               5                   10                  15

Trp Lys Trp His Lys Xaa
            20

<210> SEQ ID NO 528

<400> SEQUENCE: 528

000

<210> SEQ ID NO 529
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(20)
<223> OTHER INFORMATION: Xaa = 6-aminohexanoic acid
```

```
<220> FEATURE:
<221> NAME/KEY: MOD_RES
<222> LOCATION: (22)..(22)
<223> OTHER INFORMATION: Xaa = glycine or proline

<400> SEQUENCE: 529

Arg Ala Arg Arg Xaa Arg Arg Ala Arg Ile Leu Ile Gln Tyr Arg Xaa
1               5                   10                  15

Arg Ala Arg Xaa Arg Xaa
            20

<210> SEQ ID NO 530
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(20)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 530

Arg Ala Arg Arg Xaa Arg Arg Ala Arg Ile Leu Ile Gln Tyr Arg Xaa
1               5                   10                  15

Arg Xaa Arg Xaa Arg Xaa
            20

<210> SEQ ID NO 531
<211> LENGTH: 21
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(19)
<223> OTHER INFORMATION: Xaa = 6-aminohexanoic acid
<220> FEATURE:
<221> NAME/KEY: MOD_RES
<222> LOCATION: (21)..(21)
<223> OTHER INFORMATION: Xaa = glycine or proline

<400> SEQUENCE: 531

Arg Ala Arg Arg Xaa Arg Arg Ala Arg Ile Leu Ile Gln Tyr Arg Xaa
1               5                   10                  15

Arg Arg Xaa Arg Xaa
            20

<210> SEQ ID NO 532
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(18)
<223> OTHER INFORMATION: Xaa = 6-aminohexanoic acid
<220> FEATURE:
<221> NAME/KEY: MOD_RES
<222> LOCATION: (22)..(22)
<223> OTHER INFORMATION: Xaa = glycine or proline

<400> SEQUENCE: 532
```

-continued

Arg Ala Arg Arg Xaa Arg Arg Ala Arg Ile Leu Ile Gln Tyr Arg Ala
1               5                   10                  15

Arg Xaa Arg Ala Arg Xaa
            20

<210> SEQ ID NO 533
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)..(16)
<223> OTHER INFORMATION: Xaa = 6-aminohexanoic acid
<220> FEATURE:
<221> NAME/KEY: MOD_RES
<222> LOCATION: (20)..(20)
<223> OTHER INFORMATION: Xaa = glycine or proline

<400> SEQUENCE: 533

Arg Ala Arg Arg Xaa Arg Arg Ala Arg Ile Leu Ile Gln Tyr Arg Xaa
1               5                   10                  15

Arg Ala Arg Xaa
            20

<210> SEQ ID NO 534
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(12)
<223> OTHER INFORMATION: Xaa = 6-aminohexanoic acid
<220> FEATURE:
<221> NAME/KEY: MOD_RES
<222> LOCATION: (19)..(19)
<223> OTHER INFORMATION: Xaa = glycine or proline

<400> SEQUENCE: 534

Arg Xaa Arg Arg Xaa Arg Ile Leu Phe Gln Tyr Xaa His Met Lys Trp
1               5                   10                  15

His Lys Xaa

<210> SEQ ID NO 535
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(12)
<223> OTHER INFORMATION: Xaa = 6-aminohexanoic acid
<220> FEATURE:
<221> NAME/KEY: MOD_RES
<222> LOCATION: (19)..(19)
<223> OTHER INFORMATION: Xaa = glycine or proline

<400> SEQUENCE: 535

Arg Xaa Arg Arg Xaa Arg Ile Leu Phe Gln Tyr Xaa Arg Met Lys Trp
1               5                   10                  15

His Lys Xaa

<210> SEQ ID NO 536
<211> LENGTH: 19

```
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(12)
<223> OTHER INFORMATION: Xaa = 6-aminohexanoic acid
<220> FEATURE:
<221> NAME/KEY: MOD_RES
<222> LOCATION: (19)..(19)
<223> OTHER INFORMATION: Xaa = glycine or proline

<400> SEQUENCE: 536

Arg Xaa Arg Arg Xaa Arg Ile Leu Phe Gln Tyr Xaa Arg Trp Lys Trp
1               5                   10                  15

His Lys Xaa

<210> SEQ ID NO 537

<400> SEQUENCE: 537

000

<210> SEQ ID NO 538
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (19)..(19)
<223> OTHER INFORMATION: Xaa = glycine or proline

<400> SEQUENCE: 538

Arg Xaa Arg Arg Xaa Arg Ile Leu Phe Gln Tyr Arg Xaa Arg Ala Arg
1               5                   10                  15

Xaa Arg Xaa

<210> SEQ ID NO 539
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (19)..(19)
<223> OTHER INFORMATION: Xaa = glycine or proline

<400> SEQUENCE: 539

Arg Xaa Arg Arg Xaa Arg Ile Leu Phe Gln Tyr Arg Xaa Arg Xaa Arg
1               5                   10                  15

Xaa Arg Xaa

<210> SEQ ID NO 540
<211> LENGTH: 18
<212> TYPE: PRT
<213> ORGANISM: Artificial Sequence
<220> FEATURE:
```

-continued

```
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (18)..(18)
<223> OTHER INFORMATION: Xaa = glycine or proline

<400> SEQUENCE: 540

Arg Xaa Arg Arg Xaa Arg Ile Leu Phe Gln Tyr Arg Xaa Arg Arg Xaa
1               5                   10                  15

Arg Xaa

<210> SEQ ID NO 541
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (19)..(19)
<223> OTHER INFORMATION: Xaa = glycine or proline

<400> SEQUENCE: 541

Arg Xaa Arg Arg Xaa Arg Ile Leu Phe Gln Tyr Arg Ala Arg Xaa Arg
1               5                   10                  15

Ala Arg Xaa

<210> SEQ ID NO 542
<211> LENGTH: 17
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(13)
<223> OTHER INFORMATION: Xaa = 6-aminohexanoic acid
<220> FEATURE:
<221> NAME/KEY: MOD_RES
<222> LOCATION: (17)..(17)
<223> OTHER INFORMATION: Xaa = glycine or proline

<400> SEQUENCE: 542

Arg Xaa Arg Arg Xaa Arg Ile Leu Phe Gln Tyr Arg Xaa Arg Ala Arg
1               5                   10                  15

Xaa

<210> SEQ ID NO 543
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(12)
<223> OTHER INFORMATION: Xaa = 6-aminohexanoic acid
<220> FEATURE:
<221> NAME/KEY: MOD_RES
<222> LOCATION: (19)..(19)
<223> OTHER INFORMATION: Xaa = glycine or proline
```

```
<400> SEQUENCE: 543

Arg Xaa Arg Arg Xaa Arg Ile Leu Ile Gln Tyr Xaa His Met Lys Trp
1               5                   10                  15

His Lys Xaa

<210> SEQ ID NO 544
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(12)
<223> OTHER INFORMATION: Xaa = 6-aminohexanoic acid
<220> FEATURE:
<221> NAME/KEY: MOD_RES
<222> LOCATION: (19)..(19)
<223> OTHER INFORMATION: Xaa = glycine or proline

<400> SEQUENCE: 544

Arg Xaa Arg Arg Xaa Arg Ile Leu Ile Gln Tyr Xaa Arg Met Lys Trp
1               5                   10                  15

His Lys Xaa

<210> SEQ ID NO 545
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(12)
<223> OTHER INFORMATION: Xaa = 6-aminohexanoic acid
<220> FEATURE:
<221> NAME/KEY: MOD_RES
<222> LOCATION: (19)..(19)
<223> OTHER INFORMATION: Xaa = glycine or proline

<400> SEQUENCE: 545

Arg Xaa Arg Arg Xaa Arg Ile Leu Ile Gln Tyr Xaa Arg Trp Lys Trp
1               5                   10                  15

His Lys Xaa

<210> SEQ ID NO 546

<400> SEQUENCE: 546

000

<210> SEQ ID NO 547
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (19)..(19)
<223> OTHER INFORMATION: Xaa = glycine or proline

<400> SEQUENCE: 547

Arg Xaa Arg Arg Xaa Arg Ile Leu Ile Gln Tyr Arg Xaa Arg Ala Arg
```

-continued

```
1               5                   10                  15

Xaa Arg Xaa

<210> SEQ ID NO 548
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(17)
<223> OTHER INFORMATION: Xaa = 6-aminohexanoic acid
<220> FEATURE:
<221> NAME/KEY: MOD_RES
<222> LOCATION: (19)..(19)
<223> OTHER INFORMATION: Xaa = glycine or proline

<400> SEQUENCE: 548

Arg Xaa Arg Arg Xaa Arg Ile Leu Ile Gln Tyr Arg Xaa Arg Xaa Arg
1               5                   10                  15

Xaa Arg Xaa

<210> SEQ ID NO 549
<211> LENGTH: 18
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(16)
<223> OTHER INFORMATION: Xaa = 6-aminohexanoic acid
<220> FEATURE:
<221> NAME/KEY: MOD_RES
<222> LOCATION: (18)..(18)
<223> OTHER INFORMATION: Xaa = glycine or proline

<400> SEQUENCE: 549

Arg Xaa Arg Arg Xaa Arg Ile Leu Ile Gln Tyr Arg Xaa Arg Arg Xaa
1               5                   10                  15

Arg Xaa

<210> SEQ ID NO 550
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)..(15)
<223> OTHER INFORMATION: Xaa = 6-aminohexanoic acid
<220> FEATURE:
<221> NAME/KEY: MOD_RES
<222> LOCATION: (19)..(19)
<223> OTHER INFORMATION: Xaa = glycine or proline

<400> SEQUENCE: 550

Arg Xaa Arg Arg Xaa Arg Ile Leu Ile Gln Tyr Arg Ala Arg Xaa Arg
1               5                   10                  15

Ala Arg Xaa

<210> SEQ ID NO 551
<211> LENGTH: 17
<212> TYPE: PRT
<213> ORGANISM: Artificial Sequence
<220> FEATURE:
```

-continued

```
<223> OTHER INFORMATION: cell penetrating peptide
<220> FEATURE:
<221> NAME/KEY: MOD_RES
<222> LOCATION: (2)..(13)
<223> OTHER INFORMATION: Xaa = 6-aminohexanoic acid
<220> FEATURE:
<221> NAME/KEY: MOD_RES
<222> LOCATION: (17)..(17)
<223> OTHER INFORMATION: Xaa = glycine or proline

<400> SEQUENCE: 551

Arg Xaa Arg Arg Xaa Arg Ile Leu Ile Gln Tyr Arg Xaa Arg Ala Arg
1               5                   10                  15

Xaa

<210> SEQ ID NO 552
<211> LENGTH: 18
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (4)..(14)
<223> OTHER INFORMATION: Xaa = 6-aminohexanoic acid
<220> FEATURE:
<221> NAME/KEY: MOD_RES
<222> LOCATION: (18)..(18)
<223> OTHER INFORMATION: Xaa - glycine or proline

<400> SEQUENCE: 552

Pro Arg Pro Xaa Xaa Xaa Xaa Xaa Xaa Xaa Xaa Xaa Xaa Xaa Pro Arg
1               5                   10                  15

Gly Xaa

<210> SEQ ID NO 553
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (9)..(9)
<223> OTHER INFORMATION: Xaa = glycine or proline

<400> SEQUENCE: 553

Arg Arg Arg Arg Arg Arg Arg Arg Xaa
1               5

<210> SEQ ID NO 554
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 554

Arg Arg Met Lys Trp Lys Lys Xaa
1               5

<210> SEQ ID NO 555

<400> SEQUENCE: 555
```

```
000

<210> SEQ ID NO 556
<211> LENGTH: 33
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (33)..(33)
<223> OTHER INFORMATION: Xaa = glycine or proline

<400> SEQUENCE: 556

Cys Lys Asp Glu Pro Gln Arg Arg Ser Ala Arg Leu Ser Ala Lys Pro
1               5                   10                  15

Ala Pro Pro Lys Pro Glu Pro Lys Pro Lys Lys Ala Pro Ala Lys Lys
            20                  25                  30

Xaa

<210> SEQ ID NO 557

<400> SEQUENCE: 557

000

<210> SEQ ID NO 558
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (9)..(9)
<223> OTHER INFORMATION: Xaa = glycine or proline

<400> SEQUENCE: 558

Arg Lys Lys Arg Arg Gln Arg Arg Xaa
1               5

<210> SEQ ID NO 559
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)..(8)
<223> OTHER INFORMATION: Xaa = glycine or proline

<400> SEQUENCE: 559

Arg Lys Lys Arg Arg Gln Arg Xaa
1               5

<210> SEQ ID NO 560
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (9)..(9)
<223> OTHER INFORMATION: Xaa = glycine or proline

<400> SEQUENCE: 560
```

```
Lys Lys Arg Arg Gln Arg Arg Arg Xaa
1               5
```

<210> SEQ ID NO 561

<400> SEQUENCE: 561

000

<210> SEQ ID NO 562
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)..(10)
<223> OTHER INFORMATION: Xa = glycine or proline

<400> SEQUENCE: 562

```
Ala Lys Lys Arg Arg Gln Arg Arg Arg Xaa
1               5                   10
```

<210> SEQ ID NO 563
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)..(10)
<223> OTHER INFORMATION: Xaa = glycine or proline

<400> SEQUENCE: 563

```
Arg Ala Lys Arg Arg Gln Arg Arg Arg Xaa
1               5                   10
```

<210> SEQ ID NO 564
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)..(10)
<223> OTHER INFORMATION: Xaa = glycine or proline

<400> SEQUENCE: 564

```
Arg Lys Ala Arg Arg Gln Arg Arg Arg Xaa
1               5                   10
```

<210> SEQ ID NO 565
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)..(10)
<223> OTHER INFORMATION: Xaa = glycine or proline

<400> SEQUENCE: 565

```
Arg Lys Lys Ala Arg Gln Arg Arg Arg Xaa
1               5                   10
```

```
<210> SEQ ID NO 566
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)..(11)
<223> OTHER INFORMATION: Xaa = glycine or proline

<400> SEQUENCE: 566

Cys Arg Trp Arg Trp Lys Cys Cys Lys Lys Xaa
1               5                   10

<210> SEQ ID NO 567
<211> LENGTH: 23
<212> TYPE: DNA
<213> ORGANISM: Artificial Sequence
<220> FEATURE:
<223> OTHER INFORMATION: Synthetic sequence

<400> SEQUENCE: 567
ctcatacctt ctgcttgatg atc                                          23

<210> SEQ ID NO 568
<211> LENGTH: 25
<212> TYPE: DNA
<213> ORGANISM: Artificial Sequence
<220> FEATURE:
<223> OTHER INFORMATION: Synthetic sequence

<400> SEQUENCE: 568
gggatccagt atacttacag gctcc                                        25

<210> SEQ ID NO 569
<211> LENGTH: 22
<212> TYPE: DNA
<213> ORGANISM: Artificial Sequence
<220> FEATURE:
<223> OTHER INFORMATION: Synthetic sequence

<400> SEQUENCE: 569
gaagatggca tttctagttt gg                                           22

<210> SEQ ID NO 570
<211> LENGTH: 23
<212> TYPE: DNA
<213> ORGANISM: Artificial Sequence
<220> FEATURE:
<223> OTHER INFORMATION: Synthetic sequence

<400> SEQUENCE: 570
ggaagatggc atttctagtt tgg                                          23

<210> SEQ ID NO 571
<211> LENGTH: 29
<212> TYPE: DNA
<213> ORGANISM: Artificial Sequence
<220> FEATURE:
<223> OTHER INFORMATION: Synthetic sequence

<400> SEQUENCE: 571
catcaaggaa gatggcattt ctagtttgg                                    29

<210> SEQ ID NO 572
<211> LENGTH: 24
```

<212> TYPE: DNA
<213> ORGANISM: Artificial Sequence
<220> FEATURE:
<223> OTHER INFORMATION: Synthetic sequence

<400> SEQUENCE: 572
catcaaggaa gatggcattt ctag                                              24

<210> SEQ ID NO 573
<211> LENGTH: 28
<212> TYPE: DNA
<213> ORGANISM: Artificial Sequence
<220> FEATURE:
<223> OTHER INFORMATION: Synthetic sequence

<400> SEQUENCE: 573
ccaacatcaa ggaagatggc atttctag                                          28

<210> SEQ ID NO 574
<211> LENGTH: 24
<212> TYPE: DNA
<213> ORGANISM: Artificial Sequence
<220> FEATURE:
<223> OTHER INFORMATION: Synthetic sequence

<400> SEQUENCE: 574
caacatcaag gaagatggca tttc                                              24

<210> SEQ ID NO 575
<211> LENGTH: 28
<212> TYPE: DNA
<213> ORGANISM: Artificial Sequence
<220> FEATURE:
<223> OTHER INFORMATION: Synthetic sequence

<400> SEQUENCE: 575
cctccaacat caaggaagat ggcatttc                                          28

<210> SEQ ID NO 576
<211> LENGTH: 23
<212> TYPE: DNA
<213> ORGANISM: Artificial Sequence
<220> FEATURE:
<223> OTHER INFORMATION: Synthetic sequence

<400> SEQUENCE: 576
cctccaacat caaggaagat ggc                                               23

<210> SEQ ID NO 577
<211> LENGTH: 26
<212> TYPE: DNA
<213> ORGANISM: Artificial Sequence
<220> FEATURE:
<223> OTHER INFORMATION: Synthetic sequence

<400> SEQUENCE: 577
gtacctccaa catcaaggaa gatggc                                            26

<210> SEQ ID NO 578
<211> LENGTH: 27
<212> TYPE: DNA
<213> ORGANISM: Artificial Sequence
<220> FEATURE:
<223> OTHER INFORMATION: Synthetic sequence

<400> SEQUENCE: 578
ggtacctcca acatcaagga agatggc        27

<210> SEQ ID NO 579
<211> LENGTH: 29
<212> TYPE: DNA
<213> ORGANISM: Artificial Sequence
<220> FEATURE:
<223> OTHER INFORMATION: Synthetic sequence

<400> SEQUENCE: 579
caggtacctc caacatcaag gaagatggc        29

<210> SEQ ID NO 580
<211> LENGTH: 30
<212> TYPE: DNA
<213> ORGANISM: Artificial Sequence
<220> FEATURE:
<223> OTHER INFORMATION: Synthetic sequence

<400> SEQUENCE: 580
gcaggtacct ccaacatcaa ggaagatggc        30

<210> SEQ ID NO 581
<211> LENGTH: 22
<212> TYPE: DNA
<213> ORGANISM: Artificial Sequence
<220> FEATURE:
<223> OTHER INFORMATION: Synthetic sequence

<400> SEQUENCE: 581
cctccaacat caaggaagat gg        22

<210> SEQ ID NO 582
<211> LENGTH: 25
<212> TYPE: DNA
<213> ORGANISM: Artificial Sequence
<220> FEATURE:
<223> OTHER INFORMATION: Synthetic sequence

<400> SEQUENCE: 582
gtacctccaa catcaaggaa gatgg        25

<210> SEQ ID NO 583
<211> LENGTH: 24
<212> TYPE: DNA
<213> ORGANISM: Artificial Sequence
<220> FEATURE:
<223> OTHER INFORMATION: Synthetic sequence

<400> SEQUENCE: 583
gtacctccaa catcaaggaa gatg        24

<210> SEQ ID NO 584
<211> LENGTH: 30
<212> TYPE: DNA
<213> ORGANISM: Artificial Sequence
<220> FEATURE:
<223> OTHER INFORMATION: Synthetic sequence

<400> SEQUENCE: 584
gagcaggtac ctccaacatc aaggaagatg        30

<210> SEQ ID NO 585
<211> LENGTH: 25
<212> TYPE: DNA
<213> ORGANISM: Artificial Sequence

```
<220> FEATURE:
<223> OTHER INFORMATION: Synthetic sequence

<400> SEQUENCE: 585
gcaggtacct ccaacatcaa ggaag                                          25

<210> SEQ ID NO 586
<211> LENGTH: 27
<212> TYPE: DNA
<213> ORGANISM: Artificial Sequence
<220> FEATURE:
<223> OTHER INFORMATION: Synthetic sequence

<400> SEQUENCE: 586
gagcaggtac ctccaacatc aaggaag                                        27

<210> SEQ ID NO 587
<211> LENGTH: 29
<212> TYPE: DNA
<213> ORGANISM: Artificial Sequence
<220> FEATURE:
<223> OTHER INFORMATION: Synthetic sequence

<400> SEQUENCE: 587
cagagcaggt acctccaaca tcaaggaag                                      29

<210> SEQ ID NO 588
<211> LENGTH: 30
<212> TYPE: DNA
<213> ORGANISM: Artificial Sequence
<220> FEATURE:
<223> OTHER INFORMATION: Synthetic sequence

<400> SEQUENCE: 588
ccagagcagg tacctccaac atcaaggaag                                     30

<210> SEQ ID NO 589
<211> LENGTH: 22
<212> TYPE: DNA
<213> ORGANISM: Artificial Sequence
<220> FEATURE:
<223> OTHER INFORMATION: Synthetic sequence

<400> SEQUENCE: 589
gcaggtacct ccaacatcaa gg                                             22

<210> SEQ ID NO 590
<211> LENGTH: 24
<212> TYPE: DNA
<213> ORGANISM: Artificial Sequence
<220> FEATURE:
<223> OTHER INFORMATION: Synthetic sequence

<400> SEQUENCE: 590
gagcaggtac ctccaacatc aagg                                           24

<210> SEQ ID NO 591
<211> LENGTH: 26
<212> TYPE: DNA
<213> ORGANISM: Artificial Sequence
<220> FEATURE:
<223> OTHER INFORMATION: Synthetic sequence

<400> SEQUENCE: 591
cagagcaggt acctccaaca tcaagg                                         26
```

<210> SEQ ID NO 592
<211> LENGTH: 28
<212> TYPE: DNA
<213> ORGANISM: Artificial Sequence
<220> FEATURE:
<223> OTHER INFORMATION: Synthetic sequence

<400> SEQUENCE: 592
gccagagcag gtacctccaa catcaagg                          28

<210> SEQ ID NO 593
<211> LENGTH: 25
<212> TYPE: DNA
<213> ORGANISM: Artificial Sequence
<220> FEATURE:
<223> OTHER INFORMATION: Synthetic sequence

<400> SEQUENCE: 593
cagagcaggt acctccaaca tcaag                             25

<210> SEQ ID NO 594
<211> LENGTH: 29
<212> TYPE: DNA
<213> ORGANISM: Artificial Sequence
<220> FEATURE:
<223> OTHER INFORMATION: Synthetic sequence

<400> SEQUENCE: 594
ctgccagagc aggtacctcc aacatcaag                         29

<210> SEQ ID NO 595
<211> LENGTH: 23
<212> TYPE: DNA
<213> ORGANISM: Artificial Sequence
<220> FEATURE:
<223> OTHER INFORMATION: Synthetic sequence

<400> SEQUENCE: 595
gagcaggtac ctccaacatc aag                               23

<210> SEQ ID NO 596
<211> LENGTH: 24
<212> TYPE: DNA
<213> ORGANISM: Artificial Sequence
<220> FEATURE:
<223> OTHER INFORMATION: Synthetic sequence

<400> SEQUENCE: 596
gccagagcag gtacctccaa catc                              24

<210> SEQ ID NO 597
<211> LENGTH: 24
<212> TYPE: DNA
<213> ORGANISM: Artificial Sequence
<220> FEATURE:
<223> OTHER INFORMATION: Synthetic sequence

<400> SEQUENCE: 597
gaaatctgcc agagcaggta cctc                              24

<210> SEQ ID NO 598
<211> LENGTH: 26
<212> TYPE: DNA
<213> ORGANISM: Artificial Sequence
<220> FEATURE:
<223> OTHER INFORMATION: Synthetic sequence

```
<400> SEQUENCE: 598
ggtacctcca acatcaagga agatgg                                           26

<210> SEQ ID NO 599
<211> LENGTH: 28
<212> TYPE: DNA
<213> ORGANISM: Artificial Sequence
<220> FEATURE:
<223> OTHER INFORMATION: Synthetic sequence

<400> SEQUENCE: 599
aggtacctcc aacatcaagg aagatggc                                         28

<210> SEQ ID NO 600
<211> LENGTH: 25
<212> TYPE: DNA
<213> ORGANISM: Artificial Sequence
<220> FEATURE:
<223> OTHER INFORMATION: Synthetic sequence

<400> SEQUENCE: 600
tacctccaac atcaaggaag atggc                                            25

<210> SEQ ID NO 601
<211> LENGTH: 24
<212> TYPE: DNA
<213> ORGANISM: Artificial Sequence
<220> FEATURE:
<223> OTHER INFORMATION: Synthetic sequence

<400> SEQUENCE: 601
acctccaaca tcaaggaaga tggc                                             24

<210> SEQ ID NO 602
<211> LENGTH: 21
<212> TYPE: DNA
<213> ORGANISM: Artificial Sequence
<220> FEATURE:
<223> OTHER INFORMATION: Synthetic sequence

<400> SEQUENCE: 602
tccaacatca aggaagatgg c                                                21

<210> SEQ ID NO 603
<211> LENGTH: 20
<212> TYPE: DNA
<213> ORGANISM: Artificial Sequence
<220> FEATURE:
<223> OTHER INFORMATION: Synthetic sequence

<400> SEQUENCE: 603
ccaacatcaa ggaagatggc                                                  20

<210> SEQ ID NO 604
<211> LENGTH: 19
<212> TYPE: DNA
<213> ORGANISM: Artificial Sequence
<220> FEATURE:
<223> OTHER INFORMATION: Synthetic sequence

<400> SEQUENCE: 604
caacatcaag gaagatggc                                                   19

<210> SEQ ID NO 605
```

```
<211> LENGTH: 31
<212> TYPE: DNA
<213> ORGANISM: Artificial Sequence
<220> FEATURE:
<223> OTHER INFORMATION: Synthetic sequence

<400> SEQUENCE: 605
gtacctccaa catcaaggaa gatggcattt c                              31

<210> SEQ ID NO 606
<211> LENGTH: 30
<212> TYPE: DNA
<213> ORGANISM: Artificial Sequence
<220> FEATURE:
<223> OTHER INFORMATION: Synthetic sequence

<400> SEQUENCE: 606
gtacctccaa catcaaggaa gatggcattt                                30

<210> SEQ ID NO 607
<211> LENGTH: 29
<212> TYPE: DNA
<213> ORGANISM: Artificial Sequence
<220> FEATURE:
<223> OTHER INFORMATION: Synthetic sequence

<400> SEQUENCE: 607
gtacctccaa catcaaggaa gatggcatt                                 29

<210> SEQ ID NO 608
<211> LENGTH: 28
<212> TYPE: DNA
<213> ORGANISM: Artificial Sequence
<220> FEATURE:
<223> OTHER INFORMATION: Synthetic sequence

<400> SEQUENCE: 608
gtacctccaa catcaaggaa gatggcat                                  28

<210> SEQ ID NO 609
<211> LENGTH: 27
<212> TYPE: DNA
<213> ORGANISM: Artificial Sequence
<220> FEATURE:
<223> OTHER INFORMATION: Synthetic sequence

<400> SEQUENCE: 609
gtacctccaa catcaaggaa gatggca                                   27

<210> SEQ ID NO 610
<211> LENGTH: 23
<212> TYPE: DNA
<213> ORGANISM: Artificial Sequence
<220> FEATURE:
<223> OTHER INFORMATION: Synthetic sequence

<400> SEQUENCE: 610
gtacctccaa catcaaggaa gat                                       23

<210> SEQ ID NO 611
<211> LENGTH: 22
<212> TYPE: DNA
<213> ORGANISM: Artificial Sequence
<220> FEATURE:
<223> OTHER INFORMATION: Synthetic sequence

<400> SEQUENCE: 611
```
gtacctccaa catcaaggaa ga                                                     22

<210> SEQ ID NO 612
<211> LENGTH: 21
<212> TYPE: DNA
<213> ORGANISM: Artificial Sequence
<220> FEATURE:
<223> OTHER INFORMATION: Synthetic sequence

<400> SEQUENCE: 612
gtacctccaa catcaaggaa g                                                      21

<210> SEQ ID NO 613
<211> LENGTH: 25
<212> TYPE: DNA
<213> ORGANISM: Artificial Sequence
<220> FEATURE:
<223> OTHER INFORMATION: Synthetic sequence

<400> SEQUENCE: 613
gaagaaaaag aaaaattaga aacac                                                  25

<210> SEQ ID NO 614
<211> LENGTH: 25
<212> TYPE: DNA
<213> ORGANISM: Artificial Sequence
<220> FEATURE:
<223> OTHER INFORMATION: Synthetic sequence

<400> SEQUENCE: 614
aaggaaaaaa gaagaaaaag aaaaa                                                  25

<210> SEQ ID NO 615
<211> LENGTH: 25
<212> TYPE: DNA
<213> ORGANISM: Artificial Sequence
<220> FEATURE:
<223> OTHER INFORMATION: Synthetic sequence

<400> SEQUENCE: 615
gcaaaaagga aaaagaaga aaaag                                                   25

<210> SEQ ID NO 616
<211> LENGTH: 25
<212> TYPE: DNA
<213> ORGANISM: Artificial Sequence
<220> FEATURE:
<223> OTHER INFORMATION: Synthetic sequence

<400> SEQUENCE: 616
tttttgcaaa aaggaaaaaa gaaga                                                  25

<210> SEQ ID NO 617
<211> LENGTH: 25
<212> TYPE: DNA
<213> ORGANISM: Artificial Sequence
<220> FEATURE:
<223> OTHER INFORMATION: Synthetic sequence

<400> SEQUENCE: 617
ttgggttttt gcaaaaagga aaaaa                                                  25

<210> SEQ ID NO 618
<211> LENGTH: 25
<212> TYPE: DNA

```
<213> ORGANISM: Artificial Sequence
<220> FEATURE:
<223> OTHER INFORMATION: Synthetic sequence

<400> SEQUENCE: 618
atattttggg tttttgcaaa aagga                                              25

<210> SEQ ID NO 619
<211> LENGTH: 25
<212> TYPE: DNA
<213> ORGANISM: Artificial Sequence
<220> FEATURE:
<223> OTHER INFORMATION: Synthetic sequence

<400> SEQUENCE: 619
ctaaaatatt tgggttttt gcaaa                                               25

<210> SEQ ID NO 620
<211> LENGTH: 25
<212> TYPE: DNA
<213> ORGANISM: Artificial Sequence
<220> FEATURE:
<223> OTHER INFORMATION: Synthetic sequence

<400> SEQUENCE: 620
aggagctaaa atattttggg ttttt                                              25

<210> SEQ ID NO 621
<211> LENGTH: 25
<212> TYPE: DNA
<213> ORGANISM: Artificial Sequence
<220> FEATURE:
<223> OTHER INFORMATION: Synthetic sequence

<400> SEQUENCE: 621
tgagtaggag ctaaaatatt ttggg                                              25

<210> SEQ ID NO 622
<211> LENGTH: 25
<212> TYPE: DNA
<213> ORGANISM: Artificial Sequence
<220> FEATURE:
<223> OTHER INFORMATION: Synthetic sequence

<400> SEQUENCE: 622
cagtctgagt aggagctaaa atatt                                              25

<210> SEQ ID NO 623
<211> LENGTH: 25
<212> TYPE: DNA
<213> ORGANISM: Artificial Sequence
<220> FEATURE:
<223> OTHER INFORMATION: Synthetic sequence

<400> SEQUENCE: 623
agtaacagtc tgagtaggag ctaaa                                              25

<210> SEQ ID NO 624
<211> LENGTH: 25
<212> TYPE: DNA
<213> ORGANISM: Artificial Sequence
<220> FEATURE:
<223> OTHER INFORMATION: Synthetic sequence

<400> SEQUENCE: 624
ccagagtaac agtctgagta ggagc                                              25
```

```
<210> SEQ ID NO 625
<211> LENGTH: 25
<212> TYPE: DNA
<213> ORGANISM: Artificial Sequence
<220> FEATURE:
<223> OTHER INFORMATION: Synthetic sequence

<400> SEQUENCE: 625
aaaagaaaaa ttagaaacac aagct                                  25

<210> SEQ ID NO 626
<211> LENGTH: 25
<212> TYPE: DNA
<213> ORGANISM: Artificial Sequence
<220> FEATURE:
<223> OTHER INFORMATION: Synthetic sequence

<400> SEQUENCE: 626
aaaaattaga aacacaagct aaaga                                  25

<210> SEQ ID NO 627
<211> LENGTH: 25
<212> TYPE: DNA
<213> ORGANISM: Artificial Sequence
<220> FEATURE:
<223> OTHER INFORMATION: Synthetic sequence

<400> SEQUENCE: 627
ttagaaacac aagctaaaga gccaa                                  25

<210> SEQ ID NO 628
<211> LENGTH: 25
<212> TYPE: DNA
<213> ORGANISM: Artificial Sequence
<220> FEATURE:
<223> OTHER INFORMATION: Synthetic sequence

<400> SEQUENCE: 628
aacacaagct aaagagccaa tttca                                  25

<210> SEQ ID NO 629
<211> LENGTH: 25
<212> TYPE: DNA
<213> ORGANISM: Artificial Sequence
<220> FEATURE:
<223> OTHER INFORMATION: Synthetic sequence

<400> SEQUENCE: 629
aagctaaaga gccaatttca ataac                                  25

<210> SEQ ID NO 630
<211> LENGTH: 25
<212> TYPE: DNA
<213> ORGANISM: Artificial Sequence
<220> FEATURE:
<223> OTHER INFORMATION: Synthetic sequence

<400> SEQUENCE: 630
aaagagccaa tttcaataac aataa                                  25

<210> SEQ ID NO 631
<211> LENGTH: 25
<212> TYPE: DNA
<213> ORGANISM: Artificial Sequence
<220> FEATURE:
```

```
<223> OTHER INFORMATION: Synthetic sequence

<400> SEQUENCE: 631
gccaatttca ataacaataa gtcaa                                          25

<210> SEQ ID NO 632
<211> LENGTH: 25
<212> TYPE: DNA
<213> ORGANISM: Artificial Sequence
<220> FEATURE:
<223> OTHER INFORMATION: Synthetic sequence

<400> SEQUENCE: 632
tttcaataac ataagtcaa attta                                           25

<210> SEQ ID NO 633
<211> LENGTH: 30
<212> TYPE: DNA
<213> ORGANISM: Artificial Sequence
<220> FEATURE:
<223> OTHER INFORMATION: Synthetic sequence

<400> SEQUENCE: 633
gtgtcaccag agtaacagtc tgagtaggag                                     30

<210> SEQ ID NO 634
<211> LENGTH: 30
<212> TYPE: DNA
<213> ORGANISM: Artificial Sequence
<220> FEATURE:
<223> OTHER INFORMATION: Synthetic sequence

<400> SEQUENCE: 634
ccacaggttg tgtcaccaga gtaacagtct                                     30

<210> SEQ ID NO 635
<211> LENGTH: 30
<212> TYPE: DNA
<213> ORGANISM: Artificial Sequence
<220> FEATURE:
<223> OTHER INFORMATION: Synthetic sequence

<400> SEQUENCE: 635
aggttgtgtc accagagtaa cagtctgagt                                     30

<210> SEQ ID NO 636
<211> LENGTH: 30
<212> TYPE: DNA
<213> ORGANISM: Artificial Sequence
<220> FEATURE:
<223> OTHER INFORMATION: Synthetic sequence

<400> SEQUENCE: 636
atggcatttc tagtttggag atggcagttt                                     30

<210> SEQ ID NO 637
<211> LENGTH: 25
<212> TYPE: DNA
<213> ORGANISM: Artificial Sequence
<220> FEATURE:
<223> OTHER INFORMATION: Synthetic sequence

<400> SEQUENCE: 637
accagagtaa cagtctgagt aggag                                          25
```

```
<210> SEQ ID NO 638
<211> LENGTH: 25
<212> TYPE: DNA
<213> ORGANISM: Artificial Sequence
<220> FEATURE:
<223> OTHER INFORMATION: Synthetic sequence

<400> SEQUENCE: 638
gtcaccagag taacagtctg agtag                                               25

<210> SEQ ID NO 639
<211> LENGTH: 25
<212> TYPE: DNA
<213> ORGANISM: Artificial Sequence
<220> FEATURE:
<223> OTHER INFORMATION: Synthetic sequence

<400> SEQUENCE: 639
accacaggtt gtgtcaccag agtaa                                               25

<210> SEQ ID NO 640
<211> LENGTH: 25
<212> TYPE: DNA
<213> ORGANISM: Artificial Sequence
<220> FEATURE:
<223> OTHER INFORMATION: Synthetic sequence

<400> SEQUENCE: 640
tagtaaccac aggttgtgtc accag                                               25

<210> SEQ ID NO 641
<211> LENGTH: 25
<212> TYPE: DNA
<213> ORGANISM: Artificial Sequence
<220> FEATURE:
<223> OTHER INFORMATION: Synthetic sequence

<400> SEQUENCE: 641
ttccttagta accacaggtt gtgtc                                               25

<210> SEQ ID NO 642
<211> LENGTH: 25
<212> TYPE: DNA
<213> ORGANISM: Artificial Sequence
<220> FEATURE:
<223> OTHER INFORMATION: Synthetic sequence

<400> SEQUENCE: 642
gcagtttcct tagtaaccac aggtt                                               25

<210> SEQ ID NO 643
<211> LENGTH: 25
<212> TYPE: DNA
<213> ORGANISM: Artificial Sequence
<220> FEATURE:
<223> OTHER INFORMATION: Synthetic sequence

<400> SEQUENCE: 643
agatggcagt ttccttagta accac                                               25

<210> SEQ ID NO 644
<211> LENGTH: 25
<212> TYPE: DNA
<213> ORGANISM: Artificial Sequence
<220> FEATURE:
<223> OTHER INFORMATION: Synthetic sequence
```

```
<400> SEQUENCE: 644
tttggagatg gcagtttcct tagta                                              25

<210> SEQ ID NO 645
<211> LENGTH: 25
<212> TYPE: DNA
<213> ORGANISM: Artificial Sequence
<220> FEATURE:
<223> OTHER INFORMATION: Synthetic sequence

<400> SEQUENCE: 645
tgccagagca ggtacctcca acatc                                              25

<210> SEQ ID NO 646
<211> LENGTH: 25
<212> TYPE: DNA
<213> ORGANISM: Artificial Sequence
<220> FEATURE:
<223> OTHER INFORMATION: Synthetic sequence

<400> SEQUENCE: 646
aaatctgcca gagcaggtac ctcca                                              25

<210> SEQ ID NO 647
<211> LENGTH: 25
<212> TYPE: DNA
<213> ORGANISM: Artificial Sequence
<220> FEATURE:
<223> OTHER INFORMATION: Synthetic sequence

<400> SEQUENCE: 647
ggttgaaatc tgccagagca ggtac                                              25

<210> SEQ ID NO 648
<211> LENGTH: 25
<212> TYPE: DNA
<213> ORGANISM: Artificial Sequence
<220> FEATURE:
<223> OTHER INFORMATION: Synthetic sequence

<400> SEQUENCE: 648
agcccggttg aaatctgcca gagca                                              25

<210> SEQ ID NO 649
<211> LENGTH: 25
<212> TYPE: DNA
<213> ORGANISM: Artificial Sequence
<220> FEATURE:
<223> OTHER INFORMATION: Synthetic sequence

<400> SEQUENCE: 649
gtccaagccc ggttgaaatc tgcca                                              25

<210> SEQ ID NO 650
<211> LENGTH: 25
<212> TYPE: DNA
<213> ORGANISM: Artificial Sequence
<220> FEATURE:
<223> OTHER INFORMATION: Synthetic sequence

<400> SEQUENCE: 650
gttctgtcca agcccggttg aaatc                                              25

<210> SEQ ID NO 651
<211> LENGTH: 25
```

```
<212> TYPE: DNA
<213> ORGANISM: Artificial Sequence
<220> FEATURE:
<223> OTHER INFORMATION: Synthetic sequence

<400> SEQUENCE: 651
ggtaagttct gtccaagccc ggttg                                              25

<210> SEQ ID NO 652
<211> LENGTH: 25
<212> TYPE: DNA
<213> ORGANISM: Artificial Sequence
<220> FEATURE:
<223> OTHER INFORMATION: Synthetic sequence

<400> SEQUENCE: 652
cagtcggtaa gttctgtcca agccc                                              25

<210> SEQ ID NO 653
<211> LENGTH: 25
<212> TYPE: DNA
<213> ORGANISM: Artificial Sequence
<220> FEATURE:
<223> OTHER INFORMATION: Synthetic sequence

<400> SEQUENCE: 653
aaagccagtc ggtaagttct gtcca                                              25

<210> SEQ ID NO 654
<211> LENGTH: 25
<212> TYPE: DNA
<213> ORGANISM: Artificial Sequence
<220> FEATURE:
<223> OTHER INFORMATION: Synthetic sequence

<400> SEQUENCE: 654
cagagaaagc cagtcggtaa gttct                                              25

<210> SEQ ID NO 655
<211> LENGTH: 25
<212> TYPE: DNA
<213> ORGANISM: Artificial Sequence
<220> FEATURE:
<223> OTHER INFORMATION: Synthetic sequence

<400> SEQUENCE: 655
tcaagcagag aaagccagtc ggtaa                                              25

<210> SEQ ID NO 656
<211> LENGTH: 25
<212> TYPE: DNA
<213> ORGANISM: Artificial Sequence
<220> FEATURE:
<223> OTHER INFORMATION: Synthetic sequence

<400> SEQUENCE: 656
cttgatcaag cagagaaagc cagtc                                              25

<210> SEQ ID NO 657
<211> LENGTH: 25
<212> TYPE: DNA
<213> ORGANISM: Artificial Sequence
<220> FEATURE:
<223> OTHER INFORMATION: Synthetic sequence

<400> SEQUENCE: 657
```
tataacttga tcaagcagag aaagc                    25

<210> SEQ ID NO 658
<211> LENGTH: 25
<212> TYPE: DNA
<213> ORGANISM: Artificial Sequence
<220> FEATURE:
<223> OTHER INFORMATION: Synthetic sequence

<400> SEQUENCE: 658
gattttataa cttgatcaag cagag                    25

<210> SEQ ID NO 659
<211> LENGTH: 25
<212> TYPE: DNA
<213> ORGANISM: Artificial Sequence
<220> FEATURE:
<223> OTHER INFORMATION: Synthetic sequence

<400> SEQUENCE: 659
tctgtgattt tataacttga tcaag                    25

<210> SEQ ID NO 660
<211> LENGTH: 25
<212> TYPE: DNA
<213> ORGANISM: Artificial Sequence
<220> FEATURE:
<223> OTHER INFORMATION: Synthetic sequence

<400> SEQUENCE: 660
caccctctgt gattttataa cttga                    25

<210> SEQ ID NO 661
<211> LENGTH: 25
<212> TYPE: DNA
<213> ORGANISM: Artificial Sequence
<220> FEATURE:
<223> OTHER INFORMATION: Synthetic sequence

<400> SEQUENCE: 661
accatcaccc tctgtgattt tataa                    25

<210> SEQ ID NO 662
<211> LENGTH: 25
<212> TYPE: DNA
<213> ORGANISM: Artificial Sequence
<220> FEATURE:
<223> OTHER INFORMATION: Synthetic sequence

<400> SEQUENCE: 662
cacccaccat caccctctgt gattt                    25

<210> SEQ ID NO 663
<211> LENGTH: 25
<212> TYPE: DNA
<213> ORGANISM: Artificial Sequence
<220> FEATURE:
<223> OTHER INFORMATION: Synthetic sequence

<400> SEQUENCE: 663
aaggtcaccc accatcaccc tctgt                    25

<210> SEQ ID NO 664
<211> LENGTH: 25
<212> TYPE: DNA
<213> ORGANISM: Artificial Sequence

```
<220> FEATURE:
<223> OTHER INFORMATION: Synthetic sequence

<400> SEQUENCE: 664
tcctcaaggt cacccaccat caccc                                    25

<210> SEQ ID NO 665
<211> LENGTH: 25
<212> TYPE: DNA
<213> ORGANISM: Artificial Sequence
<220> FEATURE:
<223> OTHER INFORMATION: Synthetic sequence

<400> SEQUENCE: 665
tgatatcctc aaggtcaccc accat                                    25

<210> SEQ ID NO 666
<211> LENGTH: 25
<212> TYPE: DNA
<213> ORGANISM: Artificial Sequence
<220> FEATURE:
<223> OTHER INFORMATION: Synthetic sequence

<400> SEQUENCE: 666
ctcgttgata tcctcaaggt caccc                                    25

<210> SEQ ID NO 667
<211> LENGTH: 25
<212> TYPE: DNA
<213> ORGANISM: Artificial Sequence
<220> FEATURE:
<223> OTHER INFORMATION: Synthetic sequence

<400> SEQUENCE: 667
atcatctcgt tgatatcctc aaggt                                    25

<210> SEQ ID NO 668
<211> LENGTH: 25
<212> TYPE: DNA
<213> ORGANISM: Artificial Sequence
<220> FEATURE:
<223> OTHER INFORMATION: Synthetic sequence

<400> SEQUENCE: 668
tgatgatcat ctcgttgata tcctc                                    25

<210> SEQ ID NO 669
<211> LENGTH: 25
<212> TYPE: DNA
<213> ORGANISM: Artificial Sequence
<220> FEATURE:
<223> OTHER INFORMATION: Synthetic sequence

<400> SEQUENCE: 669
ctgcttgatg atcatctcgt tgata                                    25

<210> SEQ ID NO 670
<211> LENGTH: 25
<212> TYPE: DNA
<213> ORGANISM: Artificial Sequence
<220> FEATURE:
<223> OTHER INFORMATION: Synthetic sequence

<400> SEQUENCE: 670
accttctgct tgatgatcat ctcgt                                    25
```

<210> SEQ ID NO 671
<211> LENGTH: 25
<212> TYPE: DNA
<213> ORGANISM: Artificial Sequence
<220> FEATURE:
<223> OTHER INFORMATION: Synthetic sequence

<400> SEQUENCE: 671
cataccttct gcttgatgat catct                                    25

<210> SEQ ID NO 672
<211> LENGTH: 25
<212> TYPE: DNA
<213> ORGANISM: Artificial Sequence
<220> FEATURE:
<223> OTHER INFORMATION: Synthetic sequence

<400> SEQUENCE: 672
tctcatacct tctgcttgat gatca                                    25

<210> SEQ ID NO 673
<211> LENGTH: 25
<212> TYPE: DNA
<213> ORGANISM: Artificial Sequence
<220> FEATURE:
<223> OTHER INFORMATION: Synthetic sequence

<400> SEQUENCE: 673
ttttctcata ccttctgctt gatga                                    25

<210> SEQ ID NO 674
<211> LENGTH: 25
<212> TYPE: DNA
<213> ORGANISM: Artificial Sequence
<220> FEATURE:
<223> OTHER INFORMATION: Synthetic sequence

<400> SEQUENCE: 674
attttttctc ataccttctg cttga                                    25

<210> SEQ ID NO 675
<211> LENGTH: 25
<212> TYPE: DNA
<213> ORGANISM: Artificial Sequence
<220> FEATURE:
<223> OTHER INFORMATION: Synthetic sequence

<400> SEQUENCE: 675 atcattttt ctcataccttt ctgct                                    25

<210> SEQ ID NO 676
<211> LENGTH: 25
<212> TYPE: DNA
<213> ORGANISM: Artificial Sequence
<220> FEATURE:
<223> OTHER INFORMATION: Synthetic sequence

<400> SEQUENCE: 676
tttatcattt tttctcatac cttct                                    25

<210> SEQ ID NO 677
<211> LENGTH: 25
<212> TYPE: DNA
<213> ORGANISM: Artificial Sequence
<220> FEATURE:
<223> OTHER INFORMATION: Synthetic sequence

```
<400> SEQUENCE: 677 actttatca tttttctca tacct                                          25

<210> SEQ ID NO 678
<211> LENGTH: 25
<212> TYPE: DNA
<213> ORGANISM: Artificial Sequence
<220> FEATURE:
<223> OTHER INFORMATION: Synthetic sequence

<400> SEQUENCE: 678
ccaactttta tcatttttc tcata                                         25

<210> SEQ ID NO 679
<211> LENGTH: 30
<212> TYPE: DNA
<213> ORGANISM: Artificial Sequence
<220> FEATURE:
<223> OTHER INFORMATION: Synthetic sequence

<400> SEQUENCE: 679
ctccaacatc aaggaagatg gcatttctag                                   30

<210> SEQ ID NO 680
<211> LENGTH: 20
<212> TYPE: DNA
<213> ORGANISM: Artificial Sequence
<220> FEATURE:
<223> OTHER INFORMATION: Synthetic sequence

<400> SEQUENCE: 680
tcaaggaaga tggcatttct                                              20

<210> SEQ ID NO 681
<211> LENGTH: 20
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (7)..(7)
<223> OTHER INFORMATION: Wherein n is methylated adenine
<220> FEATURE:
<221> NAME/KEY: misc_feature
<222> LOCATION: (9)..(9)
<223> OTHER INFORMATION: Wherein n is methylated guanine
<220> FEATURE:
<221> NAME/KEY: misc_feature
<222> LOCATION: (10)..(10)
<223> OTHER INFORMATION: Wherein n is methylated adenine
<220> FEATURE:
<221> NAME/KEY: misc_feature
<222> LOCATION: (12)..(12)
<223> OTHER INFORMATION: Wherein n is methylated guanine
<220> FEATURE:
<221> NAME/KEY: misc_feature
<222> LOCATION: (13)..(13)
<223> OTHER INFORMATION: Wherein n is methylated guanine

<400> SEQUENCE: 681
ucaaggnann unncauuucu                                              20

<210> SEQ ID NO 682
<211> LENGTH: 25
<212> TYPE: DNA
<213> ORGANISM: Artificial Sequence
<220> FEATURE:
```

<223> OTHER INFORMATION: Synthetic sequence

<400> SEQUENCE: 682
gttgcctccg gttctgaagg tgttc                              25

<210> SEQ ID NO 683
<211> LENGTH: 25
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(25)
<223> OTHER INFORMATION: Wherein n is 5-methylcytosine (5mC)

<400> SEQUENCE: 683
gttgnntnng gttntgaagg tgttn                              25

<210> SEQ ID NO 684
<211> LENGTH: 21
<212> TYPE: DNA
<213> ORGANISM: Artificial Sequence
<220> FEATURE:
<223> OTHER INFORMATION: Synthetic sequence

<400> SEQUENCE: 684
cctccggttc tgaaggtgtt c                                  21

<210> SEQ ID NO 685
<211> LENGTH: 25
<212> TYPE: DNA
<213> ORGANISM: Artificial Sequence
<220> FEATURE:
<223> OTHER INFORMATION: Synthetic sequence

<400> SEQUENCE: 685
cctccggttc tgaaggtgtt cttgt                              25

<210> SEQ ID NO 686
<211> LENGTH: 28
<212> TYPE: DNA
<213> ORGANISM: Artificial Sequence
<220> FEATURE:
<223> OTHER INFORMATION: Synthetic sequence

<400> SEQUENCE: 686
gttgcctccg gttctgaagg tgttcttg                           28

<210> SEQ ID NO 687
<211> LENGTH: 30
<212> TYPE: DNA
<213> ORGANISM: Artificial Sequence
<220> FEATURE:
<223> OTHER INFORMATION: Synthetic sequence

<400> SEQUENCE: 687
ttgcctccgg ttctgaaggt gttcttgtac                         30

<210> SEQ ID NO 688
<211> LENGTH: 24
<212> TYPE: DNA
<213> ORGANISM: Artificial Sequence
<220> FEATURE:
<223> OTHER INFORMATION: Synthetic sequence

<400> SEQUENCE: 688

```
ctgttgcctc cggttctgaa ggtg                                              24
```

<210> SEQ ID NO 689
<211> LENGTH: 31
<212> TYPE: DNA
<213> ORGANISM: Artificial Sequence
<220> FEATURE:
<223> OTHER INFORMATION: Synthetic sequence

<400> SEQUENCE: 689

```
cattcaactg ttgcctccgg ttctgaaggt g                                      31
```

<210> SEQ ID NO 690
<211> LENGTH: 18
<212> TYPE: DNA
<213> ORGANISM: Artificial Sequence
<220> FEATURE:
<223> OTHER INFORMATION: Synthetic sequence

<400> SEQUENCE: 690

```
ctgttgcctc cggttctg                                                     18
```

<210> SEQ ID NO 691
<211> LENGTH: 22
<212> TYPE: DNA
<213> ORGANISM: Artificial Sequence
<220> FEATURE:
<223> OTHER INFORMATION: Synthetic sequence

<400> SEQUENCE: 691

```
caatgccatc ctggagttcc tg                                                22
```

<210> SEQ ID NO 692
<211> LENGTH: 34
<212> TYPE: DNA
<213> ORGANISM: Artificial Sequence
<220> FEATURE:
<223> OTHER INFORMATION: Synthetic sequence

<400> SEQUENCE: 692

```
gctgcccaat gccatcctgg agttcctgta agat                                   34
```

<210> SEQ ID NO 693
<211> LENGTH: 28
<212> TYPE: DNA
<213> ORGANISM: Artificial Sequence
<220> FEATURE:
<223> OTHER INFORMATION: Synthetic sequence

<400> SEQUENCE: 693

```
gctgcccaat gccatcctgg agttcctg                                          28
```

<210> SEQ ID NO 694
<211> LENGTH: 31
<212> TYPE: DNA
<213> ORGANISM: Artificial Sequence
<220> FEATURE:
<223> OTHER INFORMATION: Synthetic sequence

<400> SEQUENCE: 694

```
gctgcccaat gccatcctgg agttcctgta a                                      31
```

<210> SEQ ID NO 695
<211> LENGTH: 31
<212> TYPE: DNA

```
<213> ORGANISM: Artificial Sequence
<220> FEATURE:
<223> OTHER INFORMATION: Synthetic sequence

<400> SEQUENCE: 695
caatgccatc ctggagttcc tgtaagatac c                                    31

<210> SEQ ID NO 696
<211> LENGTH: 28
<212> TYPE: DNA
<213> ORGANISM: Artificial Sequence
<220> FEATURE:
<223> OTHER INFORMATION: Synthetic sequence

<400> SEQUENCE: 696
caatgccatc ctggagttcc tgtaagat                                        28

<210> SEQ ID NO 697
<211> LENGTH: 28
<212> TYPE: DNA
<213> ORGANISM: Artificial Sequence
<220> FEATURE:
<223> OTHER INFORMATION: Synthetic sequence

<400> SEQUENCE: 697
tgccatcctg gagttcctgt aagatacc                                        28

<210> SEQ ID NO 698
<211> LENGTH: 39
<212> TYPE: DNA
<213> ORGANISM: Artificial Sequence
<220> FEATURE:
<223> OTHER INFORMATION: Synthetic sequence

<400> SEQUENCE: 698
gctgcccaat gccatcctgg agttcctgta agataccaa                            39

<210> SEQ ID NO 699
<211> LENGTH: 27
<212> TYPE: DNA
<213> ORGANISM: Artificial Sequence
<220> FEATURE:
<223> OTHER INFORMATION: Synthetic sequence

<400> SEQUENCE: 699
caatgccatc ctggagttcc tgtaaga                                         27

<210> SEQ ID NO 700
<211> LENGTH: 32
<212> TYPE: DNA
<213> ORGANISM: Artificial Sequence
<220> FEATURE:
<223> OTHER INFORMATION: Synthetic sequence

<400> SEQUENCE: 700
gctgcccaat gccatcctgg agttcctgta ag                                   32

<210> SEQ ID NO 701
<211> LENGTH: 34
<212> TYPE: DNA
<213> ORGANISM: Artificial Sequence
<220> FEATURE:
<223> OTHER INFORMATION: Synthetic sequence

<400> SEQUENCE: 701
gcccaatgcc atcctggagt tcctgtaaga tacc                                 34
```

<210> SEQ ID NO 702
<211> LENGTH: 31
<212> TYPE: DNA
<213> ORGANISM: Artificial Sequence
<220> FEATURE:
<223> OTHER INFORMATION: Synthetic sequence

<400> SEQUENCE: 702
gcccaatgcc atcctggagt tcctgtaaga t                           31

<210> SEQ ID NO 703
<211> LENGTH: 39
<212> TYPE: DNA
<213> ORGANISM: Artificial Sequence
<220> FEATURE:
<223> OTHER INFORMATION: Synthetic sequence

<400> SEQUENCE: 703
ttgccgctgc ccaatgccat cctggagttc ctgtaagat                   39

<210> SEQ ID NO 704
<211> LENGTH: 28
<212> TYPE: DNA
<213> ORGANISM: Artificial Sequence
<220> FEATURE:
<223> OTHER INFORMATION: Synthetic sequence

<400> SEQUENCE: 704
gcccaatgcc atcctggagt tcctgtaa                               28

<210> SEQ ID NO 705
<211> LENGTH: 34
<212> TYPE: DNA
<213> ORGANISM: Artificial Sequence
<220> FEATURE:
<223> OTHER INFORMATION: Synthetic sequence

<400> SEQUENCE: 705
gccgctgccc aatgccatcc tggagttcct gtaa                        34

<210> SEQ ID NO 706
<211> LENGTH: 25
<212> TYPE: DNA
<213> ORGANISM: Artificial Sequence
<220> FEATURE:
<223> OTHER INFORMATION: Synthetic sequence

<400> SEQUENCE: 706
gcccaatgcc atcctggagt tcctg                                  25

<210> SEQ ID NO 707
<211> LENGTH: 31
<212> TYPE: DNA
<213> ORGANISM: Artificial Sequence
<220> FEATURE:
<223> OTHER INFORMATION: Synthetic sequence

<400> SEQUENCE: 707
gccgctgccc aatgccatcc tggagttcct g                           31

<210> SEQ ID NO 708
<211> LENGTH: 18
<212> TYPE: DNA
<213> ORGANISM: Artificial Sequence
<220> FEATURE:

<223> OTHER INFORMATION: Synthetic sequence
<220> FEATURE:
<221> NAME/KEY: misc_feature
<222> LOCATION: (1)..(18)
<223> OTHER INFORMATION: Wherein n is 5-methylcytosine (5mC)

<400> SEQUENCE: 708
ngntgcnnaa tgnnaunn                                          18

<210> SEQ ID NO 709
<211> LENGTH: 25
<212> TYPE: DNA
<213> ORGANISM: Artificial Sequence
<220> FEATURE:
<223> OTHER INFORMATION: Synthetic sequence

<400> SEQUENCE: 709
gatctgtcaa atcgcctgca ggtaa                                  25

<210> SEQ ID NO 710
<211> LENGTH: 22
<212> TYPE: DNA
<213> ORGANISM: Artificial Sequence
<220> FEATURE:
<223> OTHER INFORMATION: Synthetic sequence

<400> SEQUENCE: 710
gatctgtcaa atcgcctgca gg                                     22

<210> SEQ ID NO 711
<211> LENGTH: 24
<212> TYPE: DNA
<213> ORGANISM: Artificial Sequence
<220> FEATURE:
<223> OTHER INFORMATION: Synthetic sequence

<400> SEQUENCE: 711
cagatctgtc aaatcgcctg cagg                                   24

<210> SEQ ID NO 712
<211> LENGTH: 23
<212> TYPE: DNA
<213> ORGANISM: Artificial Sequence
<220> FEATURE:
<223> OTHER INFORMATION: Synthetic sequence

<400> SEQUENCE: 712
gatctgtcaa atcgcctgca ggt                                    23

<210> SEQ ID NO 713
<211> LENGTH: 21
<212> TYPE: DNA
<213> ORGANISM: Artificial Sequence
<220> FEATURE:
<223> OTHER INFORMATION: Synthetic sequence

<400> SEQUENCE: 713
gatctgtcaa atcgcctgca g                                      21

<210> SEQ ID NO 714
<211> LENGTH: 25
<212> TYPE: DNA
<213> ORGANISM: Artificial Sequence
<220> FEATURE:
<223> OTHER INFORMATION: Synthetic sequence

<400> SEQUENCE: 714
cagatctgtc aaatcgcctg caggt                                               25

<210> SEQ ID NO 715
<211> LENGTH: 23
<212> TYPE: DNA
<213> ORGANISM: Artificial Sequence
<220> FEATURE:
<223> OTHER INFORMATION: Synthetic sequence

<400> SEQUENCE: 715
cagatctgtc aaatcgcctg cag                                                 23

<210> SEQ ID NO 716
<211> LENGTH: 22
<212> TYPE: DNA
<213> ORGANISM: Artificial Sequence
<220> FEATURE:
<223> OTHER INFORMATION: Synthetic sequence

<400> SEQUENCE: 716
gggatccagt atacttacag gc                                                  22

<210> SEQ ID NO 717
<211> LENGTH: 23
<212> TYPE: DNA
<213> ORGANISM: Artificial Sequence
<220> FEATURE:
<223> OTHER INFORMATION: Synthetic sequence

<400> SEQUENCE: 717
gatccagtat acttacaggc tcc                                                 23

<210> SEQ ID NO 718
<211> LENGTH: 24
<212> TYPE: DNA
<213> ORGANISM: Artificial Sequence
<220> FEATURE:
<223> OTHER INFORMATION: Synthetic sequence

<400> SEQUENCE: 718
ggatccagta tacttacagg ctcc                                                24

<210> SEQ ID NO 719
<211> LENGTH: 26
<212> TYPE: DNA
<213> ORGANISM: Artificial Sequence
<220> FEATURE:
<223> OTHER INFORMATION: Synthetic sequence

<400> SEQUENCE: 719
acttcctctt taacagaaaa gcatac                                              26

<210> SEQ ID NO 720
<211> LENGTH: 22
<212> TYPE: DNA
<213> ORGANISM: Artificial Sequence
<220> FEATURE:
<223> OTHER INFORMATION: Synthetic sequence

<400> SEQUENCE: 720
atccagtata cttacaggct cc                                                  22

<210> SEQ ID NO 721
<211> LENGTH: 25
<212> TYPE: DNA

```
<213> ORGANISM: Artificial Sequence
<220> FEATURE:
<223> OTHER INFORMATION: Synthetic sequence

<400> SEQUENCE: 721
gagctcagat cttctaactt cctct                                    25

<210> SEQ ID NO 722
<211> LENGTH: 24
<212> TYPE: DNA
<213> ORGANISM: Artificial Sequence
<220> FEATURE:
<223> OTHER INFORMATION: Synthetic sequence

<400> SEQUENCE: 722
gggatccagt atacttacag gctc                                     24

<210> SEQ ID NO 723
<211> LENGTH: 27
<212> TYPE: DNA
<213> ORGANISM: Artificial Sequence
<220> FEATURE:
<223> OTHER INFORMATION: Synthetic sequence

<400> SEQUENCE: 723
atgggatcca gtatacttac aggctcc                                  27

<210> SEQ ID NO 724
<211> LENGTH: 25
<212> TYPE: DNA
<213> ORGANISM: Artificial Sequence
<220> FEATURE:
<223> OTHER INFORMATION: Synthetic sequence

<400> SEQUENCE: 724
ctgttccaaa tcctgcattg ttgcc                                    25

<210> SEQ ID NO 725
<211> LENGTH: 30
<212> TYPE: DNA
<213> ORGANISM: Artificial Sequence
<220> FEATURE:
<223> OTHER INFORMATION: Synthetic sequence

<400> SEQUENCE: 725
acatcaagga agatggcatt tctagtttgg                               30

<210> SEQ ID NO 726
<211> LENGTH: 30
<212> TYPE: DNA
<213> ORGANISM: Artificial Sequence
<220> FEATURE:
<223> OTHER INFORMATION: Synthetic sequence

<400> SEQUENCE: 726
ggtacctcca acatcaagga agatggcatt                               30

<210> SEQ ID NO 727
<211> LENGTH: 26
<212> TYPE: DNA
<213> ORGANISM: Artificial Sequence
<220> FEATURE:
<223> OTHER INFORMATION: Synthetic sequence

<400> SEQUENCE: 727
atttctagtt tggagatggc agtttc                                   26
```

```
<210> SEQ ID NO 728
<211> LENGTH: 25
<212> TYPE: DNA
<213> ORGANISM: Artificial Sequence
<220> FEATURE:
<223> OTHER INFORMATION: Synthetic sequence

<400> SEQUENCE: 728
ggaagatggc atttctagtt tggag                                          25

<210> SEQ ID NO 729
<211> LENGTH: 26
<212> TYPE: DNA
<213> ORGANISM: Artificial Sequence
<220> FEATURE:
<223> OTHER INFORMATION: Synthetic sequence

<400> SEQUENCE: 729
catcaaggaa gatggcattt ctagtt                                         26

<210> SEQ ID NO 730
<211> LENGTH: 25
<212> TYPE: DNA
<213> ORGANISM: Artificial Sequence
<220> FEATURE:
<223> OTHER INFORMATION: Synthetic sequence

<400> SEQUENCE: 730
atctgccaga gcaggtacct ccaac                                          25

<210> SEQ ID NO 731
<211> LENGTH: 20
<212> TYPE: DNA
<213> ORGANISM: Artificial Sequence
<220> FEATURE:
<223> OTHER INFORMATION: Synthetic sequence

<400> SEQUENCE: 731
tagtttggag atggcagttt                                                20

<210> SEQ ID NO 732
<211> LENGTH: 20
<212> TYPE: DNA
<213> ORGANISM: Artificial Sequence
<220> FEATURE:
<223> OTHER INFORMATION: Synthetic sequence

<400> SEQUENCE: 732
ggaagatggc atttctagtt                                                20

<210> SEQ ID NO 733
<211> LENGTH: 20
<212> TYPE: DNA
<213> ORGANISM: Artificial Sequence
<220> FEATURE:
<223> OTHER INFORMATION: Synthetic sequence

<400> SEQUENCE: 733
tacctccaac atcaaggaag                                                20

<210> SEQ ID NO 734
<211> LENGTH: 20
<212> TYPE: DNA
<213> ORGANISM: Artificial Sequence
<220> FEATURE:
```

<223> OTHER INFORMATION: Synthetic sequence

<400> SEQUENCE: 734
atctgccaga gcaggtacct                                              20

<210> SEQ ID NO 735
<211> LENGTH: 20
<212> TYPE: DNA
<213> ORGANISM: Artificial Sequence
<220> FEATURE:
<223> OTHER INFORMATION: Synthetic sequence

<400> SEQUENCE: 735
ccaagcccgg ttgaaatctg                                              20

<210> SEQ ID NO 736
<211> LENGTH: 30
<212> TYPE: DNA
<213> ORGANISM: Artificial Sequence
<220> FEATURE:
<223> OTHER INFORMATION: Synthetic sequence

<400> SEQUENCE: 736
aggttgtgtc accagagtaa cagtctgagt                                   30

<210> SEQ ID NO 737
<211> LENGTH: 25
<212> TYPE: DNA
<213> ORGANISM: Artificial Sequence
<220> FEATURE:
<223> OTHER INFORMATION: Synthetic sequence

<400> SEQUENCE: 737
cagagaaagc cagtcggtaa gttct                                        25

<210> SEQ ID NO 738
<211> LENGTH: 25
<212> TYPE: DNA
<213> ORGANISM: Artificial Sequence
<220> FEATURE:
<223> OTHER INFORMATION: Synthetic sequence

<400> SEQUENCE: 738
tataacttga tcaagcagag aaagc                                        25

TREATMENT METHODS FOR MUSCULAR DYSTROPHY

RELATED APPLICATIONS

This application claims the benefit of U.S. Provisional Application No. 63/182,327, filed on Apr. 30, 2021 and U.S. Provisional Application No. 63/249,721, filed on Sep. 29, 2021. The entire teachings of the above-referenced applications are incorporated by reference in their entirety.

REFERENCE TO A SEQUENCE LISTING SUBMITTED ELECTRONICALLY VIA EFS-WEB

The content of the electronically submitted sequence listing in ASCII text file (Name: 4140_0510002_Seq-listing_ST25; Size: 223,522 bytes; and Date of Creation: Dec. 19, 2022) is herein incorporated by reference in its entirety.

FIELD OF THE DISCLOSURE

The present disclosure relates to new dosing regimens for treating muscular dystrophy in a patient suffering from Duchenne muscular dystrophy (DMD) with an antisense oligonucleotide conjugate that causes skipping of an exon in the human dystrophin gene. It also provides methods for reducing toxicity associated with the treatments involving antisense oligonucleotide CPP conjugates.

BACKGROUND OF THE DISCLOSURE

Dystrophin is a critical structural protein that protects muscle from repeated strain-induced injury, affecting skeletal, diaphragmatic, and cardiac muscles. Duchenne muscular dystrophy is a rare, serious, life-threatening, X-linked recessive degenerative neuromuscular disease caused by mutations in the dystrophin gene. These mutations disrupt the reading frame of dystrophin messenger ribonucleic acid (mRNA), preventing the translation of functional dystrophin protein. Any exonic mutation that changes the reading frame of the exon, or introduces a stop codon, or is characterized by removal of an entire out of frame exon or exons, or duplications of one or more exons, has the potential to disrupt production of functional dystrophin, resulting in DMD. The absence of dystrophin protein is the direct cause of the disease and patients follow a predictable disease course with a relentlessly progressive deterioration of skeletal muscle function from early childhood leading to premature death, usually before 30 years of age.

Duchenne muscular dystrophy (DMD) is caused by a defect in the expression of the protein dystrophin. The gene encoding the protein contains 79 exons spread out over more than 2 million nucleotides of DNA. Any exonic mutation that changes the reading frame of the exon, or introduces a stop codon, or is characterized by removal of an entire out of frame exon or exons, or duplications of one or more exons, has the potential to disrupt production of functional dystrophin, resulting in DMD.

A less severe form of muscular dystrophy, Becker muscular dystrophy (BMD) has been found to arise where a mutation, typically a deletion of one or more exons, results in a correct reading frame along the entire dystrophin transcript, such that translation of mRNA into protein is not prematurely terminated. If the joining of the upstream and downstream exons in the processing of a mutated dystrophin pre-mRNA maintains the correct reading frame of the gene, the result is an mRNA coding for a protein with a short internal deletion that retains some activity, resulting in a BMD phenotype.

For many years it has been known that deletions of an exon or exons which do not alter the reading frame of a dystrophin protein would give rise to a BMD phenotype, whereas an exon deletion that causes a frame-shift will give rise to DMD (Monaco, Bertelson et al. 1988). In general, dystrophin mutations including point mutations and exon deletions that change the reading frame and thus interrupt proper protein translation result in DMD. It should also be noted that some BMD and DMD patients have exon deletions covering multiple exons.

Antisense oligonucleotides, e.g., splice switching oligonucleotides (SSOs), have been successfully used for the treatment of DMD to induce alternative splicing of pre-mRNAs by steric blockade of the spliceosome. SSOs have been specifically designed to target specific regions of the pre-mRNA, typically exons to induce the skipping of a mutation of the DMD gene thereby restoring these out-of-frame mutations in-frame to enable the production of internally shortened, yet functional dystrophin protein. Such antisense oligomers have been known to target completely within the exon (so called exon internal sequences) or at a splice donor or splice acceptor junction that crosses from the exon into a portion of the intron.

For example, eteplirsen is a phosphorodiamidate morpholino oligomer (PMO) designed to skip exon 51 of the human dystrophin gene in patients with DMD who are amenable to exon 51 skipping to restore the read frame and produce a functional shorter form of the dystrophin protein. The United States Food and Drug Administration (FDA) approved in 2016 Exondys 51® (eteplirsen) for the treatment of DMD in patients who have a confirmed mutation of the DMD gene that is amenable to exon 51 skipping. For another example, golodirsen (Vyondys 53®), also an antisense oligonucleotide of the PMO subclass, has been recently approved for the treatment of DMD in patients with a confirmed mutation of the DMD gene that is amenable to exon 53 skipping.

The discovery and development of antisense oligomers conjugated to cell-penetrating peptides (e.g., PPMOs) for DMD has also been an area of research (see, e.g., U.S. Pat. No. 10,888,578; U.S. application Ser. No. 16/469,104; U.S. application Ser. No. 16/001,310). Cell-penetrating peptides (CPP), for example, an arginine-rich peptide transport moiety, have been shown to be effective in enhancing penetration of antisense oligomers into a cell and to cause exon skipping in different muscle groups in animal models. To date, however, the relationship between human systemic exposure to dose levels of antisense oligomer conjugates (e.g., PPMOs) has not been established.

Magnesium deficiency (or hypomagensemia) is an electrolyte disturbance in which there is a low level of magnesium in the body. Causes of hypomagnesemia can include exposure to certain drugs. Hypomagnesemia can result in multiple symptoms. Symptoms include tremor, poor coordination, muscle spasms, loss of appetite, personality changes, and nystagmus. Complications may include seizures or cardiac arrest such as from torsade de pointes. Those with low magnesium often have low potassium.

The diagnosis of hypomagnesemia is typically based on finding low blood magnesium levels. Normal magnesium levels can fluctuate between about 0.6 to about 1.1 mmol/L (about 1.5 to about 2.7 mg/dL) with levels less than about 0.6 mmol/L (about 1.5 mg/dL) usually defining hypomagnesemia. The effects of antisense oligomer conjugates, such as PPMOs, on magnesium levels of patients, including DMD patients, receiving PPMO therapy is not known.

Thus, despite the successes achieved in pre-clinical models with antisense oligomers conjugated to cell-penetrating peptides, the need remains for a safe and effective dosing paradigm for treating DMD and BMD with such conjugates in human patients.

SUMMARY OF THE DISCLOSURE

In some aspects, the disclosure relates to a method of treating a patient with Duchenne muscular dystrophy (DMD) in need thereof who has a mutation that is amenable to exon skipping, comprising administering to the patient an antisense oligomer conjugate of Formula (I):

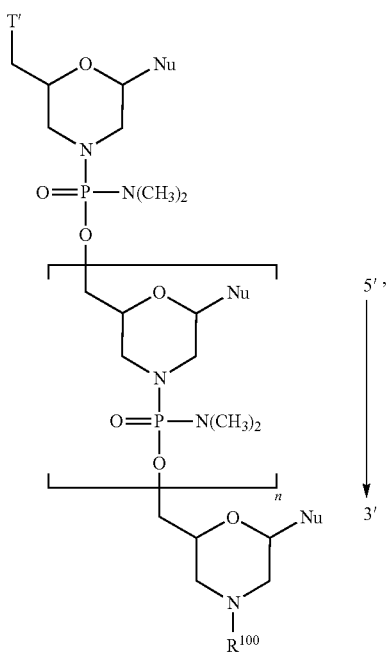

or a pharmaceutically acceptable salt thereof, wherein:
n is 1-40;
each Nu is a nucleobase, which, taken together, form a targeting sequence complementary to an exon annealing site in the dystrophin pre-mRNA;
T' is a moiety selected from:

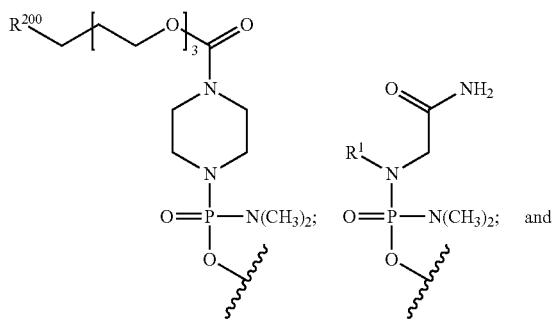

-continued $$\text{OH}$$

wherein
$R^{100}$ a cell-penetrating peptide, $R^{200}$ is hydrogen, and $R^1$ is $C_1$-$C_6$ alkyl, and wherein the conjugate is administered in a dose effective to provide a mean area under the curve (AUC) of the conjugate, or the pharmaceutically acceptable salt thereof between about 100 and about 200 ug·h/mL, between about 120 and about 240 ug·h/mL, or between about 200 and about 500 ug·h/mL.

In some aspects, $R^{100}$ is a CPP, wherein the CPP is attached to the 3'-end of the oligomer by an amide bond at the CPP carboxy terminus. In other aspects, $R^{100}$ is a substituent "Z," defined as the combination of a CPP and a linker that bridges the CPP at its carboxy terminus to the 3'-end of the oligonucleotide.

In some aspects, the present disclosure relates to a method of treating a patient with Duchenne muscular dystrophy (DMD) in need thereof who has a mutation that is amenable to exon 51 skipping, comprising administering to the patient an antisense oligomer conjugate of Formula (I):

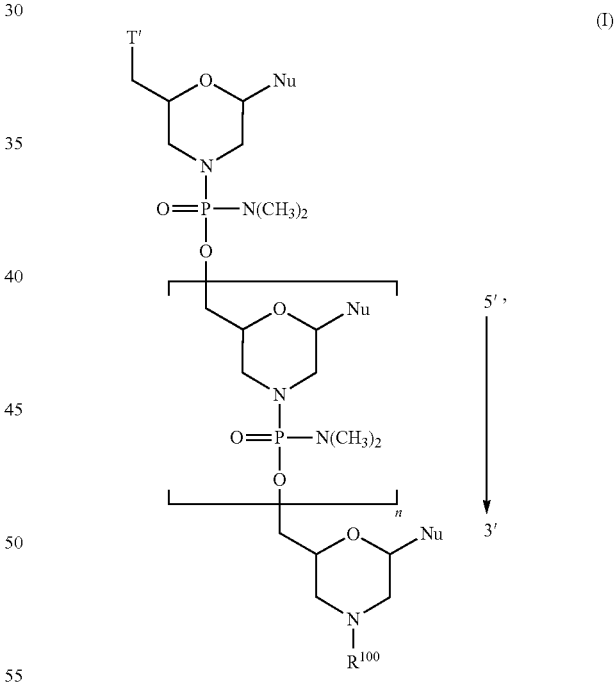

or a pharmaceutically acceptable salt thereof, wherein:
n is 1-40;
each Nu is a nucleobase, which, taken together, form a targeting sequence complementary to an exon annealing site in the dystrophin pre-mRNA;

T' is a moiety selected from:

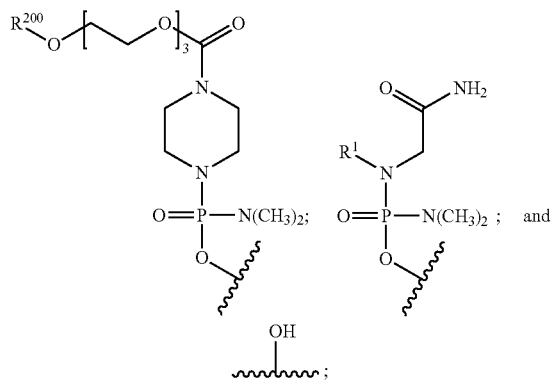

wherein
$R^{100}$ a cell-penetrating peptide, $R^{200}$ is hydrogen, and $R^1$ is $C_1$-$C_6$ alkyl, wherein the conjugate, or a pharmaceutically acceptable salt thereof, is administered at a dose equivalent to about 300 mg to about 1500 mg of the ·6HCl salt of the conjugate once every four weeks, to achieve a mean AUC of between about between about 100 and about 200 ug·h/mL, between about 120 and about 240 ug·h/mL, or between about 200 and about 500 ug·h/mL.

In some aspects, the conjugate, or a pharmaceutically acceptable salt thereof, is administered at a dose equivalent to about 300 mg to about 1200 mg, about 300 mg to about 1000 mg, about 300 mg to about 750 mg, about 300 mg to about 500 mg, about 400 mg to about 1400 mg, about 400 mg to about 1100 mg, about 400 mg to about 900 mg, about 400 mg to about 600 mg, about 500 mg to about 1500 mg, about 500 mg to about 1300 mg, about 500 mg to about 1000 mg, about 500 mg to about 950 mg, about 500 mg to about 850 mg, about 500 mg to about 750 mg, about 500 mg to about 650 mg, about 600 mg to about 1400 mg, about 600 mg to about 1300 mg, about 600 mg to about 1200 mg, about 600 mg to about 1000, or about 600 mg to about 900 mg of the ·6HCl salt of the conjugate. In some aspects, the conjugate, or a pharmaceutically acceptable salt thereof, is administered at a dose effective to provide a mean AUC of between about 100 and about 200 ug·h/mL. In some aspects, the conjugate, or a pharmaceutically acceptable salt thereof, is administered at a dose effective to provide a mean AUC of between about 120 and about 240 ug·h/mL.

In certain aspects, the conjugate, or a pharmaceutically acceptable salt thereof, is administered at a dose effective to provide a mean AUC of between about 200 and about 500 ug·h/mL.

In certain aspects, the conjugate, or a pharmaceutically acceptable salt thereof, is administered at a dose equivalent to about 300 mg, about 350 mg, about 400 mg, about 450 mg, about 500 mg, about 550 mg, about 600 mg, about 650 mg, about 700 mg, about 750 mg, about 800 mg, about 850 mg, or about 900 mg of the ·6HCl salt of the conjugate.

In some aspects, the conjugate, or a pharmaceutically acceptable salt thereof, is administered at a dose equivalent to about 950 mg, about 1000 mg, about 1050 mg, about 1100 mg, about 1150 mg, about 1200 mg, about 1250 mg, about 1300 mg, about 1350 mg, about 1400 mg, about 1450 mg, or about 1500 mg of the ·6HCl salt of the conjugate.

In some aspects, the cell-penetrating peptide is chosen from RXRRXRRXRRXR- (SEQ ID NO: 18), RFFRFFRFFR- (SEQ ID NO: 19), RXRRXRRXRRXRXB- (SEQ ID NO: 20), RFFRFFRFFRG- (SEQ ID NO: 21), RRRRRRG- (SEQ ID NO: 22), RRRRRR- (SEQ ID NO: 23), RRRRRG- (SEQ ID NO: 24), or RRRRR- (SEQ ID NO: 25), wherein R is arginine, X is 6-aminohexanoic acid, B is β-alanine, F is phenylalanine, and G is glycine.

In other aspects, the cell-penetrating peptide is chosen from RRRRRRG- (SEQ ID NO: 22), RRRRRR- (SEQ ID NO: 23), RRRRRG- (SEQ ID NO: 24), or RRRRR- (SEQ ID NO: 25), wherein R is arginine and G is glycine. In one aspect, the cell-penetrating peptide is RRRRRRG- (SEQ ID NO: 22), wherein R is arginine and G is glycine.

In some aspects, the antisense oligomer of the antisense oligomer conjugate has n+2 base pairs, where n in formula (I) is 1 to 40, optionally 13-38, optionally 13-28, optionally 13-23 or optionally 13-18. In other words, the oligomer is 15-40, 15-35, 15-30, 15-25, or 15-20 nucleotides in length.

In some aspects, the antisense oligomer conjugate causes skipping of an exon in the human dystrophin gene. In some aspects, the exon is chosen from exon 44, 45, 50, 51, 52, or 53. In certain aspects, the exon is chosen from exon 45, 51, or 53.

In certain aspects, the present disclosure provides a method of treating a patient with DMD in need thereof who has a mutation that is amenable to exon skipping, comprising administering to the patient an antisense oligomer conjugate of Formula (III):

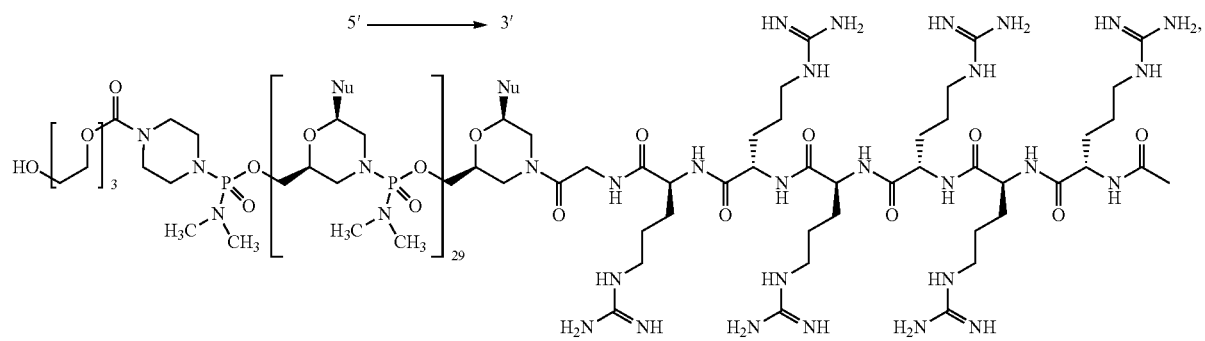

(III)

or a pharmaceutically acceptable salt thereof, wherein each Nu is a nucleobase, which, taken together, form a targeting sequence that is complementary to an exon annealing site in the dystrophin pre-mRNA.

In some embodiments, the present disclosure provides a method of treating a patient with DMD in need thereof who has a mutation that is amenable to exon 51 skipping, comprising administering to the patient an antisense oligomer conjugate has Formula (IV):

(IV)
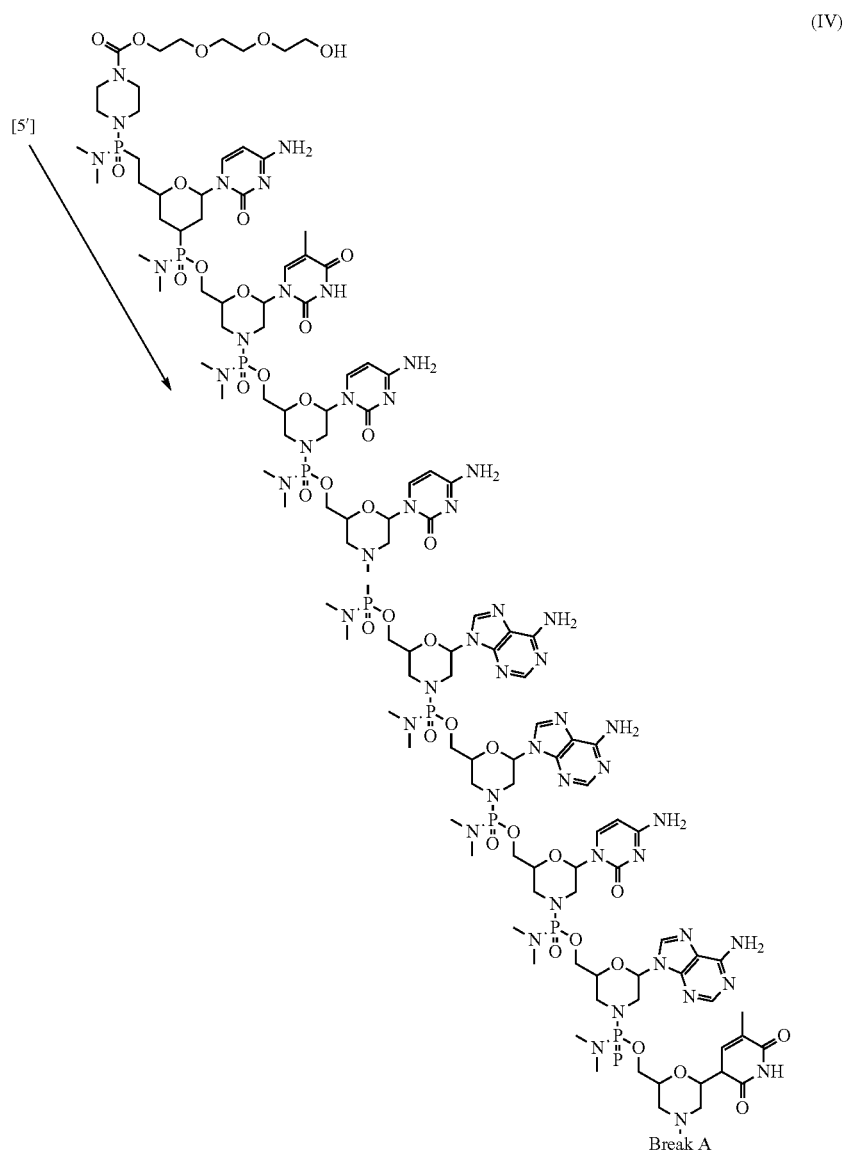

-continued
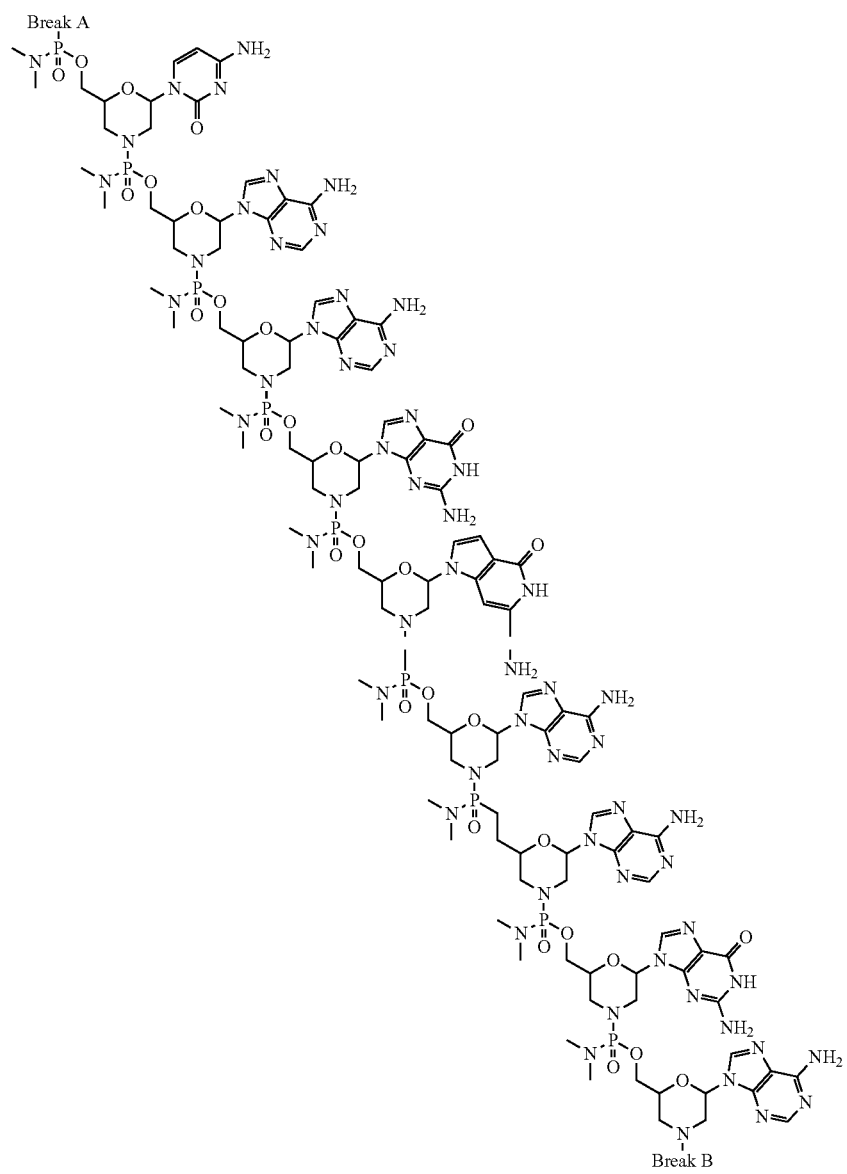

-continued
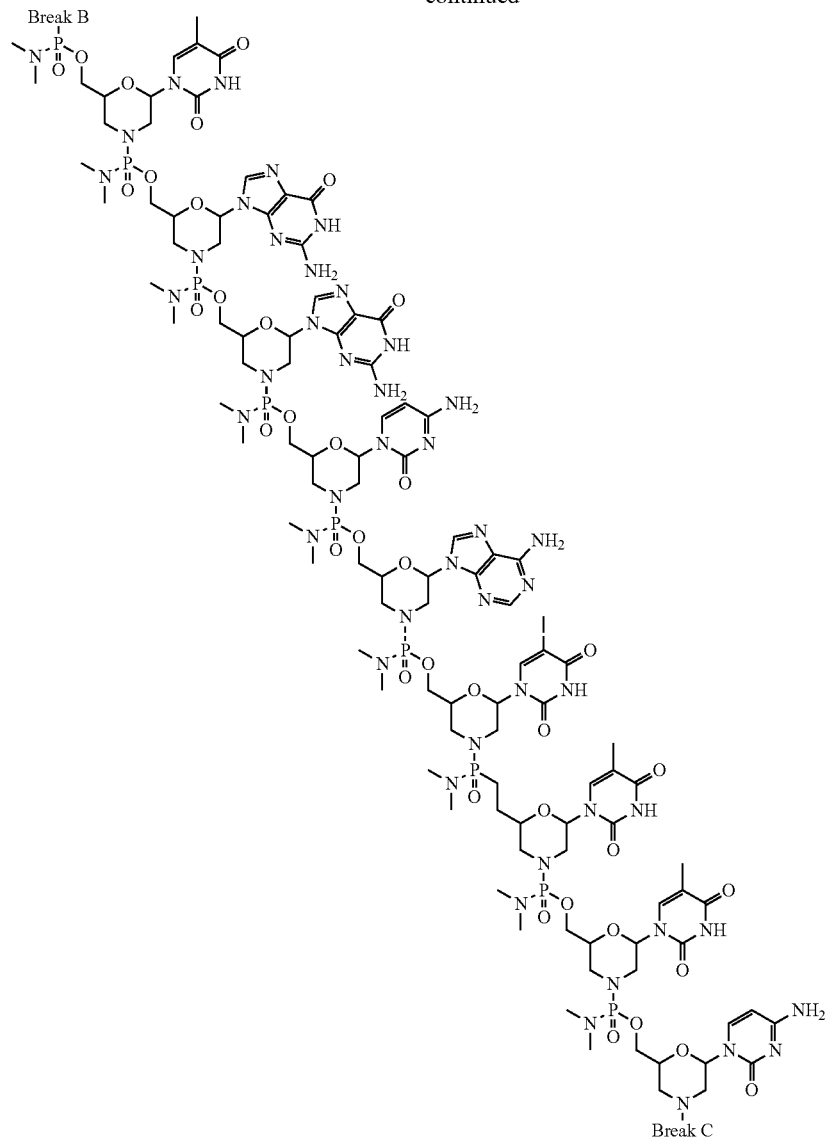
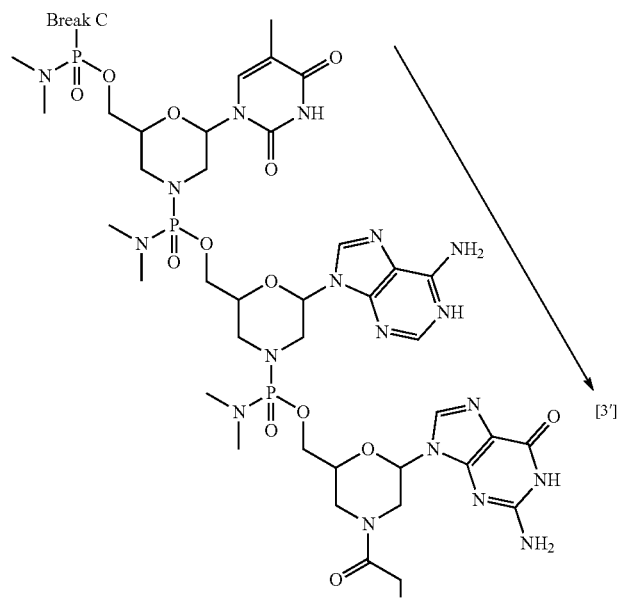

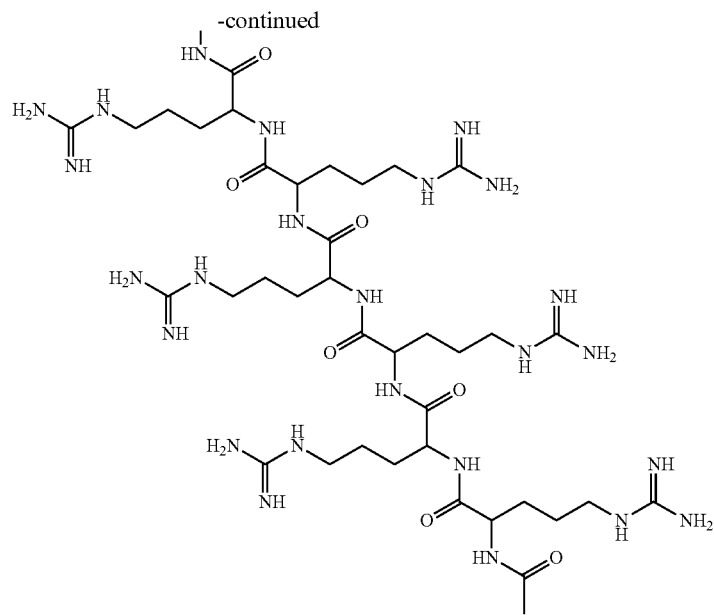
or a pharmaceutically acceptable salt thereof.
In other aspects, the antisense oligomer conjugate has Formula (IVA):
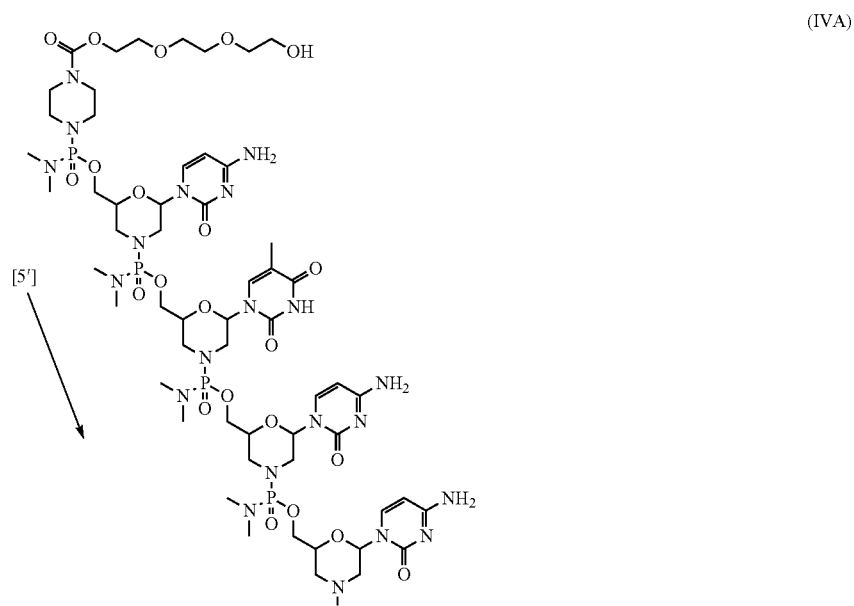
(IVA)

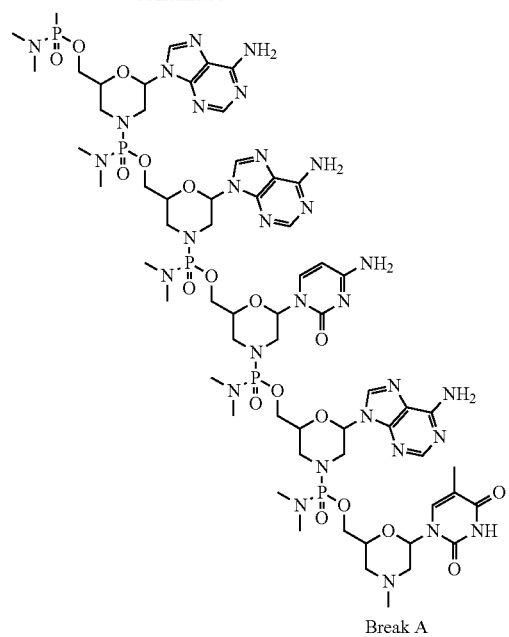
Break A
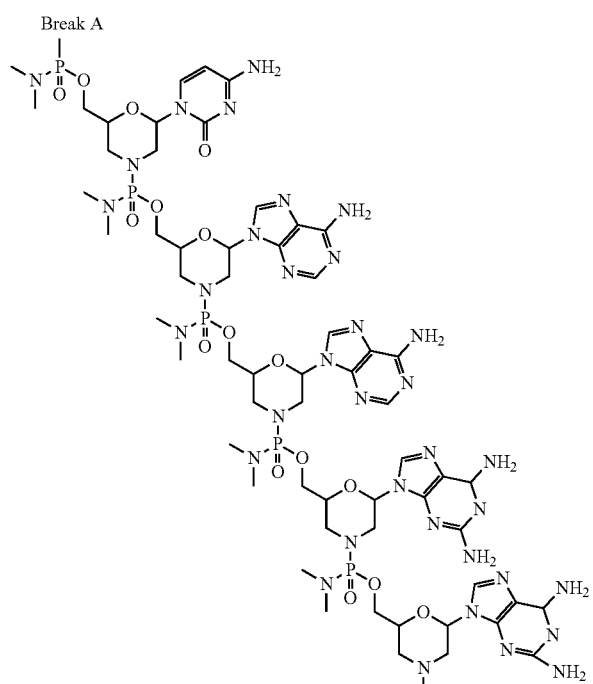
Break A

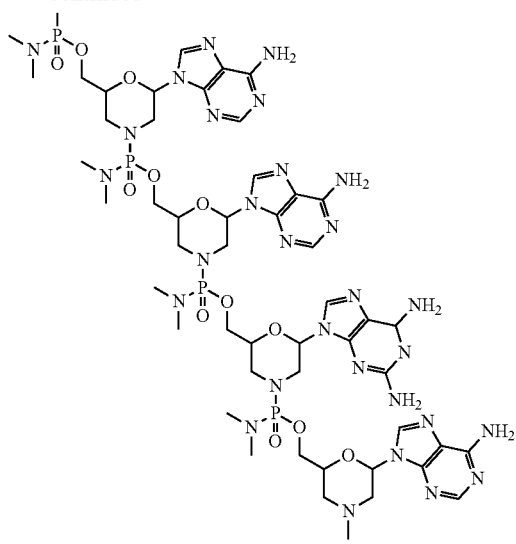

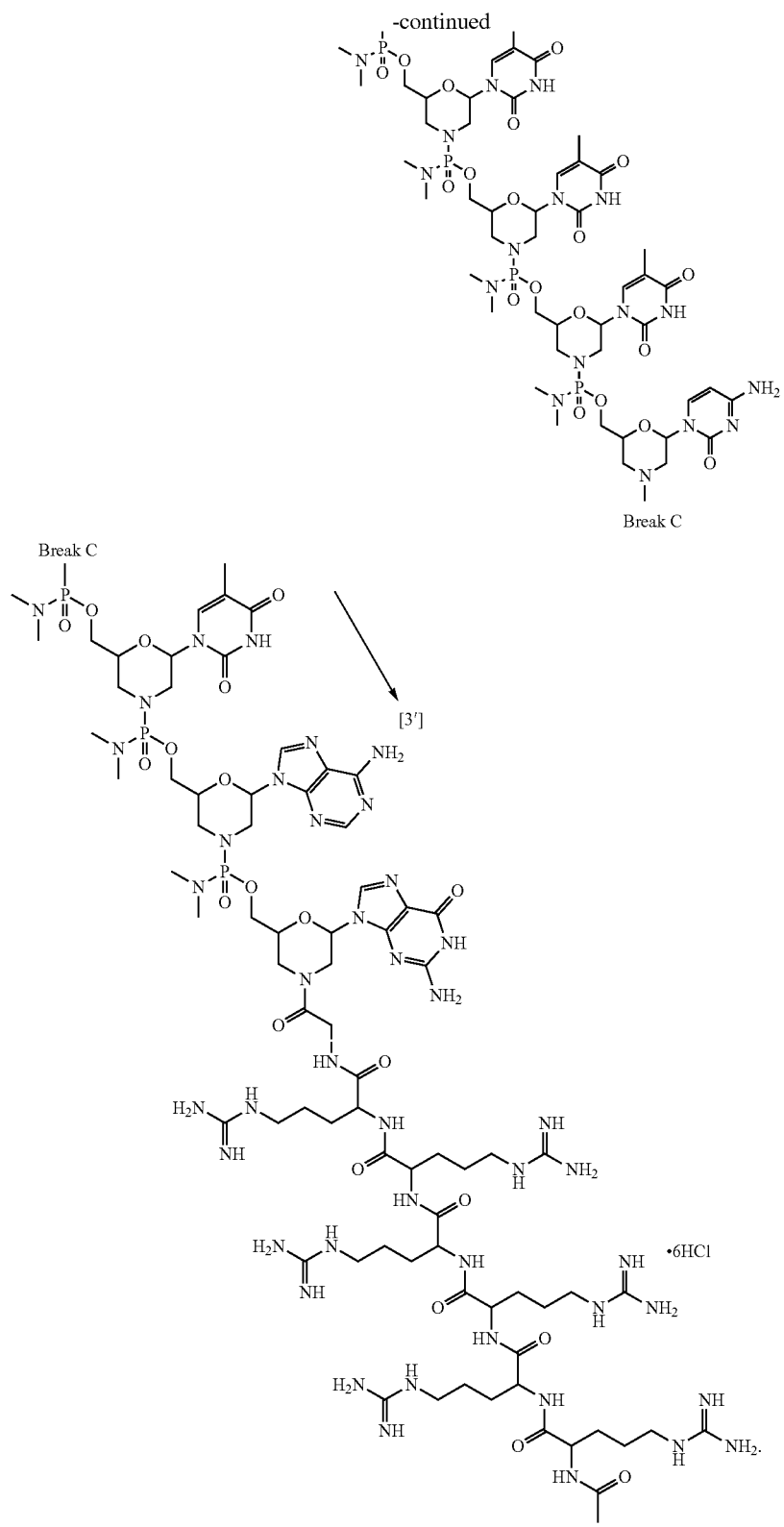
In some aspects, the antisense oligomer conjugate has Formula (IVB):

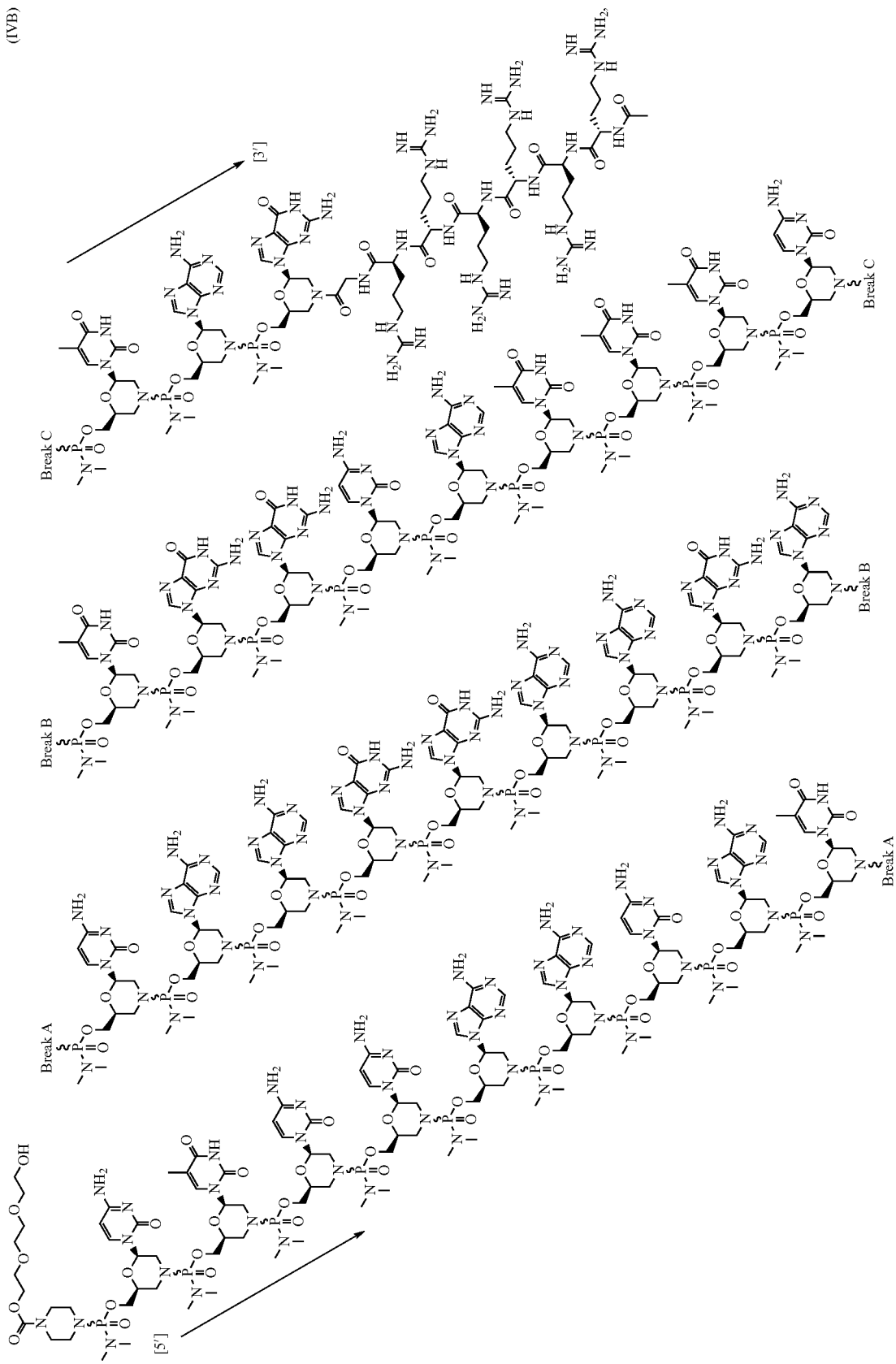

or a pharmaceutically acceptable salt thereof.

In some embodiments, an antisense oligomer conjugate of Formula (IVB) is an HCl (hydrochloric acid) salt thereof. In certain embodiments, the HCl salt is a ·6HCl salt.

Yet in other embodiments, the present disclosure provides a method of treating a patient with DMD in need thereof who has a mutation that is amenable to exon 45 skipping, comprising administering to the patient an antisense oligomer conjugate has Formula (VI):

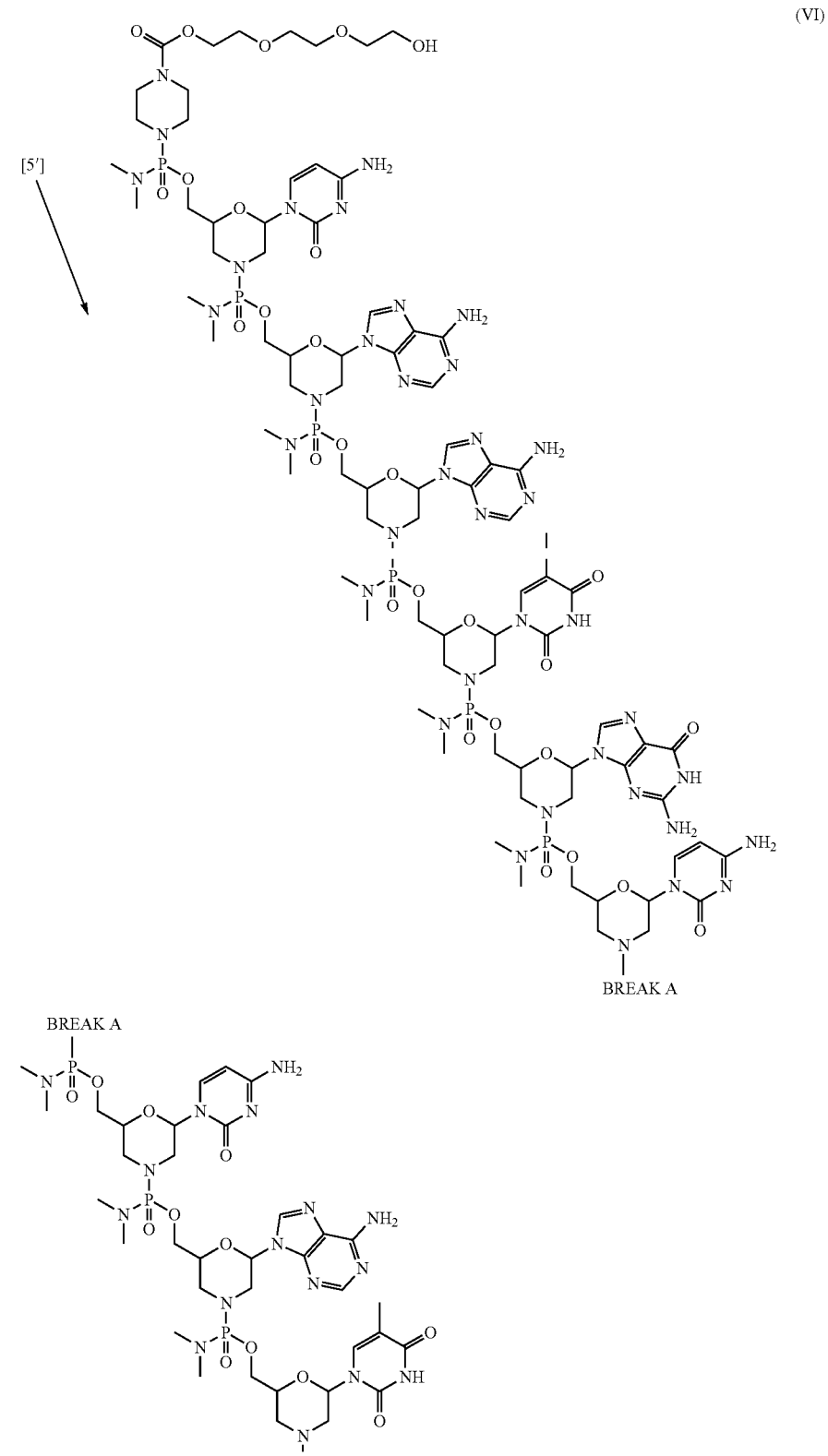

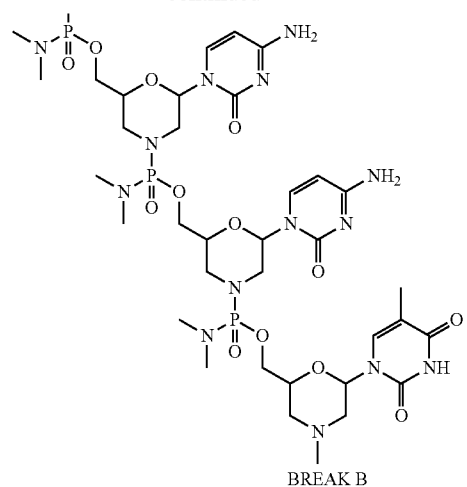
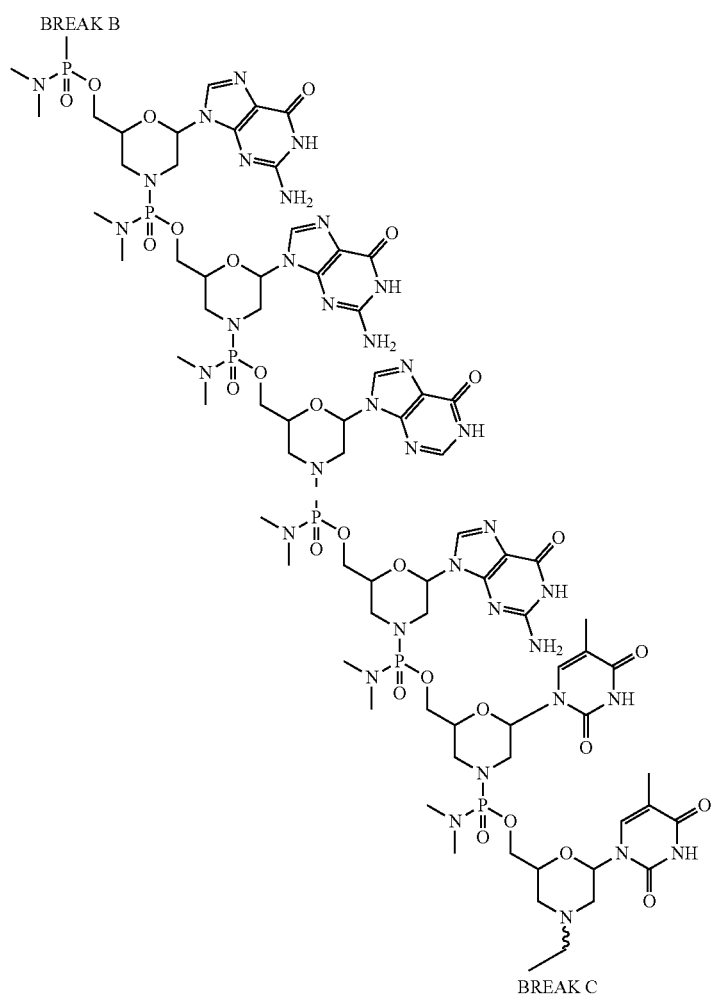

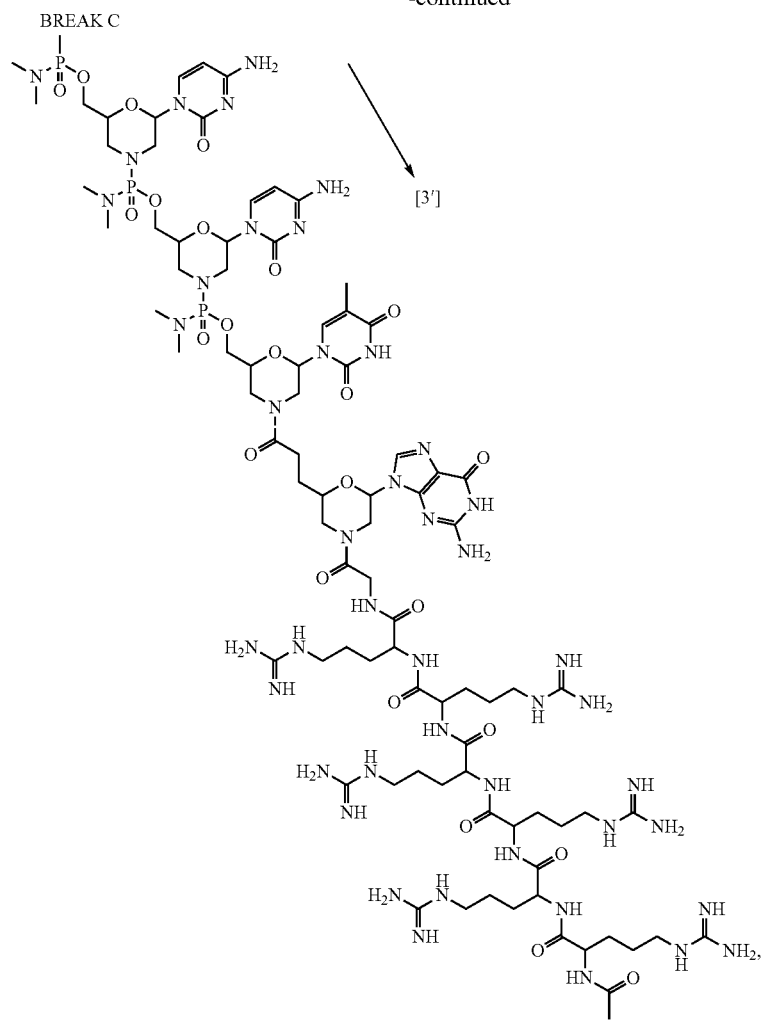
or a pharmaceutically acceptable salt thereof.
In some aspects, the antisense oligomer conjugate has Formula (VIA):

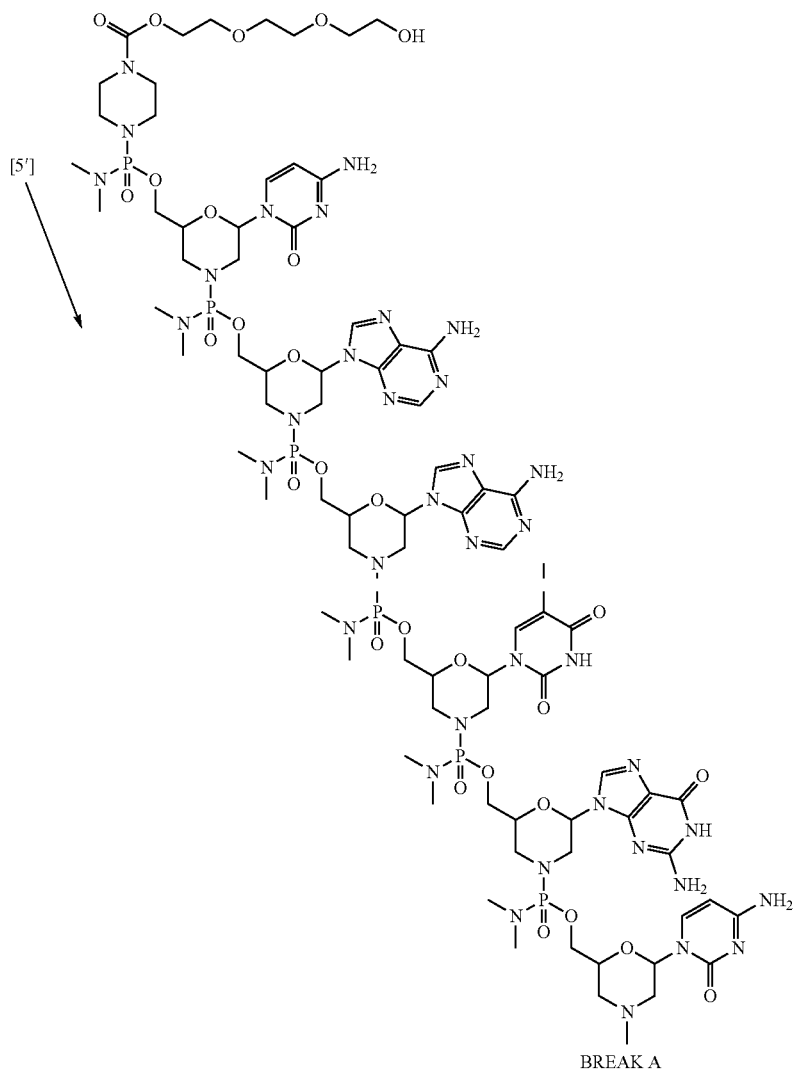 [SMILES: Cc1cn(C2CN(P(=O)(OCC3CN(P(=O)(OCC4CN(C)CC(n5ccc(N)nc5=O)O4)N(C)C)CC(n4cnc5c(=O)[nH]c(N)nc54)O3)N(C)C)CC(COP(=O)(N(C)C)N3CC(COP(=O)(N(C)C)N4CC(COP(=O)(N(C)C)N5CC(COP(=O)(N(C)C)N6CCN(C(=O)OCCOCCOCCO)CC6)OC(n6ccc(N)nc6=O)C5)OC(n5cnc6c(N)ncnc65)C4)OC(n4cnc5c(N)ncnc54)C3)O2)c(=O)[nH]c1=O]
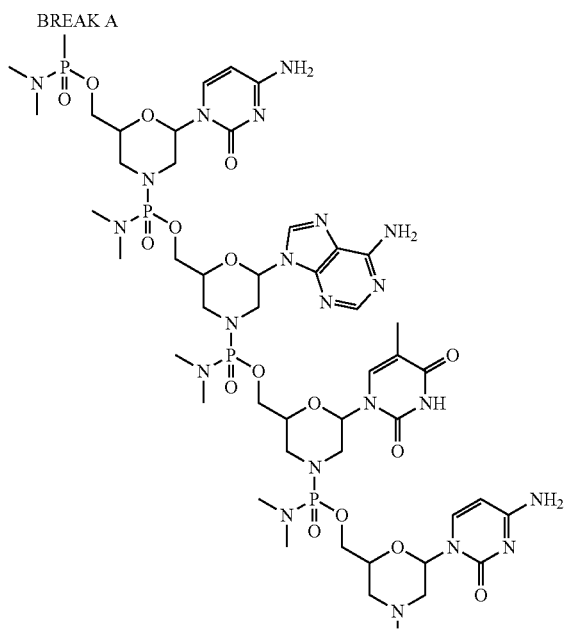

-continued
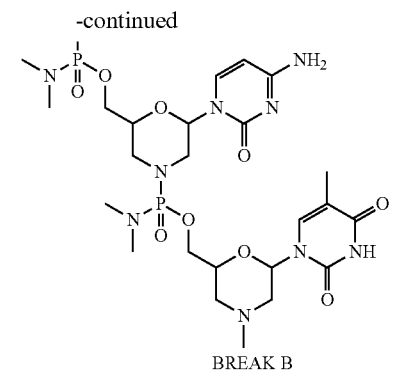
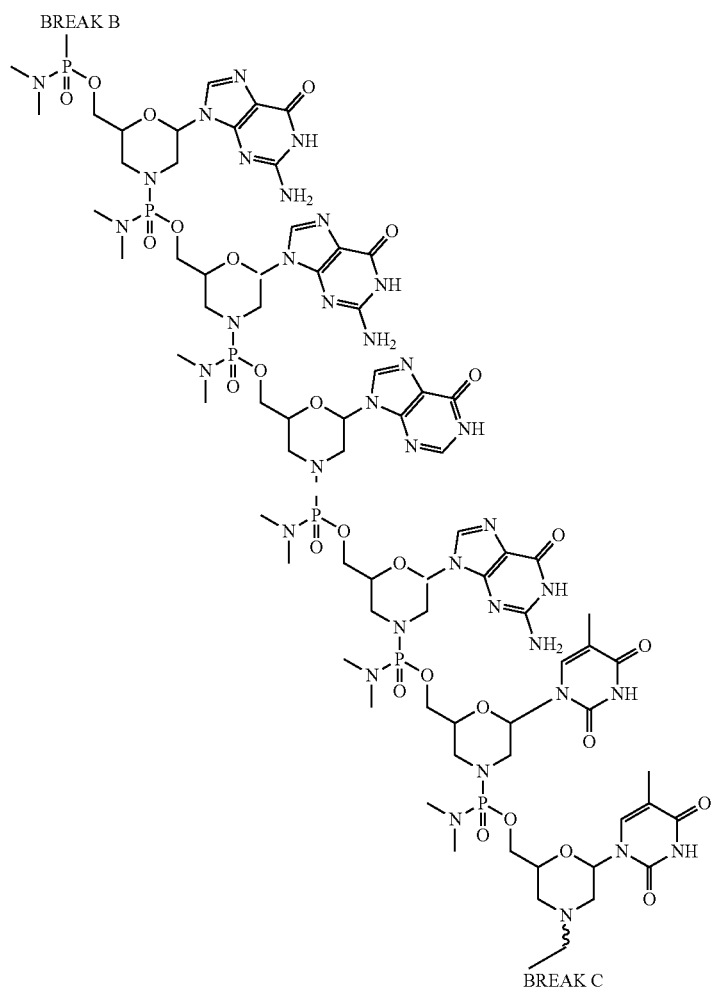

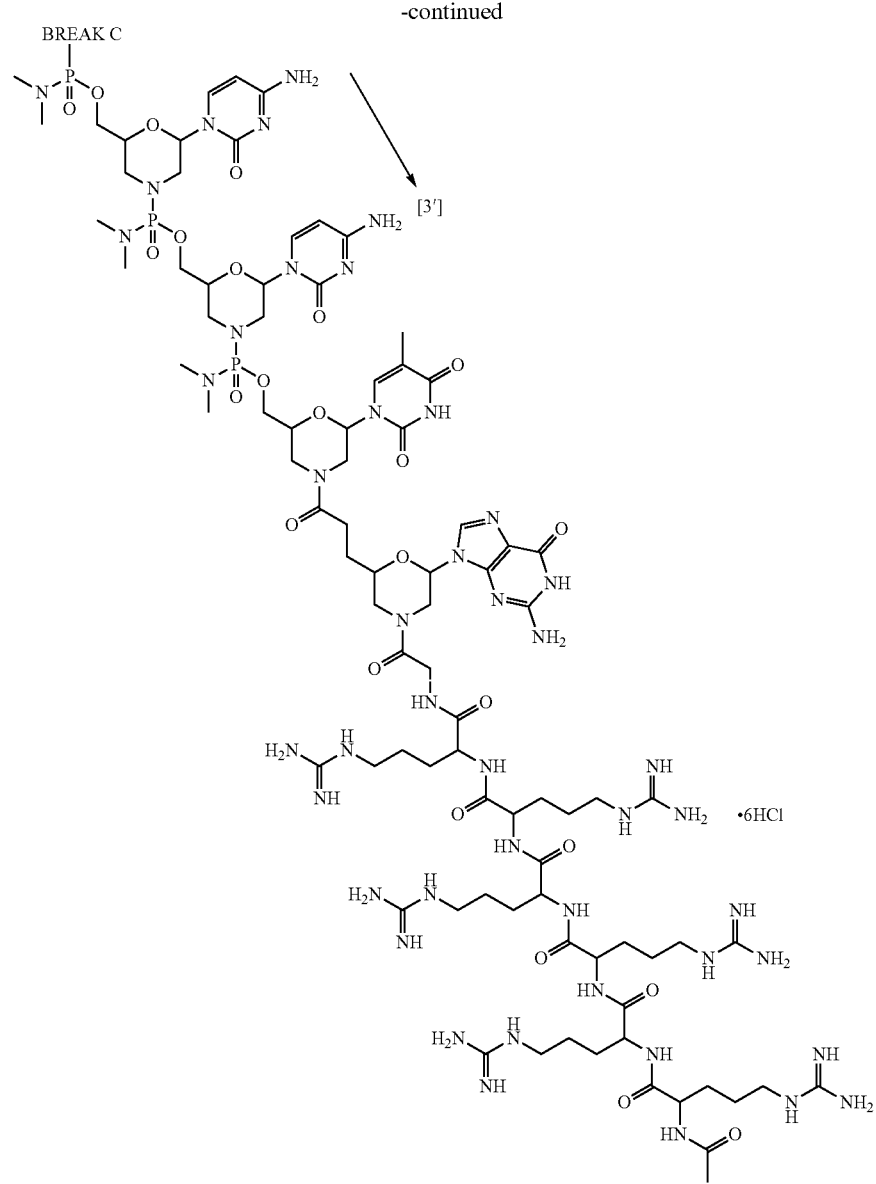
In some aspects, the antisense oligomer conjugate is according to Formula (VIB):

(VIB)
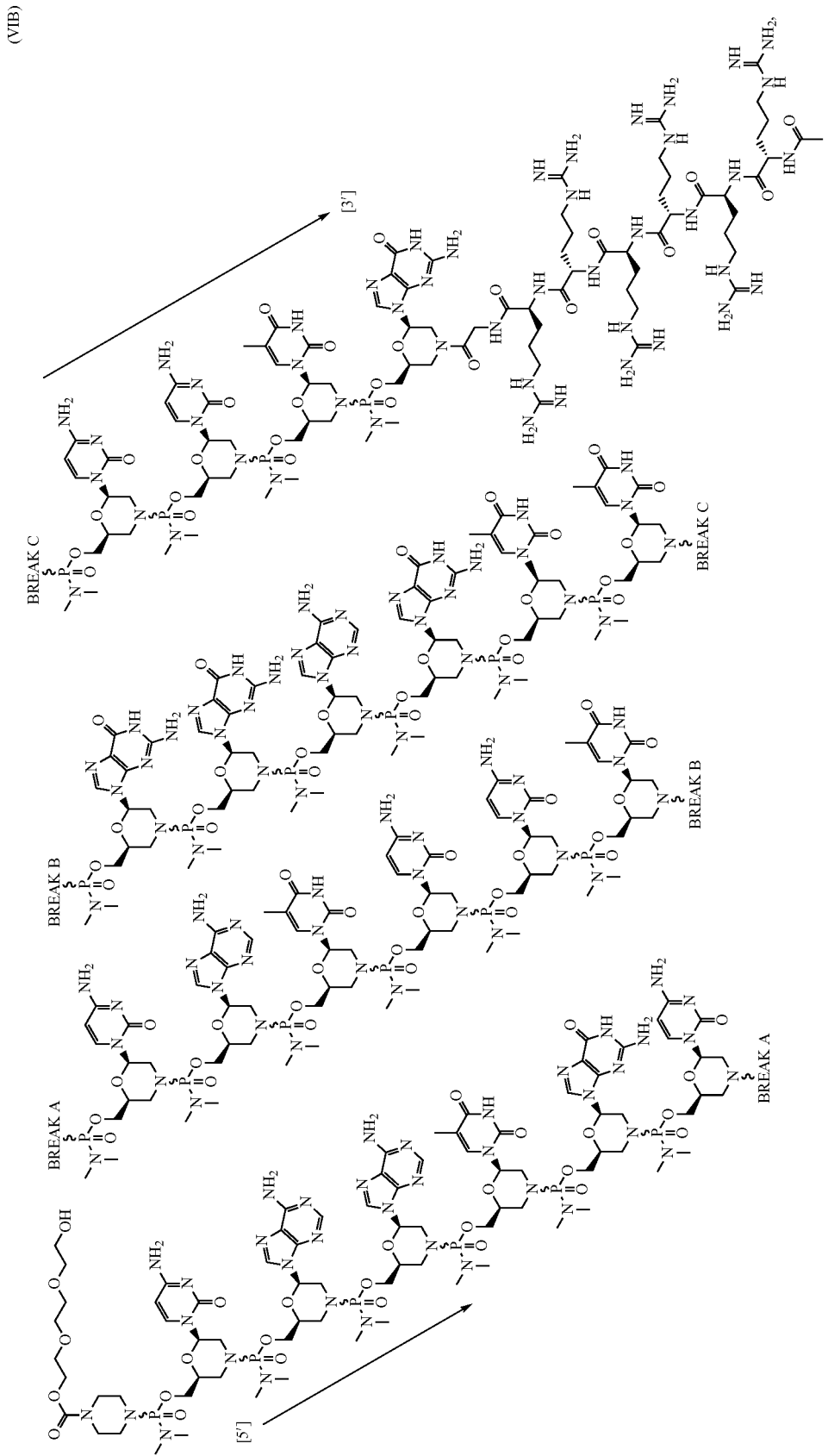

or a pharmaceutically acceptable salt thereof.

In some aspects, an antisense oligomer conjugate of Formula (VIB) is an HCl (hydrochloric acid) salt thereof. In certain embodiments, the HCl salt is a ·6HCl salt.

In some aspects, the present disclosure provides a method of treating a patient with DMD in need thereof who has a mutation that is amenable to exon 53 skipping, comprising administering to the patient an antisense oligomer conjugate has Formula (VIII):

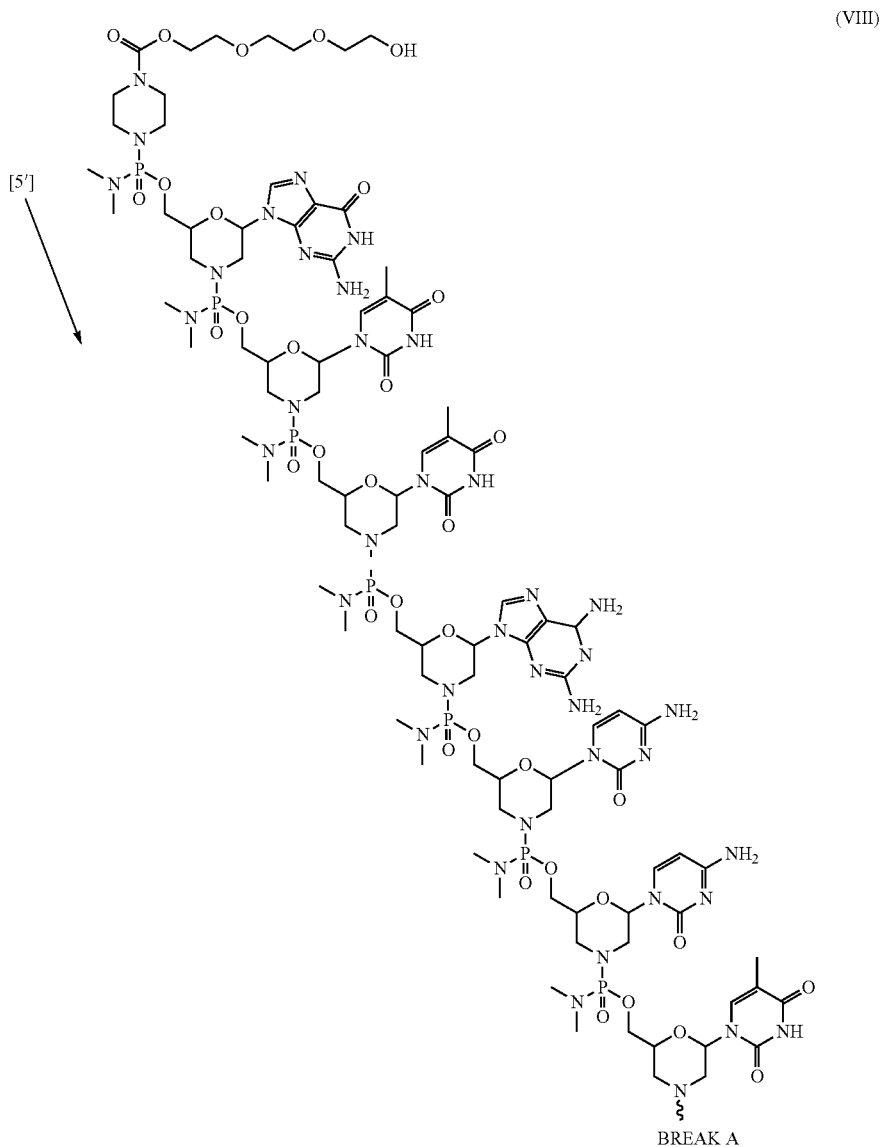

-continued
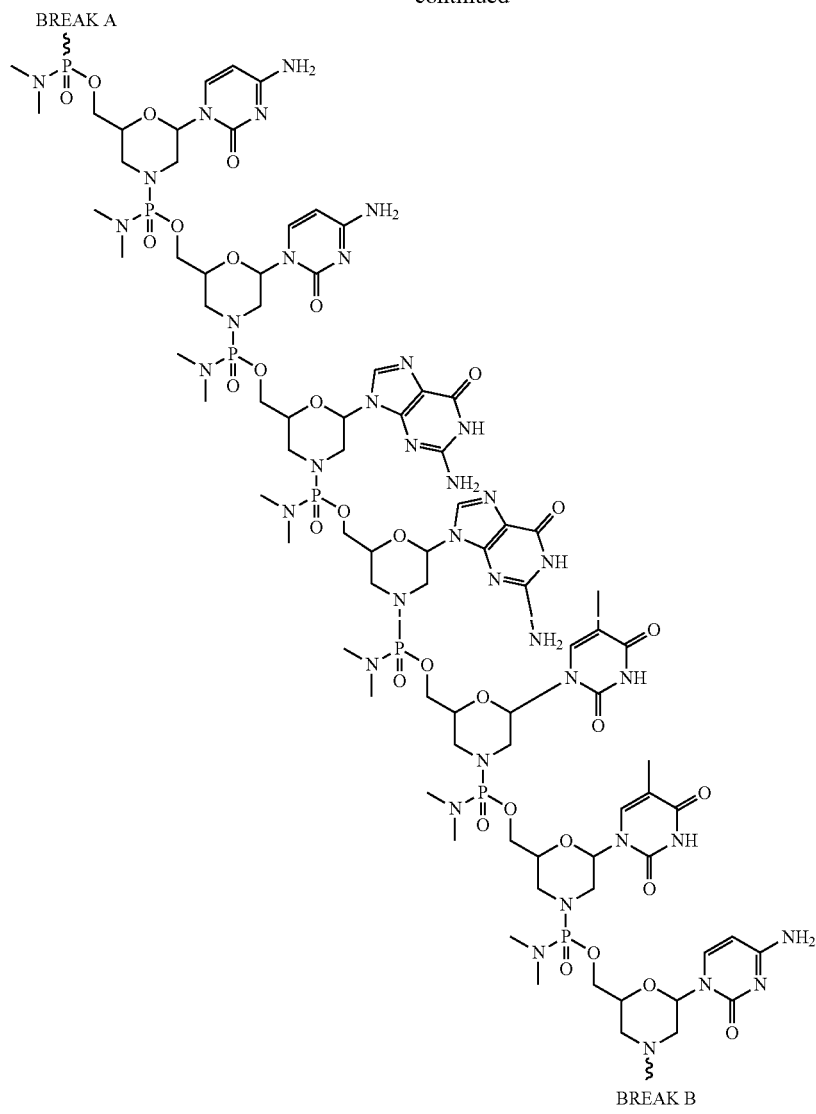
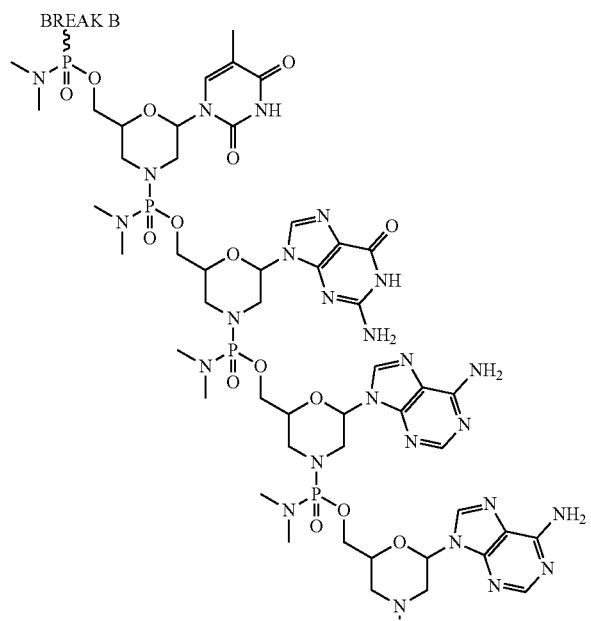

-continued
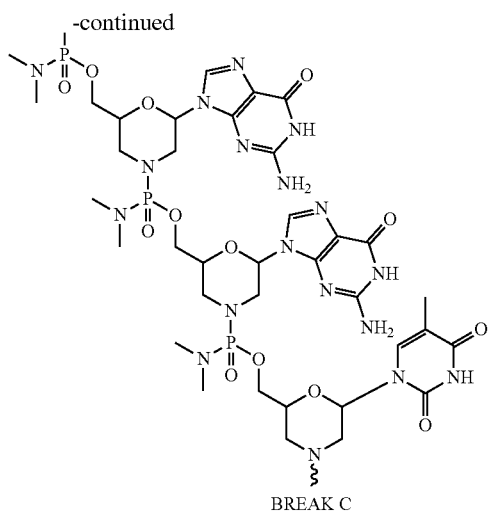
BREAK C
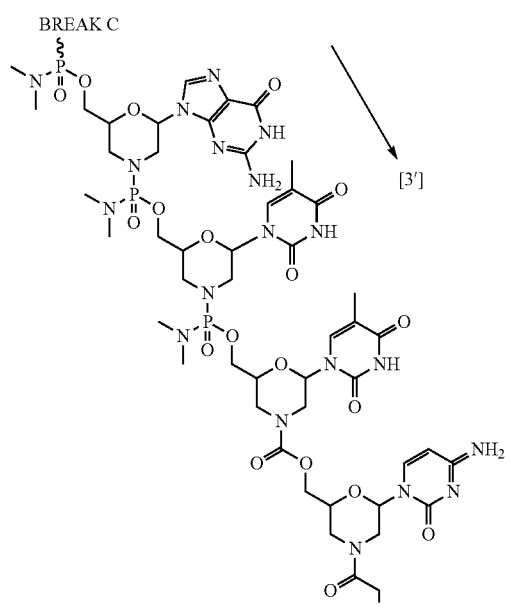
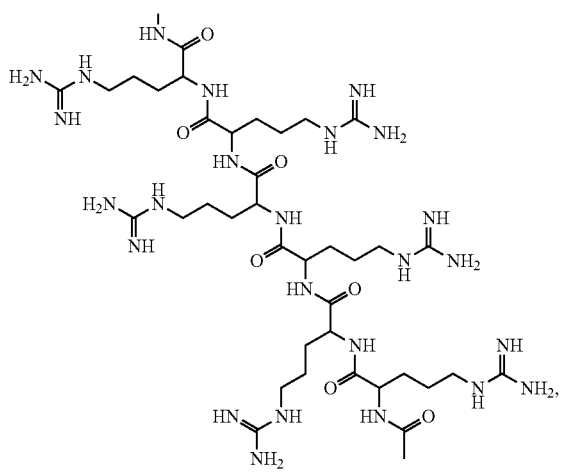
or a pharmaceutically acceptable salt thereof.
In other aspects, the antisense oligomer conjugate has Formula (VIIIA):

(VIIIA)
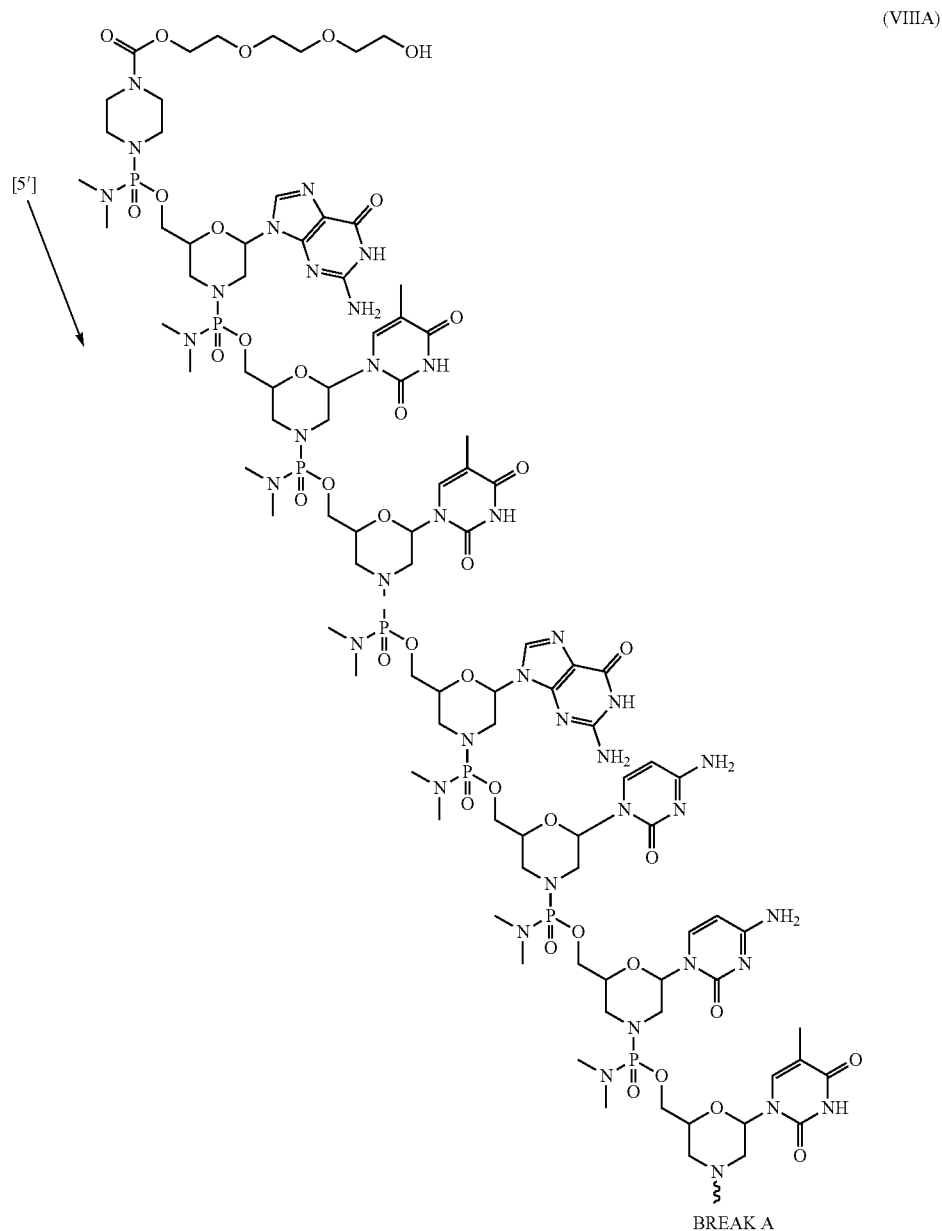
BREAK A

-continued
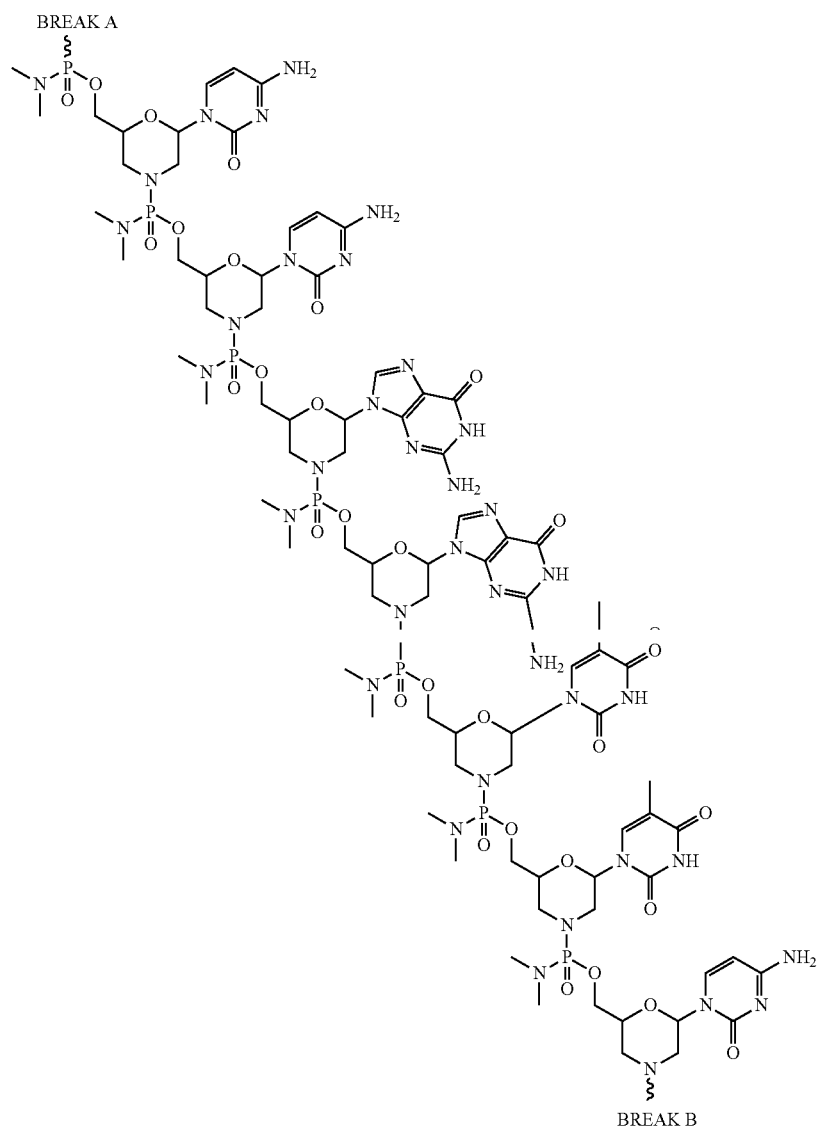

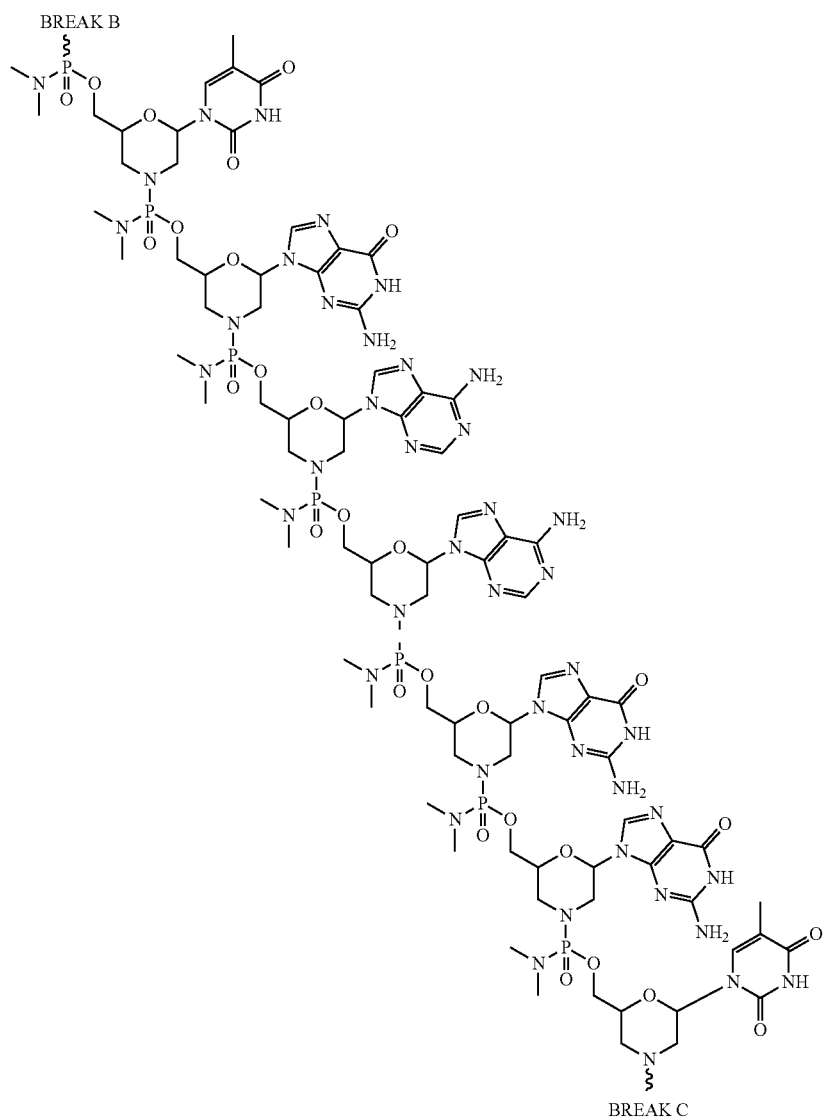

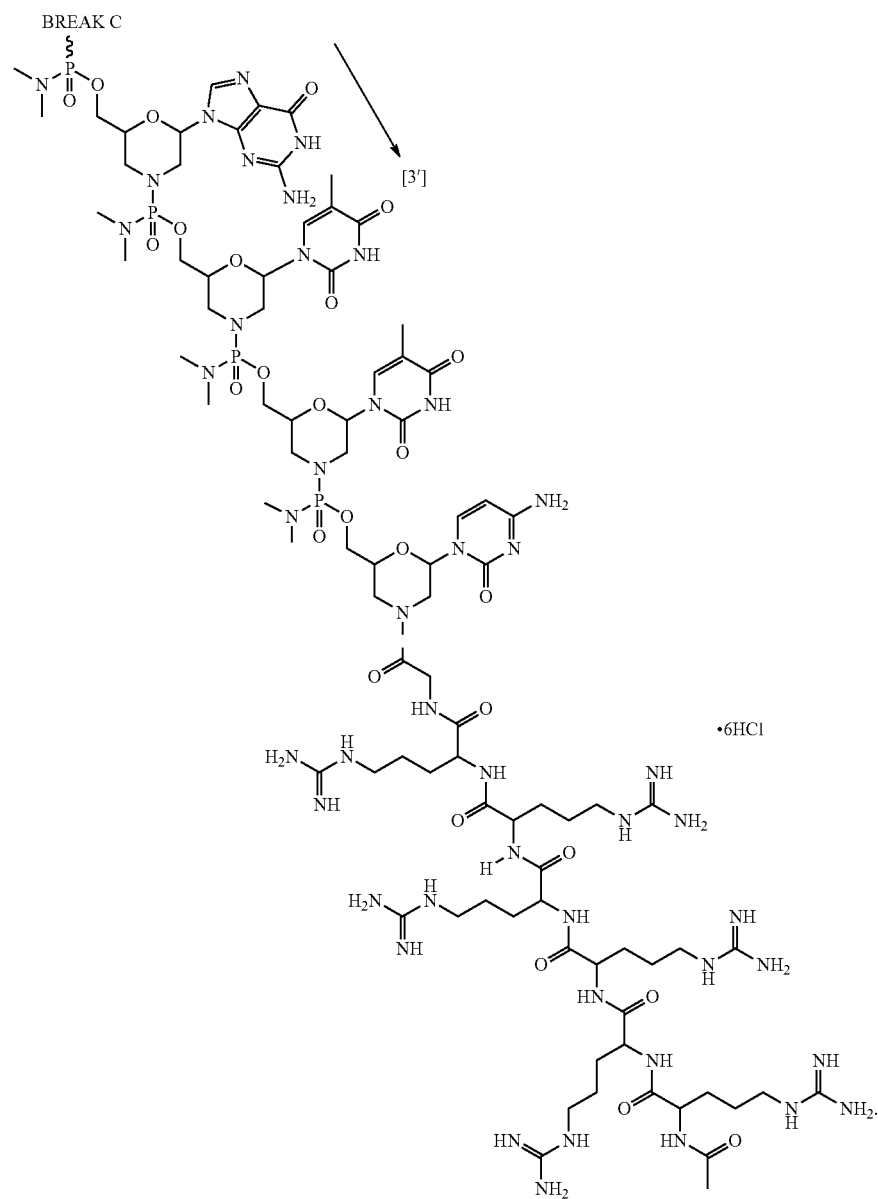 [SMILES: CC(=O)NC(CCCNC(=N)N)C(=O)NC(CCCNC(=N)N)C(=O)NC(CCCNC(=N)N)C(=O)NC(CCCNC(=N)N)C(=O)NC(CCCNC(=N)N)C(=O)NC(CCCNC(=N)N)C(=O)N(C)CC(=O)N1CC(COP(=O)(N(C)C)N2CC(COP(=O)(N(C)C)N3CC(COP(=O)(N(C)C)N4CC(COP(C)(=O)N(C)C)OC(n5cnc6c(=O)[nH]c(N)nc65)C4)OC(n4cc(C)c(=O)[nH]c4=O)C3)OC(n3cc(C)c(=O)[nH]c3=O)C2)OC(n2ccc(N)nc2=O)C1]

In other aspects, the antisense oligomer conjugate has Formula (VIIIB):
(VIIIB)
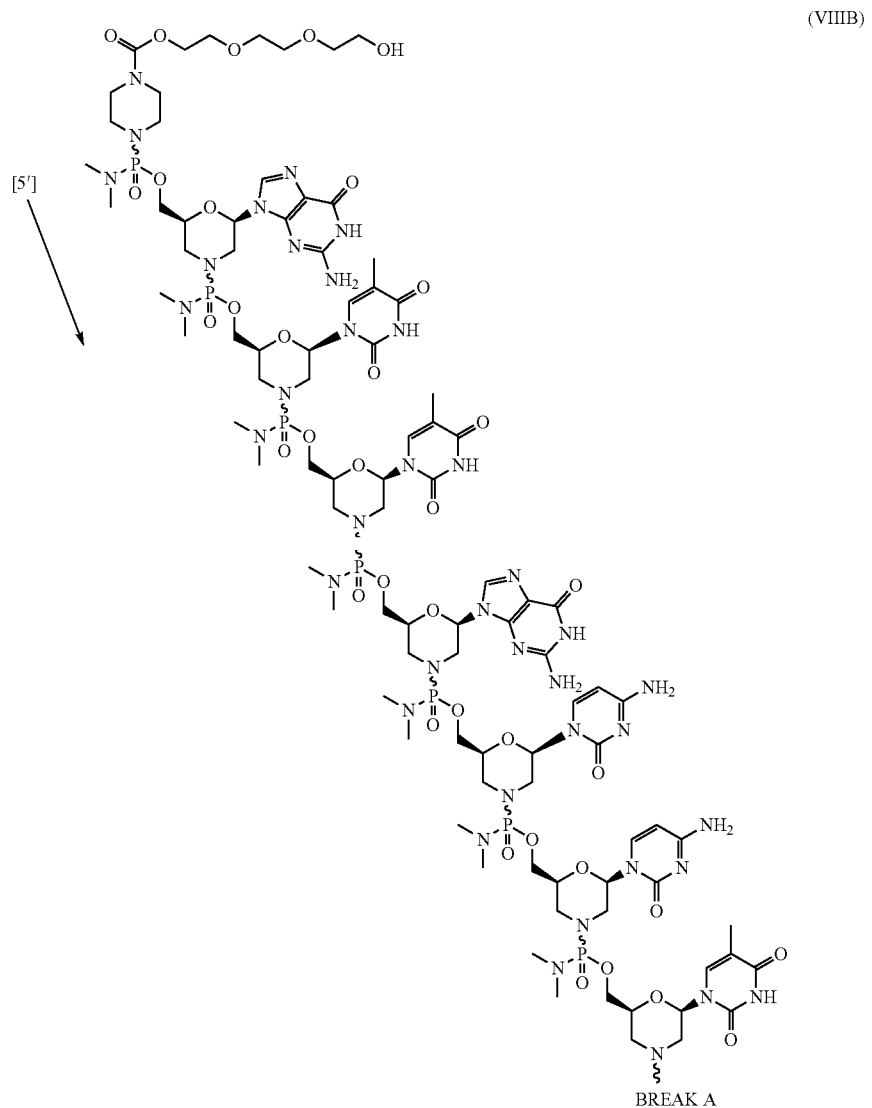

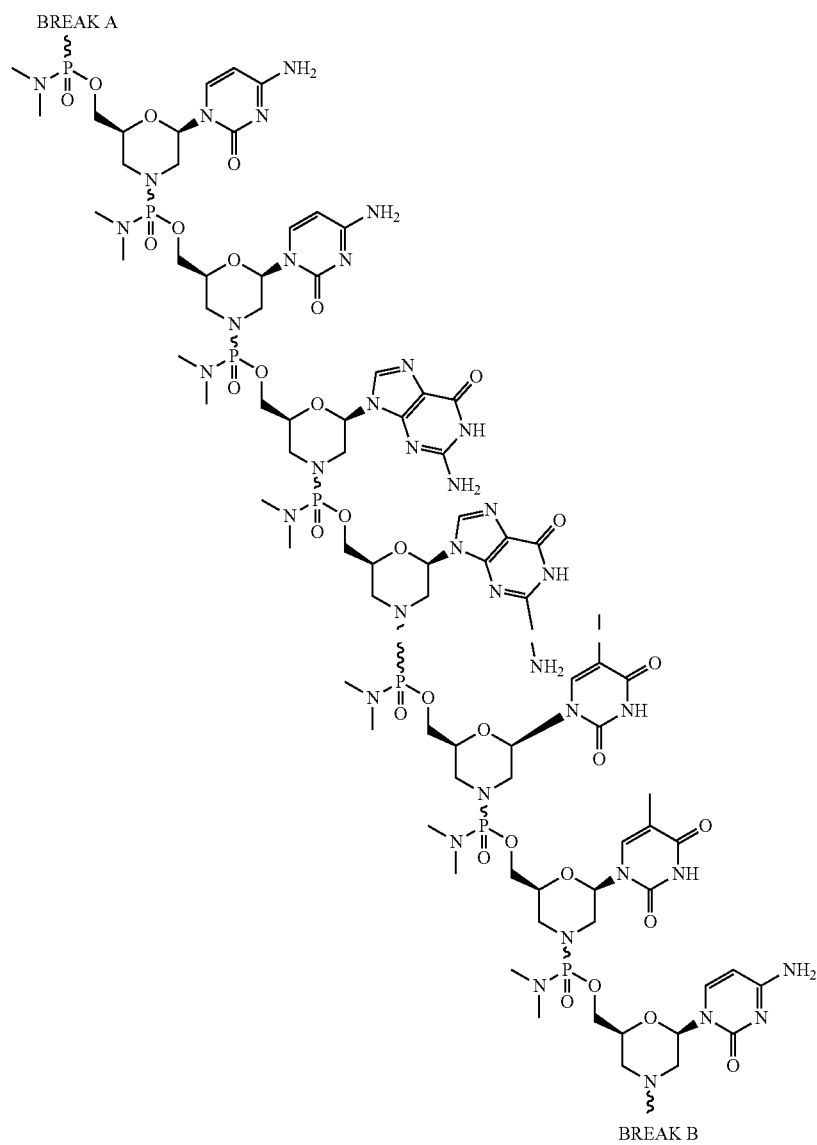

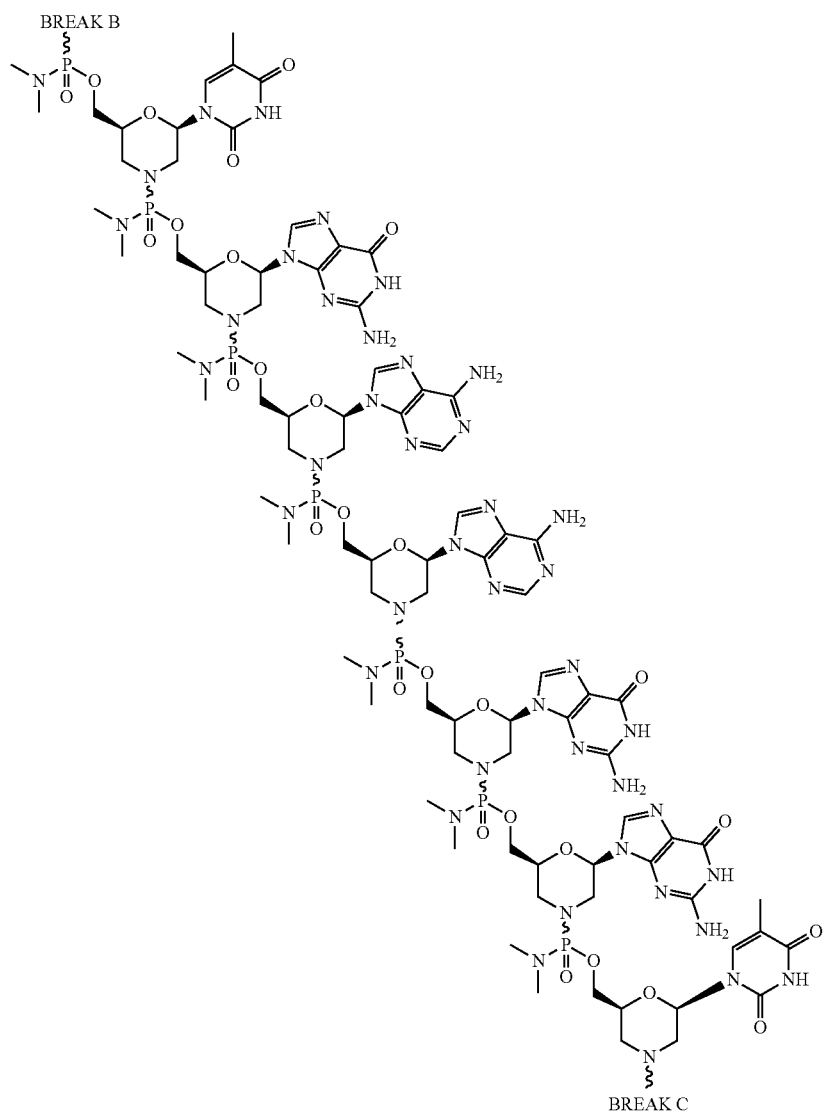
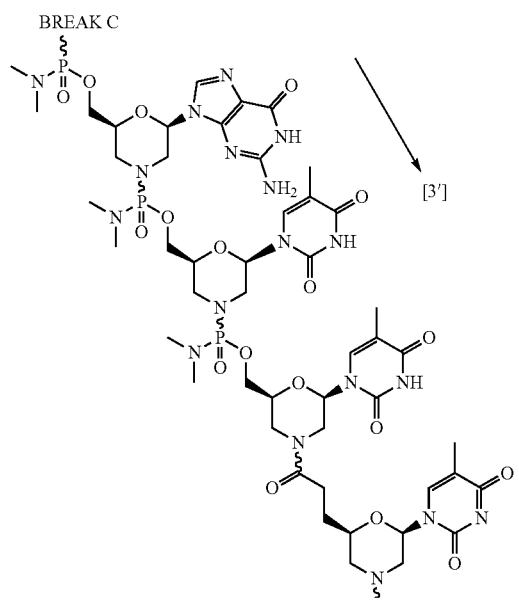

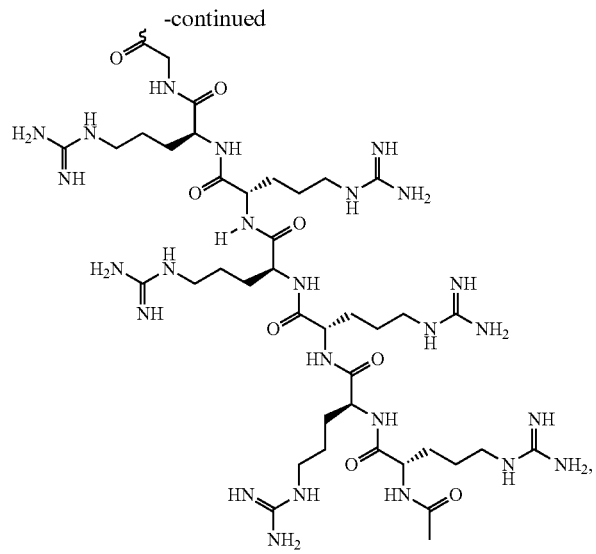

or a pharmaceutically acceptable salt thereof.

In some embodiments, an antisense oligomer conjugate of Formula (VIIIB) is an HCl (hydrochloric acid) salt thereof. In certain embodiments, the HCl salt is a ·6HCl salt.

In some aspects, the antisense oligomer conjugate, or a pharmaceutically acceptable salt thereof, is administered at a dose equivalent to about 300 mg to about 700 mg of the ·6HCl salt of the conjugate once every four weeks to a patient that weighs from about 10 kg to about 25 kg.

In some aspects, the antisense oligomer conjugate, or a pharmaceutically acceptable salt thereof, is administered at a dose equivalent to about 600 mg of the ·6HCl salt of the conjugate once every four weeks to a patient that weighs from about 10 kg to about 25 kg.

In other aspects, the antisense oligomer conjugate, or a pharmaceutically acceptable salt thereof, is administered at a dose equivalent to about 900 mg to about 1200 mg of the ·6HCl salt of the conjugate once every four weeks to a patient that weighs from about 10 kg to about 25 kg.

In one aspects, the antisense oligomer conjugate, or a pharmaceutically acceptable salt thereof, is administered at a dose equivalent to about 1100 mg of the ·6HCl salt of the conjugate once every four weeks to a patient that weighs from about 10 kg to about 25 kg.

In other aspects, the antisense oligomer conjugate, or a pharmaceutically acceptable salt thereof, is administered at a dose equivalent to about 750 mg of the ·6HCl salt of the conjugate once every four weeks to a patient that weighs greater than or equal to about 18 kg to less than about 50 kg.

In other aspects, the antisense oligomer conjugate, or a pharmaceutically acceptable salt thereof, is administered at a dose equivalent to about 1250 mg of the ·6HCl salt of the conjugate once every four weeks to a patient that weighs greater than or equal to about 18 kg to less than about 50 kg.

In some aspects, the antisense oligomer conjugate, or a pharmaceutically acceptable salt thereof is administered at a dose equivalent to about 600 mg to about 800 mg of the ·6HCl salt of the conjugate once every four weeks to a patient that weighs from about 25 kg to about 50 kg.

In one aspect, the antisense oligomer conjugate, or a pharmaceutically acceptable salt thereof, is administered at a dose equivalent to about 650 mg of the ·6HCl salt of the conjugate once every four weeks to a patient that weighs from about 25 kg to about 50 kg.

In other aspects, the antisense oligomer conjugate, or a pharmaceutically acceptable salt thereof, is administered at a dose equivalent to about 1000 mg of the ·6HCl salt of the conjugate to about 1300 mg once every four weeks to a patient that weighs from about 25 kg to about 50 kg.

In one aspect, the antisense oligomer conjugate, or a pharmaceutically acceptable salt thereof, is administered at a dose equivalent to about 1200 mg of the ·6HCl salt of the conjugate once every four weeks to a patient that weighs from about 25 kg to about 50 kg.

In other aspects, the antisense oligomer conjugate, or a pharmaceutically acceptable salt thereof, is administered at a dose equivalent to about 600 mg to about 900 mg of the ·6HCl salt of the conjugate once every four weeks to a patient that weighs from about 50 kg to about 100 kg.

In another aspects, the antisense oligomer conjugate, or a pharmaceutically acceptable salt thereof, is administered at a dose equivalent to about 700 mg to about 900 mg of the ·6HCl salt of the conjugate once every four weeks to a patient that weighs from about 50 kg to about 100 kg.

In one aspect, the antisense oligomer conjugate, or a pharmaceutically acceptable salt thereof, is administered at a dose equivalent to about 750 mg of the ·6HCl salt of the conjugate once every four weeks to a patient that weighs from about 50 kg to about 100 kg.

In yet other aspects, the antisense oligomer conjugate, or a pharmaceutically acceptable salt thereof, is administered at a dose equivalent to about 1200 mg to about 1600 mg of the ·6HCl salt of the conjugate once every four weeks to a patient that weighs from about 50 kg to about 100 kg.

In one aspect, the antisense oligomer conjugate, or a pharmaceutically acceptable salt thereof, is administered at a dose equivalent to about 1400 mg of the ·6HCl salt of the conjugate once every four weeks to a patient that weighs from about 50 kg to about 100 kg.

In yet other aspects, the antisense oligomer conjugate, or a pharmaceutically acceptable salt thereof, is administered at a dose equivalent to about 850 mg of the ·6HCl salt of the conjugate once every four weeks to a patient that weighs greater than or equal to about 50 kg.

In yet other aspects, the antisense oligomer conjugate, or a pharmaceutically acceptable salt thereof, is administered at a dose equivalent to about 1350 mg of the ·6HCl salt of the conjugate once every four weeks to a patient that weighs greater than or equal to about 50 kg.

In other aspects, the antisense oligomer conjugate, or a pharmaceutically acceptable salt thereof, is administered at a dose equivalent to about 600 mg to about 900 mg of the 6HCl salt of the conjugate once every four weeks to a patient that weighs from about 65 kg to about 150 kg.

In another aspects, the antisense oligomer conjugate, or a pharmaceutically acceptable salt thereof, is administered at a dose equivalent to about 700 mg to about 900 mg of the ·6HCl salt of the conjugate once every four weeks to a patient that weighs from about 65 kg to about 150 kg.

In one aspect, the antisense oligomer conjugate, or a pharmaceutically acceptable salt thereof, is administered at a dose equivalent to about 750 mg of the ·6HCl salt of the conjugate once every four weeks to a patient that weighs from about 65 kg to about 150 kg.

In yet other aspects, the antisense oligomer conjugate, or a pharmaceutically acceptable salt thereof, is administered at a dose equivalent to about 1200 mg to about 1600 mg of the ·6HCl salt of the conjugate once every four weeks to a patient that weighs from about 65 kg to about 150 kg.

In one aspect, the antisense oligomer conjugate, or a pharmaceutically acceptable salt thereof, is administered at a dose equivalent to about 1400 mg of the ·6HCl salt of the conjugate once every four weeks to a patient that weighs from about 65 kg to about 150 kg.

The present disclosure also provides a method of treating a patient with Duchenne muscular dystrophy (DMD) in need thereof who has a mutation that is amenable to exon 51 skipping, comprising administering to the patient an antisense oligomer conjugate of Formula (I):

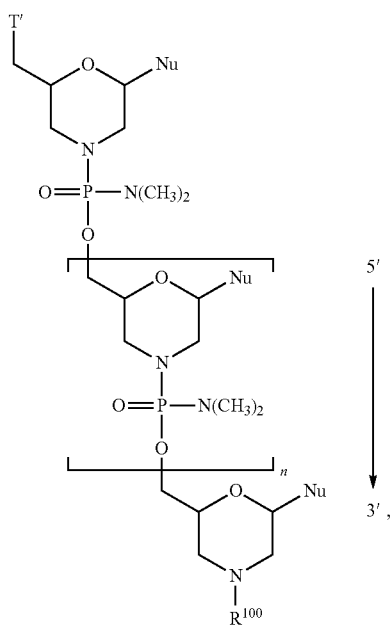

or a pharmaceutically acceptable salt thereof, wherein:
n is 1-40;
each Nu is a nucleobase, which, taken together, form a targeting sequence complementary to an exon annealing site in the dystrophin pre-mRNA;
T' is a moiety selected from:

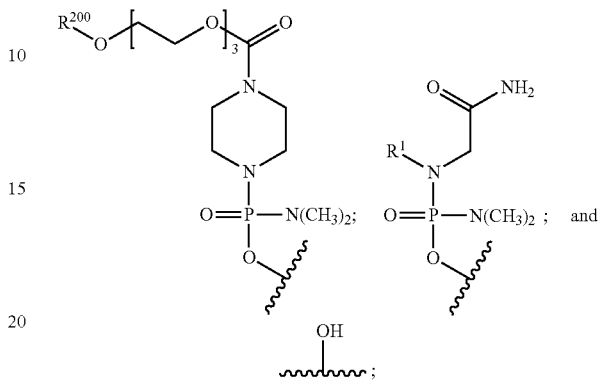

wherein
$R^{100}$ a cell-penetrating peptide, $R^{200}$ is hydrogen, and $R^1$ is $C_1$-$C_6$ alkyl,
at a dose equivalent to the dose of the ·6HCl salt of the conjugate according to the following schedule:
 i) about 300 mg to about 700 mg, or about 900 mg to about 1200 mg, once every four weeks for a patient that weighs from about 10 kg to about 25 kg;
 ii) about 600 mg to about 800 mg, or about 1000 mg to about 1300 mg, once every four weeks for a patient that weighs from about 25 kg to about 50 kg; or
 iii) about 700 mg to about 900 mg, or about 1200 mg to about 1500 mg, once every four weeks for a patient that weighs from about 50 kg to about 100 kg;
to achieve a mean AUC between about 100 and about 200 ug·h/mL, or is between about 200 and about 500 ug·h/mL, respectively.

In some embodiments, the conjugate is administered at a dose equivalent to the dose of the ·6 HCl salt of the conjugate according to the following schedule:
 iv) about 300 mg to about 700 mg, or about 900 mg to about 1200 mg, once every four weeks for a patient that weighs from about 10 kg to about 25 kg;
 v) about 500 mg to about 800 mg, or about 1000 mg to about 1300 mg, once every four weeks for a patient that weighs from about 25 kg to about 50 kg; or
 vi) about 700 mg to about 900 mg, or about 1200 mg to about 1500 mg, once every four weeks for a patient that weighs from about 50 kg to about 100 kg; to achieve a mean AUC between about 100 and about 200 ug·h/mL, or is between about 200 and about 500 ug·h/mL, respectively.

In some aspects, the antisense oligomer conjugate, or a pharmaceutically acceptable salt thereof, is administered at a dose equivalent to about 600 mg, or about 1100 mg, of the ·6HCl salt of the conjugate once every four weeks to a patient that weighs from about 10 kg to about 25 kg.

In some aspects, the antisense oligomer conjugate, or a pharmaceutically acceptable salt thereof, is administered at a dose equivalent to about 750 mg, or about 1250 mg, of the ·6HCl salt of the conjugate once every four weeks to a patient that weighs from about 18 kg to about 50 kg.

In some aspects, the antisense oligomer conjugate, or a pharmaceutically acceptable salt thereof, is administered at a dose equivalent to about 650 mg, or about 1200 mg, of the ·6HCl salt of the conjugate once every four weeks to a patient that weighs from about 25 kg to about 50 kg.

In some aspects, the antisense oligomer conjugate, or a pharmaceutically acceptable salt thereof, is administered at a dose equivalent to about 750 mg, or about 1400 mg, of the ·6HCl salt of the conjugate once every four weeks to a patient that weighs from about 50 kg to about 100 kg.

In some aspects, the antisense oligomer conjugate, or a pharmaceutically acceptable salt thereof, is administered at a dose equivalent to about 850 mg, or about 1350 mg, of the ·6HCl salt of the conjugate once every four weeks to a patient that weighs greater than or equal to 50 kg.

In one aspect, the present disclosure provides a method of treating a patient in need thereof, comprising administering to the patient an antisense oligomer conjugate, and further comprising administering a magnesium supplement to the patient.

In one particular aspect, the present disclosure also provides a method of treating a patient with Duchenne muscular dystrophy (DMD) in need thereof who has a mutation that is amenable to exon skipping, comprising administering to the patient an antisense oligomer conjugate of Formula (I), as described herein, and further comprising administering a magnesium supplement to the patient.

The present disclosure also provides a method of treating a patient with Duchenne muscular dystrophy (DMD) with an antisense oligomer conjugate, comprising administering to the patient:

i) an antisense oligomer conjugate of Formula (I):

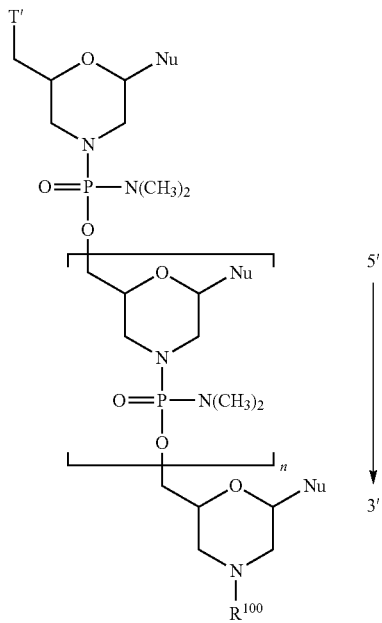

or a pharmaceutically acceptable salt thereof,
wherein:
n is 1-40;
each Nu is a nucleobase, which, taken together, form a targeting sequence complementary to an exon annealing site in the dystrophin pre-mRNA;

T' is a moiety selected from:

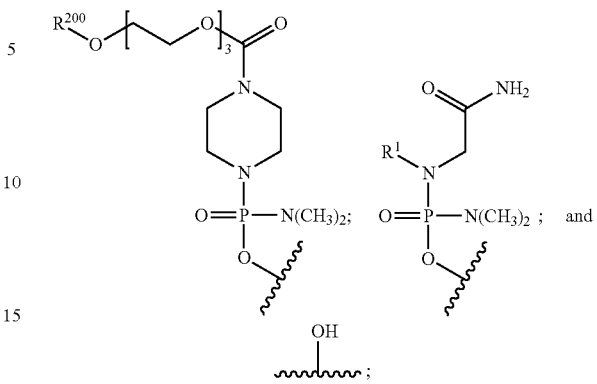

wherein
$R^{100}$ a cell-penetrating peptide, $R^{200}$ is hydrogen, and $R^1$ is $C_1$-$C_6$ alkyl; and
ii) a magnesium supplement.

In some aspects, the conjugate, or a pharmaceutically acceptable salt thereof, is administered at a dose equivalent to about 300 mg to about 1200 mg, about 300 mg to about 1000 mg, about 300 mg to about 750 mg, about 300 mg to about 500 mg, about 400 mg to about 1400 mg, about 400 mg to about 1100 mg, about 400 mg to about 900 mg, about 400 mg to about 600 mg, about 500 mg to about 1500 mg, about 500 mg to about 1300 mg, about 500 mg to about 1000 mg, about 500 mg to about 950 mg, about 500 mg to about 850 mg, about 500 mg to about 750 mg, about 500 mg to about 650 mg, about 600 mg to about 1400 mg, about 600 mg to about 1200 mg, about 600 mg to about 1200 mg, about 600 mg to about 1000, or about 600 mg to about 900 mg of the ·6HCl salt of the conjugate.

In some aspects, the conjugate, or a pharmaceutically acceptable salt thereof, is administered at a dose equivalent to about 300 mg, about 350 mg, about 400 mg, about 450 mg, about 500 mg, about 550 mg, about 600 mg, about 650 mg, about 700 mg, about 750 mg, about 800 mg, about 850 mg, or about 900 mg of the ·6HCl salt of the conjugate.

In some aspects, the conjugate, or a pharmaceutically acceptable salt thereof, is administered at a dose equivalent to about 950 mg, about 1000 mg, about 1050 mg, about 1100 mg, about 1150 mg, about 1200 mg, about 1250 mg, about 1300 mg, about 1350 mg, about 1400 mg, about 1450 mg, or about 1500 mg of the ·6HCl salt of the conjugate.

In certain aspects, the cell-penetrating peptide is chosen from RXRRXRRXRRXR (SEQ ID NO: 18), RFFRFFRFFR (SEQ ID NO: 19), RXRRXRRXRRXRXB (SEQ ID NO: 20), RFFRFFRFFRG (SEQ ID NO: 21), RRRRRRG (SEQ ID NO: 22), RRRRRR (SEQ ID NO: 23), RRRRRG (SEQ ID NO: 24), or RRRRR (SEQ ID NO: 25), wherein R is arginine, X is 6-aminohexanoic acid, B is β-alanine, F is phenylalanine, and G is glycine. In certain other aspects, the cell-penetrating peptide is chosen from RRRRRRG (SEQ ID NO: 22), RRRRRR (SEQ ID NO: 23), RRRRRG (SEQ ID NO: 24), or RRRRR (SEQ ID NO: 25), wherein R is arginine and G is glycine. In one particular aspect, the cell-penetrating peptide is RRRRRRG (SEQ ID NO: 22), wherein R is arginine and G is glycine.

In some aspects, the antisense oligomer conjugate, or a pharmaceutically acceptable salt thereof, causes skipping of an exon in the human dystrophin gene. In some aspects, the exon is chosen from exon 44, 45, 50, 51, 52, or 53. In certain aspects, the exon is chosen from exon 45, 51, or 53.

In some aspects, the magnesium supplement is administered in an amount effective to provide a normal serum magnesium level. In certain aspects, the magnesium supplement is administered at a dose equivalent to about 100 to about 2400 mg magnesium oxide per day. In other aspects, the magnesium supplement is administered at a dose equivalent to about 400 to about 2400 mg magnesium oxide per day.

In some aspects, the method of the present disclosure further comprises measuring serum magnesium level of said patient at two or more weeks from said administration. In some additional aspects, the method of the present disclosure comprises administering a second dose of magnesium supplement, at a dose based upon the measured serum magnesium level.

In some aspects, the magnesium supplement is chosen from magnesium oxide, magnesium citrate, magnesium carbonate, magnesium hydrogen phosphate, magnesium glycerophosphate, magnesium trisilicate, magnesium hydroxide, magnesium hydroxide carbonate, magnesium acetate, magnesium citrate, magnesium lactate, magnesium gluconate, magnesium chloride, magnesium aspartate, magnesium caprilate, magnesium ascorbate; magnesium taurate, magnesium malate, and magnesium diglycinate, magnesium pidulate, or magnesium sulfate. In one aspect, the magnesium supplement is from magnesium oxide.

DETAILED DESCRIPTION

Figure 1:
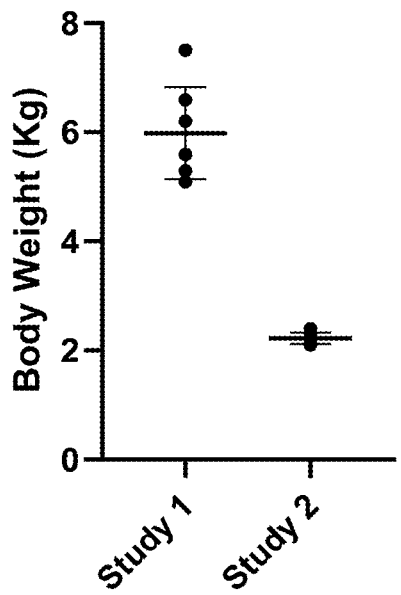
FIG. 1 demonstrates the difference in initial body weights of animals in two 12-week non-human primate (NHP) studies.

The present disclosure relates to novel dosing methods for treating muscular dystrophy, such as DMD and BMD, by administering an antisense oligomer conjugate, or a pharmaceutically acceptable salt thereof, specifically designed to induce exon skipping in the human dystrophin gene.

The present disclosure also provides therapeutically effective dosing regimens that minimize unwanted side-effects associated with administration of an antisense oligomer conjugate. Specifically, the disclosure provides methods for reducing the frequency and severity of hypomagnesemia in a patient that is being treated with administering an antisense oligomer conjugate.

Definitions

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., $C_1$ to $C_{10}$ alkyl. In certain embodiments, the alkyl group includes one to six carbon atoms, i.e., $C_1$ to $C_6$ alkyl. In certain embodiments, the alkyl group is selected from the group consisting of methyl, $CF_3$, $CCl_3$, $CFCl_2$, $CF_2C_1$, ethyl, $CH_2CF_3$, $CF_2CF_3$, propyl, isopropyl, butyl, isobutyl, sec-butyl, t-butyl, pentyl, isopentyl, neopentyl, hexyl, isohexyl, 3-methylpentyl, 2,2-dimethylbutyl, and 2,3-dimethylbutyl. The term includes both substituted and unsubstituted alkyl groups, including halogenated alkyl groups. In certain embodiments, the alkyl group is a fluorinated alkyl group. Non-limiting examples of moieties with which the alkyl group can be substituted are selected from the group consisting of halogen (fluoro, chloro, bromo, or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

"Amenable to exon skipping" as used herein with regard to a subject or patient is intended to include subjects and patients having one or more mutations in the dystrophin gene which, absent the skipping of the particular exon of the dystrophin pre-mRNA, causes the reading frame to be out-of-frame thereby disrupting translation of the pre-mRNA leading to an inability of the subject or patient to produce functional or semi-functional dystrophin. Determining whether a patient has a mutation in the dystrophin gene that is amenable to exon skipping is well within the purview of one of skill in the art (see, e.g., Aartsma-Rus et al. (2009) Hum Mutat. 30:293-299; Gurvich et al., Hum Mutat. 2009; 30(4) 633-640; and Fletcher et al. (2010) Molecular Therapy 18(6) 1218-1223.).

The terms "oligomer" and "oligonucleotide" are used interchangeably and refer to a sequence of subunits connected by intersubunit linkages. In certain instances, the term "oligomer" is used in reference to an "antisense oligomer." For "antisense oligomers," each subunit consists of: (i) a ribose sugar or a derivative thereof; and (ii) a nucleobase bound thereto, such that the order of the base-pairing moieties forms a base sequence that is complementary to a target sequence in a nucleic acid (typically an RNA) by Watson-Crick base pairing, to form a nucleic acid:oligomer heteroduplex within the target sequence with the proviso that either the subunit, the intersubunit linkage, or both are not naturally occurring. In certain embodiments, the antisense oligomer is a PMO.

The terms "complementary" and "complementarity" refer to two or more oligomers (i.e., each comprising a nucleobase sequence) that are related with one another by Watson-Crick base-pairing rules. For example, the nucleobase sequence "T-G-A (5' →3')," is complementary to the nucleobase sequence "A-C-T (3' →5')." Complementarity may be "partial," in which less than all of the nucleobases of a given nucleobase sequence are matched to the other nucleobase sequence according to base pairing rules. For example, in some embodiments, complementarity between a given nucleobase sequence and the other nucleobase sequence may be about 70%, about 75%, about 80%, about 85%, about 90% or about 95%. Or, there may be "complete" or "perfect" (100%) complementarity between a given nucleobase sequence and the other nucleobase sequence to continue the example. The degree of complementarity between nucleobase sequences has significant effects on the efficiency and strength of hybridization between the sequences.

The terms "effective amount" and "therapeutically effective amount" are used interchangeably herein and refer to an amount of therapeutic compound, such as an antisense oligomer conjugate, administered to a mammalian subject, either as a single dose or as part of a series of doses, which is effective to produce a desired therapeutic effect. For an antisense oligomer conjugate, this effect is typically brought about by inhibiting translation or natural splice-processing of a selected target sequence, or producing a clinically meaningful amount of dystrophin (statistical significance).

By "enhance" or "enhancing," or "increase" or "increasing," or "stimulate" or "stimulating," refers generally to the ability of one or more antisense oligomer conjugates or pharmaceutical compositions to produce or cause a greater physiological response (i.e., downstream effects) in a cell or a subject, as compared to the response caused by either no antisense oligomer conjugate or a control compound. A greater physiological response may include increased expression of a functional form of a dystrophin protein, or increased dystrophin-related biological activity in muscle tissue, among other responses apparent from the understanding in the art and the description herein. Increased muscle function can also be measured, including increases or improvements in muscle function by about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100%. The percentage of muscle fibers that express a functional dystrophin can also be measured, including increased dystrophin expression in about 1%, 2%, 5%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of muscle fibers. For instance, it has been shown that around 40% of muscle function improvement can occur if 25-30% of fibers express dystrophin (see, e.g., DelloRusso et al, Proc Natl Acad Sci USA 99: 12979-12984, 2002). An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times, including all integers and decimal points in between and above 1), e.g., 1.5, 1.6, 1.7, 1.8, etc.) the amount produced by no antisense oligomer conjugate (the absence of an agent) or a control compound.

As used herein, the terms "function" and "functional" and the like refer to a biological, enzymatic, or therapeutic function.

A "functional" dystrophin protein refers generally to a dystrophin protein having sufficient biological activity to reduce the progressive degradation of muscle tissue that is otherwise characteristic of muscular dystrophy, typically as compared to the altered or "defective" form of dystrophin protein that is present in certain subjects with DMD or BMD. In certain embodiments, a functional dystrophin protein may have about 10%, 20%, 30%, 40%, 50%, 60%, 70%, 80%, 90%, or 100% (including all integers in between) of the in vivo biological activity of wild-type dystrophin, as measured according to routine techniques in the art. Included are truncated forms of dystrophin, such as those forms that are produced following the administration of certain of the exon-skipping antisense oligomer conjugates of the present disclosure.

The terms "mismatch" or "mismatches" refer to one or more nucleobases (whether contiguous or separate) in an oligomer nucleobase sequence that are not matched to a target pre-mRNA according to base pairing rules. While perfect complementarity is often desired, some embodiments can include one or more but preferably 6, 5, 4, 3, 2, or 1 mismatches with respect to the target pre-mRNA. Variations at any location within the oligomer are included. In certain embodiments, antisense oligomer conjugates of the disclosure include variations in nucleobase sequence near the termini variations in the interior, and if present are typically within about 6, 5, 4, 3, 2, or 1 subunits of the 5' and/or 3' terminus.

Figure 2:
FIG. 2 depicts plasma exposure versus body weight in NHPs after administration of PPMO-1.

The terms "morpholino," "morpholino oligomer," and "PMO" refer to a phosphorodiamidate morpholino oligomer of the following general structure:

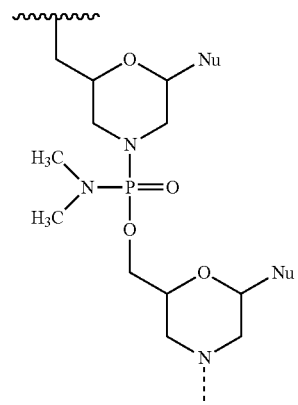

and as described in FIG. 2 of Summerton, J., et al., *Antisense & Nucleic Acid Drug Development*, 7: 187-195 (1997). Morpholinos as described herein include all stereoisomers and tautomers of the foregoing general structure. The synthesis, structures, and binding characteristics of morpholino oligomers are detailed in U.S. Pat. Nos. 5,698,685; 5,217,866; 5,142,047; 5,034,506; 5,166,315; 5,521,063; 5,506,337; 8,076,476; and 8,299,206; all of which are incorporated herein by reference.

In some aspects, a morpholino oligo (PMO) is conjugated at the 5' or 3' end of the oligomer with a "tail" moiety to increase its stability and/or solubility. Exemplary tails include:

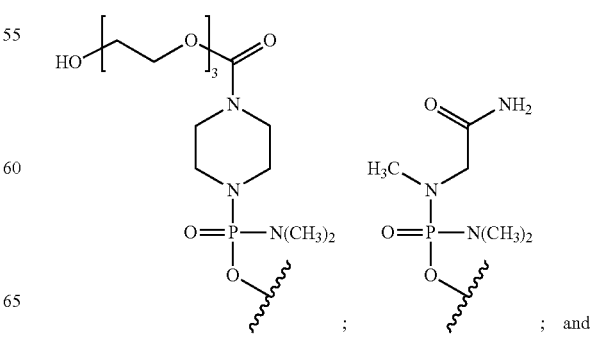

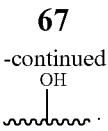

Of the above exemplary tail moieties, "TEG" or "EG3" refers to the following tail moiety:

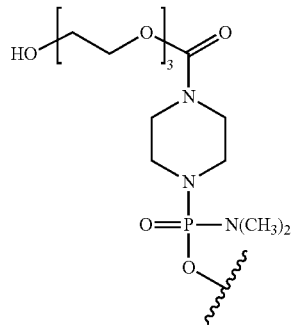

Of the above exemplary tail moieties, "GT" refers to the following tail moiety:

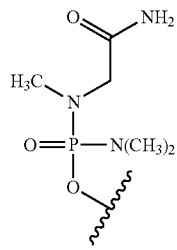

Useful morpholino oligomers are described in more detail below.

The terms "antisense oligomer CPP conjugate," "antisense oligomer conjugate," and "PPMO" refer to a conjugate where a PMO has been conjugated to a cell-penetrating peptide. CPPs are described more fully hereinbelow.

As seen in the table below, non-limiting examples of CPP's for use herein include —(RXR)$_4$—R$^a$, —R—(FFR)$_3$—R$^a$, —B—X—(RXR)$_4$—R$^a$, —B—X—R—(FFR)$_3$—R$^a$, -GLY-R—(FFR)$_3$—R$^a$, -GLY-R$_5$—R$^a$ and —R$_5$—R$^a$, -GLY-R$_6$—R$^a$ and —R$_6$—R$^a$, wherein R$^a$ is selected from H, acyl, acetyl, benzoyl, and stearoyl, and wherein R is arginine, X is 6-aminohexanoic acid, B is β-alanine, F is phenylalanine and GLY (or G) is glycine. The CPP "R$_6$" is meant to indicate a peptide of six (6) arginine residues linked together via amide bonds (and not a single substituent e.g. R$^6$). In some embodiments, R$^a$ is H or acyl. In some embodiments, R$^a$ is acetyl. Exemplary CPPs are provided in Table 1, below.

In one aspect, the CPP is chosen from one of the following sequences:

| Name | Sequence |
|---|---|
| (RXR)$_4$ | RXRRXRRXRRXR (SEQ ID NO: 18) |
| (RFF)$_3$R | RFFRFFRFFR (SEQ ID NO: 19) |
| (RXR)$_4$XB | RXRRXRRXRRXRXB (SEQ ID NO: 20) |
| (RFF)$_3$RXB | RFFRFFRFFRXB (SEQ ID NO: 26) |
| (RFF)$_3$RG | RFFRFFRFFRG (SEQ ID NO: 21) |
| R$_6$G | RRRRRRG (SEQ ID NO: 22) |
| R$_6$ | RRRRRR (SEQ ID NO: 23) |
| R$_5$G | RRRRRG (SEQ ID NO: 24) |
| R$_5$ | RRRRR (SEQ ID NO: 25) |

CPPs, their synthesis, and methods of conjugating to an oligomer are further described in U.S. Pat. Nos. 9,161,948 and 10,888,578, U.S. Application Publication No. 2012/0289457, and International Patent Application Publication Nos. WO 2004/097017, WO 2009/005793, and WO 2012/150960, the disclosures of which are incorporated herein by reference in their entirety. A more comprehensive list of CPPs is provided below.

The terms "nucleobase" (Nu), "base pairing moiety" or "base" are used interchangeably to refer to a purine or pyrimidine base found in naturally occurring, or "native" DNA or RNA (e.g., uracil, thymine, adenine, cytosine, and guanine), as well as analogs of these naturally occurring purines and pyrimidines. These analogs may confer improved properties, such as binding affinity, to the oligomer. Exemplary analogs include hypoxanthine (the base component of inosine); 2,6-diaminopurine; 5-methyl cytosine; C5-propynyl-modified pyrimidines; 10-(9-(aminoethoxy)phenoxazinyl) (G-clamp) and the like.

Further examples of base pairing moieties include, but are not limited to, uracil, thymine, adenine, cytosine, guanine and hypoxanthine (inosine) having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in: Chiu and Rana, R N A, 2003, 9, 1034-1048; Limbach et al. Nucleic Acids Research, 1994, 22, 2183-2196; and Revankar and Rao, Comprehensive Natural Products Chemistry, vol. 7, 313; are also contemplated, the contents of which are incorporated herein by reference.

Further examples of base pairing moieties include, but are not limited to, expanded-size nucleobases in which one or more benzene rings has been added. Nucleic acid base replacements described in: the Glen Research catalog (www.glenresearch.com); Krueger A T et al., Acc. Chem. Res., 2007, 40, 141-150; Kool, E T, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; and Hirao, I., Curr. Opin. Chem. Biol., 2006, 10, 622-627; the contents of which are incorporated herein by reference, are contemplated as useful in the antisense oligomer conjugates described herein. Examples of expanded-size nucleobases include those shown below, as well as tautomeric forms thereof.

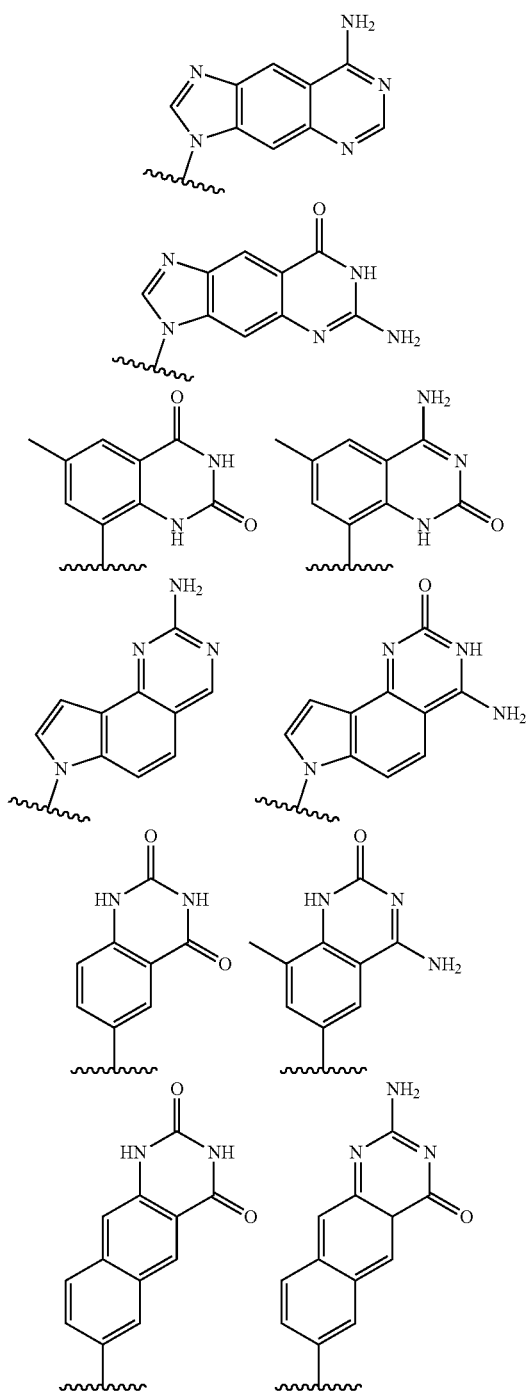

The term "exposure" refers to dose (PPMO input to the body) and various measures of acute or integrated PPMO concentrations in plasma and other biological fluid (e.g., Cmax, Cmin, Css, AUC). The term "response" refers to a direct measure of the pharmacologic effect of the drug. Response includes a broad range of endpoints or biomarkers ranging from a potential or accepted surrogate (e.g., effects on blood pressure, magnesium levels, or cardiac output) to the full range of short-term or longterm clinical effects related to efficacy and safety.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For clarity, structures of the disclosure are continuous from 5' to 3', and, for the convenience of depicting the entire structure in a compact form, various illustration breaks labeled "BREAK A," "BREAK B," and "BREAK C" have been included. As would be understood by the skilled artisan, for example, each indication of "BREAK A" shows a continuation of the illustration of the structure at these points. The skilled artisan understands that the same is true for each instance of "BREAK B" and for "BREAK C" in the structures above. None of the illustration breaks, however, are intended to indicate, nor would the skilled artisan understand them to mean, an actual discontinuation of the structure above.

As used herein, a set of brackets used within a structural formula indicate that the structural feature between the brackets is repeated. In some embodiments, the brackets used can be "[" and "]," and in certain embodiments, brackets used to indicate repeating structural features can be "(" and ")." In some embodiments, the number of repeat iterations of the structural feature between the brackets is the number indicated outside the brackets such as 2, 3, 4, 5, 6, 7, and so forth. In various embodiments, the number of repeat iterations of the structural feature between the brackets is indicated by a variable indicated outside the brackets such as "n".

As used herein, a straight bond or a squiggly bond drawn to a chiral carbon or phosphorous atom within a structural formula indicates that the stereochemistry of the chiral carbon or phosphorous is undefined and is intended to include all forms of the chiral center. Examples of such illustrations are depicted below.

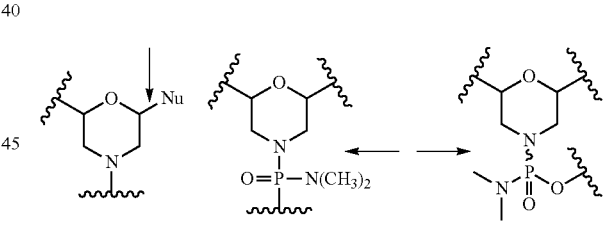

Management of Hypomagnesemia

The present description provides methods for reducing the severity and frequency of hypomagnesemia in DMD patients. The incidence rate of hypomagnesemia in DMD patients is generally no greater than that in healthy individuals. Unexpectedly, the present inventors have observed that patients treated with an antisense oligomer CPP conjugate (e.g., PPMO), higher exposure (AUC values) correlates with the severity and frequency of hypomagnesemia (magnesium deficiency). Thus, the methods described herein can result in decreased toxicity associated with abnormal magnesium levels associated with administration of with an antisense oligomer CPP conjugate (e.g., PPMO) in a human patient.

In some aspects, the present disclosure provides methods for treating hypomagnesemia associated with administering an antisense oligomer CPP conjugate (e.g., PPMO) to a patient to effect exon skipping by administering a magnesium supplement to a patient being treated with an antisense oligomer CPP conjugate. In some aspects, the patient is a DMD patient. In some aspects, the antisense oligomer CPP conjugate is an antisense oligomer CPP conjugate of Formula (I) or a pharmaceutically acceptable salt thereof. In some aspects, the antisense oligomer CPP conjugate is an antisense oligomer CPP conjugate of Formula (IVB) or a pharmaceutically acceptable salt thereof. In some aspects, the antisense oligomer CPP conjugate is an antisense oligomer CPP conjugate of Formula (VIB) or a pharmaceutically acceptable salt thereof. In some aspects, the antisense oligomer CPP conjugate is an antisense oligomer CPP conjugate of Formula (VIIIB) or a pharmaceutically acceptable salt thereof.

In some aspects, the present disclosure provides methods for preventing hypomagnesemia associated with administering an antisense oligomer CPP conjugate (e.g., PPMO) to a patient to effect exon skipping by administering a magnesium supplement to a patient being treated with an antisense oligomer CPP conjugate. In some aspects, the patient is a DMD patient. In some aspects, the antisense oligomer CPP conjugate is an antisense oligomer CPP conjugate of Formula (I) or a pharmaceutically acceptable salt thereof. In some aspects, the antisense oligomer CPP conjugate is an antisense oligomer CPP conjugate of Formula (IVB) or a pharmaceutically acceptable salt thereof. In some aspects, the antisense oligomer CPP conjugate is an antisense oligomer CPP conjugate of Formula (VIB) or a pharmaceutically acceptable salt thereof. In some aspects, the antisense oligomer CPP conjugate is an antisense oligomer CPP conjugate of Formula (VIIIB) or a pharmaceutically acceptable salt thereof.

In some aspects the present disclosure provides methods for maintaining normal serum magnesium levels in a patient to whom an antisense oligomer conjugate (e.g., PPMO) is being administered, by administering a magnesium supplement to a patient being treated with an antisense oligomer CPP conjugate. In some aspects, the patient is a DMD patient. In some aspects, the antisense oligomer CPP conjugate is an antisense oligomer CPP conjugate of Formula (I) or a pharmaceutically acceptable salt thereof. In some aspects, the antisense oligomer CPP conjugate is an antisense oligomer CPP conjugate of Formula (IVB) or a pharmaceutically acceptable salt thereof. In some aspects, the antisense oligomer CPP conjugate is an antisense oligomer CPP conjugate of Formula (VIB) or a pharmaceutically acceptable salt thereof. In some aspects, the antisense oligomer CPP conjugate is an antisense oligomer CPP conjugate of Formula (VIIIB) or a pharmaceutically acceptable salt thereof.

Hypomagnesemia in a patient (e.g., a DMD patient) can be diagnosed by a physical exam, symptoms, medical history, and a laboratory test to test the magnesium body content. Generally speaking, the means for detecting the magnesium body contents include the detection of blood levels of magnesium, in the patient's plasma or in the serum (whose anomalies generally indicate a disorder in magnesium metabolism and are, normally, the starting point for a set of further specific tests); the detection of magnesium levels in the urine (which gives a measure of the elimination of magnesium via urine, and is normally associated with protein intake, being the Mg/urea ratio in the urine quite constant); the detection of magnesium levels in the spinal fluid; the detection of erythrocytic magnesium (which shows the amount of Mg contained in the bone marrow when erythropoiesis occurs and allows, therefore, an indirect medullary exploration as concerns magnesium); the detection of lymphocytic magnesium; nuclear magnetic resonance with $^{25}$Mg (which evidences any modifications in the subcellular distribution of magnesium and in the different chemical-physical structures); and, the detection of magnesium contents in the patient's bones, muscles or any other tissue or organ of interest.

Hypomagnesemia is defined according to the CTCAE (Common Terminology Criteria for Adverse Events) or magnesium reduction level:

| Grade 1 | Grade 2 | Grade 3 | Grade 4 | Grade 5 |
|---|---|---|---|---|
| <LLN-1.2 mg/dL; <LLN-0.5 mmol/L | <1.2-0.9 mg/dL; <0.5-0.4 mmol/L | <0.9-0.7 mg/dL; <0.4-0.3 mmol/L | <0.7 mg/dL; <0.3 mmol/L; life-threatening consequences | Death |

Severe hypomagnesemia usually results in concentrations of <0.9 mg/dL (<0.4 mmol/L).

An aspect of the present disclosure includes treating a patient diagnosed with hypomagnesemia by administering to the patient a magnesium supplement. Herein throughout, in the context of magnesium-containing products, magnesium supplements, magnesium formulations and/or magnesium therapy, the term "magnesium" refers to $Mg^{+2}$ ions, either in a form of free ions in a salt or in a form of a complex.

In certain aspects, magnesium supplement is administered prophylactically, without first testing for hypomagnesemia. An aspect of the present disclosure includes treating a patient with Duchenne muscular dystrophy (DMD) with an antisense oligomer CPP conjugate, comprising administering to the patient: (i) an antisense oligonucleotide CPP conjugate that includes a morpholino phosphorodiamidate antisense oligomer that is: (a) 100% complementary to a portion of an exon of the human dystrophin pre-mRNA, and (b) 15 to 50 nucleotides in length, wherein the antisense oligonucleotide is administered intravenously; and a magnesium supplement. In another aspect, the oligomer is 15-40, 15-35, 15-30, 15-25, or 15-20 nucleotides in length. In some aspects, the oligo is 30, 29, 28, 27, 26, 25, 24, 23, 22, 21, 20, 19, 18, 17, 16, or 15 nucleotides in length. In one aspect, the oligo is 30 nucleotides in length. In some aspects, the antisense oligomer CPP conjugate is an antisense oligomer CPP conjugate of Formula (I) or a pharmaceutically acceptable salt thereof. In some aspects, the antisense oligomer CPP conjugate is an antisense oligomer CPP conjugate of Formula (IVB) or a pharmaceutically acceptable salt thereof. In some aspects, the antisense oligomer CPP conjugate is an antisense oligomer CPP conjugate of Formula (VIB) or a pharmaceutically acceptable salt thereof. In some aspects, the antisense oligomer CPP conjugate is an antisense oligomer CPP conjugate of Formula (VIIIB) or a pharmaceutically acceptable salt thereof.

In some aspects, magnesium supplement is administered to a patient orally. Magnesium-containing products for oral administration include, for example, magnesium oxide, magnesium citrate, magnesium carbonate, magnesium hydrogen phosphate, magnesium glycerophosphate, magnesium trisilicate, magnesium hydroxide, magnesium hydroxide carbonate, magnesium acetate, magnesium citrate, magnesium lactate, magnesium gluconate, magnesium chloride, magnesium aspartate, magnesium caprilate, magnesium ascorbate; magnesium taurate, magnesium malate, and magnesium diglycinate, magnesium pidulate or magnesium sulfate. In some aspects, the magnesium supplement is magnesium oxide.

In some aspects, magnesium supplement is administered to a patient intravenously. Intravenously administered magnesium includes, for example, magnesium sulfate.

Like many metal-containing complexes, the different magnesium compounds have different mechanisms of uptake in vivo. Additionally, upon administration, including ingestion, the transition metal complexes may undergo any number of reactions in vivo that affect the bioavailability and resulting therapeutic effect. By way of example, magnesium citrate is soluble in gastric fluid and thus is readily available for passive absorption in the upper gastrointestinal tract. Magnesium acetate, magnesium ascorbate and magnesium lactate are soluble in gastric fluid and share the upper gastrointestinal passive absorption potential of magnesium citrate. The ascorbate radical serves as a source of vitamin C by conversion to ascorbic acid upon exposure to hydrochloric acid in the gastric fluid, whereas the magnesium ion is converted to soluble magnesium chloride. The satisfactory water solubility of magnesium acetate, magnesium ascorbate, magnesium citrate and magnesium lactate provide for a diffusional gradient of magnesium in the upper small intestine where some passive absorption of magnesium occurs. Magnesium oxide is converted to magnesium chloride in the stomach, and offers the advantage of a high ionic magnesium content, since 60% by weight of the magnesium oxide molecule is elemental magnesium. Magnesium diglycinate represents a form of magnesium that is absorbed in part as an intact dipeptide in the proximal small intestine via a dipeptide transport pathway and therefore provides a third absorptive mechanism for magnesium.

A variety of dosages, in amount of magnesium, are contemplated by the present disclosure. Unless expressly provided otherwise, the dose amounts referred to herein refer to the amount equivalent to the amount of magnesium oxide. The dose may range from about 5 mg to about 1000 mg or more. In some aspects, the dose may range from about 5 mg to about 900 mg, about 850 mg, about 800 mg, about 750 mg, about 700 mg, about 650 mg, about 600 mg, about 550 mg, about 500 mg, about 450 mg, about 400 mg, about 350 mg, about 300 mg, about 250 mg, about 200 mg, about 150 mg, about 100 mg, or to about 50 mg. In some aspects, the dose may range from about 15 mg to about 900 mg, about 850 mg, about 800 mg, about 750 mg, about 700 mg, about 650 mg, about 600 mg, about 550 mg, about 500 mg, about 450 mg, about 400 mg, about 350 mg, about 300 mg, about 250 mg, about 200 mg, about 150 mg, about 100 mg, or to about 50 mg. In some aspects, the dose may range from about 30 mg to about 900 mg, about 850 mg, about 800 mg, about 750 mg, about 700 mg, about 650 mg, about 600 mg, about 550 mg, about 500 mg, about 450 mg, about 400 mg, about 350 mg, about 300 mg, about 250 mg, about 200 mg, about 150 mg, about 100 mg, or to about 50 mg. In some aspects, the dose may range from about 60 mg to about 900 mg, about 850 mg, about 800 mg, about 750 mg, about 700 mg, about 650 mg, about 600 mg, about 550 mg, about 500 mg, about 450 mg, about 400 mg, about 350 mg, about 300 mg, about 250 mg, about 200 mg, about 150 mg, about 100 mg, or to about 50 mg. In some aspects, the dose may range from about 100 mg to about 900 mg, about 850 mg, about 800 mg, about 750 mg, about 700 mg, about 650 mg, about 600 mg, about 550 mg, about 500 mg, about 450 mg, about 400 mg, about 350 mg, about 300 mg, about 250 mg, or about 200 mg. In some aspects, the dose may range from about 200 mg to about 900 mg, about 850 mg, about 800 mg, about 750 mg, about 700 mg, about 650 mg, about 600 mg, about 550 mg, about 500 mg, about 450 mg, about 400 mg, about 350 mg, about 300 mg, to about 250 mg. In some aspects, the dose may range from about 300 mg to about 900 mg, about 850 mg, about 800 mg, about 750 mg, about 700 mg, about 650 mg, about 600 mg, about 550 mg, about 500 mg, about 450 mg, about 400 mg, or to about 350 mg. In some aspects, the dose may range from about 400 mg to about 900 mg, about 850 mg, about 800 mg, about 750 mg, about 700 mg, about 650 mg, about 600 mg, about 550 mg, about 500 mg, or to about 450 mg.

Specific dosages of the magnesium supplement include about 5 mg, about 10 mg, about 15 mg, about 20 mg, about 25 mg, about 30 mg, about 35 mg, about 40 mg, about 45 mg, 50 mg, 55 mg, 60 mg, 65 mg, 70 mg, 75 mg, 80 mg, 85 mg, 90 mg, 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 200 mg, about 205 mg, about 210 mg, about 215 mg, about 220 mg, about 225 mg, about 230 mg, about 235 mg 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, about 505 mg, about 510 mg, about 515 mg, about 520 mg, about 525 mg, about 530 mg, about 535 mg, about 540 mg, about 545 mg, about 550 mg, about 555 mg, about 560 mg, about 565 mg, about 570 mg, about 575 mg, about 580 mg, about 585 mg, about 590 mg, about 595 mg, about 600 mg, about 605 mg, about 610 mg, about 615 mg, about 620 mg, about 625 mg, about 630 mg, about 635 mg, about 640 mg, about 645 mg, about 650 mg, about 655 mg, 660 mg, about 665 mg, about 670 mg, about 675 mg, about 680 mg, about 685 mg, about 690 mg, about 695 mg, about 700 mg, about 705 mg, about 710 mg, about 715 mg, about 720 mg, about 725 mg, about 730 mg, about 735 mg, about 740 mg, about 745 mg, about 750 mg, about 755 mg, about 760 mg, about 765 mg, 770 mg, about 780 mg, about 785 mg, about 790 mg, about 795 mg, about 800 mg, about 805 mg, about 810 mg, about 815 mg, about 820 mg, about 825 mg, about 830 mg, about 835 mg, about 840 mg, about 845 mg, 850 mg, about 855 mg, about 860 mg, about 865 mg, 880 mg, about 885 mg, about 890 mg, about 895 mg, about 900, about 905 mg, about 910 mg, about 915 mg, about 920 mg, about 925 mg, about 930 mg, about 935 mg, about 940 mg, about 945 mg, 950 mg, about 955 mg, 960 mg, about 965 mg, about 970 mg, about 975 mg, about 980 mg, about 985 mg, about 990 mg, about 995 mg, or about 1000 mg.

In some aspects, the present disclosure provides methods for treating or preventing hypomagnesemia associated with administering an antisense oligomer CPP conjugate of Formulas (IVB), or a pharmaceutically acceptable salt thereof to a patient to effect exon skipping by administering a magnesium supplement to a patient being treated with an antisense oligomer CPP conjugate, wherein the magnesium supplement dose is about 400 mg to 900 mg.

In some aspects, the present disclosure provides methods for treating or preventing hypomagnesemia associated with administering an antisense oligomer CPP conjugate of Formulas (VIB), or a pharmaceutically acceptable salt thereof to a patient to effect exon skipping by administering a magnesium supplement to a patient being treated with an antisense oligomer CPP conjugate, wherein the magnesium supplement dose is about 400 mg to 900 mg.

In some aspects, the present disclosure provides methods for treating or preventing hypomagnesemia associated with administering an antisense oligomer CPP conjugate of Formulas (VIIIB), or a pharmaceutically acceptable salt thereof to a patient to effect exon skipping by administering a magnesium supplement to a patient being treated with an antisense oligomer CPP conjugate, wherein the magnesium supplement dose is about 400 mg to 900 mg.

In an aspect, a dose of a magnesium supplement is equivalent to about 400 mg of magnesium oxide. In another aspect, a dose of a magnesium supplement is equivalent to about 800 mg of magnesium oxide.

Higher doses of magnesium are also contemplated. For example, the dose may range from about 1000 mg to about 2400 mg, about 1000 mg to about 2000 mg, about 1000 mg to about 1500 mg, about 1050 mg to about 2400 mg, about 1050 mg to about 2000 mg, about 1050 mg to about 1500 mg, 1100 mg to about 2400 mg, about 1100 mg to about 2000 mg, about 1100 mg to about 1500 mg, 1200 mg to about 2400 mg, about 120 mg to about 2000 mg, about 12 mg to about 1500 mg, 1500 mg to about 2400 mg, or about 1500 mg to about 2000 mg. Specific doses of magnesium can include about 1000 mg, about 1050 mg, about 1100 mg. about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, or about 2400 mg.

Higher dosages, may be used as short-term regimes (e.g. less than about one month) and may taper into dosages in the lower end of the ranges. In many such instances it will be advantageous to not to fall below about 40 to 100 mg per day of magnesium when tapering the dose. Alternatively, the appropriate dose of magnesium may be based on the condition of any subject, as assessed by a number of variables of import. Alternatively, the dosages may depend on the mode of administration. Alternatively, magnesium dose may vary with the amounts of an antisense oligomer CPP conjugate. Appropriate dosages may depend on numerous factors, and may be readily determined by one of skill in the art.

In some aspects, a magnesium supplement is administered once daily. In other aspect, the magnesium supplement is administered twice daily. In yet other aspects, the magnesium supplement is administered three times a day. More frequent daily administration of the magnesium supplement, as determined by a treating physician, is also contemplated by the present disclosure.

A magnesium supplement and an antisense oligomer CPP conjugate can be administered to an individual in any order. In one aspect, a magnesium supplement and an antisense oligomer CPP conjugate are administered simultaneously. For example, a magnesium supplement and an antisense oligomer CPP conjugate can be administered within the same hour of each other. In some aspects, a magnesium supplement and an antisense oligomer CPP conjugate can also be administered within about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, ab about 23 hours, or about 24 hours of each other.

In other aspects, an antisense oligomer CPP conjugate can be administered once every 2, 3, 4, 5, 6, 7, 8, 9, 10, 11, 12, 13, 14 days, or every 1, 2, 3, 4, 5, 6, 7, 8, 9, 10, 11, 12 weeks, while a magnesium supplement is administered once, twice, three time, four times, or more daily. In other aspects, an antisense oligomer CPP conjugate can be administered once every 1, 2, 3, 4, 5, 6, 7, 8, 9, 10, 11, 12 months, while a magnesium supplement is administered once, twice, three time, four times, or more daily.

Magnesium supplementation can also begin prior to initiation of a treatment regimen with an antisense oligomer CPP conjugate. For example, a patient can begin magnesium supplementation 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or more days prior to the first treatment with an antisense oligomer CPP conjugate. Alternatively, Magnesium supplementation can also begin after initiation of a treatment regimen with an antisense oligomer CPP conjugate. For example, a patient can begin magnesium supplementation 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or more days after the first treatment with an antisense oligomer CPP conjugate.

In another aspect, any of these magnesium supplement aspects can be combined with one of the PPMO dosing aspects described below.

Serum magnesium level of a patient should be measured regularly during treatment with an antisense oligomer CPP conjugate. In some aspects, serum magnesium level of a patient is measured prior to administering an antisense oligomer CPP conjugate. In some aspects, serum magnesium level of the patient is measured at two or more weeks from the administration of the conjugate. Depending on patient's serum magnesium level at a given measurement, the dose of the magnesium supplement can be adjusted up or down to maintain a normal serum magnesium level. As such, administering a second dose of magnesium supplement, at a dose based upon the measured serum magnesium level, is also contemplated by the present disclosure.

Dosing of Antisense Oligomer CPP Conjugates (PPMOs)

In previous clinical settings involving splice-switching oligomers (SSOs) for treatment of DMD (e.g., PMOs, such as eteplirsen, golodirsen), weight based (mg/kg) approaches have been used. It has now been unexpectedly discovered that both dystrophin expression and safety (hypomagnesemia) are related to exposure (dose) of PPMO.

It has been discovered that using weight-based (mg/kg) PPMO dosing approach, higher body weight (BW) is associated with higher drug exposure, resulting in a risk of underdose for lighter patients and risk of overdose for heavier patients. As such, it has been discovered that a weight-based dosing approach leads to sub-optimal dystrophin expression in lighter patients, and potential hypomagnesemia in heavier patients.

The present disclosure provides novel dosing regimens developed to optimize dystrophin expression and minimize hypomagnesemia concerns in human patients.

In some aspects, the antisense oligomer conjugate, or a pharmaceutically acceptable salt thereof, is administered at a dose effective to provide a targeted mean AUC so as to maximize dystrophin expression and minimize hypomagnesemia in a patient.

In some aspects, the antisense oligomer CPP conjugate, or a pharmaceutically acceptable salt thereof, is administered at a dose effective to provide the mean AUC of between about 100 and about 200 ug·h/mL, between about 100 and about 190 ug·h/mL, between about 100 and about 180 ug·h/mL, between about 100 and about 170 ug·h/mL, between about 100 and about 160 ug·h/mL, between about 100 and about 150 ug·h/mL, between about 100 and about 140 ug·h/mL, between about 100 and about 130 ug·h/mL, between about 100 and about 120 ug·h/mL, or between about 100 and about 110 ug·h/mL.

In some aspects, the antisense oligomer CPP conjugate, or a pharmaceutically acceptable salt thereof, is administered at a dose effective to provide the mean AUC is between about 110 and about 200 ug·h/mL, between about 120 and about 200 ug·h/mL, between about 130 and about 200 ug·h/mL, between about 140 and about 200 ug·h/mL, between about 150 and about 200 ug·h/mL, between about 160 and about 200 ug·h/mL, between about 170 and about 200 ug·h/mL, between about 180 and about 200 ug·h/mL, or between about 190 and about 200 ug·h/mL.

In some aspects, the antisense oligomer CPP conjugate, or a pharmaceutically acceptable salt thereof, is administered at a dose effective to provide the mean AUC is between about 110 and about 190 ug·h/mL, between about 120 and about 190 ug·h/mL, between about 130 and about 190 ug·h/mL, between about 140 and about 190 ug·h/mL, between about 150 and about 190 ug·h/mL, between about 160 and about 190 ug·h/mL, between about 170 and about 190 ug·h/mL, or between about 180 and about 190 ug·h/mL.

In some aspects, the antisense oligomer CPP conjugate, or a pharmaceutically acceptable salt thereof, is administered at a dose effective to provide the mean AUC is between about 110 and about 180 ug·h/mL, between about 120 and about 180 ug·h/mL, between about 130 and about 180 ug·h/mL, between about 140 and about 180 ug·h/mL, between about 150 and about 180 ug·h/mL, between about 160 and about 180 ug·h/mL, or between about 170 and about 180 ug·h/mL.

In some aspects, the antisense oligomer CPP conjugate, or a pharmaceutically acceptable salt thereof, is administered at a dose effective to provide the mean AUC is between about 110 and about 170 ug·h/mL, between about 120 and about 170 ug·h/mL, between about 130 and about 170 ug·h/mL, between about 140 and about 170 ug·h/mL, between about 150 and about 170 ug·h/mL, or between about 160 and about 170 ug·h/mL.

In some aspects, the antisense oligomer CPP conjugate, or a pharmaceutically acceptable salt thereof, is administered at a dose effective to provide the mean AUC is between about 110 and about 160 ug·h/mL, between about 120 and about 160 ug·h/mL, between about 130 and about 160 ug·h/mL, between about 140 and about 160 ug·h/mL, or between about 150 and about 160 ug·h/mL.

In some aspects, the antisense oligomer CPP conjugate, or a pharmaceutically acceptable salt thereof, is administered at a dose effective to provide the mean AUC is between about 110 and about 150 ug·h/mL, between about 120 and about 150 ug·h/mL, between about 130 and about 150 ug·h/mL, or between about 140 and about 150 ug·h/mL.

In some aspects, the antisense oligomer CPP conjugate, or a pharmaceutically acceptable salt thereof, is administered at a dose effective to provide the mean AUC is between about 120 and about 240 ug·h/mL, between about 120 and about 230 ug·h/mL, between about 120 and about 220 ug·h/mL, between about 120 and about 210 ug·h/mL, between about 120 and about 200 ug·h/mL, between about 120 and about 190 ug·h/mL, between about 120 and about 180 ug·h/mL, between about 120 and about 170 ug·h/mL, between about 120 and about 160 ug·h/mL, between about 120 and about 150 ug·h/mL, between about 120 and about 140 ug·h/mL, or between about 120 and about 130 ug·h/mL.

In some aspects, the antisense oligomer CPP conjugate, or a pharmaceutically acceptable salt thereof, is administered at a dose effective to provide the mean AUC is between about 130 and about 200 ug·h/mL, between about 130 and about 190 ug·h/mL, between about 130 and about 180 ug·h/mL, between about 130 and about 170 ug·h/mL, between about 130 and about 160 ug·h/mL, between about 130 and about 150 ug·h/mL, or between about 130 and about 140 ug·h/mL.

In some aspects, the antisense oligomer CPP conjugate, or a pharmaceutically acceptable salt thereof, is administered at a dose effective to provide the mean AUC is between about 140 and about 200 ug·h/mL, between about 140 and about 190 ug·h/mL, between about 140 and about 180 ug·h/mL, between about 140 and about 170 ug·h/mL, between about 140 and about 160 ug·h/mL, or between about 140 and about 150 ug·h/mL.

In some aspects, the antisense oligomer CPP conjugate, or a pharmaceutically acceptable salt thereof, is administered at a dose effective to provide the mean AUC is between about 150 and about 200 ug·h/mL, between about 150 and about 190 ug·h/mL, between about 150 and about 180 ug·h/mL, between about 150 and about 170 ug·h/mL, or between about 150 and about 160 ug·h/mL.

In some aspects, the antisense oligomer CPP conjugate, or a pharmaceutically acceptable salt thereof, is administered at a dose effective to provide the mean AUC is between about 160 and about 200 ug·h/mL, between about 160 and about 190 ug·h/mL, between about 160 and about 180 ug·h/mL, or between about 160 and about 170 ug·h/mL.

In some aspects, the antisense oligomer CPP conjugate, or a pharmaceutically acceptable salt thereof, is administered at a dose effective to provide the mean AUC is between about 170 and about 200 ug·h/mL, between about 170 and about 190 ug·h/mL, or between about 170 and about 180 ug·h/mL.

In some aspects, the antisense oligomer CPP conjugate, or a pharmaceutically acceptable salt thereof, is administered at a dose effective to provide the mean AUC is between about 130 and about 240 ug·h/mL, between about 140 and about 240 ug·h/mL, between about 150 and about 240 ug·h/mL, between about 160 and about 240 ug·h/mL, between about 170 and about 240 ug·h/mL, between about 180 and about 240 ug·h/mL, between about 190 and about 240 ug·h/mL, between about 200 and about 240 ug·h/mL, between about 210 and about 240 ug·h/mL, between about 220 and about 240 ug·h/mL, or between about 230 and about 240 ug·h/mL.

In some aspects, the antisense oligomer CPP conjugate, or a pharmaceutically acceptable salt thereof, is administered at a dose effective to provide the mean AUC is between about 130 and about 230 ug·h/mL, between about 140 and about 230 ug·h/mL, between about 150 and about 230 ug·h/mL, between about 160 and about 230 ug·h/mL, between about 170 and about 230 ug·h/mL, between about 180 and about 230 ug·h/mL, between about 190 and about 230 ug·h/mL, between about 200 and about 230 ug·h/mL, between about 210 and about 230 ug·h/mL, or between about 220 and about 230 ug·h/mL.

In some aspects, the antisense oligomer CPP conjugate, or a pharmaceutically acceptable salt thereof, is administered at a dose effective to provide the mean AUC is between about 130 and about 220 ug·h/mL, between about 140 and about 220 ug·h/mL, between about 150 and about 220 ug·h/mL, between about 160 and about 220 ug·h/mL, between about 170 and about 220 ug·h/mL, between about 180 and about 220 ug·h/mL, or between about 190 and about 220 ug·h/mL, between about 200 and about 220 ug·h/mL, or between about 210 and about 220 ug·h/mL.

In some aspects, the antisense oligomer CPP conjugate, or a pharmaceutically acceptable salt thereof, is administered at a dose effective to provide the mean AUC is between about 130 and about 210 ug·h/mL, between about 140 and about 210 ug·h/mL, between about 150 and about 210 ug·h/mL, between about 160 and about 210 ug·h/mL, between about 170 and about 210 ug·h/mL, between about 180 and about 210 ug·h/mL, between about 190 and about 210 ug·h/mL, or between about 200 and about 210 ug·h/mL.

In some aspects, the antisense oligomer CPP conjugate, or a pharmaceutically acceptable salt thereof, is administered at a dose effective to provide the mean AUC is between about 130 and about 200 ug·h/mL, between about 140 and about 200 ug·h/mL, between about 150 and about 200 ug·h/mL, between about 160 and about 200 ug·h/mL, between about 170 and about 200 ug·h/mL, between about 180 and about 200 ug·h/mL, or between about 190 and about 200 ug·h/mL.

In some aspects, the antisense oligomer CPP conjugate, or a pharmaceutically acceptable salt thereof, is administered at a dose effective to provide the mean AUC is between about 130 and about 190 ug·h/mL, between about 140 and about 190 ug·h/mL, between about 150 and about 190 ug·h/mL, or between about 160 and about 190 ug·h/mL, between about 170 and about 190 ug·h/mL, or between about 180 and about 190 ug·h/mL.

In some aspects, the antisense oligomer CPP conjugate, or a pharmaceutically acceptable salt thereof, is administered at a dose effective to provide the mean AUC is between about 130 and about 180 ug·h/mL, between about 140 and about 180 ug·h/mL, between about 150 and about 180 ug·h/mL, between about 160 and about 180 ug·h/mL, or between about 170 and about 180 ug·h/mL.

In some aspects, the antisense oligomer CPP conjugate, or a pharmaceutically acceptable salt thereof, is administered at a dose effective to provide the mean AUC is between about 130 and about 170 ug·h/mL, between about 140 and about 170 ug·h/mL, between about 150 and about 170 ug·h/mL, or between about 160 and about 170 ug·h/mL.

In some aspects, the antisense oligomer CPP conjugate, or a pharmaceutically acceptable salt thereof, is administered at a dose effective to provide the mean AUC is between about 130 and about 160 ug·h/mL, between about 140 and about 160 ug·h/mL, or between about 150 and about 160 ug·h/mL.

In some aspects, the antisense oligomer CPP conjugate, or a pharmaceutically acceptable salt thereof, is administered at a dose effective to provide the mean AUC is between about 130 and about 150 ug·h/mL, or between about 140 and about 150 ug·h/mL.

In some aspects, the antisense oligomer CPP conjugate, or a pharmaceutically acceptable salt thereof, is administered at a dose effective to provide the mean AUC is between about 140 and about 240 ug·h/mL, between about 140 and about 230 ug·h/mL, between about 140 and about 220 ug·h/mL, between about 140 and about 210 ug·h/mL, between about 140 and about 200 ug·h/mL, between about 140 and about 190 ug·h/mL, between about 140 and about 180 ug·h/mL, between about 140 and about 170 ug·h/mL, between about 140 and about 160 ug·h/mL, or between about 140 and about 150 ug·h/mL.

In some aspects, the antisense oligomer CPP conjugate, or a pharmaceutically acceptable salt thereof, is administered at a dose effective to provide the mean AUC is between about 150 and about 240 ug·h/mL, between about 150 and about 230 ug·h/mL, between about 150 and about 220 ug·h/mL, between about 150 and about 210 ug·h/mL, between about 150 and about 200 ug·h/mL, between about 150 and about 190 ug·h/mL, between about 150 and about 180 ug·h/mL, between about 150 and about 170 ug·h/mL, or between about 150 and about 160 ug·h/mL.

In some aspects, the antisense oligomer CPP conjugate, or a pharmaceutically acceptable salt thereof, is administered at a dose effective to provide the mean AUC is between about 160 and about 240 ug·h/mL, between about 160 and about 230 ug·h/mL, between about 160 and about 220 ug·h/mL, between about 160 and about 210 ug·h/mL, between about 160 and about 200 ug·h/mL, between about 160 and about 200 ug·h/mL, between about 160 and about 180 ug·h/mL, or between about 160 and about 170 ug·h/mL.

In some aspects, the antisense oligomer CPP conjugate, or a pharmaceutically acceptable salt thereof, is administered at a dose effective to provide the mean AUC is between about 170 and about 240 ug·h/mL, between about 170 and about 230 ug·h/mL, between about 170 and about 220 ug·h/mL, between about 170 and about 210 ug·h/mL, between about 170 and about 200 ug·h/mL, between about 170 and about 190 ug·h/mL, or between about 170 and about 180 ug·h/mL.

In some aspects, the antisense oligomer CPP conjugate, or a pharmaceutically acceptable salt thereof, is administered at a dose effective to provide the mean AUC is between about 180 and about 240 ug·h/mL, between about 180 and about 230 ug·h/mL, between about 180 and about 220 ug·h/mL, or between about 180 and about 210 ug·h/mL, between about 180 and about 200 ug·h/mL, or between about 180 and about 190 ug·h/mL.

In some aspects, the antisense oligomer CPP conjugate, or a pharmaceutically acceptable salt thereof, is administered at a dose effective to provide the mean AUC is between about 190 and about 240 ug·h/mL, between about 190 and about 230 ug·h/mL, between about 190 and about 220 ug·h/mL, between about 190 and about 210 ug·h/mL, or between about 190 and about 200 ug·h/mL.

In some aspects, the antisense oligomer CPP conjugate, or a pharmaceutically acceptable salt thereof, is administered at a dose effective to provide the mean AUC is between about 200 and about 240 ug·h/mL, between about 200 and about 230 ug·h/mL, between about 200 and about 220 ug·h/mL, or between about 200 and about 210 ug·h/mL.

In some aspects, the antisense oligomer CPP conjugate, or a pharmaceutically acceptable salt thereof, is administered at a dose effective to provide the mean AUC is between about 210 and about 240 ug·h/mL, between about 210 and about 230 ug·h/mL, or between about 210 and about 220 ug·h/mL.

In some aspects, the antisense oligomer CPP conjugate, or a pharmaceutically acceptable salt thereof, is administered at a dose effective to provide the mean AUC is between about 200 and about 500 ug·h/mL, between about 200 and about 490 ug·h/mL, between about 200 and about 480 ug·h/mL, between about 200 and about 470 ug·h/mL, between about 200 and about 460 ug·h/mL, between about 200 and about 450 ug·h/mL, between about 200 and about 440 ug·h/mL, between about 200 and about 430 ug·h/mL, between about 200 and about 420 ug·h/mL, between about 200 and about 410 ug·h/mL, between about 200 and about 400 ug·h/mL, between about 200 and about 390 ug·h/mL, between about 200 and about 380 ug·h/mL, between about 200 and about 370 ug·h/mL, between about 200 and about 360 ug·h/mL, between about 200 and about 350 ug·h/mL, between about 200 and about 340 ug·h/mL, between about 200 and about 330 ug·h/mL, between about 200 and about 320 ug·h/mL, between about 200 and about 310 ug·h/mL, between about 200 and about 300 ug·h/mL, between about 200 and about 290 ug·h/mL, between about 200 and about 280 ug·h/mL, between about 200 and about 270 ug·h/mL, between about 200 and about 260 ug·h/mL, between about 200 and about 250 ug·h/mL, between about 200 and about 240 ug·h/mL, between about 200 and about 230 ug·h/mL, between about 200 and about 220 ug·h/mL, or between about 200 and about 210 ug·h/mL.

In some aspects, the antisense oligomer CPP conjugate, or a pharmaceutically acceptable salt thereof, is administered at a dose effective to provide the mean AUC is between about 210 and about 500 ug·h/mL, between about 210 and about 490 ug·h/mL, between about 210 and about 480 ug·h/mL, between about 210 and about 470 ug·h/mL, between about 210 and about 460 ug·h/mL, between about 210 and about 450 ug·h/mL, between about 210 and about 440 ug·h/mL, between about 210 and about 430 ug·h/mL, between about 210 and about 420 ug·h/mL, between about 210 and about 410 ug·h/mL, between about 210 and about 400 ug·h/mL, between about 210 and about 390 ug·h/mL, between about 210 and about 380 ug·h/mL, between about 210 and about 370 ug·h/mL, between about 210 and about 360 ug·h/mL, between about 210 and about 350 ug·h/mL, between about 210 and about 340 ug·h/mL, between about 210 and about 330 ug·h/mL, between about 210 and about 320 ug·h/mL, between about 210 and about 310 ug·h/mL, between about 210 and about 300 ug·h/mL, between about 210 and about 290 ug·h/mL, between about 210 and about 280 ug·h/mL, between about 210 and about 270 ug·h/mL, between about 210 and about 260 ug·h/mL, between about 210 and about 250 ug·h/mL, between about 210 and about 240 ug·h/mL, between about 210 and about 230 ug·h/mL, or between about 210 and about 220 ug·h/mL.

In some aspects, the antisense oligomer CPP conjugate, or a pharmaceutically acceptable salt thereof, is administered at a dose effective to provide the mean AUC of between about 220 and about 500 ug·h/mL, between about 220 and about 490 ug·h/mL, between about 220 and about 480 ug·h/mL, between about 220 and about 470 ug·h/mL, between about 220 and about 460 ug·h/mL, between about 220 and about 450 ug·h/mL, between about 220 and about 440 ug·h/mL, between about 220 and about 430 ug·h/mL, between about 220 and about 420 ug·h/mL, between about 220 and about 410 ug·h/mL, between about 220 and about 400 ug·h/mL, between about 220 and about 390 ug·h/mL, between about 220 and about 380 ug·h/mL, between about 220 and about 370 ug·h/mL, between about 220 and about 360 ug·h/mL, between about 220 and about 350 ug·h/mL, between about 220 and about 340 ug·h/mL, between about 220 and about 330 ug·h/mL, between about 220 and about 320 ug·h/mL, between about 220 and about 310 ug·h/mL, between about 220 and about 300 ug·h/mL, between about 220 and about 290 ug·h/mL, between about 220 and about 280 ug·h/mL, between about 220 and about 270 ug·h/mL, between about 220 and about 260 ug·h/mL, between about 220 and about 250 ug·h/mL, between about 220 and about 240 ug·h/mL, or between about 220 and about 230 ug·h/mL.

In some aspects, the antisense oligomer CPP conjugate, or a pharmaceutically acceptable salt thereof, is administered at a dose effective to provide the mean AUC of between about 230 and about 500 ug·h/mL, between about 230 and about 490 ug·h/mL, between about 230 and about 480 ug·h/mL, between about 230 and about 470 ug·h/mL, between about 230 and about 460 ug·h/mL, between about 230 and about 450 ug·h/mL, between about 230 and about 440 ug·h/mL, between about 230 and about 430 ug·h/mL, between about 230 and about 420 ug·h/mL, between about 230 and about 410 ug·h/mL, between about 230 and about 400 ug·h/mL, between about 230 and about 390 ug·h/mL, between about 230 and about 380 ug·h/mL, between about 230 and about 370 ug·h/mL, between about 230 and about 360 ug·h/mL, between about 230 and about 350 ug·h/mL, between about 230 and about 340 ug·h/mL, between about 230 and about 330 ug·h/mL, between about 230 and about 320 ug·h/mL, between about 230 and about 310 ug·h/mL, between about 230 and about 300 ug·h/mL, between about 230 and about 290 ug·h/mL, between about 230 and about 280 ug·h/mL, between about 230 and about 270 ug·h/mL, between about 230 and about 260 ug·h/mL, between about 230 and about 250 ug·h/mL, or between about 230 and about 240 ug·h/mL.

In some aspects, the antisense oligomer CPP conjugate, or a pharmaceutically acceptable salt thereof, is administered at a dose effective to provide the mean AUC of between about 240 and about 500 ug·h/mL, between about 240 and about 490 ug·h/mL, between about 240 and about 480 ug·h/mL, between about 240 and about 470 ug·h/mL, between about 240 and about 460 ug·h/mL, between about 240 and about 450 ug·h/mL, between about 240 and about 440 ug·h/mL, between about 240 and about 430 ug·h/mL, between about 240 and about 420 ug·h/mL, between about 240 and about 410 ug·h/mL, between about 240 and about 400 ug·h/mL, between about 240 and about 390 ug·h/mL, between about 240 and about 380 ug·h/mL, between about 240 and about 370 ug·h/mL, between about 240 and about 360 ug·h/mL, between about 240 and about 350 ug·h/mL, between about 240 and about 340 ug·h/mL, between about 240 and about 330 ug·h/mL, between about 240 and about 320 ug·h/mL, between about 240 and about 310 ug·h/mL, between about 240 and about 300 ug·h/mL, between about 240 and about 290 ug·h/mL, between about 240 and about 280 ug·h/mL, between about 240 and about 270 ug·h/mL, between about 240 and about 260 ug·h/mL, or between about 240 and about 250 ug·h/mL.

In some aspects, the antisense oligomer CPP conjugate, or a pharmaceutically acceptable salt thereof, is administered at a dose effective to provide the mean AUC of between about 300 and about 500 ug·h/mL, between about 300 and about 490 ug·h/mL, between about 300 and about 480 ug·h/mL, between about 300 and about 470 ug·h/mL, between about 300 and about 460 ug·h/mL, between about 300 and about 450 ug·h/mL, between about 300 and about 440 ug·h/mL, between about 300 and about 430 ug·h/mL, between about 300 and about 420 ug·h/mL, between about 300 and about 410 ug·h/mL, between about 300 and about 400 ug·h/mL, between about 300 and about 390 ug·h/mL, between about 300 and about 380 ug·h/mL, between about 300 and about 370 ug·h/mL, between about 300 and about 360 ug·h/mL, between about 300 and about 350 ug·h/mL, between about 300 and about 340 ug·h/mL, between about 300 and about 330 ug·h/mL, between about 300 and about 320 ug·h/mL, or between about 300 and about 310 ug·h/mL.

In some aspects, the antisense oligomer CPP conjugate, or a pharmaceutically acceptable salt thereof, is administered at a dose effective to provide the mean AUC of between about 325 and about 500 ug·h/mL, between about 325 and about 490 ug·h/mL, between about 325 and about 480 ug·h/mL, between about 325 and about 470 ug·h/mL, between about 325 and about 460 ug·h/mL, between about 325 and about 450 ug·h/mL, between about 325 and about 440 ug·h/mL, between about 325 and about 430 ug·h/mL, between about 325 and about 420 ug·h/mL, between about 325 and about 410 ug·h/mL, between about 325 and about 400 ug·h/mL, between about 325 and about 390 ug·h/mL, between about 325 and about 380 ug·h/mL, between about 325 and about 370 ug·h/mL, between about 325 and about 360 ug·h/mL, between about 325 and about 350 ug·h/mL, between about 325 and about 340 ug·h/mL, or between about 325 and about 330 ug·h/mL.

In some aspects, the antisense oligomer CPP conjugate, or a pharmaceutically acceptable salt thereof, is administered at a dose effective to provide the mean AUC of between about 330 and about 500 ug·h/mL, between about 330 and about 490 ug·h/mL, between about 330 and about 480 ug·h/mL, between about 330 and about 470 ug·h/mL, between about 330 and about 460 ug·h/mL, between about 330 and about 450 ug·h/mL, between about 330 and about 440 ug·h/mL, between about 330 and about 430 ug·h/mL, between about 330 and about 420 ug·h/mL, between about 330 and about 410 ug·h/mL, between about 330 and about 400 ug·h/mL, between about 330 and about 390 ug·h/mL, between about 330 and about 380 ug·h/mL, between about 330 and about 370 ug·h/mL, between about 330 and about 360 ug·h/mL, between about 330 and about 350 ug·h/mL, or between about 330 and about 340 ug·h/mL.

In some aspects, the antisense oligomer CPP conjugate, or a pharmaceutically acceptable salt thereof, is administered at a dose effective to provide the mean AUC of between about 335 and about 500 ug·h/mL, between about 335 and about 490 ug·h/mL, between about 335 and about 480 ug·h/mL, between about 335 and about 470 ug·h/mL, between about 335 and about 460 ug·h/mL, between about 335 and about 450 ug·h/mL, between about 335 and about 440 ug·h/mL, between about 335 and about 430 ug·h/mL, between about 335 and about 420 ug·h/mL, between about 335 and about 410 ug·h/mL, between about 335 and about 400 ug·h/mL, between about 335 and about 390 ug·h/mL, between about 335 and about 380 ug·h/mL, between about 335 and about 370 ug·h/mL, between about 335 and about 360 ug·h/mL, between about 335 and about 350 ug·h/mL, or between about 335 and about 340 ug·h/mL.

In some aspects, the antisense oligomer CPP conjugate, or a pharmaceutically acceptable salt thereof, is administered at a dose effective to provide the mean AUC of between about 340 and about 500 ug·h/mL, between about 340 and about 490 ug·h/mL, between about 340 and about 480 ug·h/mL, between about 340 and about 470 ug·h/mL, between about 340 and about 460 ug·h/mL, between about 340 and about 450 ug·h/mL, between about 340 and about 440 ug·h/mL, between about 340 and about 430 ug·h/mL, between about 340 and about 420 ug·h/mL, between about 340 and about 410 ug·h/mL, between about 340 and about 400 ug·h/mL, between about 340 and about 390 ug·h/mL, between about 340 and about 380 ug·h/mL, between about 340 and about 370 ug·h/mL, between about 340 and about 360 ug·h/mL, or between about 340 and about 350 ug·h/mL.

In some aspects, the antisense oligomer CPP conjugate, or a pharmaceutically acceptable salt thereof, is administered at a dose effective to provide a mean AUC of about 100 ug·h/mL, about 110 ug·h/mL, about 120 ug·h/mL, about 130 ug·h/mL, about 140 ug·h/mL, about 150 ug·h/mL, about 160 ug·h/mL, about 170 ug·h/mL, about 171 ug·h/mL, about 175 ug·h/mL, about 178 ug·h/mL, about 180 ug·h/mL, about 190 ug·h/mL, about 200 ug·h/mL, about 210 ug·h/mL, about 220 ug·h/mL, about 230 ug·h/mL, about 240 ug·h/mL, about 250 ug·h/mL, about 260 ug·h/mL, about 270 ug·h/mL, about 280 ug·h/mL, about 290 ug·h/mL, about 296 ug·h/mL, about 298 ug·h/mL, about 300 ug·h/mL, about 310 ug·h/mL, about 320 ug·h/mL, about 330 ug·h/mL, about 340 ug·h/mL, about 350 ug·h/mL, about 360 ug·h/mL, about 370 ug·h/mL, about 380 ug·h/mL, about 390 ug·h/mL, about 400 ug·h/mL, about 410 ug·h/mL, about 420 ug·h/mL, about 430 ug·h/mL, about 450 ug·h/mL, about 460 ug·h/mL, about 470 ug·h/mL, about 480 ug·h/mL, about 490 ug·h/mL, or about 500 ug·h/mL.

In some aspects, the antisense oligomer CPP conjugate, or a pharmaceutically acceptable salt thereof, is administered at a dose effective to provide a targeted mean $C_{max}$ of the conjugate, or a pharmaceutically acceptable salt thereof, so as to maximize dystrophin expression and minimize hypomagnesemia in a patient.

In some aspects, the antisense oligomer CPP conjugate, or a pharmaceutically acceptable salt thereof, is administered at a dose effective to provide the mean $C_{max}$ of the conjugate, or a pharmaceutically acceptable salt thereof, of between about 70 and about 150 ug/ml, between about 70 and about 140 ug/ml, between about 70 and about 130 ug/ml, between about 70 and about 120 ug/ml, between about 70 and about 110 ug/ml, between about 70 and about 100 ug/ml, between about 70 and about 90 ug/ml, or between about 70 and about 80 ug/ml.

In some aspects, the antisense oligomer CPP conjugate, or a pharmaceutically acceptable salt thereof, is administered at a dose effective to provide the mean $C_{max}$ of the conjugate, or a pharmaceutically acceptable salt thereof, of between about 75 and about 150 ug/ml, between about 75 and about 140 ug/ml, between about 75 and about 130 ug/ml, between about 75 and about 120 ug/ml, between about 75 and about 110 ug/ml, between about 75 and about 100 ug/ml, between about 75 and about 90 ug/ml, or between about 75 and about 80 ug/ml.

In some aspects, the antisense oligomer CPP conjugate, or a pharmaceutically acceptable salt thereof, is administered at a dose effective to provide the mean $C_{max}$ of the conjugate, or a pharmaceutically acceptable salt thereof, of between about 80 and about 150 ug/ml, between about 80 and about 140 ug/ml, between about 80 and about 130 ug/ml, between about 80 and about 120 ug/ml, between about 80 and about 110 ug/ml, between about 80 and about 100 ug/ml, or between about 80 and about 90 ug/ml.

In some aspects, the antisense oligomer CPP conjugate, or a pharmaceutically acceptable salt thereof, is administered at a dose effective to provide the mean $C_{max}$ of the conjugate, or a pharmaceutically acceptable salt thereof, of between about 85 and about 150 ug/ml, between about 85 and about 140 ug/ml, between about 85 and about 130 ug/ml, between about 85 and about 120 ug/ml, between about 85 and about 110 ug/ml, between about 85 and about 100 ug/ml, or between about 85 and about 90 ug/ml.

In some aspects, the antisense oligomer CPP conjugate, or a pharmaceutically acceptable salt thereof, is administered at a dose effective to provide the mean $C_{max}$ of the conjugate, or a pharmaceutically acceptable salt thereof, of between about 90 and about 150 ug/ml, between about 90 and about 140 ug/ml, between about 90 and about 130 ug/ml, between about 90 and about 120 ug/ml, between about 90 and about 110 ug/ml, or between about 90 and about 100 ug/ml.

In some aspects, the antisense oligomer CPP conjugate, or a pharmaceutically acceptable salt thereof, is administered at a dose effective to provide the mean $C_{max}$ of the conjugate, or a pharmaceutically acceptable salt thereof, of between about 95 and about 150 ug/ml, between about 95 and about 140 ug/ml, between about 95 and about 130 ug/ml, between about 95 and about 120 ug/ml, between about 95 and about 110 ug/ml, or between about 95 and about 100 ug/ml.

In some aspects, the antisense oligomer CPP conjugate, or a pharmaceutically acceptable salt thereof, is administered at a dose effective to provide the mean $C_{max}$ of the conjugate, or a pharmaceutically acceptable salt thereof, of between about 100 and about 150 ug/ml, between about 100 and about 140 ug/ml, between about 100 and about 130 ug/ml, between about 100 and about 120 ug/ml, or between about 100 and about 110 ug/ml.

In some aspects, the antisense oligomer CPP conjugate, or a pharmaceutically acceptable salt thereof, is administered at a dose effective to provide the mean $C_{max}$ of the conjugate, or a pharmaceutically acceptable salt thereof, of between about 130 and about 250 ug/ml, between about 140 and about 250 ug/ml, between about 150 and about 250 ug/ml, between about 160 and about 250 ug/ml, between about 170 and about 250 ug/ml, between about 180 and about 250 ug/ml, between about 190 and about 250 ug/ml, between about 200 and about 250 ug/ml, between about 210 and about 250 ug/ml, between about 220 and about 250 ug/ml, between about 230 and about 250 ug/ml, or between about 240 and about 250 ug/ml.

In some aspects, the antisense oligomer CPP conjugate, or a pharmaceutically acceptable salt thereof, is administered at a dose effective to provide the mean $C_{max}$ of the conjugate, or a pharmaceutically acceptable salt thereof, of between about 130 and about 200 ug/ml, between about 140 and about 200 ug/ml, between about 150 and about 200 ug/ml, between about 160 and about 200 ug/ml, between about 170 and about 200 ug/ml, between about 180 and about 200 ug/ml, or between about 190 and about 200 ug/ml.

In some aspects, the antisense oligomer CPP conjugate, or a pharmaceutically acceptable salt thereof, is administered at a dose effective to provide the mean $C_{max}$ of the conjugate, or a pharmaceutically acceptable salt thereof, of between about 130 and about 190 ug/ml, between about 140 and about 190 ug/ml, between about 150 and about 190 ug/ml, between about 160 and about 190 ug/ml, between about 170 and about 190 ug/ml, or between about 180 and about 190 ug/ml.

In some aspects, the antisense oligomer CPP conjugate, or a pharmaceutically acceptable salt thereof, is administered at a dose effective to provide the mean $C_{max}$ of the conjugate, or a pharmaceutically acceptable salt thereof, of between about 130 and about 180 ug/ml, between about 140 and about 180 ug/ml, between about 150 and about 180 ug/ml, between about 160 and about 180 ug/ml, or between about 170 and about 180 ug/ml. In some aspects, the antisense oligomer CPP conjugate, or a pharmaceutically acceptable salt thereof, is administered at a dose effective to provide the mean $C_{max}$ of the conjugate, or a pharmaceutically acceptable salt thereof, of between about 130 and about 170 ug/ml, between about 140 and about 170 ug/ml, between about 150 and about 170 ug/ml, or between about 160 and about 170 ug/ml.

In some aspects, the antisense oligomer conjugate, or a pharmaceutically acceptable salt thereof, is administered at a dose effective to provide the mean $C_{max}$ of the conjugate, or a pharmaceutically acceptable salt thereof, of about 80 ug/ml, about 85 ug/ml, about 90 ug/ml, about 95 ug/ml, about 100 ug/ml, about 105 ug/ml, about 110 ug/ml, about 115 ug/ml, about 120 ug/ml, about 125 ug/ml, about 130 ug/ml, about 135 ug/ml, about 140 ug/ml, about 145 ug/ml, about 150 ug/ml, about 155 ug/ml, about 160 ug/ml, about 165 ug/ml, about 170 ug/ml, about 175 ug/ml, about 180 ug/ml, about 185 ug/ml, about 190 ug/ml, about 195 ug/ml, about 200 ug/ml, about 205 ug/ml, about 210 ug/ml, about 215 ug/ml, about 220 ug/ml, about 225 ug/ml, about 230 ug/ml, about 235 ug/ml, about 240 ug/ml, about 245 ug/ml, or about 250 ug/ml.

In some aspects, the antisense oligomer conjugate, or a pharmaceutically acceptable salt thereof, is administered at a dose of about 300 mg to about 900 mg, about 300 mg to about 850 mg, about 300 mg to about 800 mg, about 300 mg to about 850 mg, about 300 mg to about 800 mg, about 300 mg to about 750 mg, about 300 mg to about 700 mg, about 300 mg to about 650 mg, about 300 mg to about 600 mg, about 300 mg to about 550 mg, about 300 mg to about 500 mg, about 300 mg to about 450 mg, about 300 mg to about 400 mg, or about 300 mg.

In some aspects, the antisense oligomer conjugate, or a pharmaceutically acceptable salt thereof, is administered at a dose equivalent to the dose of the ·6HCl salt of the conjugate of about 300 mg to about 900 mg, about 300 mg to about 850 mg, about 300 mg to about 800 mg, about 300 mg to about 850 mg, about 300 mg to about 800 mg, about 300 mg to about 750 mg, about 300 mg to about 700 mg, about 300 mg to about 650 mg, about 300 mg to about 600 mg, about 300 mg to about 550 mg, about 300 mg to about 500 mg, about 300 mg to about 450 mg, about 300 mg to about 400 mg, or about 300 mg to about 350 mg.

In some aspects, the antisense oligomer conjugate, or a pharmaceutically acceptable salt thereof, is administered at a dose equivalent to the dose of the ·6HCl salt of the conjugate of about 350 mg to about 900 mg, about 400 mg to about 900 mg, about 500 mg to about 900 mg, about 550 mg to about 900 mg, about 600 mg to about 800 mg, about 650 mg to about 900 mg, about 700 mg to about 900 mg, about 750 mg to about 900 mg, about 800 mg to about 900 mg, or about 850 mg to about 900 mg.

In some aspects, the antisense oligomer conjugate, or a pharmaceutically acceptable salt thereof, is administered at a dose equivalent to the dose of the ·6HCl salt of the conjugate of about 350 mg to about 850 mg, about 400 mg to about 850 mg, about 500 mg to about 850 mg, about 550 mg to about 850 mg, about 600 mg to about 800 mg, about 650 mg to about 850 mg, about 700 mg to about 850 mg, about 750 mg to about 850 mg, or about 800 mg to about 850 mg.

In some aspects, the antisense oligomer conjugate, or a pharmaceutically acceptable salt thereof, is administered at a dose equivalent to the dose of the ·6HCl salt of the conjugate of about 350 mg to about 800 mg, about 400 mg to about 800 mg, about 500 mg to about 800 mg, about 550 mg to about 800 mg, about 600 mg to about 800 mg, about 650 mg to about 800 mg, about 700 mg to about 800 mg, or about 750 mg to about 800 mg.

In some aspects, the antisense oligomer conjugate, or a pharmaceutically acceptable salt thereof, is administered at a dose equivalent to the dose of the ·6HCl salt of the conjugate of about 350 mg to about 750 mg, about 400 mg to about 750 mg, about 500 mg to about 750 mg, about 550 mg to about 750 mg, about 600 mg to about 750 mg, about 650 mg to about 750 mg, or about 700 mg to about 750 mg.

In some aspects, the antisense oligomer conjugate, or a pharmaceutically acceptable salt thereof, is administered at a dose equivalent to the dose of the ·6HCl salt of the conjugate of about 350 mg to about 700 mg, about 400 mg to about 700 mg, about 500 mg to about 700 mg, about 550 mg to about 700 mg, about 600 mg to about 700 mg, or about 650 mg to about 700 mg.

In some aspects, the antisense oligomer conjugate, or a pharmaceutically acceptable salt thereof, is administered at a dose equivalent to the dose of the ·6HCl salt of the conjugate of about 400 mg to about 900 mg, about 400 mg to about 850 mg, about 400 mg to about 800 mg, about 400 mg to about 750 mg, about 400 mg to about 700 mg, about 400 mg to about 650 mg, about 400 mg to about 600 mg, about 400 mg to about 550 mg, about 400 mg to about 500 mg, or about 400 mg to about 450 mg.

In some aspects, the antisense oligomer conjugate, or a pharmaceutically acceptable salt thereof, is administered at a dose equivalent to the dose of the ·6HCl salt of the conjugate of about 950 mg to about 1500 mg, about 900 mg to about 1500 mg, about 850 mg to about 1500 mg, or about 800 mg to about 1500 mg.

In some aspects, the antisense oligomer conjugate, or a pharmaceutically acceptable salt thereof, is administered at a dose equivalent to the dose of the ·6HCl salt of the conjugate of about 950 mg to about 1450 mg, about 900 mg to about 1450 mg, about 850 mg to about 1450 mg, or about 800 mg to about 1450 mg.

In some aspects, the antisense oligomer conjugate, or a pharmaceutically acceptable salt thereof, is administered at a dose equivalent to the dose of the ·6HCl salt of the conjugate of about 950 mg to about 1400 mg, about 900 mg to about 1400 mg, about 850 mg to about 1400 mg, or about 800 mg to about 1400 mg.

In some aspects, the antisense oligomer conjugate, or a pharmaceutically acceptable salt thereof, is administered at a dose equivalent to the dose of the ·6HCl salt of the conjugate of about 950 mg to about 1350 mg, about 900 mg to about 1350 mg, about 850 mg to about 1350 mg, or about 800 mg to about 1350 mg.

In some aspects, the antisense oligomer conjugate, or a pharmaceutically acceptable salt thereof, is administered at a dose equivalent to the dose of the ·6HCl salt of the conjugate of about 950 mg to about 1300 mg, about 900 mg to about 1300 mg, about 850 mg to about 1300 mg, or about 800 mg to about 1300 mg.

In some aspects, the antisense oligomer conjugate, or a pharmaceutically acceptable salt thereof, is administered at a dose equivalent to the dose of the ·6HCl salt of the conjugate of about 950 mg to about 1250 mg, about 900 mg to about 1250 mg, about 850 mg to about 1250 mg, or about 800 mg to about 1250 mg.

In some aspects, the antisense oligomer conjugate, or a pharmaceutically acceptable salt thereof, is administered at a dose equivalent to the dose of the ·6HCl salt of the conjugate of about 950 mg to about 1200 mg, about 900 mg to about 1200 mg, about 850 mg to about 1200 mg, about 800 mg to about 1200 mg, about 900 mg to about 1100 mg, about 900 mg to about 1000 mg, about 800 mg to about 1100 mg, about 800 mg to about 1000 mg.

In some aspects, the antisense oligomer conjugate, or a pharmaceutically acceptable salt thereof, is administered at a dose equivalent to the dose of the ·6HCl salt of the conjugate of about 1000 mg to about 1500 mg, about 1000 mg to about 1450 mg, about 1000 mg to about 1400 mg, about 1000 mg to about 1350 mg, about 1000 mg to about 1300 mg, about 1000 mg to about 1250 mg, about 1000 mg to about 1200 mg, about 1000 mg to about 1150 mg, or about 1000 mg to about 1100 mg.

In some aspects, the antisense oligomer conjugate, or a pharmaceutically acceptable salt thereof, is administered at a dose equivalent to about 300 mg, about 350 mg, about 400 mg, about 450 mg, about 500 mg, about 550 mg, about 600 mg, about 650 mg, about 700 mg, about 750 mg, about 800 mg, about 850 mg, or about 900 mg of the ·6HCl salt of the conjugate.

In some aspects, the antisense oligomer conjugate, or a pharmaceutically acceptable salt thereof, is administered at a dose equivalent to about 950 mg, about 1000 mg, about 1050 mg, about 1100 mg, about 1150 mg, about 1200 mg, about 1250 mg, about 1300 mg, about 1350 mg, about 1400 mg, about 1450 mg, or about 1500 mg of the ·6HCl salt of the conjugate.

In some aspects, the antisense oligomer conjugate, or a pharmaceutically acceptable salt thereof, is administered according to patient weight. The following weight bands are contemplated by the present disclosure: from about 5 kg to about 25 kg, from about 10 kg to about 25 kg, from about 15 kg to about 25 kg, from about 20 kg to about 25 kg, from about 18 kg to about 50 kg, from about 25 kg to about 50 kg, from about 30 kg to about 50 kg, from about 35 kg to about 50 kg, from about 40 kg to about 50 kg, from about 50 kg to about 100 kg, from about 55 kg to about 100 kg, from about 60 kg to about 100 kg, from about 65 kg to about 100 kg, from about 70 kg to about 100 kg, from about 75 kg to about 100 kg, from about 80 kg to about 100 kg, from about 85 kg to about 100 kg, from about 90 kg to about 100 kg, from about 50 kg to about 90 kg, from about 55 kg to about 90 kg, from about 60 kg to about 90 kg, from about 65 kg to about 90 kg, from about 70 kg to about 90 kg, from about 75 kg to about 90 kg, from about 80 kg to about 90 kg, or from about 85 kg to about 90 kg.

The following weight bands are also contemplated by the present disclosure: from greater than or equal to 5 kg to less than 25 kg, from greater than or equal to 10 kg to less than 25 kg, from greater than or equal to 15 kg to less than 25 kg, from greater than or equal to 20 kg to less than 25 kg, from greater than or equal to 18 kg to less than 50 kg, from greater than or equal to 25 kg to less than 50 kg, from greater than or equal to 30 kg to less than 50 kg, from greater than or equal to 35 kg to less than 50 kg, from greater than or equal to 40 kg to less than 50 kg, greater than or equal to 50 kg, from greater than or equal to 50 kg to less than 100 kg, from greater than or equal to 55 kg to less than 100 kg, from greater than or equal to 60 kg to less than 100 kg, from greater than or equal to 65 kg to less than 100 kg, from greater than or equal to 70 kg to less than 100 kg, from greater than or equal to 75 kg to less than 100 kg, from greater than or equal to 80 kg to less than 100 kg, from greater than or equal to 85 kg to less than 100 kg, from greater than or equal to 90 kg to less than 100 kg, greater than or equal to 50 kg to less than 90 kg, from greater than or equal to 55 kg to less than 90 kg, from greater than or equal to 60 kg to less than 90 kg, from greater than or equal to 65 kg to less than 90 kg, from greater than or equal to 70 kg to less than 90 kg, from greater than or equal to 75 kg to less than 90 kg, from greater than or equal to 80 kg to less than 90 kg, or from greater than or equal to 85 kg to less than 90 kg.

The following weight bands are also contemplated by the present disclosure: from about 5 kg to about 20 kg, from about 10 kg to about 20 kg, from about 15 kg to about 20 kg, from about 25 kg to about 40 kg, from about 30 kg to about 40 kg, from about 35 kg to about 40 kg, from about 18 kg to about 50 kg, from about 50 kg to about 90 kg, from about 55 kg to about 90 kg, from about 60 kg to about 90 kg, from about 65 kg to about 90 kg, from about 70 kg to about 90 kg, from about 75 kg to about 90 kg, from about 80 kg to about 90 kg, or from about 85 kg to about 90 kg.

The following weight bands are also contemplated by the present disclosure: from greater than or equal to 5 kg to less than 20 kg, from greater than or equal to 10 kg to less than 20 kg, from greater than or equal to 15 kg to less than 20 kg, from greater than or equal to 25 kg to less than 40 kg, from greater than or equal to 30 kg to less than 40 kg, from greater than or equal to 35 kg to less than 40 kg, from greater than or equal to 50 kg to less than 90 kg, from greater than or equal to 55 kg to less than 90 kg, from greater than or equal to 60 kg to less than 90 kg, from greater than or equal to 65 kg to less than 90 kg, from greater than or equal to 70 kg to less than 90 kg, from greater than or equal to 75 kg to less than 90 kg, from greater than or equal to 80 kg to less than 90 kg, or from greater than or equal to 85 kg to less than 90 kg.

The following weight bands are also contemplated by the present disclosure: from about 5 kg to about 15 kg, from about 10 kg to about 15 kg, from about 25 kg to about 30 kg, from about 30 kg to about 35 kg, from about 30 kg to about 45 kg, from about 50 kg to about 85 kg, from about 55 kg to about 85 kg, from about 60 kg to about 85 kg, from about 65 kg to about 85 kg, from about 70 kg to about 85 kg, from about 75 kg to about 85 kg, from about 50 kg to about 75 kg, from about 55 kg to about 75 kg, from about 60 kg to about 75 kg, from about 65 kg to about 75 kg, from about 70 kg to about 75 kg or from about 80 kg to about 85 kg.

The following weight bands are also contemplated by the present disclosure: from greater than or equal to 5 kg to less than 15 kg, from greater than or equal to 10 kg to less than 15 kg, from greater than or equal to 25 kg to less than 30 kg, from greater than or equal to 30 kg to less than 35 kg, from greater than or equal to 30 kg to less than 45 kg, from greater than or equal to 50 kg to less than 85 kg, from greater than or equal to 55 kg to less than 85 kg, from greater than or equal to 60 kg to less than 85 kg, from greater than or equal to 65 kg to less than 85 kg, from greater than or equal to 70 kg to less than 85 kg, from greater than or equal to 75 kg to less than 85 kg, from greater than or equal to 50 kg to less than 75 kg, from greater than or equal to 55 kg to less than 75 kg, from greater than or equal to 60 kg to less than 75 kg, from greater than or equal to 65 kg to less than 75 kg, from greater than or equal to 70 kg to less than 75 kg or from greater than or equal to 80 kg to less than 85 kg.

The following weight bands are also contemplated by the present disclosure: from about 10 kg to about 50 kg, from about 10 kg to about 45 kg, from about 10 kg to about 40 kg, from about 10 kg to about 35 kg, from about 15 kg to about 50 kg, from about 15 kg to about 45 kg, from about 15 kg to about 40 kg, from about 15 kg to about 35 kg, from about 20 kg to about 50 kg, from about 20 kg to about 45 kg, from about 20 kg to about 40 kg, from about 20 kg to about 35 kg, from about 25 kg to about 50 kg, from about 25 kg to about 45 kg, from about 25 kg to about 40 kg, or from about 25 kg to about 35 kg.

The following weight bands are also contemplated by the present disclosure: from greater than or equal to 10 kg to less than 50 kg, from greater than or equal to 10 kg to less than 45 kg, from greater than or equal to 10 kg to less than 40 kg, from greater than or equal to 10 kg to less than 35 kg, from greater than or equal to 15 kg to less than 50 kg, from greater than or equal to 15 kg to less than 45 kg, from greater than or equal to 15 kg to less than 40 kg, from greater than or equal to 15 kg to less than 35 kg, from greater than or equal to 20 kg to less than 50 kg, from greater than or equal to 20 kg to less than 45 kg, from greater than or equal to 20 kg to less than 40 kg, from greater than or equal to 20 kg to less than 35 kg, from greater than or equal to 25 kg to less than 50 kg, from greater than or equal to 25 kg to less than 45 kg, from greater than or equal to 25 kg to less than 40 kg, or from greater than or equal to 25 kg to less than 35 kg.

The following weight bands are also contemplated by the present disclosure: from about 20 kg to about 110 kg, from about 30 kg to about 110 kg, from about 40 kg to about 110 kg, from about 50 kg to about 110 kg, from about 60 kg to about 110 kg, from about 20 kg to about 100 kg, from about 30 kg to about 100 kg, from about 40 kg to about 100 kg, from about 50 kg to about 100 kg, from about 60 kg to about 100 kg, from about 20 kg to about 90 kg, from about 30 kg to about 90 kg, from about 40 kg to about 90 kg, from about 50 kg to about 90 kg, or from about 60 kg to about 90 kg.

The following weight bands are also contemplated by the present disclosure: from greater than or equal to 20 kg to less than 110 kg, from greater than or equal to 30 kg to less than 110 kg, from greater than or equal to 40 kg to less than 110 kg, from greater than or equal to 50 kg to less than 110 kg, from greater than or equal to 60 kg to less than 110 kg, from greater than or equal to 20 kg to less than 100 kg, from greater than or equal to 30 kg to less than 100 kg, from greater than or equal to 40 kg to less than 100 kg, from greater than or equal to 50 kg to less than 100 kg, from greater than or equal to 60 kg to less than 100 kg, from greater than or equal to 20 kg to less than 90 kg, from greater than or equal to 30 kg to less than 90 kg, from greater than or equal to 40 kg to less than 90 kg, from greater than or equal to 50 kg to less than 90 kg, or from greater than or equal to 60 kg to less than 90 kg.

In some aspects, the antisense oligomer conjugate, or a pharmaceutically acceptable salt thereof, is administered according to the weight bands at a dose effective to achieve a mean AUC of between about 100 and about 200 ug·h/mL in a patient within a particular weight band. In other aspects, the antisense oligomer conjugate, or a pharmaceutically acceptable salt thereof, is administered according to the weight bands at a dose effective to achieve a mean AUC of between about 120 and about 240 ug·h/mL in a patient within a particular weight band. In other aspects, the antisense oligomer conjugate, or a pharmaceutically acceptable salt thereof, is administered according to the weight bands at a dose effective to achieve a mean AUC of between about 200 and about 500 ug·h/mL in a patient within a particular weight band.

In some aspects, the antisense oligomer conjugate, or a pharmaceutically acceptable salt thereof, is administered at a dose equivalent to the dose of the ·6HCl salt of the conjugate according to the following schedule:
    vii) about 300 mg to about 700 mg, or about 900 mg to about 1200 mg, once every four weeks for a patient that weighs from about 10 kg to about 25 kg;
    viii) about 600 mg to about 800 mg, or about 1000 mg to about 1300 mg, once every four weeks for a patient that weighs from about 25 kg to about 50 kg; or
    ix) about 700 mg to about 900 mg, or about 1200 mg to about 1500 mg, once every four weeks for a patient that weighs from about 50 kg to about 100 kg;
to achieve a mean AUC between about 100 and about 200 ug·h/mL, or is between about 200 and about 500 ug·h/mL.

In some aspects, the antisense oligomer conjugate, or a pharmaceutically acceptable salt thereof, is administered at a dose equivalent to the dose of the ·6HCl salt of the conjugate according to the following schedule:
    x) about 500 mg to about 700 mg, or about 1000 mg to about 1200 mg, once every four weeks for a patient that weighs from about 15 kg to about 40 kg; or
    xi) about 600 mg to about 800 mg, or about 1100 mg to about 1400 mg, once every four weeks for a patient that weighs from about 40 kg to about 100 kg;
to achieve a mean AUC between about 100 and about 200 ug·h/mL, or is between about 200 and about 500 ug·h/mL.

In some aspects, the antisense oligomer conjugate, or a pharmaceutically acceptable salt thereof, is administered at a dose equivalent to the dose of the ·6HCl salt of the conjugate according to the following schedule:
    xii) about 750 mg to about 1250 mg, once every four weeks for a patient that weighs greater than or equal to about 18 kg to less than about 50 kg; or xiii) about 850 mg to about 1350 mg, once every four weeks for a patient that weighs greater than or equal to about 50 kg;

to achieve a mean AUC between about 120 and about 240 ug·h/mL, or between about 200 and about 500 ug·h/mL.

In some aspects, the antisense oligomer conjugate, or a pharmaceutically acceptable salt thereof, is administered to a patient that weighs from about 5 kg to about 25 kg, from about 10 kg to about 25 kg, from about 15 kg to about 25 kg, from about 20 kg to about 25 kg, 5 kg to about 20 kg, from about 10 kg to about 20 kg, or from about 15 kg to about 20 kg at a dose equivalent to the dose of the ·6HCl salt of the conjugate of from about 300 mg to about 750 mg, about 350 mg to about 750 mg, about 400 mg to about 750 mg, about 450 mg to about 750 mg, about 400 mg to about 750 mg, about 450 mg to about 750 mg, about 500 mg to about 750 mg, about 550 mg to about 750 mg, about 600 mg to about 750 mg, about 650 mg to about 750 mg, 300 mg to about 700 mg, about 350 mg to about 700 mg, about 400 mg to about 700 mg, about 450 mg to about 700 mg, about 400 mg to about 700 mg, about 450 mg to about 700 mg, about 500 mg to about 700 mg, about 550 mg to about 700 mg, about 600 mg to about 700 mg, about 650 mg to about 700 mg, about 300 mg to about 650 mg, about 350 mg to about 650 mg, about 400 mg to about 650 mg, about 450 mg to about 650 mg, about 500 mg to about 650 mg, about 550 mg to about 650 mg, or about 600 mg to about 650 mg.

In some aspects, the antisense oligomer conjugate, or a pharmaceutically acceptable salt thereof, is administered to a patient that weighs from about 25 kg to about 50 kg, from about 30 kg to about 50 kg, from about 35 kg to about 50 kg, from about 40 kg to about 50 kg, from about 25 kg to about 40 kg, from about 30 kg to about 40 kg, from about 35 kg to about 40 kg, from about 25 kg to about 30 kg, from about 30 kg to about 45 kg, from about 35 kg to about 45 kg, from about 40 kg to about 45 kg, from about 30 kg to about 35 kg, from about 35 kg to about 45 kg, from about 25 kg to about 45 kg, from about 25 kg to about 35 kg, or from about 35 kg to about 45 kg at a dose equivalent to the dose of the ·6HCl salt of the conjugate of from about 600 mg to about 800 mg, about 650 mg to about 800 mg, about 700 mg to about 800 mg, about 750 mg to about 800 mg, about 600 mg to about 750 mg, about 650 mg to about 750 mg, about 700 mg to about 750 mg, 600 mg to about 700 mg, or about 650 mg to about 700 mg.

In some aspects, the antisense oligomer conjugate, or a pharmaceutically acceptable salt thereof, is administered to a patient that weighs greater than or equal to about 18 kg to less than about 50 kg at a dose equivalent to the dose of the ·6HCl salt of the conjugate of from about 750 mg to about 1250 mg. In some aspects, the antisense oligomer conjugate, or a pharmaceutically acceptable salt thereof, is administered to a patient that weighs greater than about 50 kg, at a dose equivalent to the dose of the ·6HCl salt of the conjugate of from about 850 mg to about 1350 mg.

In some aspects, the antisense oligomer conjugate, or a pharmaceutically acceptable salt thereof, is administered to a patient that weighs from about 50 kg to about 100 kg, from about 55 kg to about 100 kg, from about 60 kg to about 100 kg, from about 65 kg to about 100 kg, from about 70 kg to about 100 kg, from about 75 kg to about 100 kg, from about 80 kg to about 100 kg, from about 85 kg to about 100 kg, or from about 90 kg to about 100 kg, from about 50 kg to about 90 kg, from about 55 kg to about 90 kg, from about 60 kg to about 90 kg, from about 65 kg to about 90 kg, from about 70 kg to about 90 kg, from about 75 kg to about 90 kg, from about 80 kg to about 90 kg, or from about 85 kg to about 90 kg at a dose equivalent to the dose of the ·6HCl salt of the conjugate of from about 700 mg to about 900 mg, about 750 mg to about 900 mg, about 800 mg to about 900 mg, or about 850 mg to about 900 mg, about 700 mg to about 850 mg, about 750 mg to about 850 mg, or about 800 mg to about 850 mg, about 700 mg to about 750 mg, about 750 mg to about 800 mg, about 750 mg to about 900 mg, or about 800 mg to about 900 mg.

In some aspects, the antisense oligomer conjugate, or a pharmaceutically acceptable salt thereof, is administered to a patient that weighs from about 5 kg to about 25 kg, from about 10 kg to about 25 kg, from about 15 kg to about 25 kg, from about 20 kg to about 25 kg, 5 kg to about 20 kg, from about 10 kg to about 20 kg, or from about 15 kg to about 20 kg at a dose equivalent to the dose of the ·6HCl salt of the conjugate of from about 900 mg to about 1200 mg, about 850 mg to about 1200 mg, about 800 mg to about 1200 mg, about 900 mg to about 1100 mg, about 900 mg to about 1000 mg, about 800 mg to about 1100 mg, or about 800 mg to about 1000 mg.

In some aspects, the antisense oligomer conjugate, or a pharmaceutically acceptable salt thereof, is administered to a patient that weighs from about 25 kg to about 50 kg, from about 30 kg to about 50 kg, from about 35 kg to about 50 kg, from about 40 kg to about 50 kg, from about 25 kg to about 40 kg, from about 30 kg to about 40 kg, from about 35 kg to about 40 kg, from about 25 kg to about 30 kg, from about 30 kg to about 45 kg, from about 35 kg to about 45 kg, from about 40 kg to about 45 kg, from about 30 kg to about 35 kg, from about 35 kg to about 45 kg, from about 25 kg to about 45 kg, from about 25 kg to about 35 kg, or from about 35 kg to about 45 kg at a dose equivalent to the dose of the ·6HCl salt of the conjugate of from about 1000 mg to about 1300 mg, about 1000 mg to about 1250 mg, about 1000 mg to about 1200 mg, about 1000 mg to about 1150 mg, about 1050 mg to about 1100 mg, about 1050 mg to about 1300 mg, about 1050 mg to about 1250 mg, about 1050 mg to about 1200 mg, about 1050 mg to about 1150 mg, about 1050 mg to about 1100 mg, about 1050 mg to about 1250, about 1100 mg to about 1250, about 1150 mg to about 1250, about 1200 mg to about 1250, or about 1250 mg to about 1300.

In some aspects, the antisense oligomer conjugate, or a pharmaceutically acceptable salt thereof, is administered to a patient that weighs from about 50 kg to about 100 kg, from about 55 kg to about 100 kg, from about 60 kg to about 100 kg, from about 65 kg to about 100 kg, from about 70 kg to about 100 kg, from about 75 kg to about 100 kg, from about 80 kg to about 100 kg, from about 85 kg to about 100 kg, or from about 90 kg to about 100 kg, from about 50 kg to about 90 kg, from about 55 kg to about 90 kg, from about 60 kg to about 90 kg, from about 65 kg to about 90 kg, from about 70 kg to about 90 kg, from about 75 kg to about 90 kg, from about 80 kg to about 90 kg, or from about 85 kg to about 90 kg at a dose equivalent to the dose of the ·6HCl salt of the conjugate of from about 1200 mg to about 1500 mg, 1000 mg to about 1500 mg, about 1000 mg to about 1450 mg, about 1000 mg to about 1400 mg, about 1000 mg to about 1350 mg, about 1000 mg to about 1300 mg, about 1000 mg to about 1250 mg, about 1200 mg to about 1450 mg, about 1200 mg to about 1400 mg, about 1200 mg to about 1350 mg, about 1200 mg to about 1300 mg, or about 1200 mg to about 1250 mg.

In some aspects, the antisense oligomer conjugate, or a pharmaceutically acceptable salt thereof, is administered to a patient that weighs from about 5 kg to about 25 kg, from about 10 kg to about 25 kg, from about 15 kg to about 25 kg, from about 20 kg to about 25 kg, 5 kg to about 20 kg, from about 10 kg to about 20 kg, or from about 15 kg to about 20 kg at a dose equivalent to the dose of the ·6HCl salt of the conjugate of about 550 mg, 600 mg, about 650 mg, or about 700 mg.

In some aspects, the antisense oligomer conjugate, or a pharmaceutically acceptable salt thereof, is administered to a patient that weighs from about 5 kg to about 25 kg, from about 10 kg to about 25 kg, from about 15 kg to about 25 kg, from about 20 kg to about 25 kg, 5 kg to about 20 kg, from about 10 kg to about 20 kg, or from about 15 kg to about 20 kg at a dose equivalent to the dose of the ·6HCl salt of the conjugate of about 1050 mg, 1100 mg, 1150 mg, or about 1200 mg.

In some aspects, the antisense oligomer conjugate, or a pharmaceutically acceptable salt thereof, is administered to a patient that weighs from about 25 kg to about 50 kg, from about 30 kg to about 50 kg, from about 35 kg to about 50 kg, from about 40 kg to about 50 kg, from about 25 kg to about 40 kg, from about 30 kg to about 40 kg, from about 35 kg to about 40 kg, from about 25 kg to about 30 kg, from about 30 kg to about 45 kg, from about 35 kg to about 45 kg, from about 40 kg to about 45 kg, from about 30 kg to about 35 kg, from about 35 kg to about 45 kg, from about 25 kg to about 45 kg, from about 25 kg to about 35 kg, or from about 35 kg to about 45 kg at a dose equivalent to the dose of the ·6HCl salt of the conjugate of about 600 mg, about 650 mg, about 700 mg, or about 700 mg.

In some aspects, the antisense oligomer conjugate, or a pharmaceutically acceptable salt thereof, is administered to a patient that weighs from about 25 kg to about 50 kg, from about 30 kg to about 50 kg, from about 35 kg to about 50 kg, from about 40 kg to about 50 kg, from about 25 kg to about 40 kg, from about 30 kg to about 40 kg, from about 35 kg to about 40 kg, from about 25 kg to about 30 kg, from about 30 kg to about 45 kg, from about 35 kg to about 45 kg, from about 40 kg to about 45 kg, from about 30 kg to about 35 kg, from about 35 kg to about 45 kg, from about 25 kg to about 45 kg, from about 25 kg to about 35 kg, or from about 35 kg to about 45 kg at a dose equivalent to the dose of the ·6HCl salt of the conjugate of about 1100 mg, about 1150 mg, about 1200 mg, about 1250 mg, or about 1300 mg.

In some aspects, the antisense oligomer conjugate, or a pharmaceutically acceptable salt thereof, is administered to a patient that weighs from about 50 kg to about 100 kg, from about 55 kg to about 100 kg, from about 60 kg to about 100 kg, from about 65 kg to about 100 kg, from about 70 kg to about 100 kg, from about 75 kg to about 100 kg, from about 80 kg to about 100 kg, from about 85 kg to about 100 kg, or from about 90 kg to about 100 kg, from about 50 kg to about 90 kg, from about 55 kg to about 90 kg, from about 60 kg to about 90 kg, from about 65 kg to about 90 kg, from about 70 kg to about 90 kg, from about 75 kg to about 90 kg, from about 80 kg to about 90 kg, or from about 85 kg to about 90 kg at a dose equivalent to the dose of the ·6HCl salt of the conjugate of about 700 mg, about 750 mg, about 800 mg, or about 850 mg.

In some aspects, the antisense oligomer conjugate, or a pharmaceutically acceptable salt thereof, is administered to a patient that weighs from about 50 kg to about 100 kg, from about 55 kg to about 100 kg, from about 60 kg to about 100 kg, from about 65 kg to about 100 kg, from about 70 kg to about 100 kg, from about 75 kg to about 100 kg, from about 80 kg to about 100 kg, from about 85 kg to about 100 kg, or from about 90 kg to about 100 kg, from about 50 kg to about 90 kg, from about 55 kg to about 90 kg, from about 60 kg to about 90 kg, from about 65 kg to about 90 kg, from about 70 kg to about 90 kg, from about 75 kg to about 90 kg, from about 80 kg to about 90 kg, or from about 85 kg to about 90 kg at a dose equivalent to the dose of the ·6HCl salt of the conjugate of about 1300 mg, about 1350 mg, about 1400 mg, about 1450 mg, about 1500 mg, or about 1550 mg.

In some aspects, the antisense oligomer conjugate, or a pharmaceutically acceptable salt thereof, is administered to a patient that weighs from about 80 kg to about 100 kg, from about 85 kg to about 100 kg, from about 90 kg to about 100 kg, from about 95 kg to about 100 kg, from about 80 kg to about 90 kg, from about 75 kg to about 90 kg, from about 75 kg to about 95 kg, from about 75 kg to about 80 kg, or from about 80 kg to about 90 kg, at a dose equivalent to the dose of the ·6HCl salt of the conjugate of about 700 mg, about 750 mg, about 800 mg, about 850 mg, about 900 mg, about 950 mg, or about 1100 mg.

In some aspects, the antisense oligomer conjugate, or a pharmaceutically acceptable salt thereof, is administered to a patient that weighs from about 80 kg to about 100 kg, from about 85 kg to about 100 kg, from about 90 kg to about 100 kg, from about 95 kg to about 100 kg, from about 80 kg to about 90 kg, from about 75 kg to about 90 kg, from about 75 kg to about 95 kg, from about 75 kg to about 80 kg, or from about 80 kg to about 90 kg, at a dose equivalent to the dose of the ·6HCl salt of the conjugate of about 1100 mg, about 1150 mg, about 1200 mg, about 1250 mg, about 1300 mg, about 1350 mg, or about 1400 mg.

In some aspects, the antisense oligomer conjugate, or a pharmaceutically acceptable salt thereof, is administered to a patient that weighs from more that about 45 kg, about 50 kg, about 55 kg, about 60 kg, or about 65 kg, at a dose equivalent to the dose of the ·6HCl salt of the conjugate of about 700 mg, about 750 mg, about 800 mg, about 850 mg, about 900 mg, about 950 mg, or about 1000 mg.

In some aspects, the antisense oligomer conjugate, or a pharmaceutically acceptable salt thereof, is administered to a patient that weighs from more that about 45 kg, about 50 kg, about 55 kg, about 60 kg, or about 65 kg, at a dose equivalent to the dose of the ·6HCl salt of the conjugate of about 1100 mg, about 1150 mg, about 1200 mg, about 1250 mg, about 1300 mg, about 1350 mg, about 1400 mg, or about 1450 mg.

If desired, the antisense oligomer conjugate, or a pharmaceutically acceptable salt thereof, may be administered as two, three, four, five, six or more sub-doses administered separately at appropriate intervals throughout the day, optionally, in unit dosage forms. In certain situations, dosing is one administration per day. In certain embodiments, dosing is one or more administration per every 2, 3, 4, 5, 6, 7, 8, 9, 10, 11, 12, 13, 14 days, or every 1, 2, 3, 4, 5, 6, 7, 8, 9, 10, 11, 12 weeks, or every 1, 2, 3, 4, 5, 6, 7, 8, 9, 10, 11, 12 months, as needed, to maintain the desired expression of a functional dystrophin protein. In certain embodiments, dosing is one or more administrations once every two weeks. In some embodiments, dosing is one administration once every two weeks. In various embodiments, dosing is one or more administrations every month. In certain embodiments, dosing is one administration every month.

Cell Penetrating Peptides (CPPs)

As described, cell-penetrating peptides (CPP), for example, an arginine-rich peptide transport moiety, have been shown to be effective in enhancing penetration of antisense oligomers into a cell and to cause exon skipping in different muscle groups in animal models.

Exemplary CPPs are provided in Table 1.

TABLE 1

Exemplary Carrier Peptide Sequences

| Name | Sequence (Amino to Carboxy Terminus or 5' to 3') |
| --- | --- |
| (RFF)$_3$; CP0407 | RFFRFFRFF-aa (SEQ ID NO: 89) |
| RTR | RTRTRFLRRT-aa (SEQ ID NO: 90) |
| RFFR | RFFRFFRFFR-aa (SEQ ID NO: 91) |
| KTR | KTRTKFLKKT-aa (SEQ ID NO: 92) |
| KFF | KFFKFFKFF-aa (SEQ ID NO: 93) |
| KFFK | KFFKFFKFFK-aa (SEQ ID NO: 94) |
| (RFF)$_2$ | RFFRFF-aa (SEQ ID NO: 95) |
| (RFF)$_2$R | RFFRFFR-aa (SEQ ID NO: 96) |
| RX | RXXRXXR-aa (SEQ ID NO: 97) |
| (RXR)$_4$; P007 | RXRRXRRXRRXR-aa (SEQ ID NO: 98) |
| Tat$_{47\_58}$ | YGRKKRRQRRR-aa (SEQ ID NO: 99) |
| Tat$_{48\_58}$ | GRKKRRQRRR-aa (SEQ ID NO: 100) |
| Tat$_{49\_58}$ | RKKRRQRRR-aa (SEQ ID NO: 101) |
| Penetratin | RQIKIWFQNRRMKWKKGG-aa (SEQ ID NO: 102) |
| Transportan | GWTLNSAGYLLGKINLKALAALAKKIL-aa (SEQ ID NO: 103) |
| 2XHph-1 | YARVRRRGPRGYARVRRRGPRR-aa (SEQ ID NO: 104) |
| Hph-1 | YARVRRRGPRR-aa (SEQ ID NO: 105) |
| Sim-2 | AKAARQAAR-aa (SEQ ID NO: 106) |
| HSV1 VP22 | DAATATRGRSAASRPTERPRAPARSASRPRRPVE-aa (SEQ ID NO: 107) |
| Pep-1 | KETWWETWWTEWSQPKKKRKV-aa (SEQ ID NO: 108) |
| Pep-2 | KETWFETWFTEWSQPKKKRKV-aa (SEQ ID NO: 109) |
| ANTP | RQIKIWFQNRRMKWKK-aa (SEQ ID NO: 110) |
| R$_6$Pen | RRRRRR-RQIKIWFQNRRMKWKKGG-aa (SEQ ID NO: 111) |
| rTat | RRRQRRKKRC-aa (SEQ ID NO: 112) |
| pTat | CYGRKKRRQRRR-aa (SEQ ID NO: 113) |
| R$_9$F$_2$ | RRRRRRRRRFFC-aa (SEQ ID NO: 114) |
| R$_9$CF$_2$, RRRRRRRRRCFF | RRRRRRRRRCFF-aa (SEQ ID NO: 115) |
| R$_8$CF$_2$R | RRRRRRRRCFFR-aa (SEQ ID NO: 116) |
| R$_6$CF$_2$R$_3$ | RRRRRRCFFRRR-aa (SEQ ID NO: 117) |
| R$_5$FCFR$_4$ | RRRRRFCFRRRR-aa (SEQ ID NO: 118) |
| R$_5$F$_2$R$_4$ | RRRRRFFRRRR-aa (SEQ ID NO: 119) |
| R$_4$CF$_2$R$_5$ | RRRRCFFRRRRR-aa (SEQ ID NO: 120) |
| R$_2$CF$_2$R$_7$ | RRCFFRRRRRRR-aa (SEQ ID NO: 121) |
| CF$_2$R$_9$ | CFFRRRRRRRRR-aa (SEQ ID NO: 122) |
| CR$_9$F$_2$ | CRRRRRRRRRFF-aa (SEQ ID NO: 123) |

TABLE 1-continued

Exemplary Carrier Peptide Sequences

| Name | Sequence (Amino to Carboxy Terminus or 5' to 3') |
|---|---|
| $F_2R_9$ | FFRRRRRRRRR-aa (SEQ ID NO: 124) |
| $R_5F_2CF_2R_4$ | RRRRRFFCFFRRRR-aa (SEQ ID NO: 125) |
| $R_9I_2$ | RRRRRRRRRII-aa (SEQ ID NO: 126) |
| $R_8F_3$ | RRRRRRRRFFF-aa (SEQ ID NO: 127) |
| $R_9F_4$ | RRRRRRRRRFFFF-aa (SEQ ID NO: 128) |
| $R_5F_2$ | RRRRRRRRFF-aa (SEQ ID NO: 129) |
| $R_6F_2$ | RRRRRRFF-aa (SEQ ID NO: 130) |
| $R_5F_2$ | RRRRRFF-aa (SEQ ID NO: 131) |
| $(RRX)_3RR$ | RRXRRXRRXRR-aa (SEQ ID NO: 132) |
| $(RXR)_4$ | RXRRXRRXRRXR-aa (SEQ ID NO: 98) |
| $(XRR)_4$ | XRRXRRXRRXRR-aa (SEQ ID NO: 134) |
| $(RX)_5RR$ | RXRXRXRXRXRR-aa (SEQ ID NO: 135) |
| $(RXR)_3$ | RXRRXRRXR-aa (SEQ ID NO: 136) |
| $(RXR)_2R$ | RXRRXRR-aa (SEQ ID NO: 137) |
| $(RXR)_2$ | RXRRXR-aa (SEQ ID NO: 138) |
| $(RKX)_3RK$ | RKXRKXRKXRK-aa (SEQ ID NO: 139) |
| $(RHX)_3RH$ | RHXRHXRHXRH-aa (SEQ ID NO: 140) |
| $R_8CF_2R$ | RRRRRRRRCFFR-aa (SEQ ID NO: 116) |
| $(RRX)_3RR$ | RRXRRXRRXRR-aa (SEQ ID NO: 132) |
| $(RXR)_4$; P007 | RXRRXRRXRRXR-aa (SEQ ID NO: 98) |
| $(XRR)_4$ | XRRXRRXRRXRR-aa (SEQ ID NO: 134) |
| $(RX)_5R$ | RXRXRXRXRXR-aa (SEQ ID NO: 135) |
| $(RX)_7R$ | RXRXRXRXRXRXRXR-aa (SEQ ID NO: 146) |
| $(RXR)_5$ | RXRRXRRXRRXRRXR-aa (SEQ ID NO: 147) |
| $(RXRRBR)_2$; B | RXRRBRRXRRBR-aa (SEQ ID NO: 148) |
| $(RXR)_3RBR$ | RXRRXRRXRRBR-aa (SEQ ID NO: 149) |
| $(RB)_5RXRBR$ | RBRBRBRBRBRXRBR-aa (SEQ ID NO: 150) |
| RBRBRBRXRBRBRBR | RBRBRBRXRBRBRBR-aa (SEQ ID NO: 151) |
| $X(RB)_3RX(RB)_3R-X$ | XRBRBRBRXRBRBRBR-aa (SEQ ID NO: 152) |
| $(RBRX)_4$ | RBRXRBRXRBRXRBR-aa (SEQ ID NO: 153) |
| $(RB)_4 (RX)_3R$ | RBRBRBRBRXRXRXR-aa (SEQ ID NO: 154) |
| $RX(RB)_2RX(RB)_3R$ | RXRBRBRXRBRBRBR-aa (SEQ ID NO: 155) |
| $(RB)_7R$ | RBRBRBRBRBRBRBR-aa (SEQ ID NO: 156) |
| $R_4$ | tg-RRRR-aa (SEQ ID NO: 157) |
| $R_5$ | tg-RRRRR-aa (SEQ ID NO: 158) |
| $R_6$ | tg-RRRRRR-aa (SEQ ID NO: 159) |
| $R_7$ | tg-RRRRRRR-aa (SEQ ID NO: 160) |
| $R_8$ | tg-RRRRRRRR-aa (SEQ ID NO: 161) |

TABLE 1-continued

Exemplary Carrier Peptide Sequences

| Name | Sequence (Amino to Carboxy Terminus or 5' to 3') |
|---|---|
| $R_5GR_4$ | tg-RRRRRGRRRR-aa (SEQ ID NO: 162) |
| $R_5F_2R_4$ | tg-RRRRRFFRRRR-aa (SEQ ID NO: 163) |
| Tat | tg-RKKRRQRRR-aa (SEQ ID NO: 164) |
| rTat | tg-RRRQRRKKR-aa (SEQ ID NO: 165) |
| | RXRRXR-aa (SEQ ID NO: 138) |
| | RBRRBR-aa (SEQ ID NO: 167) |
| | RXRRBR-aa (SEQ ID NO: 168) |
| | RBRRXR-aa (SEQ ID NO: 169) |
| | RXRY$^b$RXR-aa (SEQ ID NO: 170) |
| | RBRY$^b$RBR-aa (SEQ ID NO: 171) |
| | RXRY$^b$RBR-aa (SEQ ID NO: 172) |
| | RBRY$^b$RXR-aa (SEQ ID NO: 173) |
| | RXRILFQYRXR-aa (SEQ ID NO: 174) |
| | RBRILFQYRBR-aa (SEQ ID NO: 175) |
| | RXRILFQYRBR-aa (SEQ ID NO: 176) |
| | RBRILFQYRXR-aa (SEQ ID NO: 177) |
| | RXRRXRRXR-aa (SEQ ID NO: 136) |
| | RBRRBRRBR-aa (SEQ ID NO: 179) |
| | RXRRBRRXR-aa (SEQ ID NO: 180) |
| | RXRRBRRBR-aa (SEQ ID NO: 181) |
| | RXRRXRRBR-aa (SEQ ID NO: 182) |
| | RBRRXRRBR-aa (SEQ ID NO: 183) |
| | RBRRXRRXR-aa (SEQ ID NO: 184) |
| | RBRRBRRXR-aa (SEQ ID NO: 185) |
| | RXRY$^b$RXRRXR-aa (SEQ ID NO: 186) |
| | RXRRXRY$^b$RXR-aa (SEQ ID NO: 187) |
| | RXRILFQYRXRRXR-aa (SEQ ID NO: 188) |
| | RXRRXRILFQYRXR-aa (SEQ ID NO: 189) |
| | RXRY$^b$RXRYRXR-aa (SEQ ID NO: 190) |
| | RXRILFQYRXRILFQYRXR-aa (SEQ ID NO: 191) |
| | RXRILFQYRXRY$^b$RXR-aa (SEQ ID NO: 192) |
| | RXRY$^b$RXRILFQYRXR-aa (SEQ ID NO: 193) |
| | RBRY$^b$RBRRBR-aa (SEQ ID NO: 194) |
| | RBRRBRY$^b$RBR-aa (SEQ ID NO: 195) |
| | RBRILFQYRBRRBR-aa (SEQ ID NO: 196) |
| | RBRRBRILFQYRBR-aa (SEQ ID NO: 197) |
| | RBRYRBRY$^b$RBR-aa (SEQ ID NO: 198) |
| | RBRILFQYRBRILFQYRBR-aa (SEQ ID NO: 199) |
| | RBRY$^b$RBRILFQYRBR-aa (SEQ ID NO: 200) |
| | RBRILFQYRBRY$^b$RBR-aa (SEQ ID NO: 201) |
| | RXRY$^b$RBRRXR-aa (SEQ ID NO: 202) |
| | RXRRBRY$^b$RXR-aa (SEQ ID NO: 203) |
| | RXRILFQYRBRRXR-aa (SEQ ID NO: 204) |
| | RXRRBRILFQYRXR-aa (SEQ ID NO: 205) |
| | RXRY$^b$RBRY$^b$RXR-aa (SEQ ID NO: 206) |
| | RXRILFQYRBRILFQYRXR-aa (SEQ ID NO: 207) |
| | RXRY$^b$RBRILFQYRXR-aa (SEQ ID NO: 208) |
| | RXRILFQYRBRY$^b$RXR-aa (SEQ ID NO: 209) |
| | RXRY$^b$RBRRBR-aa (SEQ ID NO: 210) |
| | RXRRBRY$^b$RBR-aa (SEQ ID NO: 211) |
| | RXRILFQYRBRRBR-aa (SEQ ID NO: 212) |
| | RXRRBRILFQYRBR-aa (SEQ ID NO: 213) |
| | RXRY$^b$RBRY$^b$RBR-aa (SEQ ID NO: 214) |
| | RXRILFQYRBRILFQYRBR-aa (SEQ ID NO: 215) |
| | RXRY$^b$RBRILFQYRBR-aa (SEQ ID NO: 216) |
| | RXRILFQYRBRY$^b$RBR-aa (SEQ ID NO: 217) |
| | RXRY$^b$RXRRBR-aa (SEQ ID NO: 218) |
| | RXRRXRY$^b$RBR-aa (SEQ ID NO: 219) |
| | RXRILFQYRXRRBR-aa (SEQ ID NO: 220) |
| | RXRRXRILFQYRBR-aa (SEQ ID NO: 221) |
| | RXRY$^b$RXRY$^b$RBR-aa (SEQ ID NO: 222) |
| | RXRILFQYRXRILFQYRBR-aa (SEQ ID NO: 223) |
| | RXRY$^b$RXRILFQYRBR-aa (SEQ ID NO: 224) |
| | RXRILFQYRXRY$^b$RBR-aa (SEQ ID NO: 225) |
| | RBRY$^b$RXRRBR-aa (SEQ ID NO: 226) |
| | RBRRXRY$^b$RBR-aa (SEQ ID NO: 227) |
| | RBRILFQYRXRRBR-aa (SEQ ID NO: 228) |
| | RBRRXRILFQYRBR-aa (SEQ ID NO: 229) |
| | RBRY$^b$RXRY$^b$RBR-aa (SEQ ID NO: 230) |
| | RBRILFQYRXRILFQYRBR-aa (SEQ ID NO: 231) |
| | RBRY$^b$RXRILFQYRBR-aa (SEQ ID NO: 232) |
| | RBRILFQYRXRY$^b$RBR-aa (SEQ ID NO: 233) |

TABLE 1-continued

Exemplary Carrier Peptide Sequences

| Name | Sequence (Amino to Carboxy Terminus or 5' to 3') |
|---|---|
| | RBRY$^b$RXRRXR-aa (SEQ ID NO: 234) |
| | RBRRXRY$^b$RXR-aa (SEQ ID NO: 235) |
| | RBRILFQYRXRRXR-aa (SEQ ID NO: 236) |
| | RBRRXRILFQYRXR-aa (SEQ ID NO: 237) |
| | RBRY$^b$RXRY$^b$RXR-aa (SEQ ID NO: 238) |
| | RBRILFQYRXRILFQYRXR-aa (SEQ ID NO: 239) |
| | RBRY$^b$RXRILFQYRXR-aa (SEQ ID NO: 240) |
| | RBRILFQYRXRY$^b$RXR-aa (SEQ ID NO: 241) |
| | RBRY$^b$RBRRXR-aa (SEQ ID NO: 242) |
| | RBRRBRY$^b$RXR-aa (SEQ ID NO: 243) |
| | RBRILFQYRBRRXR-aa (SEQ ID NO: 244) |
| | RBRRBRILFQYRXR-aa (SEQ ID NO: 245) |
| | RBRY$^b$RBRY$^b$RXR-aa (SEQ ID NO: 246) |
| | RBRILFQYRBRILFQYRXR-aa (SEQ ID NO: 247) |
| | RBRY$^b$RBRILFQYRXR-aa (SEQ ID NO: 248) |
| | RBRILFQYRBRY$^b$RXR-aa (SEQ ID NO: 249) |
| | RXRRXRRXRRXR-aa (SEQ ID NO: 98) |
| | RXRRBRRXRILFQYRXRBRXR-aa (SEQ ID NO: 251) |
| | RXRRBRRXRRBR-aa (SEQ ID NO: 148) |
| | YGRKKRRQRRRP-aa (SEQ ID NO: 253) |
| | RXRRXRRXRRXRXBASSLNIAXC-aa (SEQ ID NO: 254) |
| | RXRRBRRXRILFQYRXRBRXRBASSLNIAXC-aa (SEQ ID NO: 255) |
| | RXRRBRRXRASSLNIARXRBRXRBC-aa (SEQ ID NO: 256) |
| | RXRRBRRXRRBRXBASSLNIA-aa (SEQ ID NO: 257) |
| | THRPPMWSPVWP-aa (SEQ ID NO: 258) |
| | HRPPMWSPVWP-aa (SEQ ID NO: 259) |
| | THRPPMWSPV-aa (SEQ ID NO: 260) |
| | THRPPMWSP-aa (SEQ ID NO: 261) |
| | THRPPMWSPVFP-aa (SEQ ID NO: 262) |
| | THRPPMWSPVYP-aa (SEQ ID NO: 263) |
| | THRPPMWSPAWP-aa (SEQ ID NO: 264) |
| | THRPPMWSPLWP-aa (SEQ ID NO: 265) |
| | THRPPMWSPIWP-aa (SEQ ID NO: 266) |
| | THRPPMWTPVVWP-aa (SEQ ID NO: 267) |
| | THRPPMFSPVWP-aa (SEQ ID NO: 268) |
| | THRPPMWS-aa (SEQ ID NO: 269) |
| | HRPPMWSPVW-aa (SEQ ID NO: 270) |
| | THRPPMYSPVWP-aa (SEQ ID NO: 271) |
| | THRPPnleWSPVWP-aa (nle = norleucine)(SEQ ID NO: 272) |
| | THKPPMWSPVWP-aa (SEQ ID NO: 273) |
| | SHRPPMWSPVWP-aa (SEQ ID NO: 274) |
| | STFTHPR-aa (SEQ ID NO: 275) |
| | YDIDNRR-aa (SEQ ID NO: 276) |
| | AYKPVGR-aa (SEQ ID NO: 277) |
| | HAIYPRH-aa (SEQ ID NO: 278) |
| | HTPNSTH-aa (SEQ ID NO: 279) |
| | ASSPVHR-aa (SEQ ID NO: 280) |
| | SSLPLRK-aa (SEQ ID NO: 281) |
| | KKRS-aa (SEQ ID NO: 282) |
| | KRSK-aa (SEQ ID NO: 283) |
| | KKRSK-aa (SEQ ID NO: 284) |
| | KSRK-aa (SEQ ID NO: 285) |
| | SRKR-aa (SEQ ID NO: 286) |
| | RKRK-aa (SEQ ID NO: 287) |
| | KSRKR-aa (SEQ ID NO: 288) |
| | QHPPWRV-aa (SEQ ID NO: 289) |
| | THPPTTH-aa (SEQ ID NO: 290) |
| | YKHTPTT-aa (SEQ ID NO: 291) |
| | QGMHRGT-aa (SEQ ID NO: 292) |
| | SRKRK-aa (SEQ ID NO: 293) |
| | KSRKRK-aa (SEQ ID NO: 294) |
| | PKKKRKV-aa (SEQ ID NO: 295) |
| | GKKRSKV-aa (SEQ ID NO: 296) |
| | KSRKRKL-aa (SEQ ID NO: 297) |
| | HSPSKIP-aa (SEQ ID NO: 298) |
| | HMATFHY-aa (SEQ ID NO: 299) |
| | AQPNKFK-aa (SEQ ID NO: 300) |
| | NLTRLHT-aa (SEQ ID NO: 301) |
| | KKKR-aa (SEQ ID NO: 302) |
| | KKKK-aa (SEQ ID NO: 303) |
| | KKKRK-aa (SEQ ID NO: 304) |
| | RRRRRQIKIWFQNRRMKWKKGGC-aa (SEQ ID NO: 305) |

TABLE 1-continued

Exemplary Carrier Peptide Sequences

| Name | Sequence (Amino to Carboxy Terminus or 5' to 3') |
|---|---|
| | RRRRRRRQIKIWFQNRRMKWKKGGC-aa (SEQ ID NO: 306) |
| | RQIKIWFQNRRMKWKKGGC-aa (SEQ ID NO: 307) |
| | RRRRRRRQIKIWFQNRRMKWKKC-aa (SEQ ID NO: 308) |
| | RXRRXRRXRRQIKIWFQNRRMKWKKGGC-aa (SEQ ID NO: 309) |
| | RRRRRRRQIKILFQNRXRXRXRXC-aa (SEQ ID NO: 310) |
| | RXRRXRRXRRXRC-aa (SEQ ID NO: 311) |
| | RXRRXRRXRRXRXC-aa (SEQ ID NO: 312) |
| | RXRRXRRXRIKILFQNRRMKWKKGGC-aa (SEQ ID NO: 313) |
| | RXRRXRRXRIKILFQNRRMKWKKC-aa (SEQ ID NO: 314) |
| | RXRRXRRXRIKILFQNRMKWKKC-aa (SEQ ID NO: 315) |
| | RXRRXRRXRIKILFQNXRMKWKKC-aa (SEQ ID NO: 316) |
| | RXRRXRRXRIKILFQNHRMKWKKC-aa (SEQ ID NO: 317) |
| | RXRRXRRXRIKILFQNXRMKWKKC-aa (SEQ ID NO: 316) |
| | RXRRXRRXRIKILFQNXRMKWKKC-aa (SEQ ID NO: 316) |
| | RXRRXRRXRIKILFQNXRMKWKAC-aa (SEQ ID NO: 320) |
| | RXRRXRRXRIKILFQNXRMKWHKAC-aa (SEQ ID NO: 321) |
| | RXRRXRRXRIKILFQNXRMKWHRC-aa (SEQ ID NO: 322) |
| | RXRXRXRXRIKILFQNRRMKWKKC-aa (SEQ ID NO: 323) |
| | RARARARARIKILFQNRRMKWKKC-aa (SEQ ID NO: 324) |
| | RXRRXRRXRIXILFQNXRMKWHKAC-aa (SEQ ID NO: 3253) |
| | RXRRXRRXRIHILFQNXRMKWHKAC-aa (SEQ ID NO: 326) |
| | RXRRXRRXRIRILFQNXRMKWHKAC-aa (SEQ ID NO: 327) |
| | RXRRXRRXRIXILFQYXRMKWHKAC-aa (SEQ ID NO: 328) |
| | RXRRXRRXRLYSPLSFQXRMKWHKAC-aa (SEQ ID NO: 329) |
| | RXRRXRRXRISILFQYXRMKWHKAC-aa (SEQ ID NO: 330) |
| | RXRRXRRXRILFQYXRMKWHKAC-aa (SEQ ID NO: 331) |
| | RXRRXRIXILFQYXRMKWHKAC-aa (SEQ ID NO: 332) |
| | RXRRARRXRIHILFQYXRMKWHKAC-aa (SEQ ID NO: 333) |
| | RARRXRRARIHILFQYXRMKWHKAC-aa (SEQ ID NO: 334) |
| | RXRRXRRXRIHILFQYXRMKWHKAC-aa (SEQ ID NO: 335) |
| | RXRRXRRXRIXILFQNXRMKWHKAC-aa (SEQ ID NO: 325) |
| | RXRRXRRXRIHILFQNXRMKWHKAC-aa (SEQ ID NO: 326) |
| | RXRRXRRXRIKILFQNRRMKWHK-aa (SEQ ID NO: 338) |
| | RXRRXRRXRIKILFQNXRMKWHK-aa (SEQ ID NO: 339) |
| | RXRRXRRXRIXILFQNRRMKWHK-aa (SEQ ID NO: 340) |
| | RXRRXRRXRIXILFQNXRMKWHK-aa (SEQ ID NO: 341) |
| | RXRRXRRXRIHILFQNRRMKWHK-aa (SEQ ID NO: 342) |
| | RXRRXRRXRIHILFQNXRMKWHK-aa (SEQ ID NO: 343) |
| | RXRRXRRXRIRILFQNRRMKWHK-aa (SEQ ID NO: 344) |
| | RXRRXRRXRIRILFQNXRMKWHK-aa (SEQ ID NO: 345) |
| | RXRRXRRXRIILFQNRRMKWHK-aa (SEQ ID NO: 346) |
| | RXRRXRRXRIILFQNXRMKWHK-aa (SEQ ID NO: 347) |
| | RXRRXRRXRKILFQNRRMKWHK-aa (SEQ ID NO: 348) |
| | RXRRXRRXRKILFQNXRMKWHK-aa (SEQ ID NO: 349) |
| | RXRRXRRXRXILFQNXRMKWHK-aa (SEQ ID NO: 350) |
| | RXRRXRRXRXILFQNXRMKWHK-aa (SEQ ID NO: 351) |
| | RXRRXRRXRHILFQNRRMKWHK-aa (SEQ ID NO: 352) |
| | RXRRXRRXRHILFQNXRMKWHK-aa (SEQ ID NO: 353) |
| | RXRRXRRXRRILFQNRRMKWHK-aa (SEQ ID NO: 354) |

TABLE 1-continued

Exemplary Carrier Peptide Sequences

| Name | Sequence (Amino to Carboxy Terminus or 5' to 3') |
| --- | --- |
| | RXRRXRRXRRILFQNXRMKWHK-aa (SEQ ID NO: 355) |
| | RXRRXRRXRILFQNRRMKWHK-aa (SEQ ID NO: 356) |
| | RXRRXRRXRILFQNXRMKWHK-aa (SEQ ID NO: 357) |
| | RXRRXRRXRIKILFQYRRMKWHK-aa (SEQ ID NO: 358) |
| | RXRRXRRXRIKILFQYXRMKWHK-aa (SEQ ID NO: 359) |
| | RXRRXRRXRIXILFQYRRMKWHK-aa (SEQ ID NO: 360) |
| | RXRRXRRXRIXILFQYXRMKWHK-aa (SEQ ID NO: 361) |
| | RXRRXRRXRIHILFQYRRMKWHK-aa (SEQ ID NO: 362) |
| | RXRRXRRXRIHILFQYXRMKWHK-aa (SEQ ID NO: 363) |
| | RXRRXRRXRIRILFQYRRMKWHK-aa (SEQ ID NO: 364) |
| | RXRRXRRXRIRILFQYXRMKWHK-aa (SEQ ID NO: 365) |
| | RXRRXRRXRIILFQYRRMKWHK-aa (SEQ ID NO: 366) |
| | RXRRXRRXRIILFQYXRMKWHK-aa (SEQ ID NO: 367) |
| | RXRRXRRXRKILFQYRRMKWHK-aa (SEQ ID NO: 368) |
| | RXRRXRRXRKILFQYXRMKWHK-aa (SEQ ID NO: 369) |
| | RXRRXRRXRXILFQYRRMKWHK-aa (SEQ ID NO: 370) |
| | RXRRXRRXRXILFQYXRMKWHK-aa (SEQ ID NO: 371) |
| | RXRRXRRXRHILFQYRRMKWHK-aa (SEQ ID NO: 372) |
| | RXRRXRRXRHILFQYXRMKWHK-aa (SEQ ID NO: 373) |
| | RXRRXRRXRRILFQYRRMKWHK-aa (SEQ ID NO: 374) |
| | RXRRXRRXRRILFQYXRMKWHK-aa (SEQ ID NO: 375) |
| | RXRRXRRXRILFQYRRMKWHK-aa (SEQ ID NO: 376) |
| | RXRRXRRXRILFQYXRMKWHK-aa (SEQ ID NO: 377) |
| | RXRRXRRXR-aa (SEQ ID NO: 136) |
| | RXRRXRRXRRXR-aa (SEQ ID NO: 98) |
| | RARRAR-aa (SEQ ID NO: 380) |
| | RARRARRAR-aa (SEQ ID NO: 381) |
| | RARRARRARRAR-aa (SEQ ID NO: 382) |
| | RXRRXRI-aa (SEQ ID NO: 383) |
| | RXRRARRXR-aa (SEQ ID NO: 384) |
| | RARRXRRAR-aa (SEQ ID NO: 385) |
| | RRRRR-aa (SEQ ID NO: 386) |
| | RRRRRR-aa (SEQ ID NO: 387) |
| | RRRRRRR-aa (SEQ ID NO: 388) |
| | RXRRXRRXRRXRC-aa (SEQ ID NO: 311) |
| | RXRRXRRXRRXRXC-aa (SEQ ID NO: 312) |
| | RXRRXRRXRIKILFQNRRMKWKKGGC-aa (SEQ ID NO: 313) |
| | RXRRXRRXRIKILFQNRRMKWKKC-aa (SEQ ID NO: 314) |
| | RXRRXRRXRIKILFQNRMKWKKC-aa (SEQ ID NO: 315) |
| | RXRRXRRXRIKILFQNXRMKWKKC-aa (SEQ ID NO: 316) |
| | RXRRXRRXRIKILFQNHRMKWKKC-aa (SEQ ID NO: 317) |
| | RXRRXRRXRIKILFQNXRMKWKKC-aa (SEQ ID NO: 316) |
| | RXRRXRRXRIKILFQNXRMKWKKC-aa (SEQ ID NO: 316) |
| | RXRRXRRXRIKILFQNXRMKWKAC-aa (SEQ ID NO: 320) |
| | RXRRXRRXRIKILFQNXRMKWHKAC-aa (SEQ ID NO: 321) |
| | RXRRXRRXRIKILFQNXRMKWHRC-aa (SEQ ID NO: 322) |
| | RXRXRXRIKILFQNRRMKWKKC-aa (SEQ ID NO: 323) |
| | RARARARARIKILFQNRRMKWKKC-aa (SEQ ID NO: 324) |
| | RXRRXRRXRIXILFQNXRMKWHKAC-aa (SEQ ID NO: 325) |
| | RXRRXRRXRIHILFQNXRMKWHKAC-aa (SEQ ID NO: 326) |
| | RXRRXRRXRIRILFQNXRMKWHKAC-aa (SEQ ID NO: 327) |
| | RXRRXRRXRIXILFQYXRMKWHKAC-aa (SEQ ID NO: 328) |
| | RXRRXRRXRLYSPLSFQXRMKWHKAC-aa (SEQ ID NO: 329) |
| | RRMKWHK-aa (SEQ ID NO: 408) |
| | XRMKWHK-aa (SEQ ID NO: 409) |
| | XXXXXXXXXXXXXILFQXXRMKWHK-aa (SEQ ID NO: 410) |
| | XXXXXXXXXXXXXILFQXXRMKWHK-aa (SEQ ID NO: 410) |

TABLE 1-continued

Exemplary Carrier Peptide Sequences

| Name | Sequence (Amino to Carboxy Terminus or 5' to 3') |
|---|---|
| | RRRRRRRQIKILFQNPKKKRKVGGC-aa (SEQ ID NO: 412) |
| | HHFFRRRRRRRRRFFC-aa (SEQ ID NO: 413) |
| | HHHHHHRRRRRRRRRRFFC-aa (SEQ ID NO: 414) |
| | HHHHHHFFRRRRRRRRRRFFC-aa (SEQ ID NO: 415) |
| | HHHHHHXRRRRRRRRRRFFC-aa (SEQ ID NO: 416) |
| | HHHHHHXXFFRRRRRRRRRRFFC-aa (SEQ ID NO: 417) |
| | HHHXRRRRRRRRRFFXHHHC-aa (SEQ ID NO: 418) |
| | XRMKWHK-aa (SEQ ID NO: 409) |
| | XRWKWHK-aa (SEQ ID NO: 420) |
| | RXRARXR-aa (SEQ ID NO: 421) |
| | RXRXRXR-aa (SEQ ID NO: 422) |
| | RARXRAR-aa (SEQ ID NO: 423) |
| | RXRAR-aa (SEQ ID NO: 424) |
| | XXXXXXXXXXXXXXILFQXXHMKWHK-aa (SEQ ID NO: 425) |
| | XXXXXXXXXXXXXXILFQXXRWKWHK-aa (SEQ ID NO: 426) |
| | XXXXXXXXXXXXXXILFQXXHWKWHK-aa (SEQ ID NO: 427) |
| | XXXXXXXXXXXXXXILFQXRXRARXR-aa (SEQ ID NO: 428) |
| | XXXXXXXXXXXXXXILFQXRXRXRXR-aa (SEQ ID NO: 429) |
| | XXXXXXXXXXXXXXILFQXRXRRXR-aa (SEQ ID NO: 430) |
| | XXXXXXXXXXXXXXILFQXRARXRAR-aa (SEQ ID NO: 431) |
| | XXXXXXXXXXXXXXILFQXRXRARXR-aa (SEQ ID NO: 428) |
| | XXXXXXXXXXXXXXILFQXRXRAR-aa (SEQ ID NO: 433) |
| | XXXXXXXXXXXXXXILIQXXRMKWHK-aa (SEQ ID NO: 434) |
| | XXXXXXXXXXXXXXILIQXXHMKWHK-aa (SEQ ID NO: 435) |
| | XXXXXXXXXXXXXXILIQXXRWKWHK-aa (SEQ ID NO: 436) |
| | XXXXXXXXXXXXXXILIQXXHWKWHK-aa (SEQ ID NO: 437) |
| | XXXXXXXXXXXXXXILIQXRXRARXR-aa (SEQ ID NO: 438) |
| | XXXXXXXXXXXXXXILIQXRXRXRXR-aa (SEQ ID NO: 439) |
| | XXXXXXXXXXXXXXILIQXRXRRXR-aa (SEQ ID NO: 440) |
| | XXXXXXXXXXXXXXILIQXRARXRAR-aa (SEQ ID NO: 441) |
| | XXXXXXXXXXXXXXILIQXRXRARXR-aa (SEQ ID NO: 438) |
| | XXXXXXXXXXXXXXILIQXRXRAR-aa (SEQ ID NO: 443) |
| | XXXXXXXXXXXXXXILFQXXHMKWHK-aa (SEQ ID NO: 425) |
| | XXXXXXXXXXXXXXILFQXXRWKWHK-aa (SEQ ID NO: 426) |
| | XXXXXXXXXXXXXXILFQXXHWKWHK-aa (SEQ ID NO: 427) |
| | XXXXXXXXXXXXXXILFQXRXRARXR-aa (SEQ ID NO: 428) |
| | XXXXXXXXXXXXXXILFQXRXRXRXR-aa (SEQ ID NO: 429) |
| | XXXXXXXXXXXXXXILFQXRXRRXR-aa (SEQ ID NO: 430) |
| | XXXXXXXXXXXXXXILFQXRARXRAR-aa (SEQ ID NO: 431) |
| | XXXXXXXXXXXXXXILFQXRXRARXR-aa (SEQ ID NO: 428) |
| | XXXXXXXXXXXXXXILFQXRXRAR-aa (SEQ ID NO: 433) |
| | XXXXXXXXXXXXXXILIQXXRMKWHK-aa (SEQ ID NO: 434) |
| | XXXXXXXXXXXXXXILIQXXHMKWHK-aa (SEQ ID NO: 435) |
| | XXXXXXXXXXXXXXILIQXXRWKWHK-aa (SEQ ID NO: 436) |

TABLE 1-continued

Exemplary Carrier Peptide Sequences

| Name | Sequence (Amino to Carboxy Terminus or 5' to 3') |
|---|---|
| | XXXXXXXXXXXXXXILIQXXHWKWHK-aa (SEQ ID NO: 437) |
| | XXXXXXXXXXXXXXILIQXRXRARXR-aa (SEQ ID NO: 438) |
| | XXXXXXXXXXXXXXILIQXRXRXRXR-aa (SEQ ID NO: 439) |
| | XXXXXXXXXXXXXXILIQXRXRRXR-aa (SEQ ID NO: 440) |
| | XXXXXXXXXXXXXXILIQXRARXRAR-aa (SEQ ID NO: 441) |
| | XXXXXXXXXXXXXXILIQXRXRARXR-aa (SEQ ID NO: 438) |
| | XXXXXXXXXXXXXXILIQXRXRAR-aa (SEQ ID NO: 443) |
| | RXRRARRXRRARXA-aa (SEQ ID NO: 463) |
| | RXRRARRXRILFQYXHMKWHKAC-aa (SEQ ID NO: 464) |
| | RXRRARRXRILFQYXRMKWHKAC-aa (SEQ ID NO: 465) |
| | RXRRARRXRILFQYXRWKWHKAC-aa (SEQ ID NO: 466) |
| | RXRRXRRXRRXC-aa (SEQ ID NO: 311) |
| | RXRRXRRXRIXILFQNXRMKWHKAC-aa (SEQ ID NO: 325) |
| | RXRRXRRXRIHILFQNXRMKWHKAC-aa (SEQ ID NO: 326) |
| | RXRRXRRXRIXILFQYXRMKWHKAC-aa (SEQ ID NO: 328) |
| | RXRRXRRXRLYSPLSFQXRMKWHKAC-aa (SEQ ID NO: 329) |
| | RXRRXRRXRILFQYXRMKWHKAC-aa (SEQ ID NO: 331) |
| | RXRRXRIXILFQYXRMKWHKAC-aa (SEQ ID NO: 332) |
| | RARRXRRARILFQYXRMKWHKAC-aa (SEQ ID NO: 474) |
| | RXRRARRXRILFQYXRMKWHKAC-aa (SEQ ID NO: 465) |
| | RARRXRRARILFQYXRMKWHKAC-aa (SEQ ID NO: 474) |
| | RXRRARRXRILFQYXRMKWHKAC-aa (SEQ ID NO: 465) |
| | RXRRARRXRILFQYXHMKWHKAC-aa (SEQ ID NO: 464) |
| | RXRRARRXRILFQYXRMKWHKAC-aa (SEQ ID NO: 465) |
| | RXRRARRXRILFQYXRWKWHKAC-aa (SEQ ID NO: 466) |
| | RXRRARRXRILFQYXHWKWHKAC-aa (SEQ ID NO: 481) |
| | RXRRARRXRILFQYRXRARXRAC-aa (SEQ ID NO: 482) |
| | RXRRARRXRILFQYRXRXRXRAC-aa (SEQ ID NO: 483) |
| | RXRRARRXRILIQYXRMKWHKAC-aa (SEQ ID NO: 484) |
| | RXRRXRILFQYRXRRXRC-aa (SEQ ID NO: 485) |
| | RXRRARRXRILFQYRXRARXRAC-aa (SEQ ID NO: 482) |
| | RXRRARRXRILFQYRXRXRXRAC-aa (SEQ ID NO: 483) |
| | RXRRARRXRILIQYXRMKWHKAC-aa (SEQ ID NO: 484) |
| | RXRRXRILFQYRXRRXRCYS-aa (SEQ ID NO: 489) |
| | RARRXRRARILFQYRARXRARAC-aa (SEQ ID NO: 490) |
| | RARRXRRARILFQYRXRARXRAC-aa (SEQ ID NO: 491) |
| | RARRXRRARILFQYRXRRXRAC-aa (SEQ ID NO: 492) |
| | RARRXRRARILFQYRXRARXAC-aa (SEQ ID NO: 493) |
| | RXRRARRXRILFQYRXRRXRAC-aa (SEQ ID NO: 494) |
| | RXRRARRXRILFQYRXRARXAC-aa (SEQ ID NO: 495) |
| | RXRRARRXRIHILFQNXRMKWHKAC-aa (SEQ ID NO: 496) |
| | RXRRARRXRRARXAC-aa (SEQ ID NO: 497) |
| | RXRRARRXRILFQYXHMKWHK-aa (SEQ ID NO: 498) |
| | RXRRARRXRILFQYXRMKWHK-aa (SEQ ID NO: 499) |
| | RXRRARRXRILFQYXRWKWHK-aa (SEQ ID NO: 500) |
| | RXRRARRXRILFQYXRMKWHK-aa (SEQ ID NO: 499) |
| | RXRRARRXRILFQYRXRARXR-aa (SEQ ID NO: 502) |
| | RXRRARRXRILFQYRXRXRXR-aa (SEQ ID NO: 503) |
| | RXRRARRXRILFQYRXRRXR-aa (SEQ ID NO: 504) |
| | RXRRARRXRILFQYRARXRAR-aa (SEQ ID NO: 505) |

TABLE 1-continued

Exemplary Carrier Peptide Sequences

| Name | Sequence (Amino to Carboxy Terminus or 5' to 3') |
|---|---|
| | RXRRARRXRILFQYRXRAR-aa (SEQ ID NO: 506) |
| | RXRRARRXRILIQYXHMKWHK-aa (SEQ ID NO: 507) |
| | RXRRARRXRILIQYXRMKWHK-aa (SEQ ID NO: 508) |
| | RXRRARRXRILIQYXRWKWHK-aa (SEQ ID NO: 509) |
| | RXRRARRXRILIQYXRMKWHK-aa (SEQ ID NO: 508) |
| | RXRRARRXRILIQYRXRARXR-aa (SEQ ID NO: 511) |
| | RXRRARRXRILIQYRXRXRXR-aa (SEQ ID NO: 512) |
| | RXRRARRXRILIQYRXRRXR-aa (SEQ ID NO: 513) |
| | RXRRARRXRILIQYRARXRAR-aa (SEQ ID NO: 514) |
| | RXRRARRXRILIQYRXRAR-aa (SEQ ID NO: 515) |
| | RARRXRRARILFQYXHMKWHK-aa (SEQ ID NO: 516) |
| | RARRXRRARILFQYXRMKWHK-aa (SEQ ID NO: 517) |
| | RARRXRRARILFQYXRWKWHK-aa (SEQ ID NO: 518) |
| | RARRXRRARILFQYXRMKWHK-aa (SEQ ID NO: 517) |
| | RARRXRRARILFQYRXRARXR-aa (SEQ ID NO: 520) |
| | RARRXRRARILFQYRXRXRXR-aa (SEQ ID NO: 521) |
| | RARRXRRARILFQYXRRXR-aa (SEQ ID NO: 522) |
| | RARRXRRARILFQYRARXRAR-aa (SEQ ID NO: 523) |
| | RARRXRRARILFQYRXRAR-aa (SEQ ID NO: 524) |
| | RARRXRRARILIQYXHMKWHK-aa (SEQ ID NO: 525) |
| | RARRXRRARILIQYXRMKWHK-aa (SEQ ID NO: 526) |
| | RARRXRRARILIQYXRWKWHK-aa (SEQ ID NO: 527) |
| | RARRXRRARILIQYXRMKWHK-aa (SEQ ID NO: 526) |
| | RARRXRRARILIQYRXRARXR-aa (SEQ ID NO: 529) |
| | RARRXRRARILIQYRXRXRXR-aa (SEQ ID NO: 530) |
| | RARRXRRARILIQYXRRXR-aa (SEQ ID NO: 531) |
| | RARRXRRARILIQYRARXRAR-aa (SEQ ID NO: 532) |
| | RARRXRRARILIQYRXRAR-aa (SEQ ID NO: 533) |
| | RXRRXRILFQYXHMKWHK-aa (SEQ ID NO: 534) |
| | RXRRXRILFQYXRMKWHK-aa (SEQ ID NO: 535) |
| | RXRRXRILFQYXRWKWHK-aa (SEQ ID NO: 536) |
| | RXRRXRILFQYXRMKWHK-aa (SEQ ID NO: 535) |
| | RXRRXRILFQYRXRARXR-aa (SEQ ID NO: 538) |
| | RXRRXRILFQYRXRXRXR-aa (SEQ ID NO: 539) |
| | RXRRXRILFQYRXRRXR-aa (SEQ ID NO: 540) |
| | RXRRXRILFQYRARXRAR-aa (SEQ ID NO: 541) |
| | RXRRXRILFQYRXRAR-aa (SEQ ID NO: 542) |
| | RXRRXRILIQYXHMKWHK-aa (SEQ ID NO: 543) |
| | RXRRXRILIQYXRMKWHK-aa (SEQ ID NO: 544) |
| | RXRRXRILIQYXRWKWHK-aa (SEQ ID NO: 545) |
| | RXRRXRILIQYXRMKWHK-aa (SEQ ID NO: 544) |
| | RXRRXRILIQYRXRARXR-aa (SEQ ID NO: 547) |
| | RXRRXRILIQYRXRXRXR-aa (SEQ ID NO: 548) |
| | RXRRXRILIQYRXRRXR-aa (SEQ ID NO: 549) |
| | RXRRXRILIQYRARXRAR-aa (SEQ ID NO: 550) |
| | RXRRXRILIQYRXRAR-aa (SEQ ID NO: 551) |
| | PRPXXXXXXXXXXXPRG-aa (SEQ ID NO: 552) |
| | RRRRRRRR-aa (SEQ ID NO: 553) |
| | RRMKWKK-aa (SEQ ID NO: 554) |
| | PKKKRKV-aa (SEQ ID NO: 295) |
| | CKDEPQRRSARLSAKPAPPKPEPKPKKAPAKK-aa (SEQ ID NO: 556) |
| | RKKRRQRRR-aa (SEQ ID NO: 101) |
| | RKKRRQRR-aa (SEQ ID NO: 558) |
| | RKKRRQR-aa (SEQ ID NO: 559) |
| | KKRRQRRR-aa (SEQ ID NO: 560) |
| | KKRRQRRR-aa (SEQ ID NO: 560) |
| | AKKRRQRRR-aa (SEQ ID NO: 562) |
| | RAKRRQRRR-aa (SEQ ID NO: 563) |
| | RKARRQRRR-aa (SEQ ID NO: 564) |
| | RKKARQRRR-aa (SEQ ID NO: 565) |
| | CRWRWKCCKK-aa (SEQ ID NO: 566) | aa = glycine or proline; B = 3-alanine; X = 6-aminohexanoic acid; tg. = unmodified amino terminus, or the amino terminal capped with an acetyl, benzoyl or stearoyl group (i.e., an acetyl amide, benzoyl amide or stearoyl amide) and $Y^b$ is: NH-(CHR)-C(O) - wherein n is 2 to 7 and each R is independently, at each occurrence, hydrogen or methyl. For simplicity, not all sequences are noted with a terminal tg group; however, each of the above sequences may comprise an unmodified amino terminus or an amino terminus capped with an acetyl, benzoyl or stearoyl group.

In some embodiments, an antisense oligonucleotide comprises a substituent "Z," defined as the combination of a CPP and a linker. The linker bridges the CPP at its carboxy terminus to the 3'-end and/or the 5'-end of the oligonucleotide. In various embodiments, an antisense oligonucleotide may comprise only one CPP linked to the 3' end of the oligomer. In other embodiments, an antisense oligonucleotide may comprise only one CPP linked to the 5' end of the oligomer.

The linker within Z may comprise, for example, 1, 2, 3, 4, or 5 amino acids. For example, the linker may comprise 1, 2, 3, 4, or 5 of a glycine moiety, wherein the CPP is attached to the glycine moiety by an amide bond at the CPP carboxy terminus. In one aspect, the linker comprises one glycine moiety.

In particular embodiments, Z is selected from:
—C(O)(CH$_2$)$_5$NH—CPP;
—C(O)(CH$_2$)$_2$NH—CPP;
—C(O)(CH$_2$)$_2$NHC(O)(CH$_2$)$_5$NH—CPP;
—C(O)CH$_2$NH—CPP; and the formula:

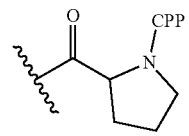

wherein the CPP is attached to the linker moiety by an amide bond at the CPP carboxy terminus.

In various embodiments, the CPP is an arginine-rich peptide as defined above and seen in Table 1. In certain embodiments, the arginine-rich CPP is —R$_6$—R$^a$, (i.e., six arginine residues), wherein R$^a$ is selected from H, acyl, acetyl, benzoyl, and stearoyl. In certain embodiments, R$^a$ is acetyl.

In certain embodiments, Z is —C(O)CH$_2$NH-R$_6$—R$^a$ covalently bonded to an antisense oligomer of the disclosure at the 5' and/or 3' end of the oligomer, wherein R$^a$ is H, acyl, acetyl, benzoyl, or stearoyl to cap the amino terminus of the R$_6$. In certain embodiments, R$^a$ is acetyl. In these non-limiting examples, the CPP is —R$_6$—R$^a$ and the linker is —C(O)CH$_2$NH—, (i.e. GLY). This particular example of Z=—C(O)CH$_2$NH-R$_6$—R$^a$ is also exemplified by the following structure:

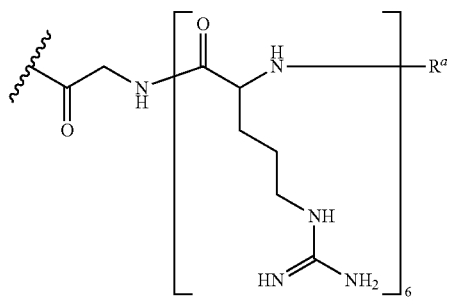

wherein R$^a$ is selected from H, acyl, acetyl, benzoyl, and stearoyl. In some embodiments, R$^a$ H or acyl. In some embodiments, R$^a$ is acetyl.

In various embodiments, the CPP is —R$_6$—R$^a$, also exemplified as the following formula:

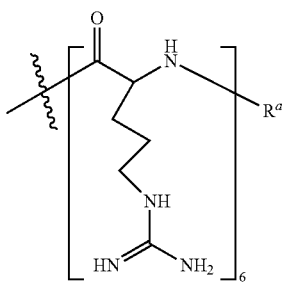

wherein R$^a$ is selected from H, acyl, acetyl, benzoyl, and stearoyl. In certain embodiments, the CPP is SEQ ID NO: 128. In some embodiments, R$^a$ is H or acyl. In some embodiments, R$^a$ is acetyl.

In some embodiments, the CPP is —(RXR)$_4$—R$^a$, also exemplified as the following formula:

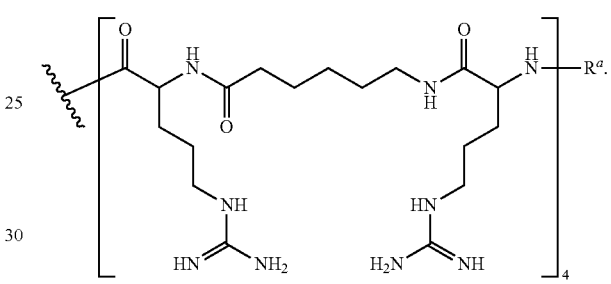

In various embodiments, the CPP is —R—(FFR)$_3$—R$^a$, also exemplified as the following formula:

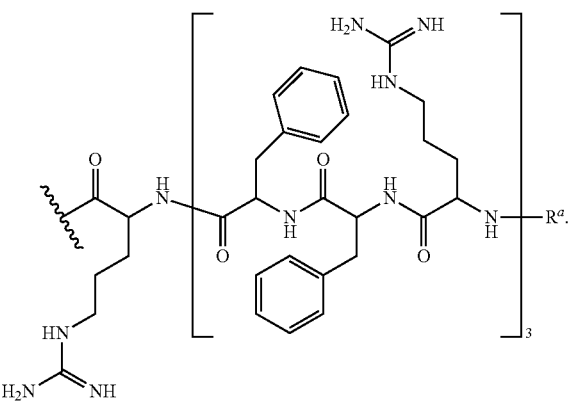

In various embodiments, Z is selected from:
—C(O)(CH$_2$)$_5$NH—CPP;
—C(O)(CH$_2$)$_2$NH—CPP;
—C(O)(CH$_2$)$_2$NHC(O)(CH$_2$)$_5$NH—CPP;
—C(O)CH$_2$NH—CPP, and the formula:

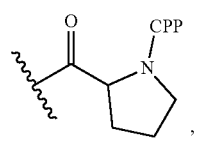

wherein the CPP is attached to the linker moiety by an amide bond at the CPP carboxy terminus, and wherein the CPP is selected from:

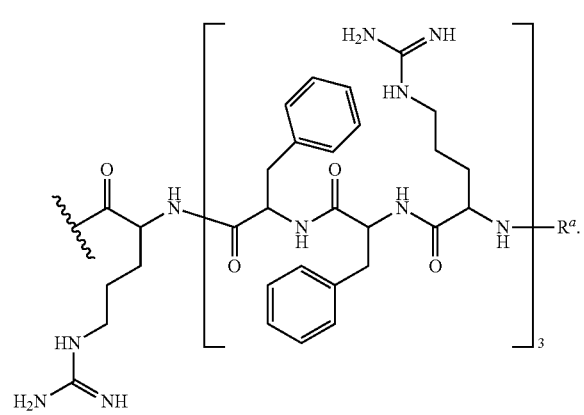

(—R—(FFR)$_3$—R$^a$),

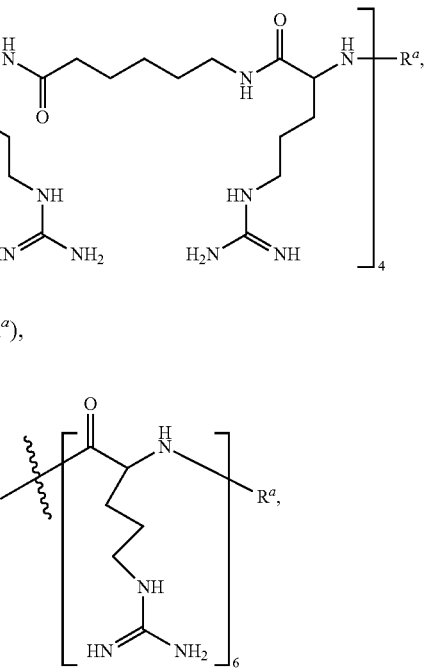

(—(RXR)$_4$—R$^a$), and (—R$_6$—R$^a$). In some embodiments, R$^a$ is H or acyl. In some embodiments, R$^a$ is acetyl.

In some embodiments, "-G-R$_6$" or "-G-R$_6$-Ac" is conjugated to the 3' end of an antisense oligomer of the disclosure and is of the following formula:

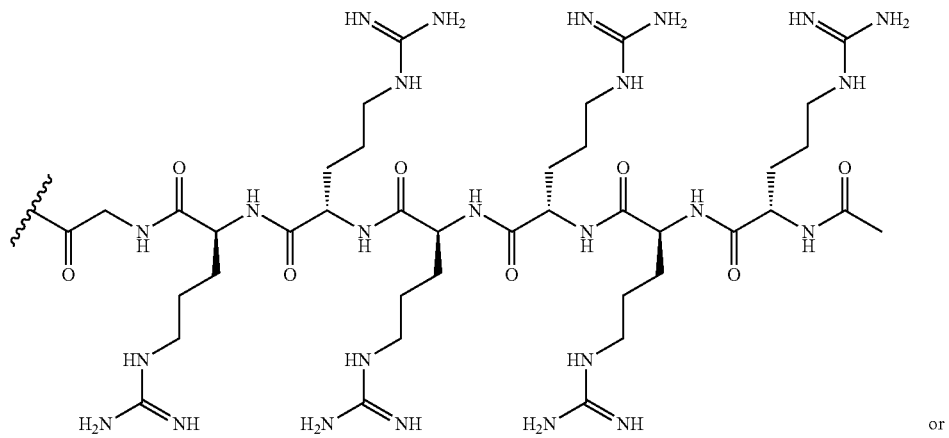

or

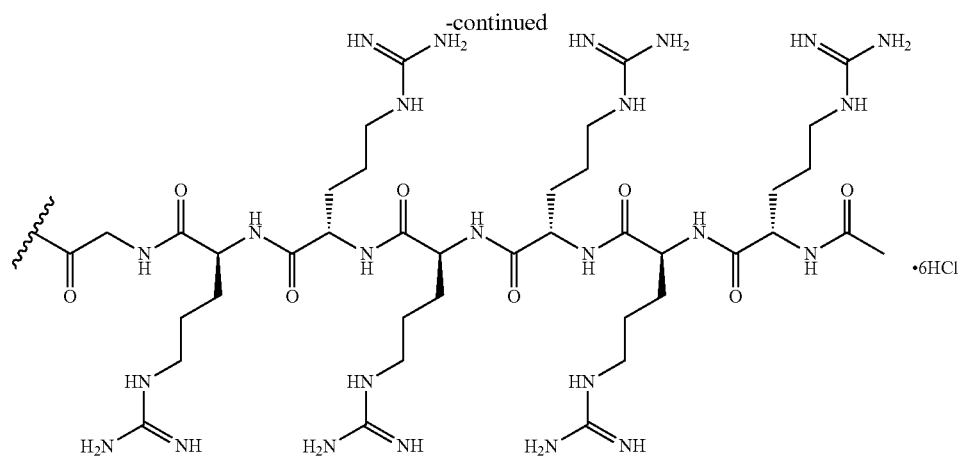
-continued

Antisense Oligomer CPP Conjugates

In various aspects, the disclosure provides antisense oligomers according to Formula (I):

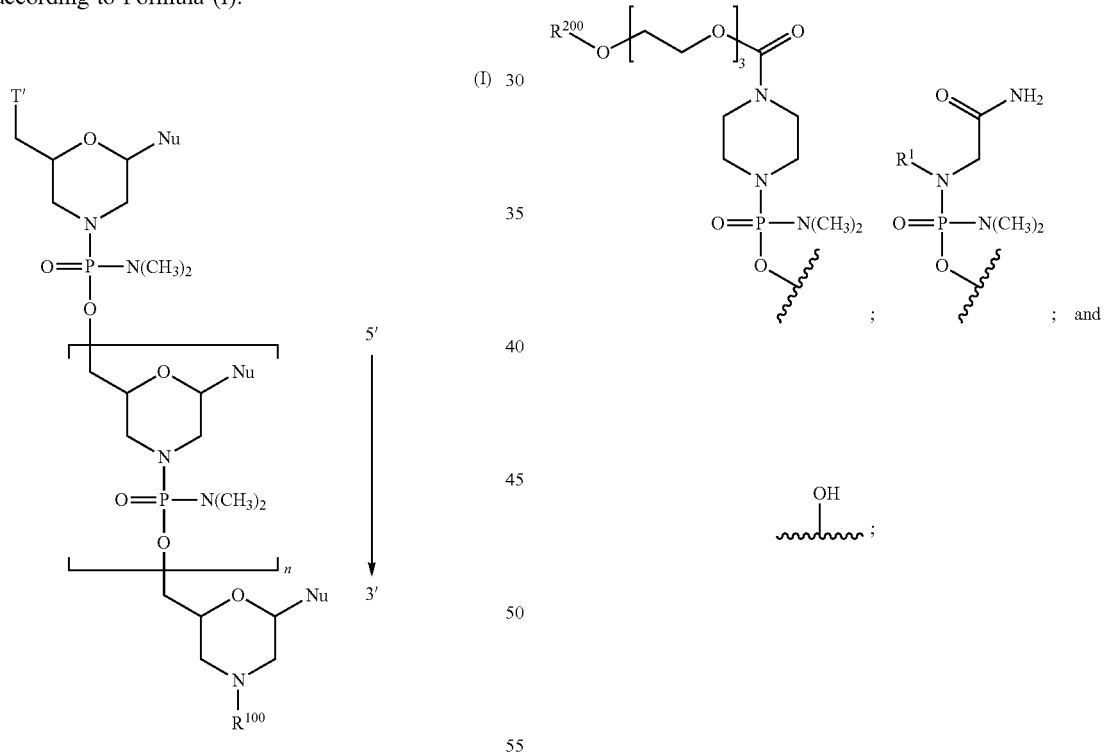

or a pharmaceutically acceptable salt thereof, wherein:

n is 1-40;

each Nu is a nucleobase, which, taken together form a targeting sequence that is complementary to an exon annealing site in the dystrophin pre-mRNA;

T' is a moiety selected from:

wherein $R^{100}$ a cell-penetrating peptide, $R^{200}$ is hydrogen, and

IV is $C_1$-$C_6$ alkyl.

In various aspects, an antisense oligomer conjugate of the disclosure is according to Formula (II):

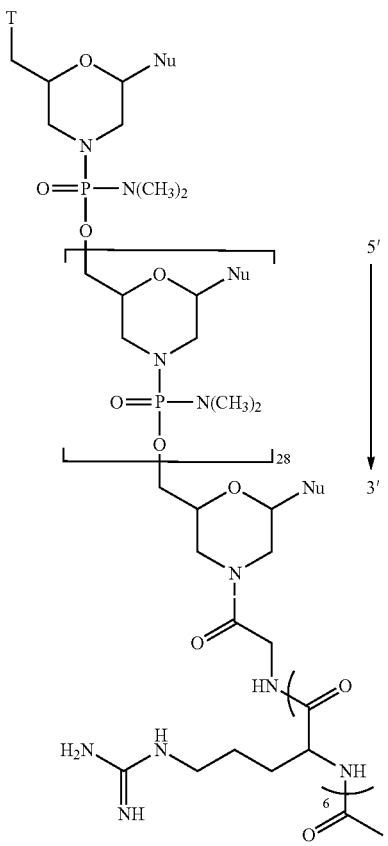

(II)

or a pharmaceutically acceptable salt thereof, wherein:
each Nu is a nucleobase which taken together form a targeting sequence;
T is a moiety selected from:

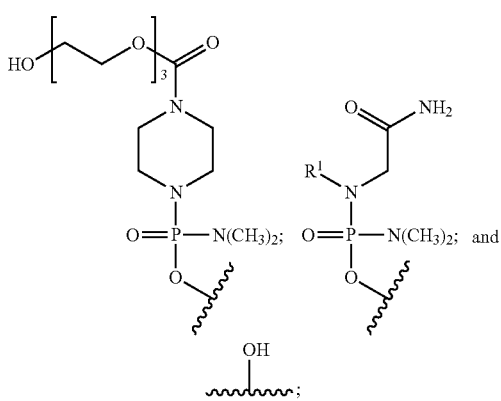

$R^1$ is $C_1$-$C_6$ alkyl;
wherein the targeting sequence is complementary to an annealing site in the dystrophin pre-RNA.

In some aspects, the antisense oligonucleotide conjugate in the composition comprises a sequence that is complementary to 15 to 35 nucleobases of an exon 44, exon 45, exon 50, exon 51, exon 52, or exon 53 target region of the dystrophin pre-mRNA. Oligonucleotide sequences designed to target and skip these dystrophin exons have been described in the art. See for example, the following PCT published applications and issued US patents: WO2018/129384, WO2019/060775, WO2020/219820 WO2018/007475, WO2018/091544, WO2020/089325, WO2004/048570, WO2020/028832, WO2017/062862, U.S. Pat. Nos. 10,683,322, 8,969,551, 10,781,448, 9,988,629, 9,840,706, 10,851,373, WO2020/004675, and WO2020/0158792, the sequence disclosure of which is incorporated herein.

A number of exemplary targeting sequences are described below. These sequences can be provided as morpholino targeting sequences and incorporated into the antisense oligonucleotide conjugates of Formula I.

In some aspects, the targeting sequence is complementary to an exon 51 annealing site in the dystrophin pre-mRNA. In some aspects, the site is designated as H51A(+66+95). In some aspects, the targeting sequence is complementary to an exon 45 annealing site in the dystrophin pre-mRNA. In some aspects, the site is designated as H45A(−03+19). In some aspects, the targeting sequence is complementary to an exon 53 annealing site in the dystrophin pre-mRNA. In some aspects, the site is designated as H53A(+36+60).

In various embodiments, T is

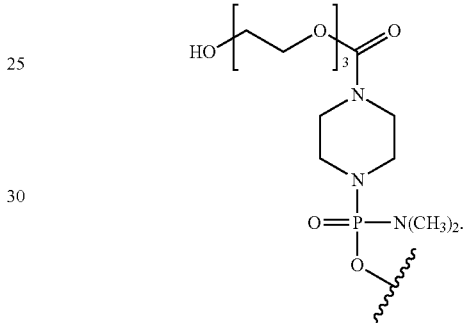

In various embodiments, $R^1$ is methyl, $CF_3$, $CCl_3$, $CFCl_2$, $CF_2Cl$, ethyl, $CH_2CF_3$, $CF_2CF_3$, propyl, isopropyl, butyl, isobutyl, sec-butyl, t-butyl, pentyl, isopentyl, neopentyl, hexyl, isohexyl, 3-methylpentyl, 2,2-dimethylbutyl, or 2,3-dimethylbutyl.

In some embodiments, an antisense oligomer conjugate of Formula (I) is an HCl (hydrochloric acid) salt thereof. In certain embodiments, the HCl salt is a ·6HCl salt.

In some embodiments, each Nu is independently selected from cytosine (C), guanine (G), thymine (T), adenine (A), 5-methylcytosine (5mC), uracil (U), and hypoxanthine (I).

In some embodiments, the targeting sequence is 5'-CTC-CAACATCAAGGAAGATGGCATTTCTAG-3', wherein each thymine (T) is optionally uracil (U) (SEQ ID NO: 31).

In various embodiments, T is

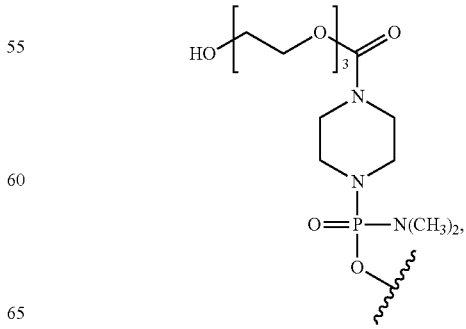

and the targeting sequence is 5'-CTCCAACATCAAGGAA-GATGGCATTTCTAG-3', wherein each thymine (T) is optionally uracil (U) (SEQ ID NO: 31).

In various embodiments, T is

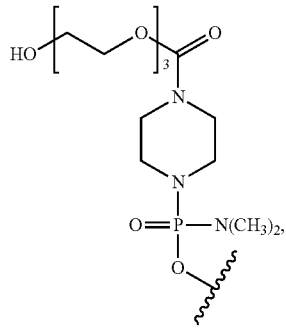

and the targeting sequence is 5'-CTCCAACATCAAGGAA-GATGGCATTTCTAG-3' (SEQ ID NO: 32).

In some embodiments, the targeting sequence is 5'-CAATGCCATCCTGGAGTTCCTG-3', wherein each thymine (T) is optionally uracil (U) (SEQ ID NO: 28).

In various embodiments, T is

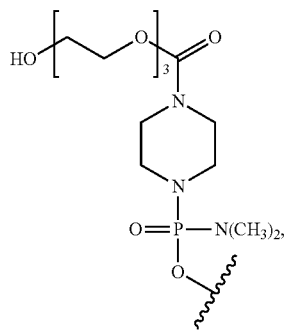

and the targeting sequence is 5'-CAATGCCATCCTG-GAGTTCCTG-3', wherein each thymine (T) is optionally uracil (U) (SEQ ID NO: 28).

In various embodiments, T is

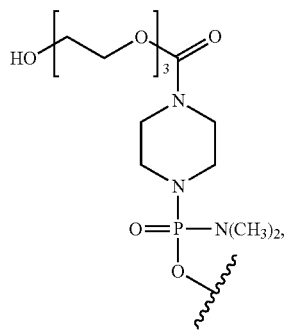

and the targeting sequence is 5'-CAATGCCATCCTG-GAGTTCCTG-3' (SEQ ID NO: 27).

In some embodiments, the targeting sequence is 5'-GTTGCCTCCGGTTCTGAAGGTGTTC-3', wherein each thymine (T) is optionally uracil (U) (SEQ ID NO: 30).

In various embodiments, T is

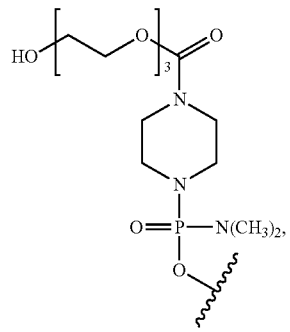

and the targeting sequence is 5'-GTTGCCTCCGGTTCT-GAAGGTGTTC-3', wherein each thymine (T) is optionally uracil (U) (SEQ ID NO: 30).

In various embodiments, T is

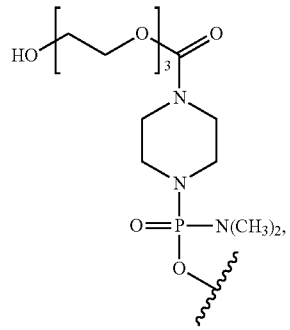

and the targeting sequence is 5'-GTTGCCTCCGGTTCT-GAAGGTGTTC-3' (SEQ ID NO: 29).

In some embodiments, including, for example, some embodiments of Formula (I), an antisense oligomer conjugate of the disclosure is according to Formula (III):

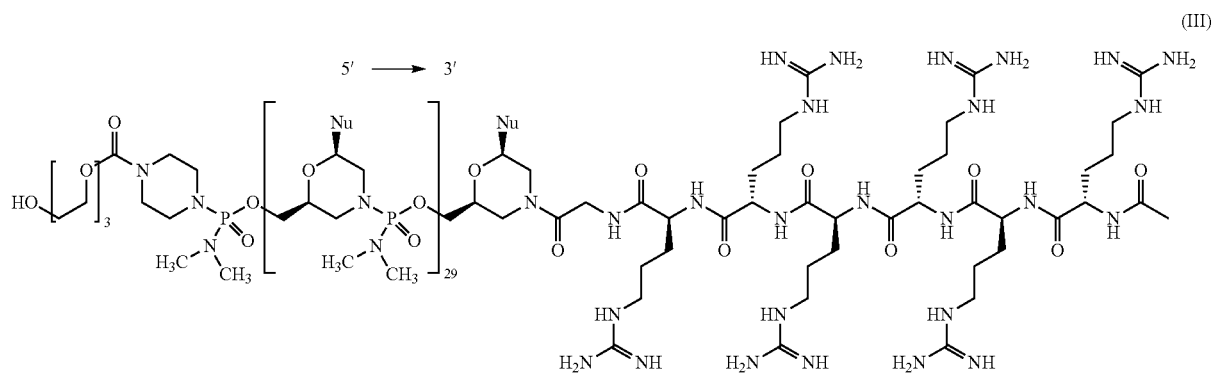

or a pharmaceutically acceptable salt thereof, wherein:

each Nu is a nucleobase which taken together to form a targeting sequence that is complementary to an exon 51 annealing site in the dystrophin pre-mRNA designated as H51A(+66+95).

In some embodiments, each Nu is independently selected from cytosine (C), guanine (G), thymine (T), adenine (A), 5-methylcytosine (5mC), uracil (U), and hypoxanthine (I).

In various embodiments, each Nu from 1 to 30 and 5' to 3' is:

| Position No. 5' to 3' | Nu |
|---|---|
| 1 | C |
| 2 | X |
| 3 | C |
| 4 | C |
| 5 | A |
| 6 | A |
| 7 | C |
| 8 | A |
| 9 | X |
| 10 | C |
| 11 | A |
| 12 | A |
| 13 | G |
| 14 | G |
| 15 | A |
| 16 | A |
| 17 | G |
| 18 | A |
| 19 | X |
| 20 | G |
| 21 | G |
| 22 | C |
| 23 | A |
| 24 | X |
| 25 | X |
| 26 | X |
| 27 | C |
| 28 | X |
| 29 | A |
| 30 | G | wherein A is

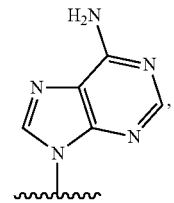 [SMILES: *n1cnc2c(N)ncnc21]

C is

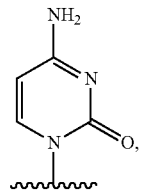 [SMILES: *n1ccc(N)nc1=O]

G is

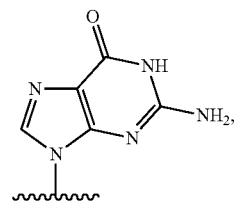 [SMILES: *n1cnc2c(=O)[nH]c(N)nc21]

and X is

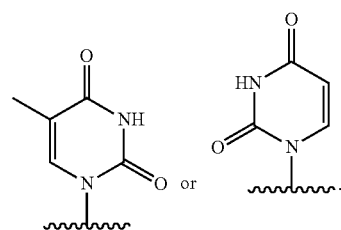

In certain embodiments, each X is independently

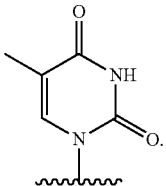 [SMILES: *n1cc(C)c(=O)[nH]c1=O]

In some embodiments, an antisense oligomer conjugate of Formula (III) is an HCl (hydrochloric acid) salt thereof. In certain embodiments, the HCl salt is a ·6HCl salt.

In some embodiments, including, for example, some embodiments of Formula (III), an antisense oligomer conjugate of the disclosure is according to Formula (IIIA):

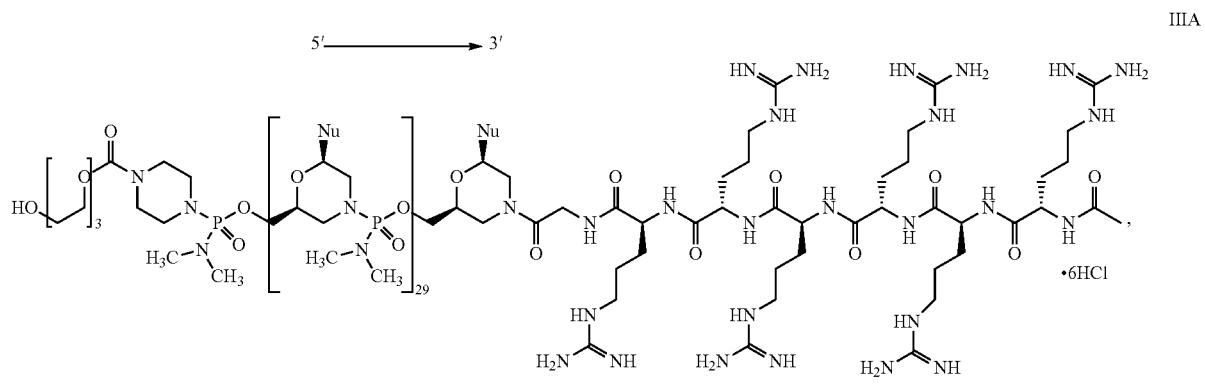

IIIA wherein each Nu is a nucleobase which taken together to form a targeting sequence that is complementary to an exon 51 annealing site in the dystrophin pre-mRNA designated as H51A(+66+95).

In some embodiments, each Nu is independently selected from cytosine (C), guanine (G), thymine (T), adenine (A), 5-methylcytosine (5mC), uracil (U), and hypoxanthine (I).

In various embodiments, each Nu from 1 to 30 and 5' to 3' is:

| Position No. 5' to 3' | Nu |
|---|---|
| 1 | C |
| 2 | X |
| 3 | C |
| 4 | C |
| 5 | A |
| 6 | A |
| 7 | C |
| 8 | A |
| 9 | X |
| 10 | C |
| 11 | A |
| 12 | A |
| 13 | G |
| 14 | G |
| 15 | A |
| 16 | A |
| 17 | G |
| 18 | A |
| 19 | X |
| 20 | G |
| 21 | G |
| 22 | C |
| 23 | A |
| 24 | X |
| 25 | X |
| 26 | X |
| 27 | C |
| 28 | X |
| 29 | A |
| 30 | G | wherein A is

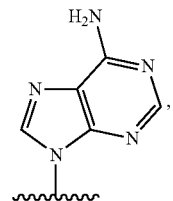 [SMILES: *n1cnc2c(N)ncnc21]

C is

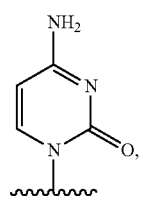 [SMILES: *n1ccc(N)nc1=O]

G is

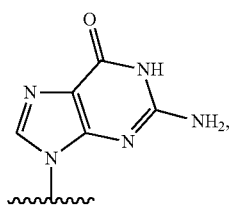 [SMILES: *n1cnc2c(=O)[nH]c(N)nc21]

and X is

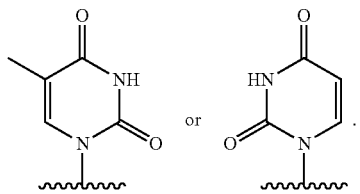

In certain embodiments, each X is

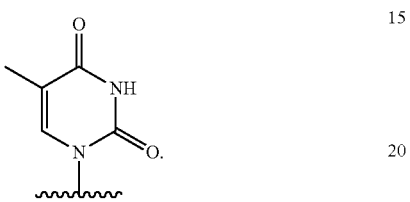

In some embodiments including, for example, embodiments of antisense oligomer conjugates of Formula (III) and Formula (IIIA), the targeting sequence is 5'-CTCCAACAT-CAAGGAAGATGGCATTTCTAG-3' wherein each thymine (T) is optionally uracil (U) (SEQ ID NO: 31). In various embodiments including, for example, embodiments of antisense oligomer conjugates of Formula (III) and Formula (IIIA), the targeting sequence is 5'-CTCCAACAT-CAAGGAAGATGGCATTTCTAG-3' (SEQ ID NO: 32).

In some embodiments, including, for example, embodiments of antisense oligomer conjugates of Formula (I), an antisense oligomer conjugate of the disclosure is according to Formula (IV):

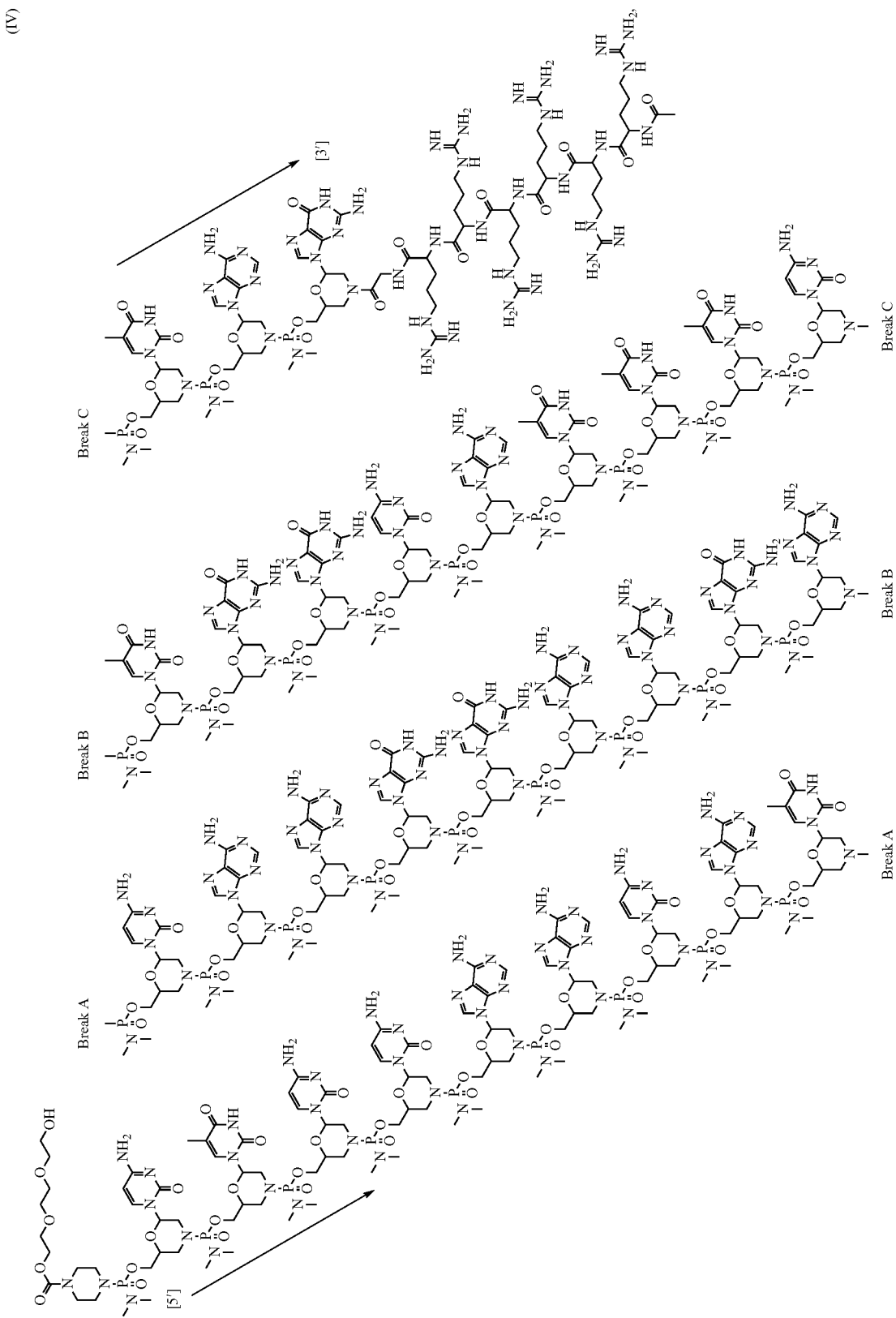
(IV)

or a pharmaceutically acceptable salt thereof.

In some embodiments, an antisense oligomer conjugate of Formula (IV) is an HCl (hydrochloric acid) salt thereof. In certain embodiments, the HCl salt is a ·6HCl salt.

In some embodiments, including, for example, embodiments of antisense oligomer conjugates of Formula (IV), an antisense oligomer conjugate of the disclosure is according to Formula (IVA):

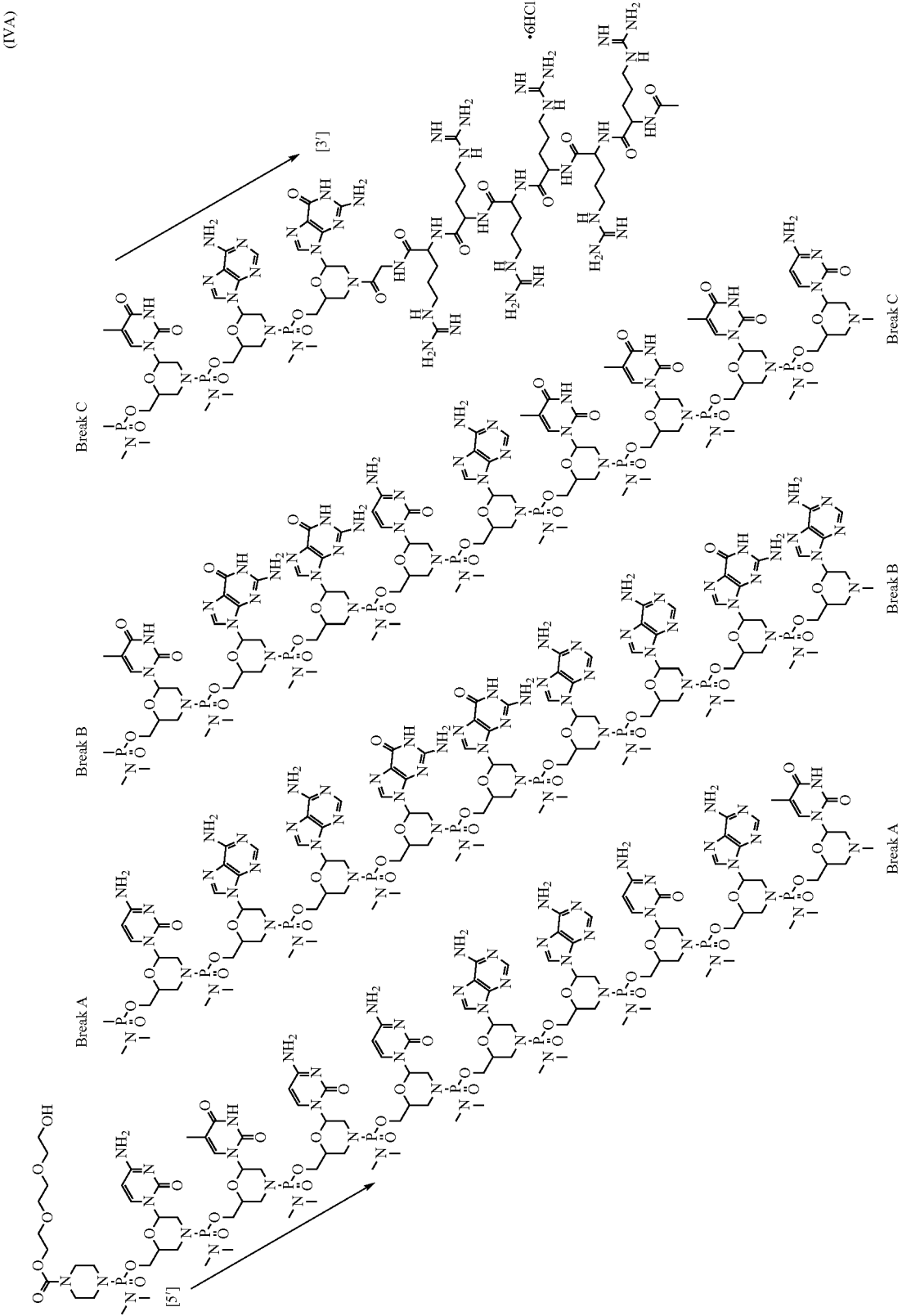
(IVA)

In some embodiments of the disclosure, including some embodiments of antisense oligomer conjugates of Formula (I) and embodiments of antisense oligomer conjugates of Formula (IV), the antisense oligomer conjugate is according to Formula (IVB):

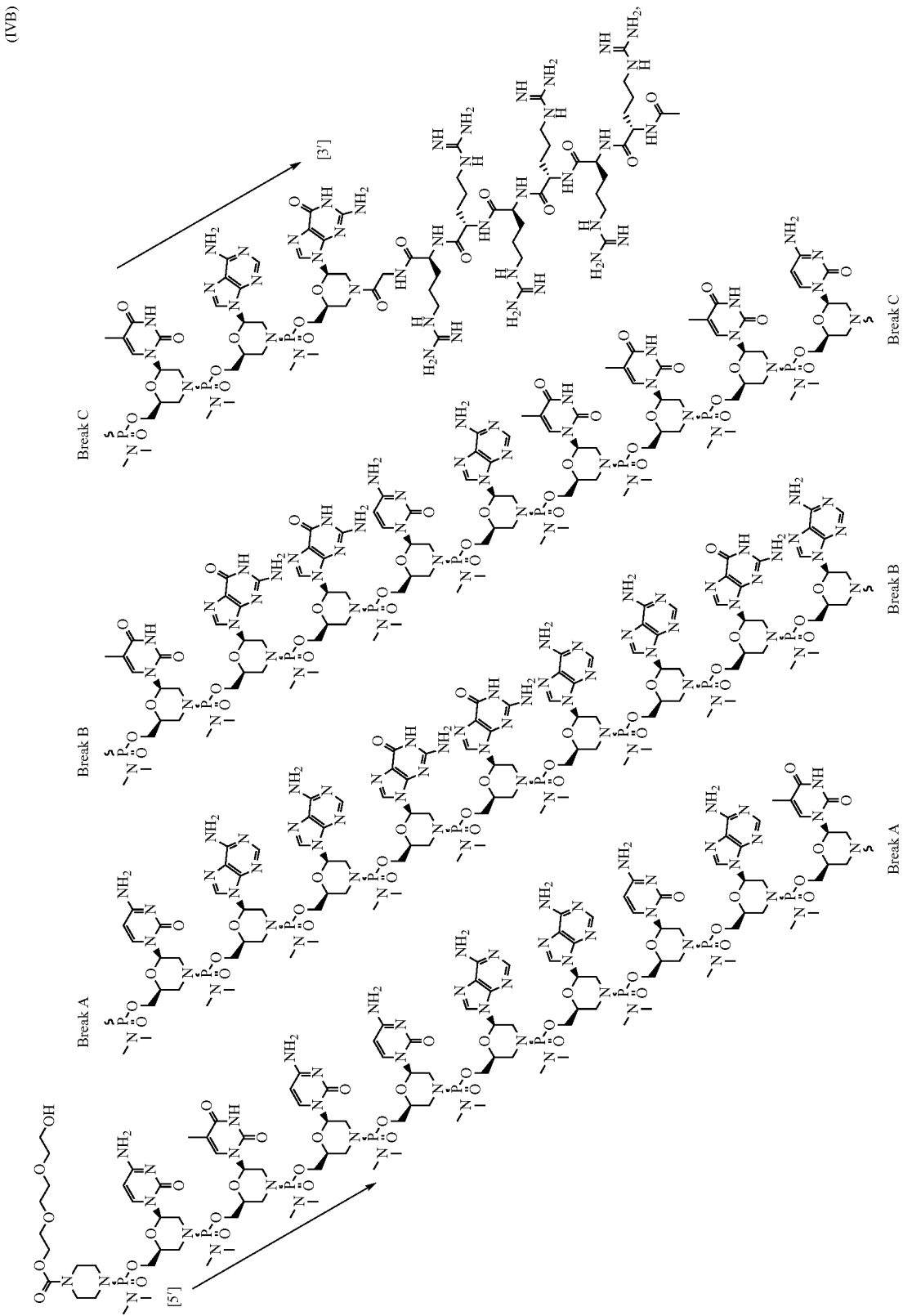

or a pharmaceutically acceptable salt thereof.

In some embodiments, an antisense oligomer conjugate of Formula (IVB) is an HCl (hydrochloric acid) salt thereof. In certain embodiments, the HCl salt is a ·6HCl salt.

In some embodiments, including, for example, embodiments of antisense oligomer conjugates of Formula (IVB), an antisense oligomer conjugate of the disclosure is according to Formula (IVC):

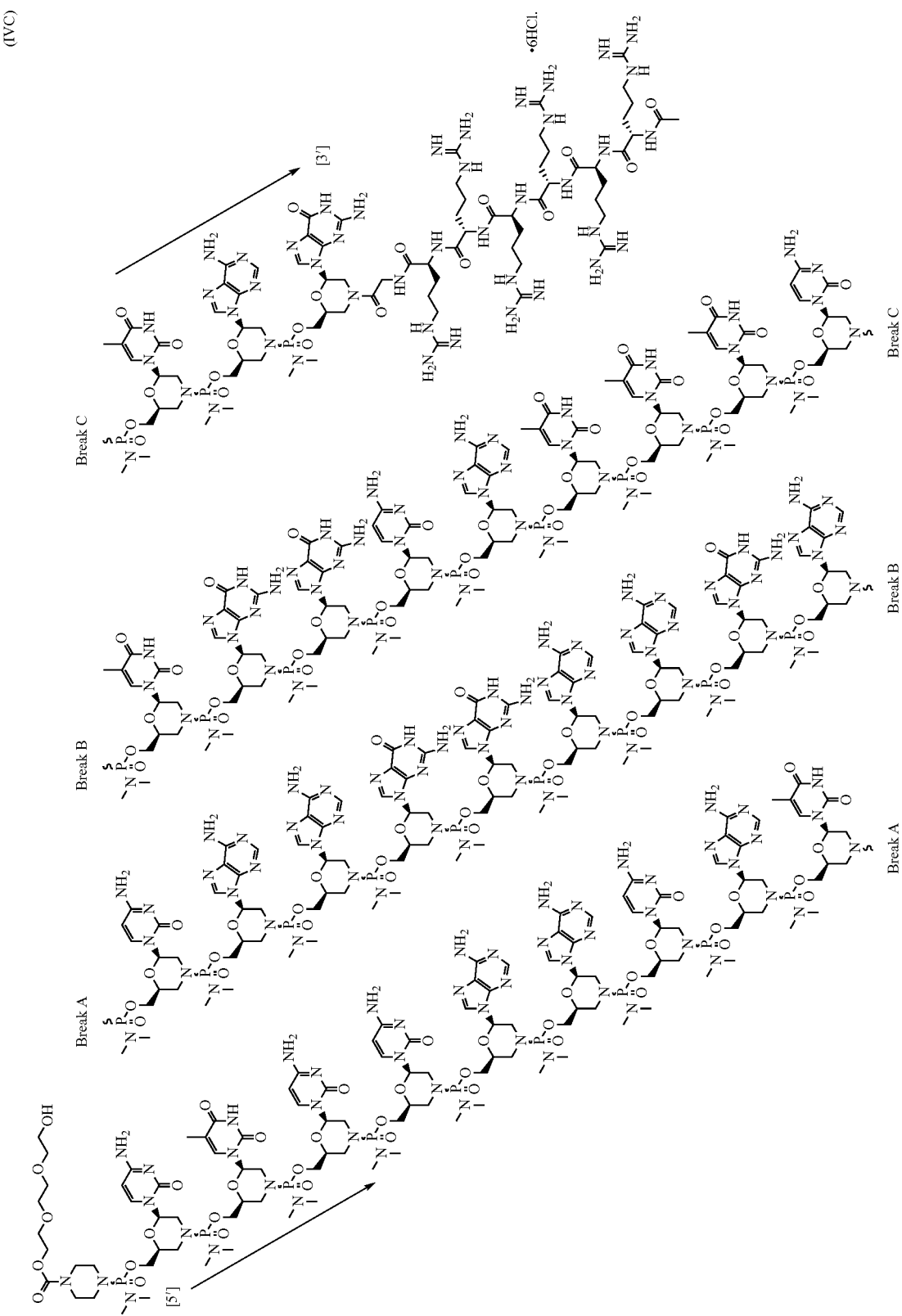

In some embodiments, including, for example, some embodiments of Formula (I), an antisense oligomer conjugate of the disclosure is according to Formula (V):

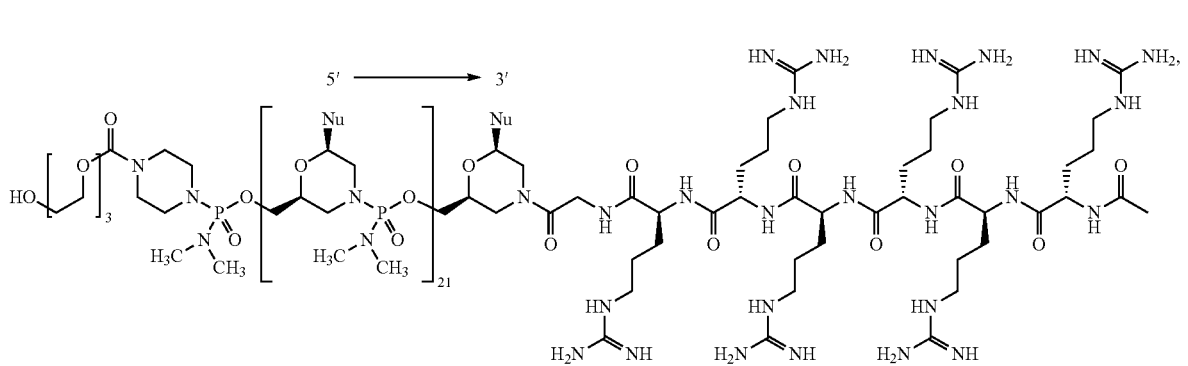

or a pharmaceutically acceptable salt thereof, wherein:

each Nu is a nucleobase which taken together form a targeting sequence that is complementary to an exon 45 annealing site in the dystrophin pre-mRNA designated as H45A(−03-+19).

In some embodiments, each Nu is independently selected from cytosine (C), guanine (G), thymine (T), adenine (A), 5-methylcytosine (5mC), uracil (U), and hypoxanthine (I). In various embodiments, each Nu from 1 to 22 and 5' to 3' is:

| Position No. 5' to 3' | Nu |
|---|---|
| 1 | C |
| 2 | X |
| 3 | C |
| 4 | C |
| 5 | A |
| 6 | A |
| 7 | C |
| 8 | A |
| 9 | X |
| 10 | C |
| 11 | A |
| 12 | A |
| 13 | G |
| 14 | G |
| 15 | A |
| 16 | A |
| 17 | G |
| 18 | A |
| 19 | X |
| 20 | G |
| 21 | G |
| 22 | C |
| 23 | A |
| 24 | X |
| 25 | X |
| 26 | X |
| 27 | C |
| 28 | X |
| 29 | A |
| 30 | G | wherein A is

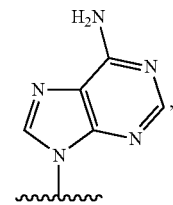 [SMILES: *n1cnc2c(N)ncnc21]

C is

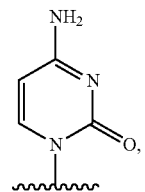 [SMILES: *n1ccc(N)nc1=O]

G is

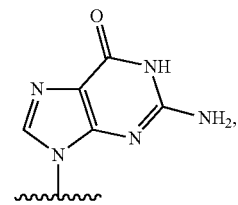 [SMILES: *n1cnc2c(=O)[nH]c(N)nc21]

and X is

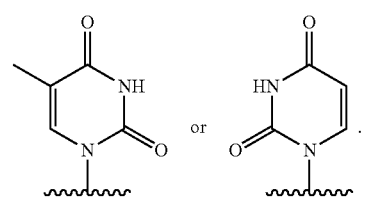

In certain embodiments, each X is independently

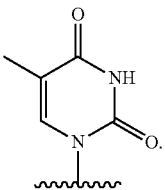 [SMILES: *n1cc(C)c(=O)[nH]c1=O]

In Some embodiments, an antisense oligomer conjugate of Formula (V) is an HCl (hydrochloric acid) salt thereof. In certain embodiments, the HCl salt is a ·6HCl salt.

In some embodiments, including, for example, some embodiments of Formula (V), an antisense oligomer conjugate of the disclosure is according to Formula (VA):

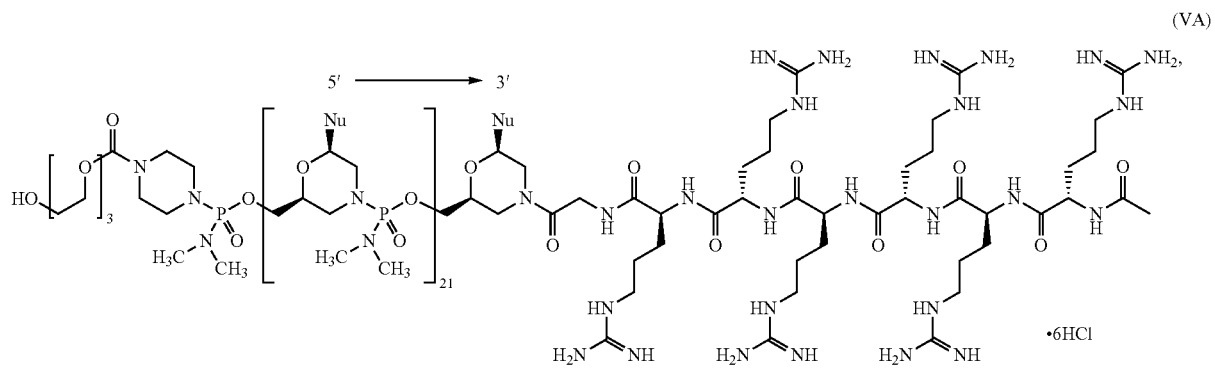

(VA)

wherein each Nu is a nucleobase which taken together form a targeting sequence that is complementary to an exon 45 annealing site in the dystrophin pre-mRNA designated as H45A(−03+19).

In some embodiments, each Nu is independently selected from cytosine (C), guanine (G), thymine (T), adenine (A), 5-methylcytosine (5mC), uracil (U), and hypoxanthine (I). In various embodiments, each Nu from 1 to 30 and 5' to 3' is:

| Position No. 5' to 3' | Nu |
|---|---|
| 1 | C |
| 2 | A |
| 3 | A |
| 4 | X |
| 5 | G |
| 6 | C |
| 7 | C |
| 8 | A |
| 9 | X |
| 10 | C |
| 11 | C |
| 12 | X |
| 13 | G |
| 14 | G |
| 15 | A |
| 16 | G |
| 17 | X |
| 18 | X |
| 19 | C |
| 20 | C |
| 21 | X |
| 22 | G | wherein A is

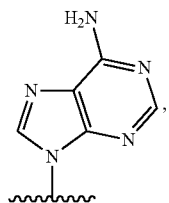 [SMILES: *n1cnc2c(N)ncnc21]

C is

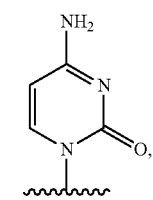 [SMILES: *n1ccc(N)nc1=O]

G is

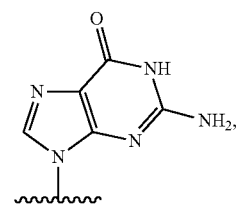 [SMILES: *n1cnc2c(=O)[nH]c(N)nc21]

and X is

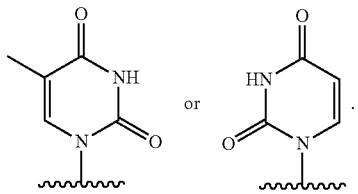

In certain embodiments, each X is

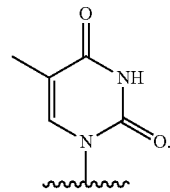 [SMILES: *n1cc(C)c(=O)[nH]c1=O]

In some embodiments including, for example, embodiments of antisense oligomer conjugates of Formula (V) and Formula (VA), the targeting sequence is 5'-CAATGC-CATCCTGGAGTTCCTG-3' wherein each thymine (T) is optionally uracil (U) (SEQ ID NO: 28). In various embodiments including, for example, embodiments of antisense oligomer conjugates of Formula (V) and Formula (VA), the targeting sequence is 5'-CAATGCCATCCTG-GAGTTCCTG-3' (SEQ ID NO: 27).

In some embodiments, including, for example, embodiments of antisense oligomer conjugates of Formula (I), an antisense oligomer conjugate of the disclosure is according to Formula (VI):

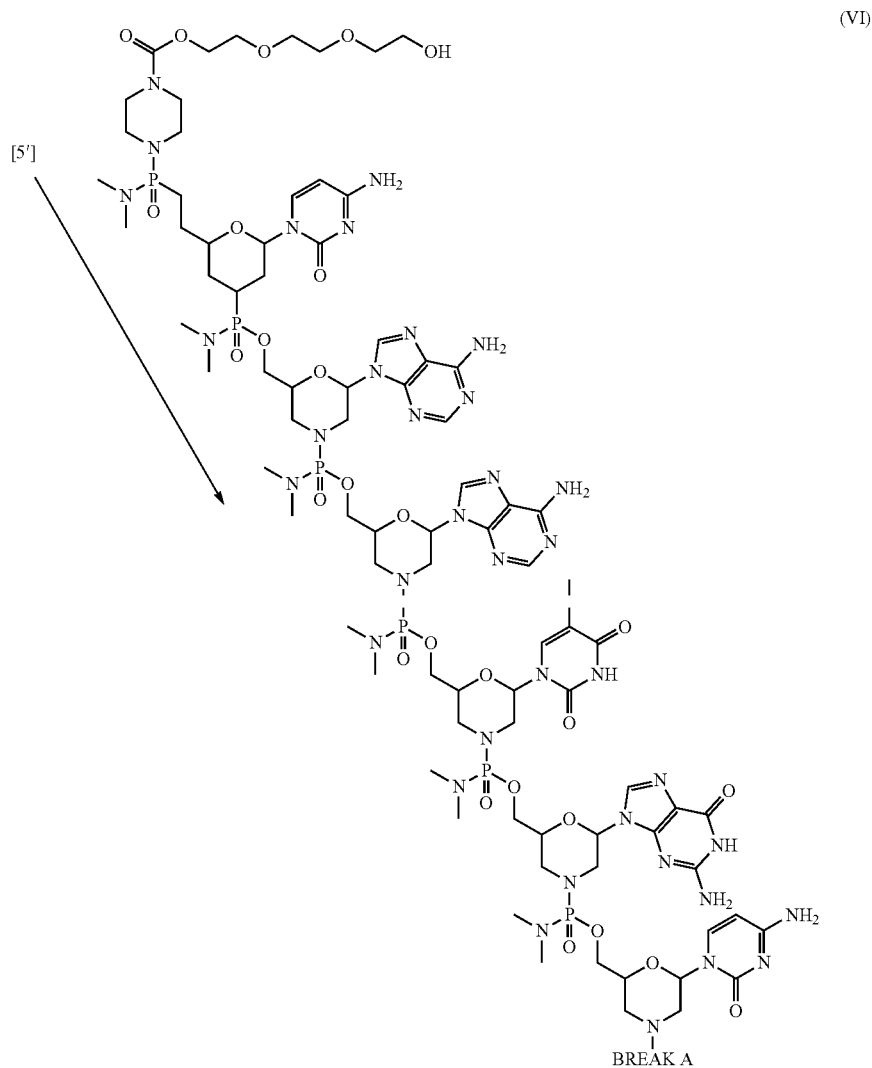

(VI)

BREAK A

-continued
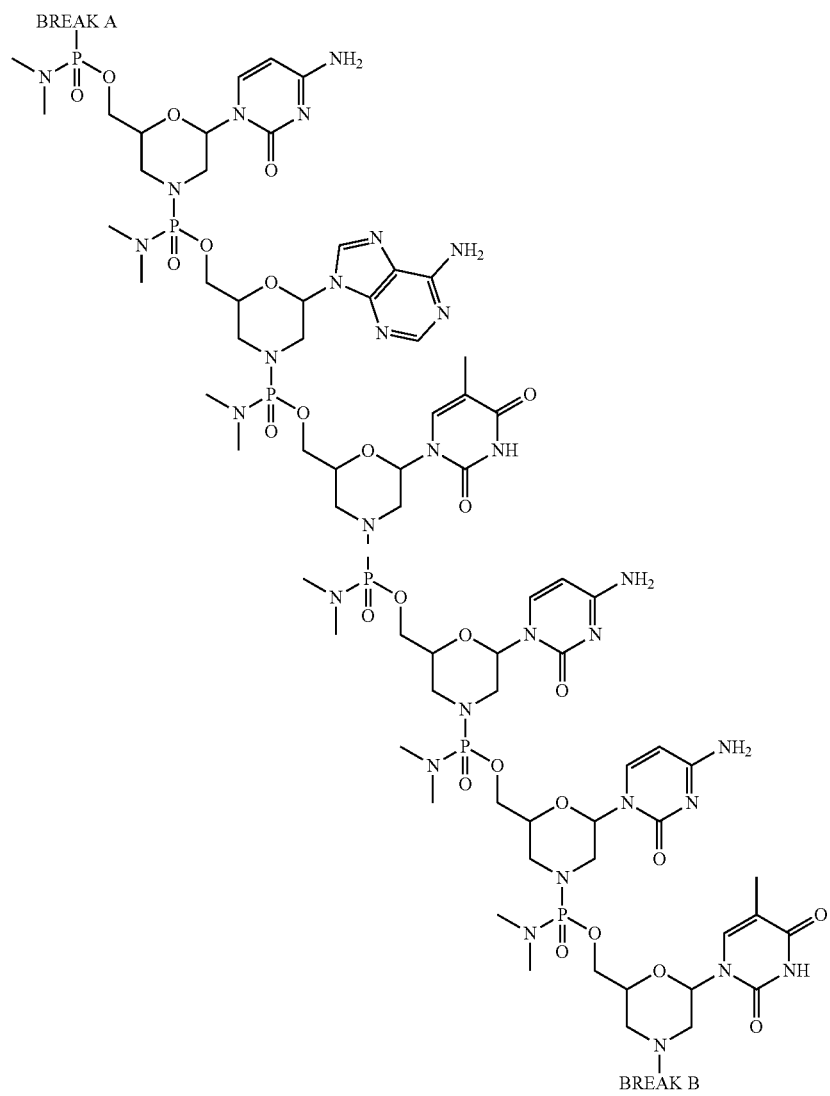
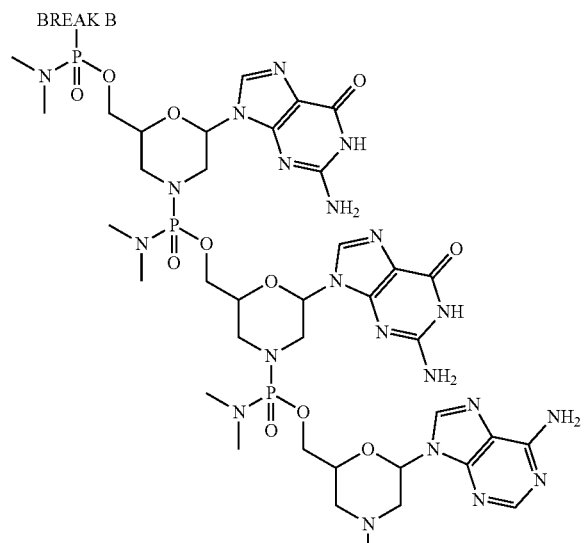

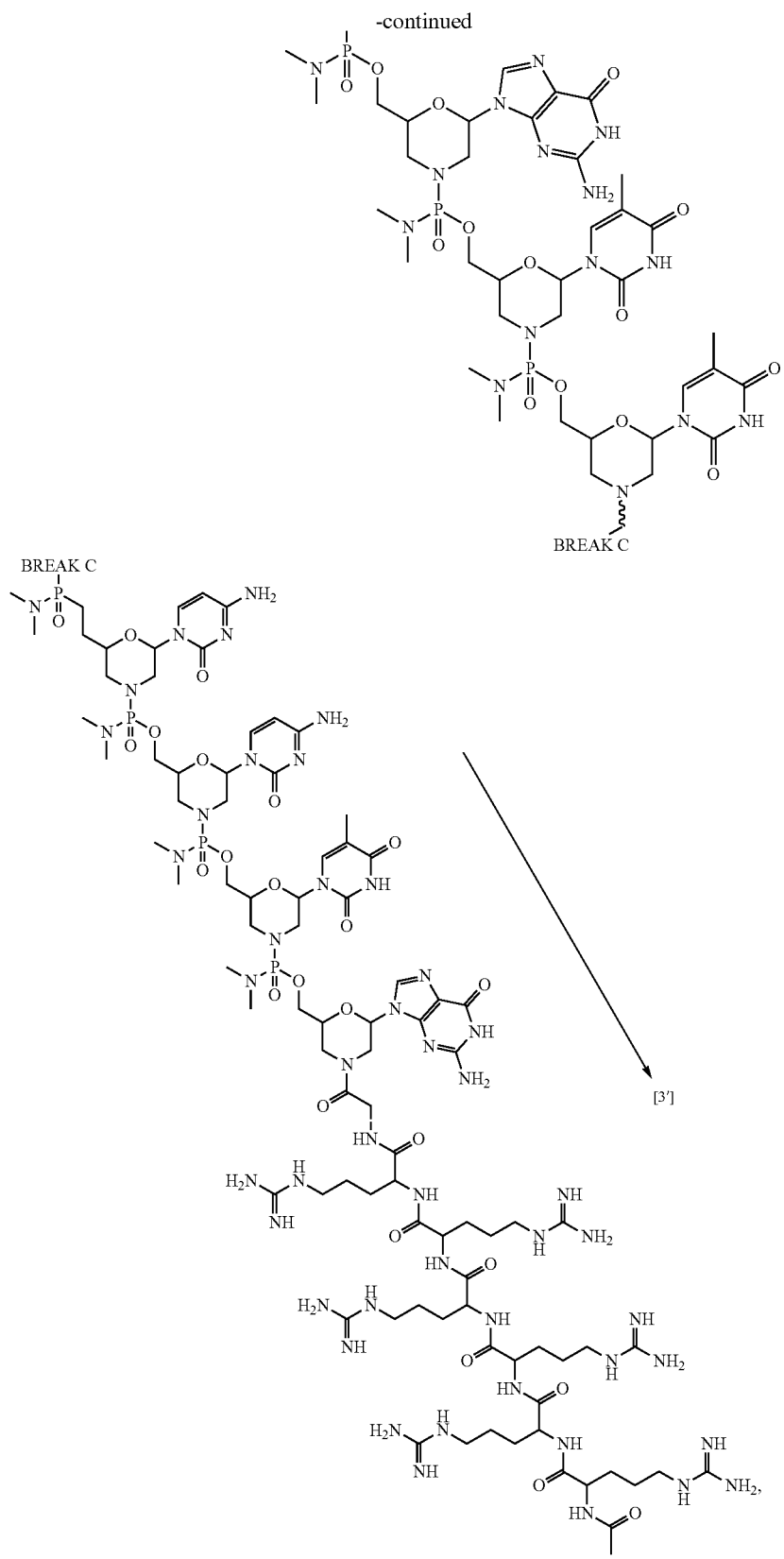
or a pharmaceutically acceptable salt thereof.

In some embodiments, an antisense oligomer conjugate of Formula (VI) is an HCl (hydrochloric acid) salt thereof. In certain embodiments, the HCl salt is a ·6HCl salt.

In some embodiments, including, for example, embodiments of antisense oligomer conjugates of Formula (VI), an antisense oligomer conjugate of the disclosure is according to Formula (VIA):

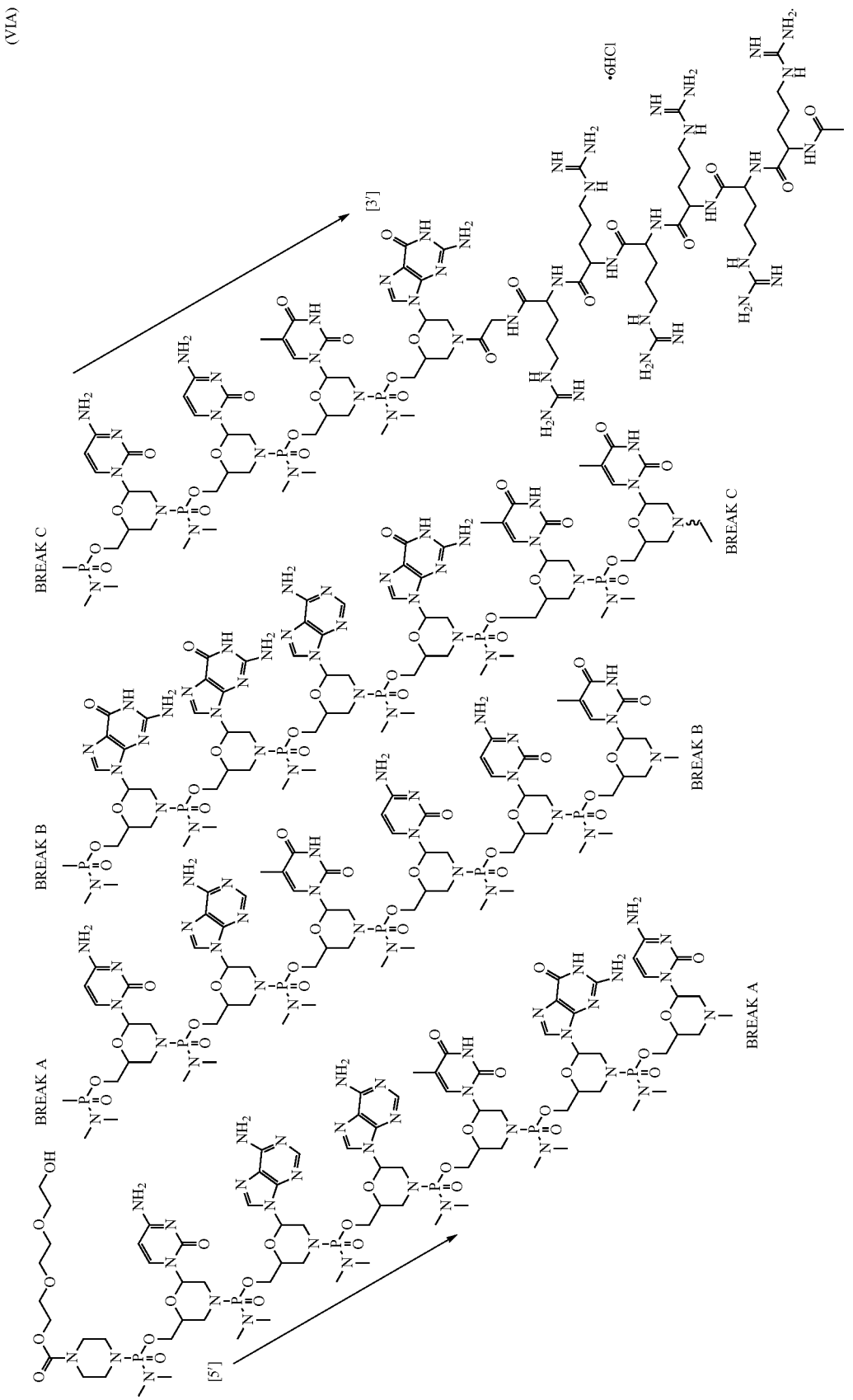

In some embodiments of the disclosure, including some embodiments of antisense oligomer conjugates of Formula (I) and embodiments of antisense oligomer conjugates of Formula (VI), the antisense oligomer conjugate is according to Formula (VIB):

(VIB)
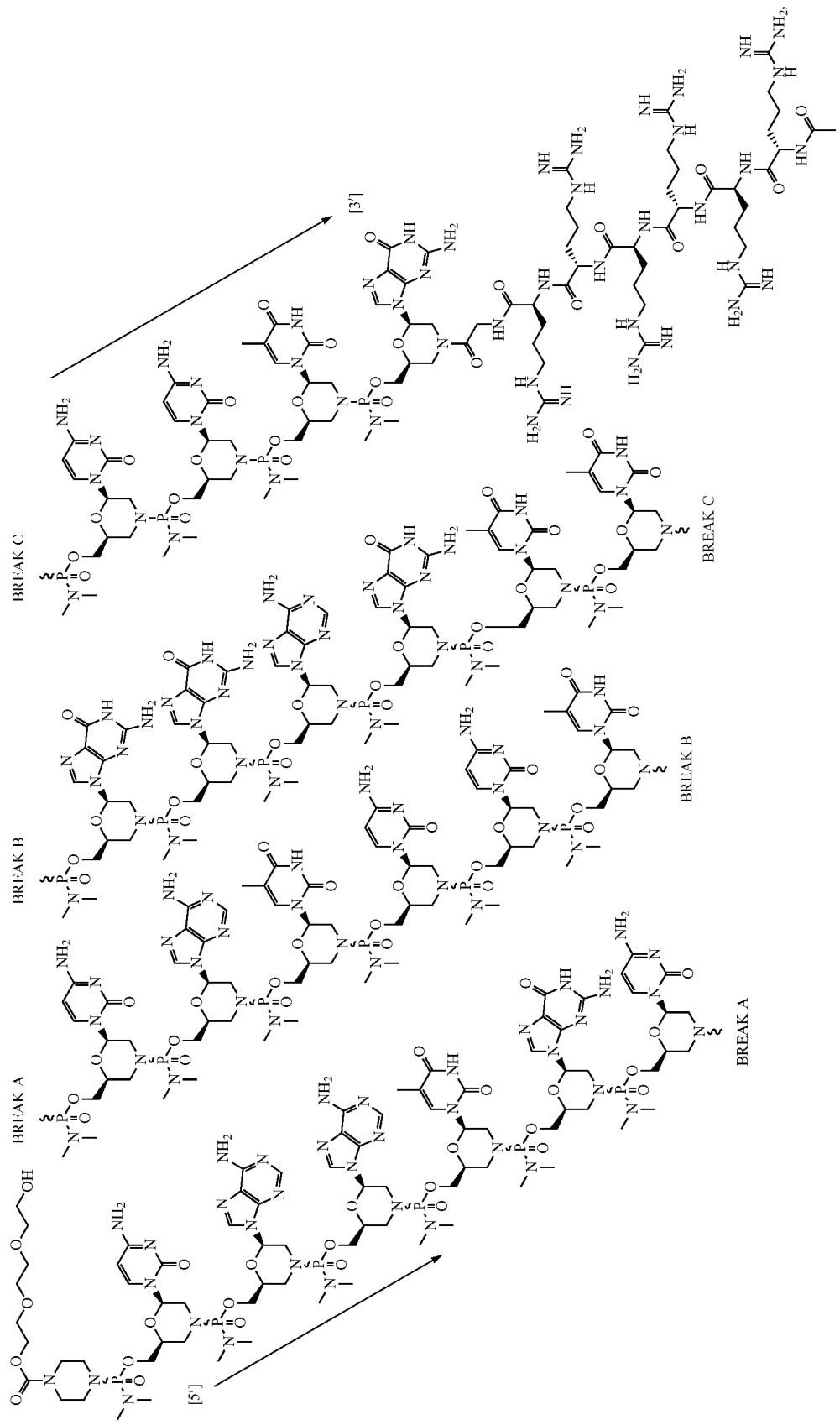

or a pharmaceutically acceptable salt thereof.

In some embodiments, an antisense oligomer conjugate of Formula (VIB) is an HCl (hydrochloric acid) salt thereof. In certain embodiments, the HCl salt is a ·6HCl salt.

In some embodiments, including, for example, embodiments of antisense oligomer conjugates of Formula (VIB), an antisense oligomer conjugate of the disclosure is according to Formula (VIC):

(VIC)
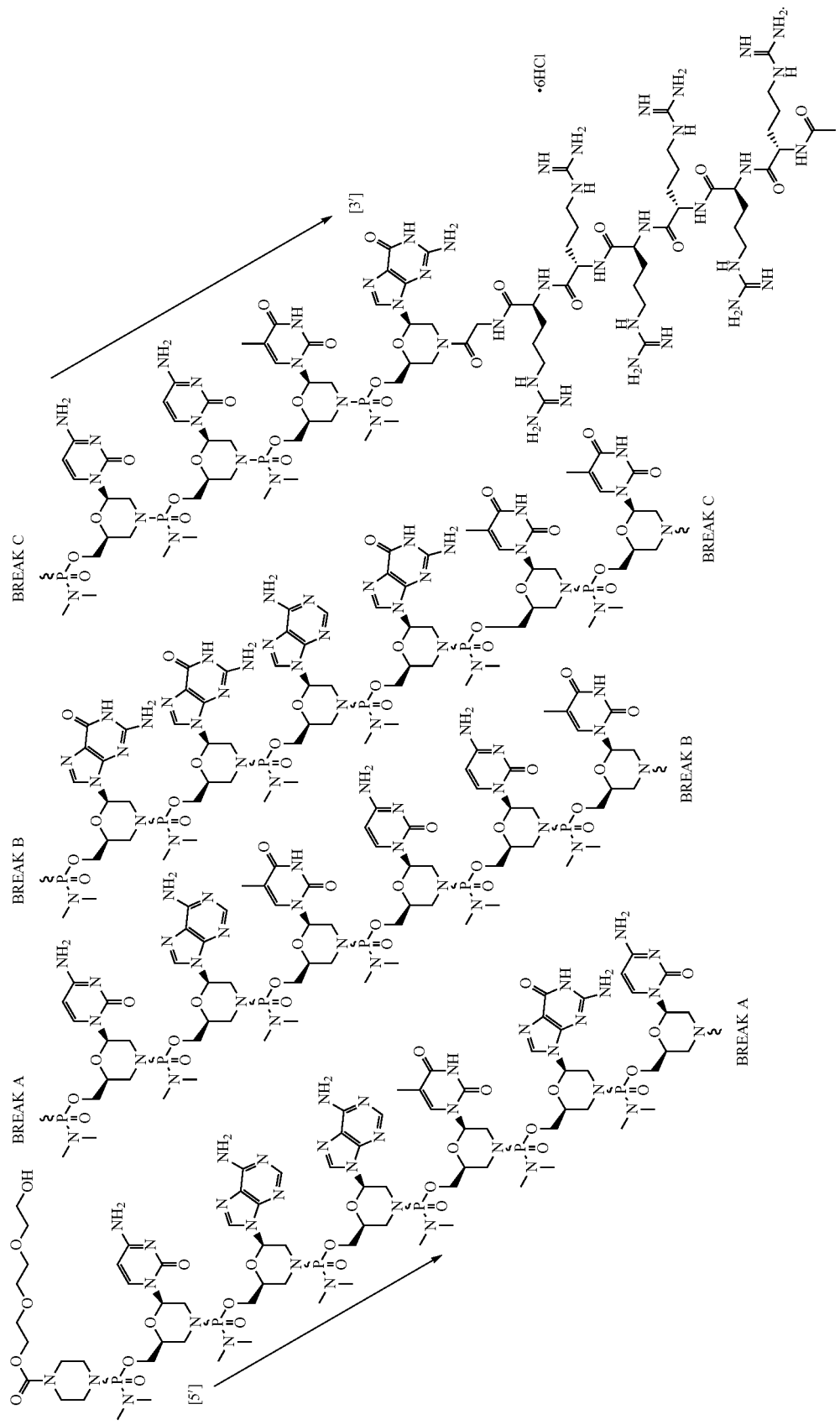

In some embodiments, including, for example, some embodiments of Formula (I), an antisense oligomer conjugate of the disclosure is according to Formula (VII):

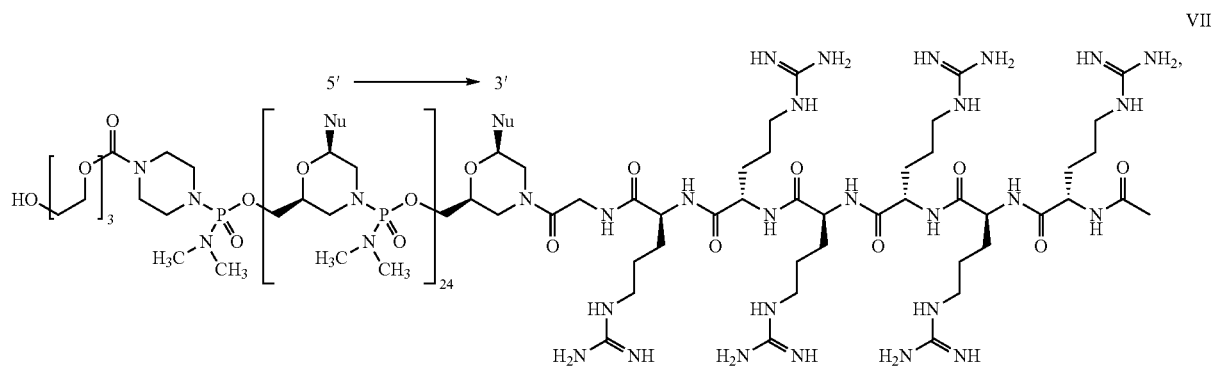

or a pharmaceutically acceptable salt thereof, wherein:

each Nu is a nucleobase which taken together form a targeting sequence that is complementary to an exon 53 annealing site in the dystrophin pre-mRNA designated as H53A(+36+60).

In some embodiments, each Nu is independently selected from cytosine (C), guanine (G), thymine (T), adenine (A), 5-methylcytosine (5mC), uracil (U), and hypoxanthine (I). In various embodiments, each Nu from 1 to 25 and 5' to 3' is:

| Position No. 5' to 3' | Nu |
|---|---|
| 1 | G |
| 2 | X |
| 3 | X |
| 4 | G |
| 5 | C |
| 6 | C |
| 7 | X |
| 8 | C |
| 9 | C |
| 10 | G |
| 11 | G |
| 12 | X |
| 13 | X |
| 14 | C |
| 15 | X |
| 16 | G |
| 17 | A |
| 18 | A |
| 19 | G |
| 20 | G |
| 21 | X |
| 22 | G |
| 23 | X |
| 24 | X |
| 25 | C | wherein A is

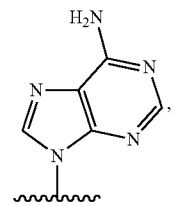 [SMILES: *n1cnc2c(N)ncnc21]

C is

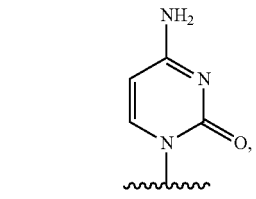 [SMILES: *n1ccc(N)nc1=O]

G is

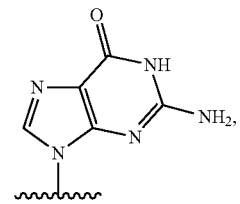 [SMILES: *n1cnc2c(=O)[nH]c(N)nc21]

and X is

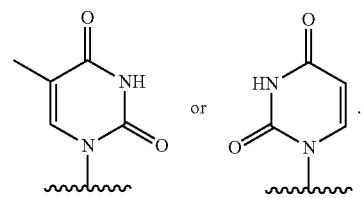

In certain embodiments, each X is independently

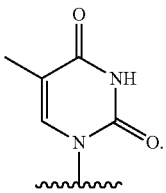 [SMILES: *n1cc(C)c(=O)[nH]c1=O]

In Some embodiments, an antisense oligomer conjugate of Formula (VII) is an HCl (hydrochloric acid) salt thereof. In certain embodiments, the HCl salt is a ·6HCl salt. In some embodiments, including, for example, some embodiments of Formula (VII), an antisense oligomer conjugate of the disclosure is according to Formula (VIIA):

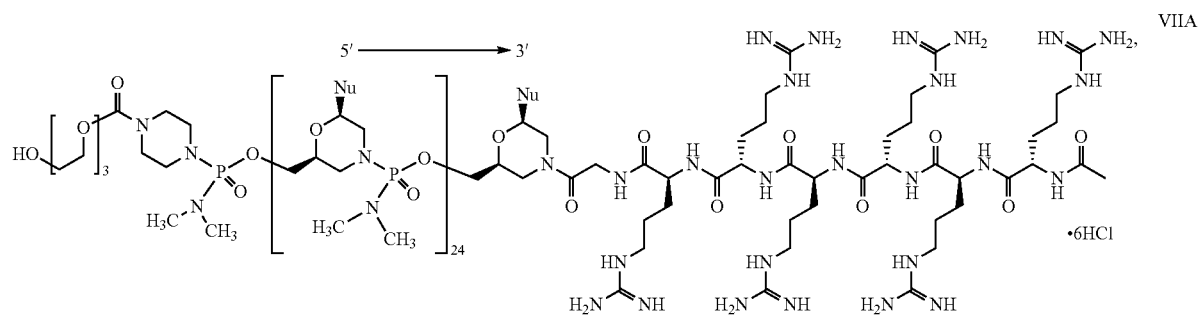

wherein each Nu is a nucleobase which taken together form a targeting sequence that is complementary to an exon 53 annealing site in the dystrophin pre-mRNA designated as H53A(+36+60).

In some embodiments, each Nu is independently selected from cytosine (C), guanine (G), thymine (T), adenine (A), 5-methylcytosine (5mC), uracil (U), and hypoxanthine (I). In various embodiments, each Nu from 1 to 25 and 5' to 3' is:

| Position No. 5' to 3' | Nu |
|---|---|
| 1 | G |
| 2 | X |
| 3 | X |
| 4 | G |
| 5 | C |
| 6 | C |
| 7 | X |
| 8 | C |
| 9 | C |
| 10 | G |
| 11 | G |
| 12 | X |
| 13 | X |
| 14 | C |
| 15 | X |
| 16 | G |
| 17 | A |
| 18 | A |
| 19 | G |
| 20 | G |
| 21 | X |
| 22 | G |
| 23 | X |
| 24 | X |
| 25 | C | wherein A is

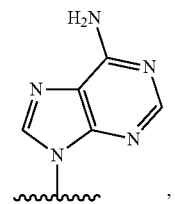

C is

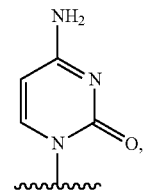 [SMILES: *n1ccc(N)nc1=O]

G is

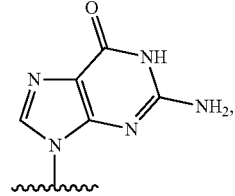 [SMILES: *n1cnc2c(=O)[nH]c(N)nc21]

and X is

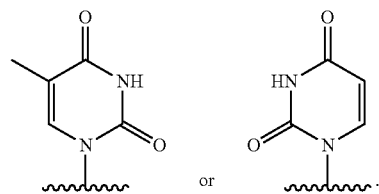

In certain embodiments, each X is

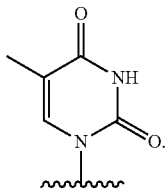 [SMILES: *n1cc(C)c(=O)[nH]c1=O]

In some embodiments including, for example, embodiments of antisense oligomer conjugates of Formula (VII) and Formula (VITA), the targeting sequence is 5'-GTTGCCTCCGGTTCTGAAGGTGTTC-3' wherein each thymine (T) is optionally uracil (U) (SEQ ID NO: 30). In various embodiments including, for example, embodiments of antisense oligomer conjugates of Formula (VII) and Formula (VITA), the targeting sequence is 5'-GTTGCCTCCGGTTCTGAAGGTGTTC-3' (SEQ ID NO: 29).

In some embodiments, including, for example, embodiments of antisense oligomer conjugates of Formula (I), an antisense oligomer conjugate of the disclosure is according to Formula (VIII):

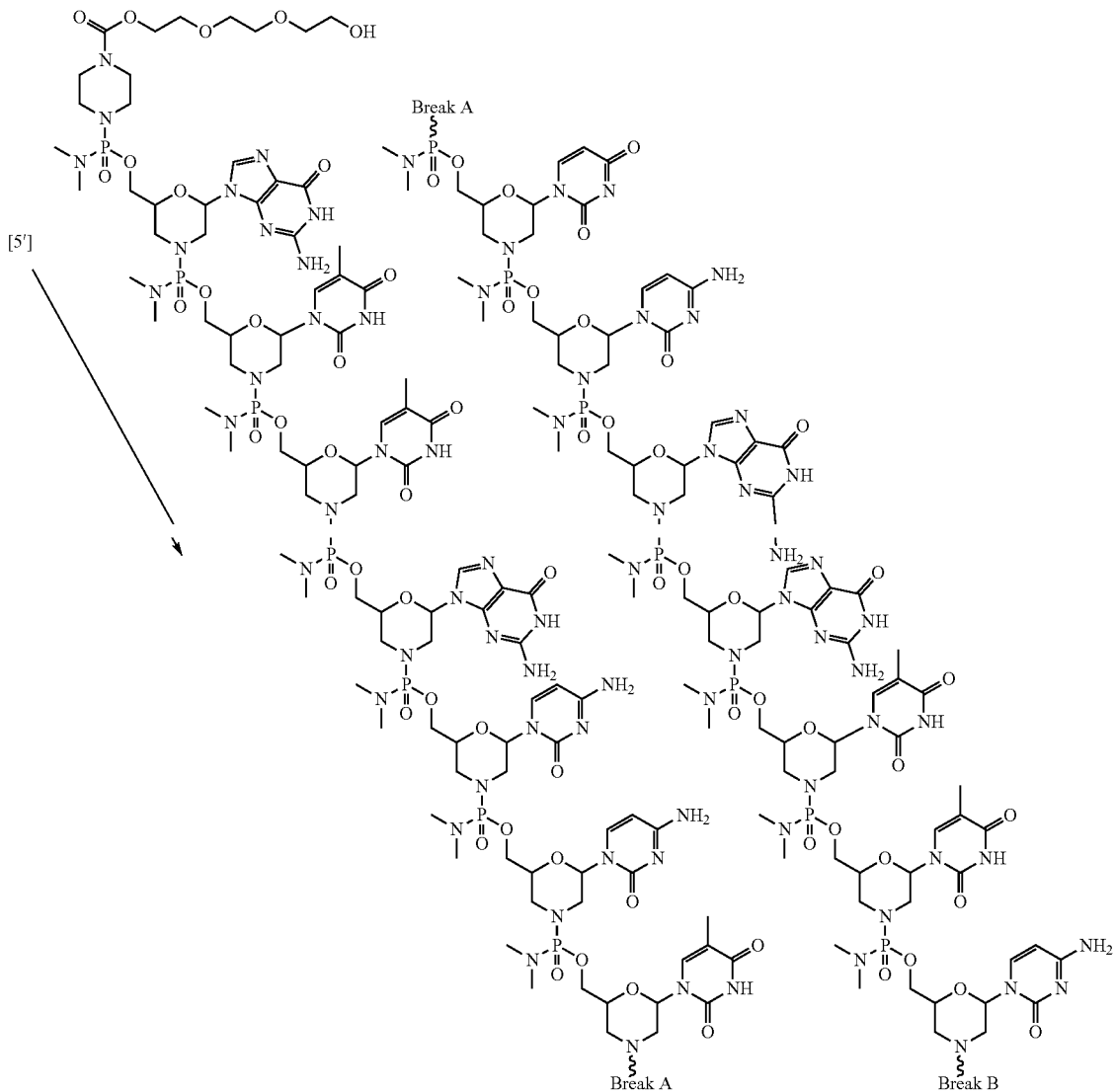

VIII

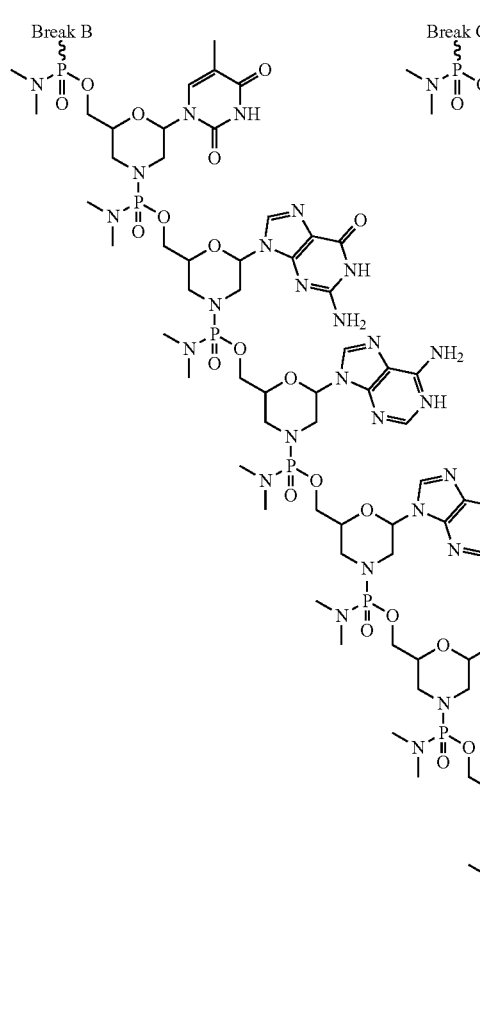
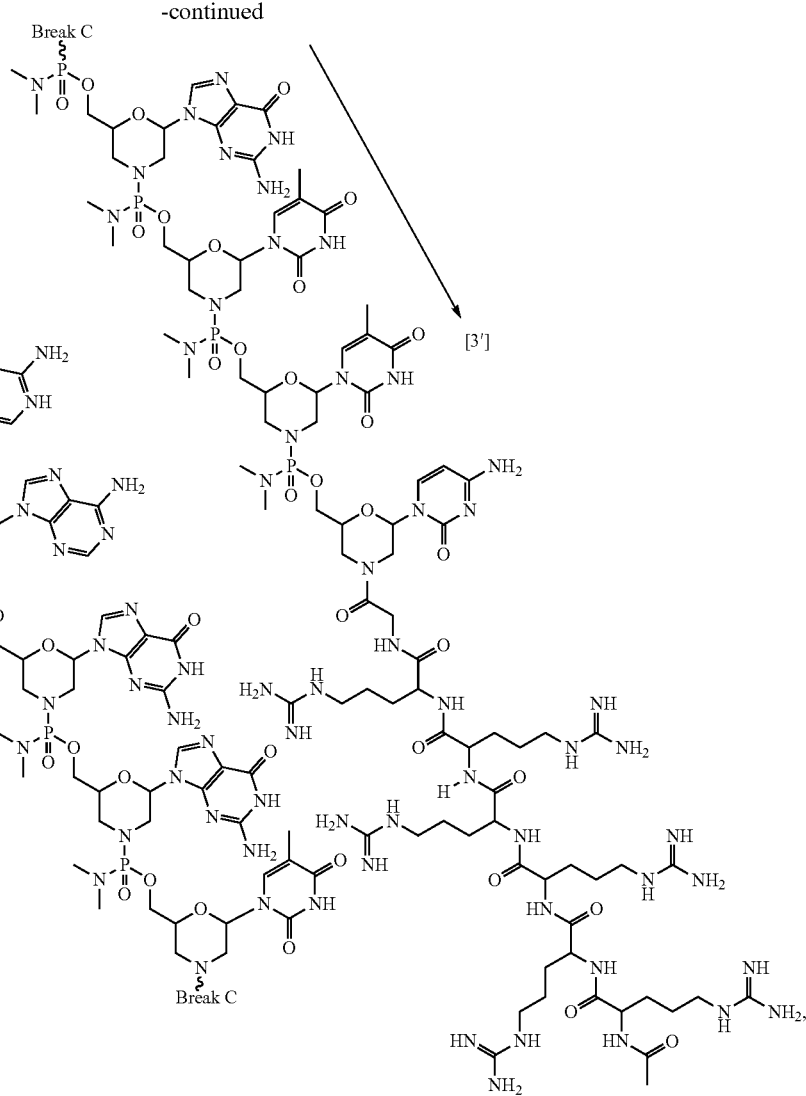

or a pharmaceutically acceptable salt thereof.

In some embodiments, an antisense oligomer conjugate of Formula (VIII) is an HCl (hydrochloric acid) salt thereof. In certain embodiments, the HCl salt is a ·6HCl salt. In some embodiments, including, for example, embodiments of antisense oligomer conjugates of Formula (VIII), an antisense oligomer conjugate of the disclosure is according to Formula (VIIIA):

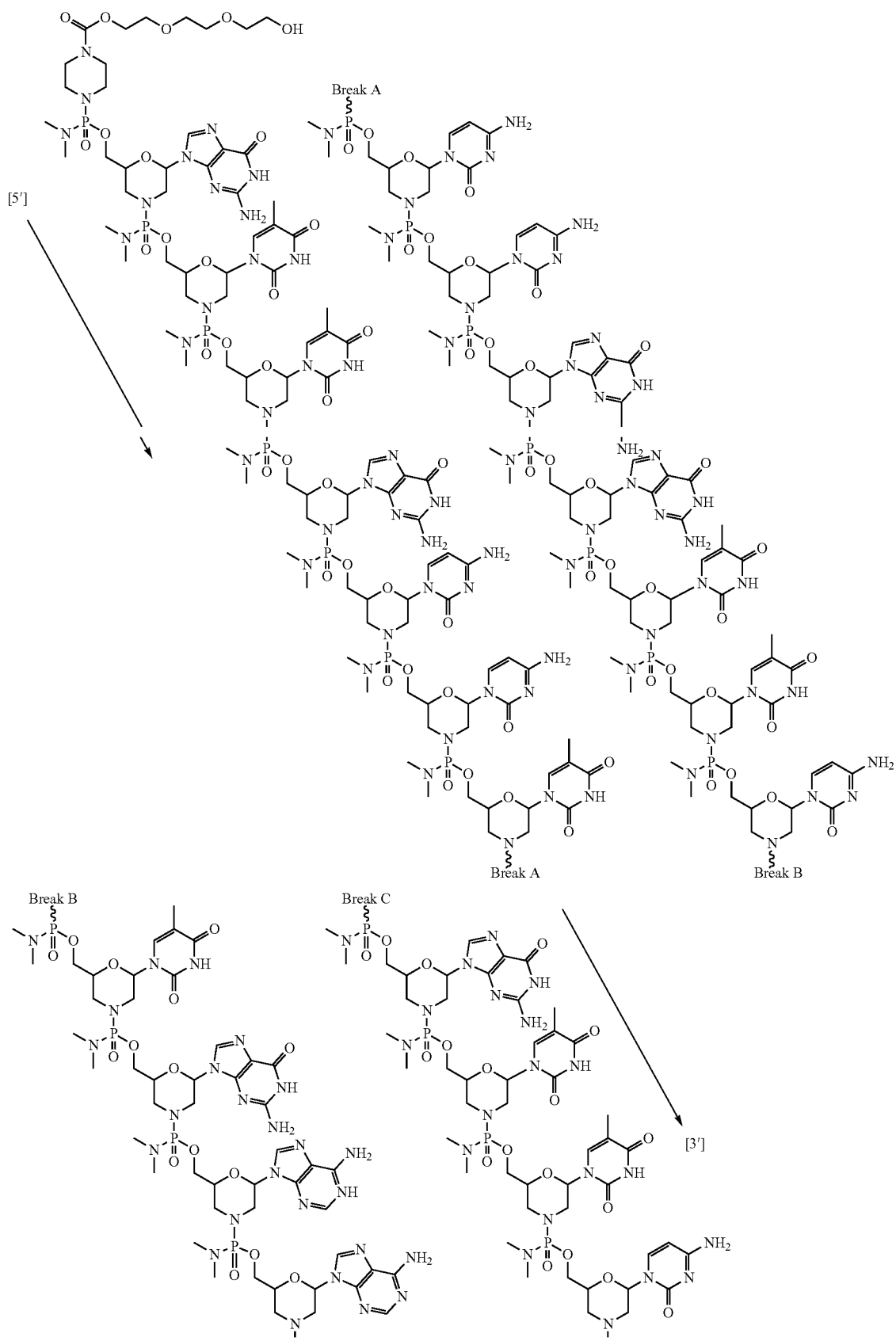

-continued
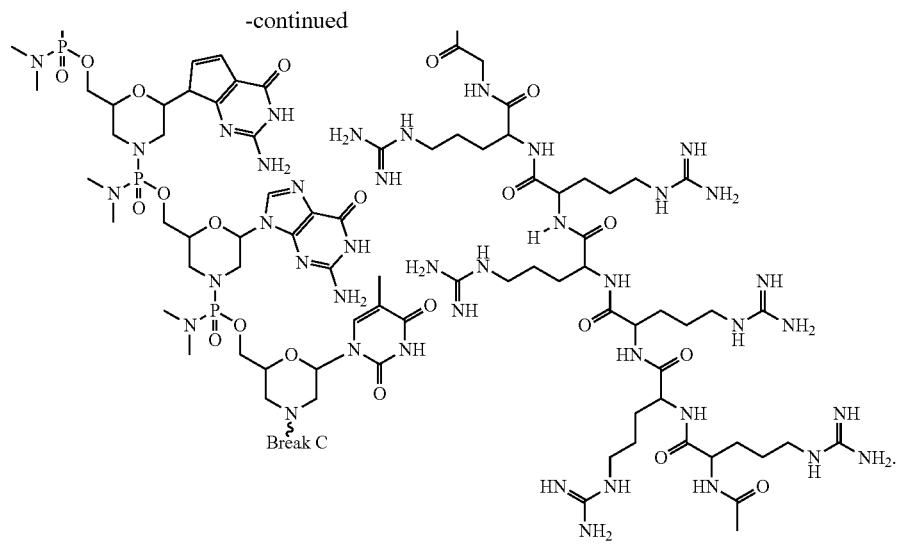
Break C
In some embodiments of the disclosure, including some embodiments of antisense oligomer conjugates of Formula (I) and embodiments of antisense oligomer conjugates of Formula (VIII), the antisense oligomer conjugate is according to Formula (VIIIB):
VIIIB
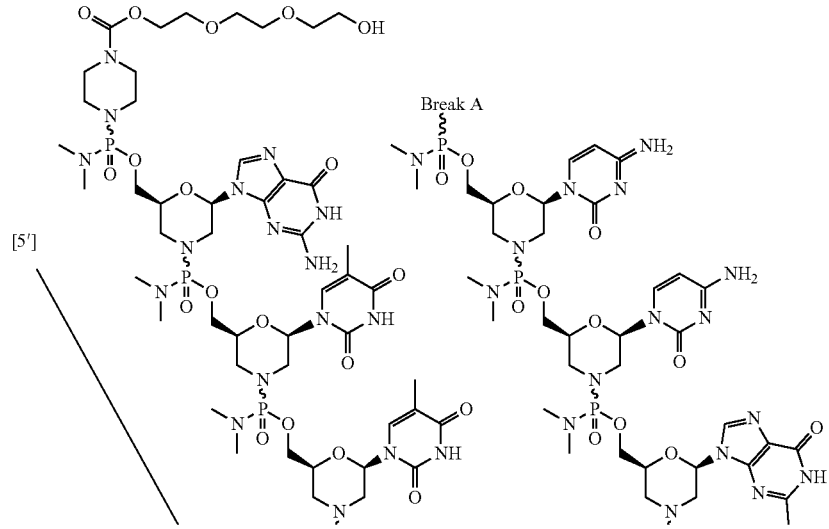

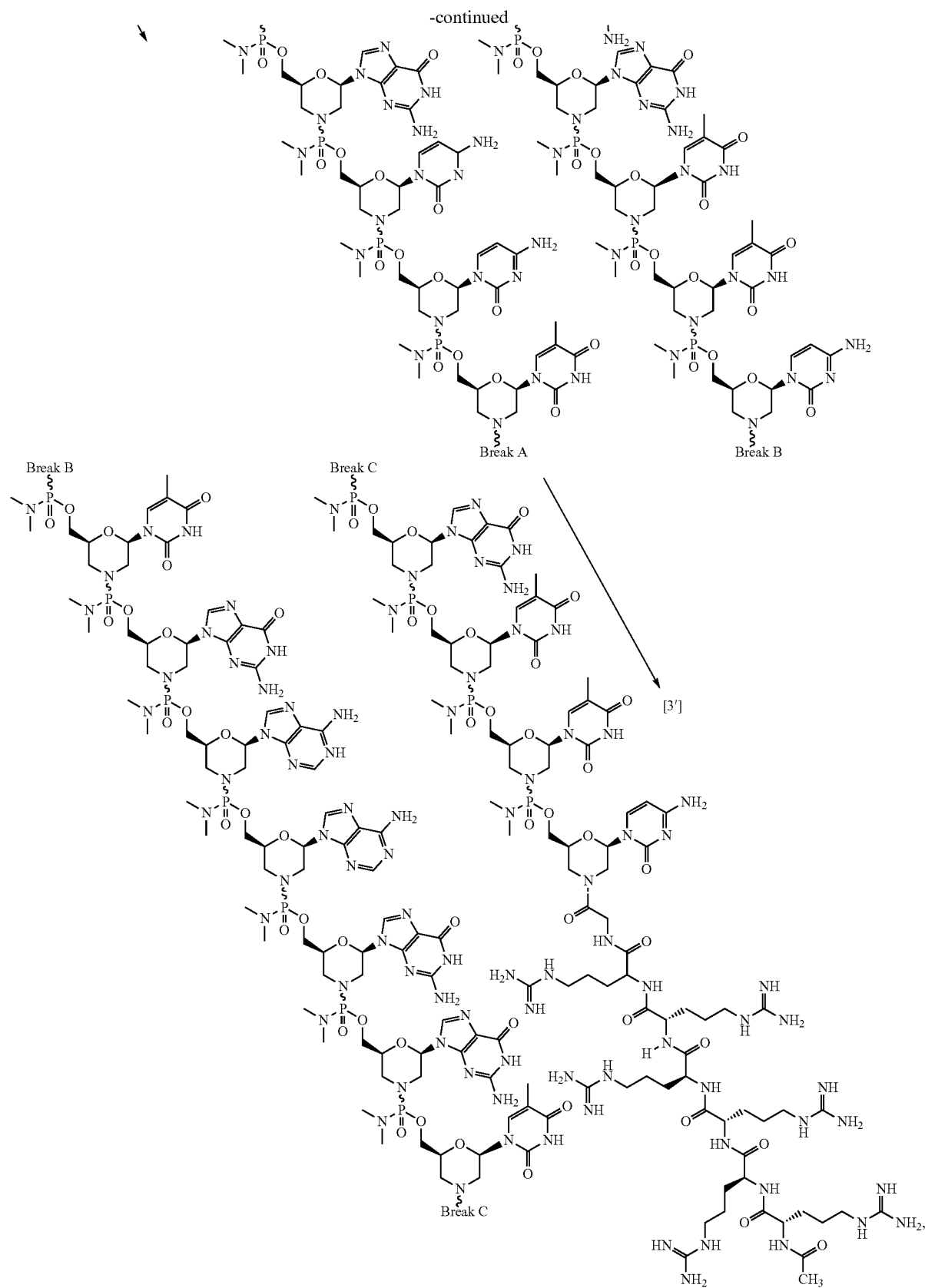
or a pharmaceutically acceptable salt thereof.

In some embodiments, an antisense oligomer conjugate of Formula (VIIIB) is an HCl (hydrochloric acid) salt thereof. In certain embodiments, the HCl salt is a ·6HCl salt. In some embodiments, including, for example, embodiments of antisense oligomer conjugates of Formula (VIIIB), an antisense oligomer conjugate of the disclosure is according to Formula (VIIIC):
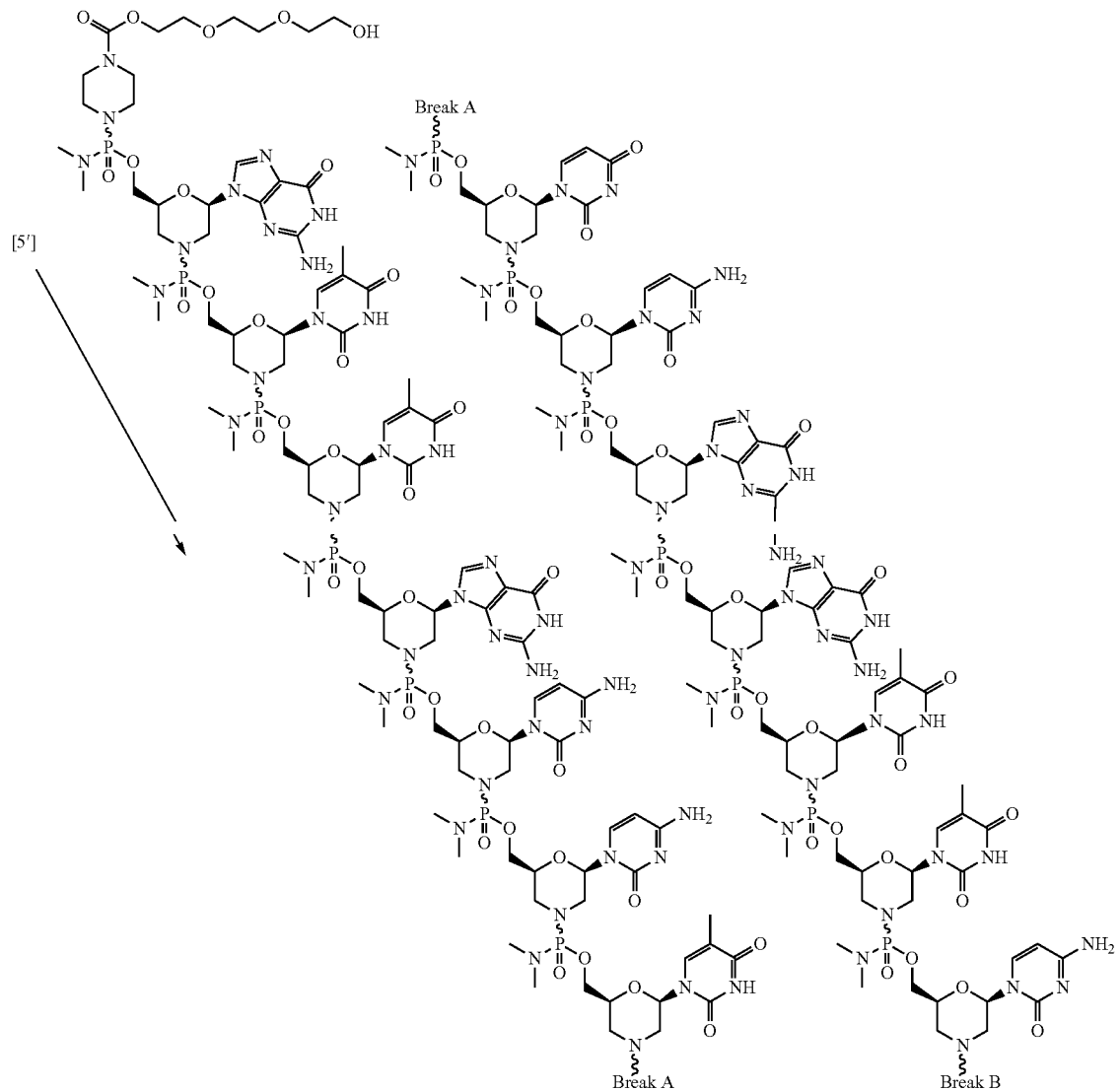
VIIIC

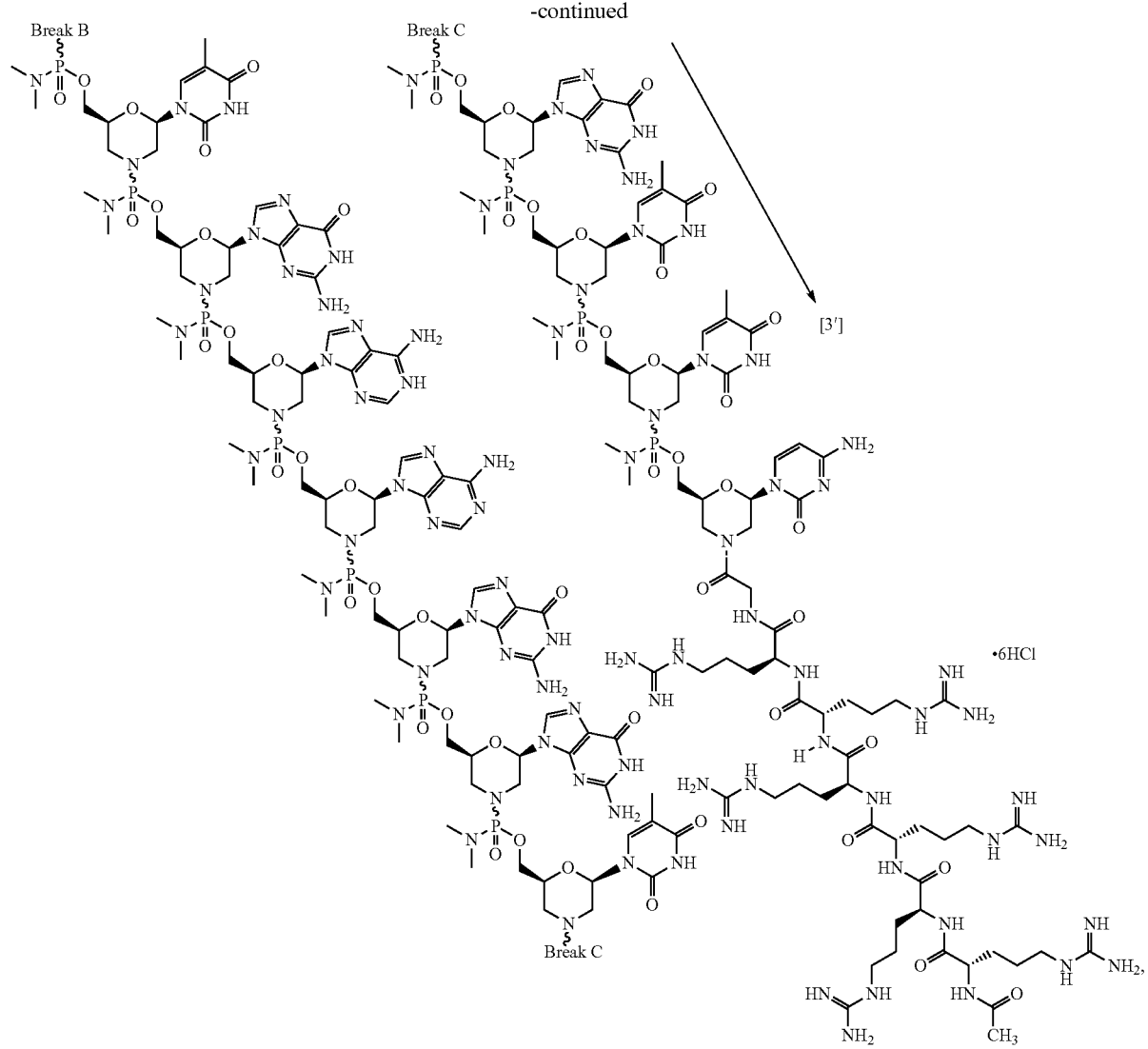

In one aspect, the disclosure provides an antisense oligomer conjugate, or a pharmaceutically acceptable salt thereof, capable of binding a selected target to induce exon skipping in the human dystrophin gene, wherein the antisense oligomer conjugate, or a pharmaceutically acceptable salt thereof, comprises a sequence of bases that is complementary to an exon 51 target region of the dystrophin pre-mRNA designated as an annealing site; wherein the base sequence and annealing site are selected from one of the following:

| Annealing Site | Base Sequence [5' to 3'] |
|---|---|
| H51D(+16-07) | CTC ATA CCT TCT GCT TGA TGA TC (SEQ ID NO: 567) |
| H50D(+103+127) | GGG ATC AGT AT ACT TAC AGG CTC C (SEQ ID NO: 568) |
| H51A(+61+82) | GAA GAT GGC ATT TCT AGT TTG G (SEQ ID NO: 569) |
| H51A(+61+83) | GGA AGA TGG CAT TTC TAG TTT GG (SEQ ID NO: 570) |
| H51A(+61+89) | CAT CAA GGA AGA TGG CAT TTC TAG TTT GG (SEQ ID NO: 571) |
| H51A(+66+89) | CAT CAA GGA AGA TGG CAT TTC TAG (SEQ ID NO: 572) |
| H51A(+66+93) | CCA ACA TCA AGG AAG ATG GCA TTT CTA G (SEQ ID NO: 573) |
| H51A(+69+92) | CAA CAT CAA GGA AGA TGG CAT TTC (SEQ ID NO: 574) |
| H51A(+69+96) | CCT CCA ACA TCA AGG AAG ATG GCA TTT C (SEQ ID NO: 575) |

-continued

| Annealing Site | Base Sequence [5' to 3'] |
| --- | --- |
| H51A(+74+96) | CCT CCA ACA TCA AGG AAG ATG GC (SEQ ID NO: 576) |
| H51A(+74+99) | GTA CCT CCA ACA TCA AGG AAG ATG GC (SEQ ID NO: 577) |
| H51A(+74+100) | GGT ACC TCC AAC ATC AAG GAA GAT GGC (SEQ ID NO: 578) |
| H51A(+74+102) | CAG GTA CCT CCA ACA TCA AGG AAG ATG GC (SEQ ID NO: 579) |
| H51A(+74+103) | GCA GGT ACC TCC AAC ATC AAG GAA GAT GGC (SEQ ID NO: 580) |
| H51A(+75+96) | CCT CCA ACA TCA AGG AAG ATG G (SEQ ID NO: 581) |
| H51A(+75+99) | GTA CCT CCA ACA TCA AGG AAG ATG G (SEQ ID NO: 582) |
| H51A(+76+99) | GTA CCT CCA ACA TCA AGG AAG ATG (SEQ ID NO: 583) |
| H51A(+76+105) | GAG CAG GTA CCT CCA ACA TCA AGG AAG ATG (SEQ ID NO: 584) |
| H51A(+80+103) | GCA GGT ACC TCC AAC ATC AAG GAA G (SEQ ID NO: 585) |
| H51A(+80+105) | GAG CAG GTA CCT CCA ACA TCA AGG AAG (SEQ ID NO: 586) |
| H51A(+80+107) | CAG AGC AGG TAC CTC CAA CAT CAA GGA AG (SEQ ID NO: 587) |
| H51A(+80+108) | CCA GAG CAG GTA CCT CCA ACA TCA AGG AAG (SEQ ID NO: 588) |
| H51A(+83+103) | GCA GGT ACC TCC AAC ATC AAG G (SEQ ID NO: 589) |
| H51A(+83+105) | GAG CAG GTA CCT CCA ACA TCA AGG (SEQ ID NO: 590) |
| H51A(+83+107) | CAG AGC AGG TAC CTC CAA CAT CAA GG (SEQ ID NO: 591) |
| H51A(+83+109) | GCC AGA GCA GGT ACC TCC AAC ATC AAG G (SEQ ID NO: 592) |
| H51A(+84+107) | CAG AGC AGG TAC CTC CAA CAT CAA G (SEQ ID NO: 593) |
| H51A(+84+111) | CTG CCA GAG CAG GTA CCT CCA ACA TCA AG (SEQ ID NO: 594) |
| H51A(+84+105) | GAG CAG GTA CCT CCA ACA TCA AG (SEQ ID NO: 595) |
| H51A(+87+109) | GCC AGA GCA GGT ACC TCC AAC ATC (SEQ ID NO: 596) |
| H51A(+93+116) | GAA ATC TGC AGC AGG TAC CTC (SEQ ID NO: 597) |
| H51A(+75+100) | GGT ACC TCC AAC ATC AAG GAA GAT GG (SEQ ID NO: 598) |
| H51A(+74+101) | AGG TAC CTC CAA CAT CAA GGA AGA TGG C (SEQ ID NO: 599) |
| H51A(+74+98) | TAC CTC CAA CAT CAA GGA AGA TGG C (SEQ ID NO: 600) |
| H51A(+74+97) | ACC TCC AAC ATC AAG GAA GAT GGC (SEQ ID NO: 601) |
| H51A(+74+94) | TCC AAC ATC AAG GAA GAT GGC (SEQ ID NO: 602) |
| H51A(+74+93) | CCA ACA TCA AGG AAG ATG GC (SEQ ID NO: 603) |
| H51A(+74+92) | CAA CAT CAA GGA AGA TGG C (SEQ ID NO: 604) |
| H51A(+69+99) | GTA CCT CCA ACA TCA AGG AAG ATG GCA TTT C (SEQ ID NO: 605) |
| H51A(+70+99) | GTA CCT CCA ACA TCA AGG AAG ATG GCA TTT (SEQ ID NO: 606) |
| H51A(+71+99) | GTA CCT CCA ACA TCA AGG AAG ATG GCA TT (SEQ ID NO: 607) |
| H51A(+72+99) | GTA CCT CCA ACA TCA AGG AAG ATG GCA T (SEQ ID NO: 608) |
| H51A(+73+99) | GTA CCT CCA ACA TCA AGG AAG ATG GCA (SEQ ID NO: 609) |
| H51A(+77+99) | GTA CCT CCA ACA TCA AGG AAG AT (SEQ ID NO: 610) |
| H51A(+78+99) | GTA CCT CCA ACA TCA AGG AAG A (SEQ ID NO: 611) |
| H51A(+79+99) | GTA CCT CCA ACA TCA AGG AAG |
| H51.SA.(-60-36) | GAA GAA AAA GAA AAA TTA GAA ACA C (SEQ ID NO: 613) |

-continued

| Annealing Site | Base Sequence [5' to 3'] |
|---|---|
| H51.SA.(-50-26) | AAG GAA AAA AGA AGA AAA AGA AAA A (SEQ ID NO: 614) |
| H51.SA.(-45-21) | GCA AAA AGG AAA AAA GAA GAA AAA G (SEQ ID NO: 615) |
| H51.SA.(-40-16) | TTT TTG CAA AAA GGA AAA AAG AAG A (SEQ ID NO: 616) |
| H51.SA.(-35-11) | TTG GGT TTT TGC AAA AAG GAA AAA A (SEQ ID NO: 617) |
| H51.SA.(-30-6) | ATA TTT TGG GTT TTT GCA AAA AGG A (SEQ ID NO: 618) |
| H51.SA.(-25-1) | CTA AAA TAT TTT GGG TTT TGC AAA A (SEQ ID NO: 619) |
| H51.SA.(-20+5) | AGG AGC TAA AAT ATT TTG GGT TTT T (SEQ ID NO: 620) |
| H51.SA.(-15+10) | TGA GTA GGA GCT AAA ATA TTT TGG G (SEQ ID NO: 621) |
| H51.SA.(-10+15) | CAG TCT GAG TAG GAG CTA AAA TAT T (SEQ ID NO: 622) |
| H51.SA.(-5+20) | AGT AAC AGT CTG AGT AGG AGC TAA A (SEQ ID NO: 623) |
| H51.SA.(-1+24) | CCA GAG TAA CAG TCT GAG TAG GAG C (SEQ ID NO: 624) |
| H51.SA.(-65-41) | AAA AGA AAA ATT AGA AAC ACA AGC T (SEQ ID NO: 625) |
| H51.SA.(-70-46) | AAA AAT TAG AAA CAC AAG CTA AAG A (SEQ ID NO: 626) |
| H51.SA.(-75-51) | TTA GAA ACA CAA GCT AAA GAG CCA A (SEQ ID NO: 627) |
| H51.SA.(-80-56) | AAC ACA AGC TAA AGA GCC AAT TTC A (SEQ ID NO: 628) |
| H51.SA.(-85-61) | AAG CTA AAG AGC CAA TTT CAA TAA C (SEQ ID NO: 629) |
| H51.SA.(-90-66) | AAA GAG CCA ATT TCA ATA ACA ATA A (SEQ ID NO: 630) |
| H51.SA.(-95-71) | GCC AAT TTC AAT AAC AAT AAG TCA A (SEQ ID NO: 631) |
| H51.SA.(-100-76) | TTT CAA TAA CAA TAA GTC AAA TTT A (SEQ ID NO: 632) |
| H51A(+1+30) | GTG TCA CCA GAG TAA CAG TCT GAG TAG GAG (SEQ ID NO: 633) |
| H51A(+10+39) | CCA CAG GTT GTG TCA CCA GAG TAA CAG TCT (SEQ ID NO: 634) |
| H51A(+6+35) | AG GTT GTG TCA CCA GA GTA ACA GTC TGA GT (SEQ ID NO: 635) |
| H51A(+49+78) | ATG GCA TTT CTA GTT TGG AGA TGG CAG TTT (SEQ ID NO: 636) |
| H51A(+1+25) | ACC AGA GTA ACA GTC TGA GTA GGA G (SEQ ID NO: 637) |
| H51A(+4+28) | GTC ACC AGA GTA ACA GTC TGA GTA G (SEQ ID NO: 638) |
| H51A(+16+40) | ACC ACA GGT TGT GTC ACC AGA GTA A (SEQ ID NO: 639) |
| H51A(+21+45) | TAG TAA CCA CAG GTT GTG TCA CCA G (SEQ ID NO: 640) |
| H51A(+26+50) | TTC CTT AGT AAC CAC AGG TTG TGT C (SEQ ID NO: 641) |
| H51A(+31+55) | GCA GTT TCC TTA GTA ACC ACA GGT T (SEQ ID NO: 642) |
| H51A(+36+60) | AGA TGG CAG TTT CCT TAG TAA CCA C (SEQ ID NO: 643) |
| H51A(+41+65) | TTT GGA GAT GGC AGT TTC CTT AGT A (SEQ ID NO: 644) |
| H51A(+86+110) | TGC CAG AGC AGG TAC CTC CAA CAT C (SEQ ID NO: 645) |
| H51A(+91+115) | AAA TCT GCC AGA GCA GGT ACC TCC A (SEQ ID NO: 646) |
| H51A(+96+120) | GGT TGA AAT CTG CCA GAG CAG GTA C (SEQ ID NO: 647) |
| H51A(+101+125) | AGC CCG GTT GAA ATC TGC CAG AGC A (SEQ ID NO: 648) |
| H51A(+106+130) | GTC CAA GCC CGG TTG AAA TCT GCC A (SEQ ID NO: 649) |
| H51A(+111+135) | GTT CTG TCC AAG CCC GGT TGA AAT C (SEQ ID NO: 650) |

| Annealing Site | Base Sequence [5' to 3'] |
|---|---|
| H51A(+116+140) | GGT AAG TTC TGT CCA AGC CCG GTT G (SEQ ID NO: 651) |
| H51A(+121+145) | CAG TCG GTA AGT TCT GTC CAA GCC C (SEQ ID NO: 652) |
| H51A(+126+150) | AAA GCC AGT CGG TAA GTT CTG TCC A (SEQ ID NO: 653) |
| H51A(+131+155) | CAG AGA AAG CCA GTC GGT AAG TTC T (SEQ ID NO: 654) |
| H51A(+136+160) | TCA AGC AGA GAA AGC CAG TCG GTA A (SEQ ID NO: 655) |
| H51A(+141+165) | CTT GAT CAA GCA GAG AAA GCC AGT C (SEQ ID NO: 656) |
| H51A(+146+170) | TAT AAC TTG ATC AAG CAG AGA AAG C (SEQ ID NO: 657) |
| H51A(+151+175) | GAT TTT ATA ACT TGA TCA AGC AGA G (SEQ ID NO: 658) |
| H51A(+156+180) | TCT GTG ATT TTA TAA CTT GAT CAA G (SEQ ID NO: 659) |
| H51A(+161+185) | CAC CCT CTG TGA TTT TAT AAC TTG A (SEQ ID NO: 660) |
| H51A(+166+190) | ACC ATC ACC CTC TGT GAT TTT ATA A (SEQ ID NO: 661) |
| H51A(+171+195) | CAC CCA CCA TCA CCC TCT GTG ATT T (SEQ ID NO: 662) |
| H51A(+176+200) | AAG TCA CCC CAC CAT CAC CCT CTG T (SEQ ID NO: 663) |
| H51A(+181+205) | TCC TCA AGG TCA CCC ACC ATC ACC C (SEQ ID NO: 664) |
| H51A(+186+210) | TGA TAT CCT CAA GGT CAC CCA CCA T (SEQ ID NO: 665) |
| H51A(+191+215) | CTC GTT GAT ATC CTC AAG GTC ACC C (SEQ ID NO: 666) |
| H51A(+196+220) | ATC ATC TCG TTG ATA TCC TCA AGG T (SEQ ID NO: 667) |
| H51A(+201+225) | TGA TGA TCA TCT CGT TGA TAT CCT C (SEQ ID NO: 668) |
| H51A(+206+230) | CTG CTT GAT GAT CAT CTC GTT GAT A (SEQ ID NO: 669) |
| H51D(+211-02) | ACC TTC TGC TTG ATG ATC ATC TCG T (SEQ ID NO: 670) |
| H51D(+214-05) | CAT ACC TTC TGC TTG ATG ATC ATC T (SEQ ID NO: 671) |
| H51D(+217-08) | TCT CAT ACC TTC TGC TTG ATG ATC A (SEQ ID NO: 672) |
| H51D(+220-11) | TTT TCT CAT ACC TTC TGC TTG ATG A (SEQ ID NO: 673) |
| H51D(+223-14) | ATT TTT TCT CAT ACC TTC TGC TTG A (SEQ ID NO: 674) |
| H51D(+226-17) | ATC ATT TTT TCT CAT ACC TTC TGC T (SEQ ID NO: 675) |
| H51D(+229-20) | TTT ATC ATT TTT TCT CAT ACC TTC T (SEQ ID NO: 676) |
| H51D(+232-23) | ACT TTT ATC ATT TTT TCT CAT ACC T (SEQ ID NO: 677) |
| H51D(-02-26) | CCA ACT TTT ATC ATT TTT TCT CAT A (SEQ ID NO: 678) |
| H51A(+1+30) | GTG TCA CCA GAG TAA CAG TCT GAG TAG GAG (SEQ ID NO: 633) | wherein A is

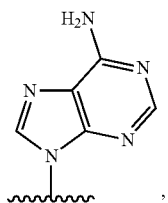 [SMILES: *n1cnc2c(N)ncnc21]

,

C is

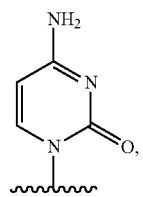 [SMILES: *n1ccc(N)nc1=O]

,

G is

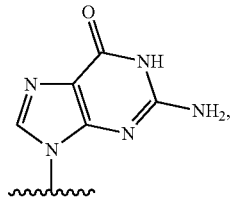 [SMILES: *n1cnc2c(=O)[nH]c(N)nc21]

and T is

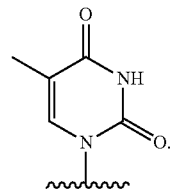 [SMILES: *n1cc(C)c(=O)[nH]c1=O]

In one aspect, the base sequence and annealing site are selected from one of the following:

| Annealing Site | Base Sequence [5' to 3'] |
|---|---|
| H51A(+66+95) | CTC AAC CAT CAA GGA AGA TGG CAT TTC TAG (SEQ ID NO: 679) |
| H51A(+74+97) | ACC TCC AAC ATC AAG GAA GAT GGC (SEQ ID NO: 601) |
| H51A(+70+99) | GTA CCT CCA ACA TCA AGG AAG ATG GCA TTT (SEQ ID NO: 606) |
| H51A(+72+99) | GTA CCT CCA ACA TCA AGG AAG ATG GCA T (SEQ ID NO: 608) |
| H51A(+68+87) | TCA AGG AAG ATG GCA TTT CT (SEQ ID NO: 680) |
| H51A(+68+87) | UCA AGG AmAGm AmUGm GmCA UUU CU (SEQ ID NO: 681) |
| H53A(+36+60) | GTT GCC TCC GGT TCT GAA GGT GTT C (SEQ ID NO: 682) |
| H53A(+36+60) | GTT G5mC5mC T5mC5mC GGT T5mC T GAA GGT GTT 5Mc (SEQ ID NO: 683) |
| H53A(+36+56) | CCT CCG GTT CTG AAG GTG TTC (SEQ ID NO: 684) |
| H53A(+23+47) | CTG AAG GTG TTC TTG TAC TTC ATC C (SEQ ID NO: 34) |
| H53A(+32+56) | CCT CCG GTT CTG AAG GTG TTC TTG T (SEQ ID NO: 685) |
| H53A(+33+60) | GTT GCC TCC GGT TCT GAA GGT GTT CTT G (SEQ ID NO: 686) |
| H53A(+30+59) | TTG CCT CCG GTT CTG AAG GTG TTC TTG TAC (SEQ ID NO: 687) |
| H53A(+39+62) | CTG TTG CCT CCG GTT CTG AAG GTG (SEQ ID NO: 688) |
| H53A(+36+69) | CAT TCA ACT GTT GCC TCC GGT TCT GAA GGT G (SEQ ID NO: 689) |
| H53A(+45+62) | CTG TTG CCT CCG GTT CTG (SEQ ID NO: 690) |
| H45A(-03+19) | CAA TGC CAT CCT GGA GTT CCT G (SEQ ID NO: 691) |
| H45A(-09+25) | GCT GCC AAT GCA TCC TGG AGT TCC TGT AGA T (SEQ ID NO: 692) |
| H45A(-03+25) | GCT GCC AAT GCA TCC TGG AGT TCC T G (SEQ ID NO: 693) |
| H45A(-06+25) | GCT GCC AAT GCA TCC TGG AGT TCC TGT A A (SEQ ID NO: 694) |
| H45A(-12+19) | CAA TGC CAT CCT GGA GTT CCT GTA AGA TAC C (SEQ ID NO: 695) |
| H45A(-09+19) | CAA TGC CAT CCT GGA GTT CCT GTA AGA T (SEQ ID NO: 696) |
| H45A(-12+16) | TGC CAT CCT GGA GTT CCT GTA AGA TAC C (SEQ ID NO: 697) |
| H45A(-14+25) | GCT GCC AAT GCA TCC TGG AGT TCC TGT AGA TAC CAA (SEQ ID NO: 698) |
| H45A(-08+19) | CAA TGC CAT CCT GGA GTT CCT GTA AGA (SEQ ID NO: 699) |
| HM45A(-07+25) | GCT GCC AAT GCA TCC TGG AGT TCC TGT A AG (SEQ ID NO: 700) |
| H45A(-12+22) | GCC AAT GCA TCC TGG AGT TCC TGT AGA TAC C (SEQ ID NO: 701) |
| H45A(-09+22) | GCC AAT GCA TCC TGG AGT TCC TGT AGA T (SEQ ID NO: 702) |
| H45A(-09+30) | TTG CCG CTG CCC AAT GCC ATC CTG GAG TTC CTG TAA GAT (SEQ ID NO: 703) |

-continued

| Annealing Site | Base Sequence [5' to 3'] |
|---|---|
| H45A(-06+22) | GCC CAA TGC CAT CCT GGA GTT CCT GTA A (SEQ ID NO: 704) |
| H45A(-06+28) | GCC GCT GCC CAA TGC CAT CCT GGA GTT CCT GTA A (SEQ ID NO: 705) |
| H45A(-03+22) | GCC CAA TGC CAT CCT GGA GTT CCT G (SEQ ID NO: 706) |
| H45A(-03+28) | GCC GCT GCC CAA TGC CAT CCT GGA GTT CCT G (SEQ ID NO: 707) |
| H45A(+9+26) | m5C-G-m5C-T-G-C-m5C-m5C-A-A-T-G-m5C-m5C-A-U-m5C-m5C (SEQ ID NO: 708) |
| H44A(-10+15) | GAT CTG TCA AAT CGC CTG CAG GTA A (SEQ ID NO: 709) |
| H44A(-07+15) | GAT CTG TCA AAT CGC CTG CAG G (SEQ ID NO: 710) |
| H44M(-07+17) | CAG ATC TGT CAA ATC GCC TGC AGG (SEQ ID NO: 711) |
| H44A(-08+15) | GAT CTG TCA AAT CGC CTG CAG GT (SEQ ID NO: 712) |
| H44A(-06+15) | GAT CTG TCA AAT CGC CTG CAG (SEQ ID NO: 713) |
| H44A(-08+17) | CAG ATC TGT CAA ATC GCC TGC AGG T (SEQ ID NO: 714) |
| H44A(-06+17) | CAG ATC TGT CAA ATC GCC TGC AG (SEQ ID NO: 715) |
| H50D(+04-18) | GGG ATC CAG TAT ACT TAC AGG C (SEQ ID NO: 716) |
| H50D(+07-18) | GGG ATC CAG TAT ACT TAC AGG CTC C (SEQ ID NO: 568) |
| H50D(+07-16) | GAT CCA GTA TAC TTA CAG GCT CC (SEQ ID NO: 717) |
| H50D(+07-17) | GGA TCC AGT ATA CTT ACA GGC TCC (SEQ ID NO: 718) |
| H50A(-19+07) | ACT TCC TCT TTA ACA GAA AAG CAT AC (SEQ ID NO: 719) |
| H50D(+07-15) | ATC CAG TAT ACT TAC AGG CTC C (SEQ ID NO: 720) |
| H50A(-02+23) | GAG CTC AGA TCT TCT AAC TTC CTC T (SEQ ID NO: 721) |
| H50D(+06-18) | GGG ATC CAG TAT ACT TAC AGG CTC (SEQ ID NO: 722) |
| H50D(+07-20) | ATG GGA TCC AGT ATA CTT ACA GGC TCC (SEQ ID NO: 723) |
| H52A(-01+24) | CTG TTC AAA TCT GCA TTG TTG C (SEQ ID NO: 724) | wherein A is

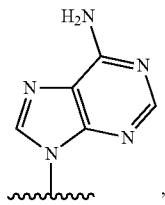 [SMILES: *n1cnc2c(N)ncnc21]

G is

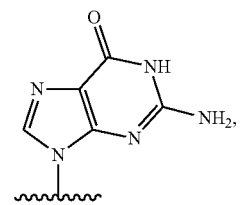

C is

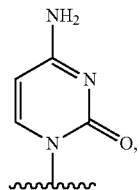 [SMILES: *n1ccc(N)nc1=O]

T is

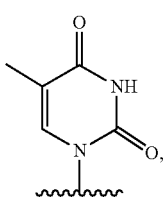 [SMILES: *n1cc(C)c(=O)[nH]c1=O]

U is

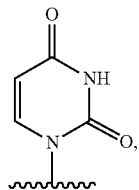

Gm is methylated guanine, Am is methylated adenine, and m5C is

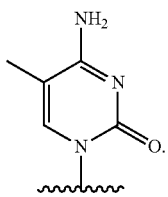 [SMILES: *n1cc(C)c(N)nc1=O]

In another aspect, the disclosure provides antisense oligomers of Formula (IX):

IX

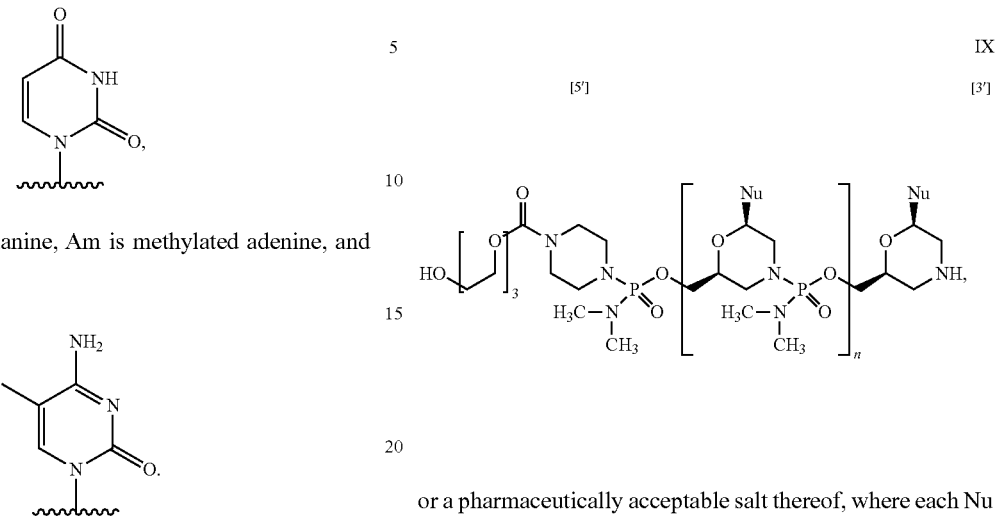

or a pharmaceutically acceptable salt thereof, where each Nu from 1 to n and 5' to 3' corresponds to the nucleobases in the following sequences:

| Annealing Site | Sequence [5' to 3'] |
|---|---|
| H51A(+61+90) | ACA TCA AGG AAG ATG GCA TTT CTA GTT TGG (SEQ ID NO: 725) |
| H51D(+16-07) | CTC ATA CCT TCT GCT TGA TGA TC (SEQ ID NO: 567) |
| H50D(+103+127) | GGG ATC AG TAT ACT TAC AGG CTC C (SEQ ID NO: 568) |
| H51A(+81+105) | GAG CAG GTA CCT CCA ACA TCA AGG AA (SEQ ID NO: 33) |
| H51A(+71+100) | GGT ACC TCC AAC ATC AAG GAA GAT GGC ATT (SEQ ID NO: 726) |
| H51A(+48+73) | ATT TCT AGT TTG GAG ATG GCA GTT TC (SEQ ID NO: 727) |
| H51A(+59+84) | GGA AGA TGG CAT TTC TAG TTT GGA G (SEQ ID NO: 728) |
| H51A(+64+88) | CAT CAA GGA AGA TGG CAT TTC TAG TT (SEQ ID NO: 729) |
| H51A(+89+113) | ATC TGC CAG AGC AGG TAC CTC CAA C (SEQ ID NO: 730) |
| H51A(+49+68) | TAG TTT GGA GAT GGC AGT TT (SEQ ID NO: 731) |
| H51A(+64+83) | GGA AGA TGG CAT TTC TAG TT (SEQ ID NO: 732) |
| H51A(+80+98) | TAC CTC CAA CAT CAA GGA AG (SEQ ID NO: 733) |
| H51A(+94+113) | ATC TGC CAG AGC AGG TAC CT (SEQ ID NO: 734) |
| H51A(+109+128) | CCA AGC CCG GTT GAA ATC TG (SEQ ID NO: 735) |
| H51A(+61+82) | GAA GAT GGC ATT TCT AGT TTG G (SEQ ID NO: 569) |
| H51A(+61+83) | GGA AGA TGG CAT TTC TAG TTT GG (SEQ ID NO: 570) |
| H51A(+61+89) | CAT CAA GGA AGA TGG CAT TTC TAG TTT GG (SEQ ID NO: 571) |
| H51A(+66+89) | CAT CAA GGA AGA TGG CAT TTC TAG (SEQ ID NO: 572) |
| H51A(+66+93) | CCA ACA TCA AGG AAG ATG GCA TTT CTA G (SEQ ID NO: 573) |
| H51A(+69+92) | CAA CAT CAA GGA AGA TGG CAT TTC (SEQ ID NO: 574) |
| H51A(+69+96) | CCT CCA ACA TCA AGG AAG ATG GCA TTT C (SEQ ID NO: 575) |
| H51A(+74+96) | CCT CCA ACA TCA AGG AAG ATG GC (SEQ ID NO: 576) |
| H51A(+74+99) | GTA CCT CCA ACA TCA AGG AAG ATG GC (SEQ ID NO: 577) |
| H51A(+74+100) | GGT ACC TCC AAC ATC AAG GAA GAT GGC (SEQ ID NO: 578) |

| Annealing Site | Sequence [5' to 3'] |
|---|---|
| H51A(+74+102) | CAG GTA CCT CCA ACA TCA AGG AAG ATG GC (SEQ ID NO: 579) |
| H51A(+74+103) | GCA GGT ACC TCC AAC ATC AAG GAA GAT GGC (SEQ ID NO: 580) |
| H51A(+75+96) | CCT CCA ACA TCA AGG AAG ATG G (SEQ ID NO: 581) |
| H51A(+75+99) | GTA CCT CCA ACA TCA AGG AAG ATG G (SEQ ID NO: 582) |
| H51A(+76+99) | GTA CCT CCA ACA TCA AGG AAG ATG (SEQ ID NO: 583) |
| H51A(+76+105) | GAG CAG GTA CCT CCA ACA TCA AGG AAG ATG (SEQ ID NO: 584) |
| H51A(+80+103) | GCA GGT ACC TCC AAC ATC AAG GAA G (SEQ ID NO: 585) |
| H51A(+80+105) | GAG CAG GTA CCT CCA ACA TCA AGG AAG (SEQ ID NO: 586) |
| H51A(+80+107) | CAG AGC AGG TAC CTC CAA CAT CAA GGA AG (SEQ ID NO: 587) |
| H51A(+80+108) | CCA GAG CAG GTA CCT CCA ACA TCA AGG AAG (SEQ ID NO: 588) |
| H51A(+83+103) | GCA GGT ACC TCC AAC ATC AAG G (SEQ ID NO: 589) |
| H51A(+83+105) | GAG CAG GTA CCT CCA ACA TCA AGG (SEQ ID NO: 590) |
| H51A(+83+107) | CAG AGC AGG TAC CTC CAA CAT CAA GG (SEQ ID NO: 591) |
| H51A(+83+109) | GCC AGA GCA GGT ACC TCC AAC ATC AAG G (SEQ ID NO: 592) |
| H51A(+84+107) | CAG AGC AGG TAC CTC CAA CAT CAA G (SEQ ID NO: 593) |
| H51A(+84+111) | CTG CCA GAG CAG GTA CCT CCA ACA TCA AG (SEQ ID NO: 594) |
| H51A(+84+105) | GAG CAG GTA CCT CCA ACA TCA AG (SEQ ID NO: 595) |
| H51A(+87+109) | GCC AGA GCA GGT ACC TCC AAC ATC (SEQ ID NO: 596) |
| H51A(+93+116) | GAA ATC TGC CAG AGC AGG TAC CTC (SEQ ID NO: 597) |
| H51A(+75+100) | GGT ACC TCC AAC ATC AAG GAA GAT GG (SEQ ID NO: 598) |
| H51A(+74+101) | AGG TAC CTC CAA CAT CAA GGA AGA TGG C (SEQ ID NO: 599) |
| H51A(+74+98) | TAC CTC CAA CAT CAA GGA AGA TGG C (SEQ ID NO: 600) |
| H51A(+74+97) | ACC TCC AAC ATC AAG GAA GAT GGC (SEQ ID NO: 601) |
| H51A(+74+94) | TCC AAC ATC AAG GAA GAT GGC (SEQ ID NO: 602) |
| H51A(+74+93) | CCA ACA TCA AGG AAG ATG GC (SEQ ID NO: 603) |
| H51A(+74+92) | CAA CAT CAA GGA AGA TGG C (SEQ ID NO: 604) |
| H51A(+69+99) | GTA CCT CCA ACA TCA AGG AAG ATG GCA TTT C (SEQ ID NO: 605) |
| H51A(+70+99) | GTA CCT CCA ACA TCA AGG AAG ATG GCA TTT (SEQ ID NO: 606) |
| H51A(+71+99) | GTA CCT CCA ACA TCA AGG AAG ATG GCA TT (SEQ ID NO: 607) |
| H51A(+72+99) | GTA CCT CCA ACA TCA AGG AAG ATG GCA T (SEQ ID NO: 608) |
| H51A(+73+99) | GTA CCT CCA ACA TCA AGG AAG ATG GCA (SEQ ID NO: 609) |
| H51A(+77+99) | GTA CCT CCA ACA TCA AGG AAG AT (SEQ ID NO: 610) |
| H51A(+78+99) | GTA CCT CCA ACA TCA AGG AAG A (SEQ ID NO: 611) |
| H51A(+79+99) | GTA CCT CCA ACA TCA AGG AAG |
| H51.SA.(-60-36) | GAA GAA AAA GAA AAA TTA GAA ACA C (SEQ ID NO: 613) |
| H51.SA.(-50-26) | AAG GAA AAA AGA AGA AAA AGA AAA A (SEQ ID NO: 614) |
| H51.SA.(-45-21) | GCA AAA GGA AAA AAA GAA GAA AAA G (SEQ ID NO: 615) |
| H51.SA.(-40-16) | TTT TTG CAA AAA GGA AAA AAG AAG A (SEQ ID NO: 616) |
| H51.SA.(-35-11) | TTG GGT TTT TGC AAA AAG GAA AAA A (SEQ ID NO: 617) |

-continued

| Annealing Site | Sequence [5' to 3'] |
| --- | --- |
| H51.SA.(-30-6) | ATA TTT TGG GTT TTT GCA AAA AGG A (SEQ ID NO: 618) |
| H51.SA.(-25-1) | CTA AAA TAT TTT GGG TTT TTG CAA A (SEQ ID NO: 619) |
| H51.SA.(-20+5) | AGG AGC TAA AAT ATT TTG GGT TTT T (SEQ ID NO: 620) |
| H51.SA.(-15+10) | TGA GTA GGA GCT AAA ATA TTT TGG G (SEQ ID NO: 621) |
| H51.SA.(-10+15) | CAG TCT GAG TAG GAG CTA AAA TAT T (SEQ ID NO: 622) |
| H51.SA.(-5+20) | AGT AAC AGT CTG AGT AGG AGC TAA A (SEQ ID NO: 623) |
| H51.SA.(-1+24) | CCA GAG TAA CAG TCT GAG TAG GAG C (SEQ ID NO: 624) |
| H51.SA.(-65-41) | AAA AGA AAA ATT AGA AAC ACA AGC T (SEQ ID NO: 625) |
| H51.SA.(-70-46) | AAA AAT TAG AAA CAC AAG CTA AAG A (SEQ ID NO: 626) |
| H51.SA.(-75-51) | TTA GAA ACA CAA GCT AAA GAG CCA A (SEQ ID NO: 627) |
| H51.SA.(-80-56) | AAC ACA AGC TAA AGA GCC AAT TTC A (SEQ ID NO: 628) |
| H51.SA.(-85-61) | AAG CTA AAG AGC CAA TTT CAA TAA C (SEQ ID NO: 629) |
| H51.SA.(-90-66) | AAA GAG CCA ATT TCA ATA ACA ATA A (SEQ ID NO: 630) |
| H51.SA.(-95-71) | GCC AAT TTC AAT AAC AAT AAG TCA A (SEQ ID NO: 631) |
| H51.SA.(-100-76) | TTT CAA TAA CAA TAA GTC AAA TTT A (SEQ ID NO: 632) |
| H51A(+1+30) | GTG TCA CCA GAG TAA CAG TCT GAG TAG GAG (SEQ ID NO: 633) |
| H51A(+10+39) | CCA CAG GTT GTG TCA CCA GAG TAA CAG TCT (SEQ ID NO: 634) |
| H51A(+6+35) | AGG TTG TGT CAC CAG AGT AAC AGT CTG AGT (SEQ ID NO: 736) |
| H51A(+49+78) | ATG GCA TTT CTA GTT TGG AGA TGG CAG TTT (SEQ ID NO: 636) |
| H51A(+1+25) | ACC AGA GTA ACA GTC TGA GTA GGA G (SEQ ID NO: 637) |
| H51A(+4+28) | GTC ACC AGA GTA ACA GTC TGA GTA G (SEQ ID NO: 638) |
| H51A(+16+40) | ACC ACA GGT TGT GTC ACC AGA GTA A (SEQ ID NO: 639) |
| H51A(+21+45) | TAG TAA CCA CAG GTT GTG TCA CCA G (SEQ ID NO: 640) |
| H51A(+26+50) | TTC CTT AGT AAC CAC AGG TTG TGT C (SEQ ID NO: 641) |
| H51A(+31+55) | GCA GTT TCC TTA GTA ACC ACA GGT T (SEQ ID NO: 642) |
| H51A(+36+60) | AGA TGG CAG TTT CCT TAG TAA CCA C (SEQ ID NO: 643) |
| H51A(+41+65) | TTT GGA GAT GGC AGT TTC CTT AGT A (SEQ ID NO: 644) |
| H51A(+86+110) | TGC CAG AGC AGG TAC CTC CAA CAT C (SEQ ID NO: 645) |
| H51A(+91+115) | AAA TCT GCC AGA GCA GGT ACC TCC A (SEQ ID NO: 646) |
| H51A(+96+120) | GGT TGA AAT CTG CCA GAG CAG GTA C (SEQ ID NO: 647) |
| H51A(+101+125) | AGC CCG GTT GAA ATC TGC CAG AGC A (SEQ ID NO: 648) |
| H51A(+106+130) | GTC CAA GCC CGG TTG AAA TCT GCC A (SEQ ID NO: 649) |
| H51A(+111+135) | GTT CTG TCC AAG CCC GGT TGA AAT C (SEQ ID NO: 650) |
| H51A(+116+140) | GGT AAG TTC TGT CCA AGC CCG GTT G (SEQ ID NO: 651) |
| H51A(+121+145) | CAG TCG GTA AGT TCT GTC CAA GCC C (SEQ ID NO: 652) |
| H51A(+126+150) | AAA GCC AGT CGG TAA GTT CTG TCC A (SEQ ID NO: 653) |
| H51A(+131+155) | CAG AGA AAG CCA GTC GGTA AGT TCT (SEQ ID NO: 737) |
| H51A(+136+160) | TCA AGC AGA GAA AGC CAG TCG GTA A (SEQ ID NO: 655) |

-continued

| Annealing Site | Sequence [5' to 3'] |
|---|---|
| H51A(+141+165) | CTT GAT CAA GCA GAG AAA GCC AGT C (SEQ ID NO: 656) |
| H51A(+146+170) | TAT AAC TTGA TCA AGC AGA GAA AGC (SEQ ID NO: 738) |
| H51A(+151+175) | GAT TTT ATA ACT TGA TCA AGC AGA G (SEQ ID NO: 658) |
| H51A(+156+180) | TCT GTG ATT TTA TAA CTT GAT CAA G (SEQ ID NO: 659) |
| H51A(+161+185) | CAC CCT CTG TGA TTT TAT AAC TTG A (SEQ ID NO: 660) |
| H51A(+166+190) | ACC ATC ACC CTC TGT GAT TTT ATA A (SEQ ID NO: 661) |
| H51A(+171+195) | CAC CCA CCA TCA CCC TCT GTG ATT T (SEQ ID NO: 662) |
| H51A(+176+200) | AAG GTC ACC CAC CAT CAC CCT CTG T (SEQ ID NO: 663) |
| H51A(+181+205) | TCC TCA AGG TCA CCC ACC ATC ACC C (SEQ ID NO: 664) |
| H51A(+186+210) | TGA TAT CCT CAA GGT CAC CCA CCA T (SEQ ID NO: 665) |
| H51A(+191+215) | CTC GTT GAT ATC CTC AAG GTC ACC C (SEQ ID NO: 666) |
| H51A(+196+220) | ATC ATC TCG TTG ATA TCC TCA AGG T (SEQ ID NO: 667) |
| H51A(+201+225) | TGA TGA TCA TCT CGT TGA TAT CCT C (SEQ ID NO: 668) |
| H51A(+206+230) | CTG CTT GAT GAT CAT CTC GTT GAT A (SEQ ID NO: 669) |
| H51D(+211-02) | ACC TTC TGC TTG ATG ATC ATC TCG T (SEQ ID NO: 670) |
| H51D(+214-05) | CAT ACC TTC TGC TTG ATG ATC ATC T (SEQ ID NO: 671) |
| H51D(+217-08) | TCT CAT ACC TTC TGC TTG ATG ATC A (SEQ ID NO: 672) |
| H51D(+220-11) | TTT TCT CAT ACC TTC TGC TTG ATG A (SEQ ID NO: 673) |
| H51D(+223-14) | ATT TTT TCT CAT ACC TTC TGC TTG A (SEQ ID NO: 674) |
| H51D(+226-17) | ATC ATT TTT TCT CAT ACC TTC TGC T (SEQ ID NO: 675) |
| H51D(+229-20) | TTT ATC ATT TTT TCT CAT ACC TTC T (SEQ ID NO: 676) |
| H51D(+232-23) | ACT TTT ATC ATT TTT TCT CAT ACC T (SEQ ID NO: 677) |
| H51D(-02-26) | CCA ACT TTT ATC ATT TTT TCT CAT A (SEQ ID NO: 678) |
| H51A(+1+30) | GTG TCA CCA GAG TAA CAG TCT GAG TAG GAG (SEQ ID NO: 633) | wherein A is

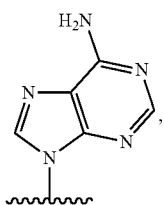 [SMILES: *n1cnc2c(N)ncnc21]

G is

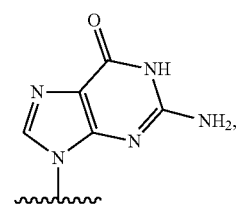

C is

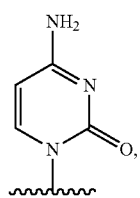 [SMILES: *n1ccc(N)nc1=O]

and T is

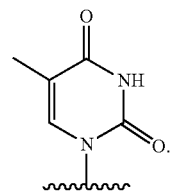 [SMILES: *n1cc(C)c(=O)[nH]c1=O]

In one aspect, the base sequence and annealing site are selected from one of the following:

| Annealing Site | Base Sequence [5' to 3'] |
|---|---|
| H51A(+66+95) | CTC AAC CAT CAA GGA AGA TGG CAT TTC TAG (SEQ ID NO: 679) |
| H51A(+74+97) | ACC TCC AAC ATC AAG GAA GAT GGC (SEQ ID NO: 601) |
| H51A(+70+99) | GTA CCT CCA ACA TCA AGG AAG ATG GCA TTT (SEQ ID NO: 606) |
| H51A(+72+99) | GTA CCT CCA ACA TCA AGG AAG ATG GCA T (SEQ ID NO: 608) |
| H51A(+68+87) | TCA AGG AAG ATG GCA TTT CT (SEQ ID NO: 680) |
| H51A(+68+87) | UCA AGG AmAGm AmUGm GmCA UUU CU (SEQ ID NO: 681) |
| H53A(+36+60) | GTT GCC TCC GGT TCT GAA GGT GTT C (SEQ ID NO: 682) |
| H53A(+36+60) | GTT G5mC5mC T5mC5mC GGT T5mC T GAA GGT GTT 5mC (SEQ ID NO: 683) |
| H53A(+36+56) | CCT CCG GTT CTG AAG GTG TTC (SEQ ID NO: 684) |
| H53A(+23+47) | CTG AAG GTG TTC TTG TAC TTC ATC C (SEQ ID NO: 34) |
| H53A(+32+56) | CCT CCG GTT CTG AAG GTG TTC TTG T (SEQ ID NO: 685) |
| H53A(+33+60) | GTT GCC TCC GGT TCT GAA GGT GTT CTT G (SEQ ID NO: 686) |
| H53A(+30+59) | TTG CCT CCG GTT CTG AAG GTG TTC TTG TAC (SEQ ID NO: 687) |
| H53A(+39+62) | CTG TTG CCT CCG GTT CTG AAG GTG (SEQ ID NO: 688) |
| H53A(+36+69) | CAT TCA ACT GTT GCC TCC GGT TCT GAA GGT G (SEQ ID NO: 689) |
| H53A(+45+62) | CTG TTG CCT CCG GTT CTG (SEQ ID NO: 690) |
| H45A(-03+19) | CAA TGC CAT CCT GGA GTT CCT G (SEQ ID NO: 691) |
| H45A(-09+25) | GCT GCC AAC TGC CAT CCT GGA GTT CCT GT A AGA T (SEQ ID NO: 692) |
| H45A(-03+25) | GCT GCC AAC TGC CAT CCT GGA GTT CCT G (SEQ ID NO: 693) |
| H45A(-06+25) | GCT GCC AAC TGC CAT CCT GGA GTT CCT GT A A (SEQ ID NO: 694) |
| H45A(-12+19) | CAA TGC CAT CCT GGA GTT CCT GTA AGA TAC C (SEQ ID NO: 695) |
| H45A(-09+19) | CAA TGC CAT CCT GGA GTT CCT GTA AGA T (SEQ ID NO: 696) |
| H45A(-12+16) | TGC CAT CCT GGA GTT CCT GTA AGA TAC C (SEQ ID NO: 697) |
| H45A(-14+25) | GCT GCC AAC TGC CAT CCT GGA GTT CCT GTA AGA TAC CAA (SEQ ID NO: 698) |
| H45A(-08+19) | CAA TGC CAT CCT GGA GTT CCT GTA AGA (SEQ ID NO: 699) |
| HM45A(-07+25) | GCT GCC AAC TGC CAT CCT GGA GTT CCT GTA AG (SEQ ID NO: 700) |
| H45A(-12+22) | GCC AAC TGC CAT CCT GGA GTT CCT GTA AGA TAC C (SEQ ID NO: 701) |
| H45A(-09+22) | GCC AAC TGC CAT CCT GGA GTT CCT GTA AGA T (SEQ ID NO: 702) |
| H45A(-09+30) | TTG CCG CTG CCC AAT GCC ATC CTG GAG TTC CTG TAA GAT (SEQ ID NO: 703) |
| H45A(-06+22) | GCC AAC TGC CAT CCT GGA GTT CCT GTA A (SEQ ID NO: 704) |
| H45A(-06+28) | GCC GCT GCC AAC TGC CAT CCT GGA GTT CCT GTA A (SEQ ID NO: 705) |
| H45A(-03+22) | GCC AAC TGC CAT CCT GGA GTT CCT G (SEQ ID NO: 706) |
| H45A(-03+28) | GCC GCT GCC AAC TGC CAT CCT GGA GTT CCT G (SEQ ID NO: 707) |
| H45A(+9+26) | m5C-G-m5C-T-G-C-m5C-m5C-A-A-T-G-m5C-m5C-A-U-m5C-m5C (SEQ ID NO: 708) |
| H44A(-10+15) | GAT CTG TCA AAT CGC CTG CAG GTA A (SEQ ID NO: 709) |

-continued

| Annealing Site | Base Sequence [5' to 3'] |
|---|---|
| H44A(-07+15) | GAT CTG TCA AAT CGC CTG CAG G (SEQ ID NO: 710) |
| H44M(-07+17) | CAG ATC TGT CAA ATC GCC TGC AGG (SEQ ID NO: 711) |
| H44A(-08+15) | GAT CTG TCA AAT CGC CTG CAG GT (SEQ ID NO: 712) |
| H44A(-06+15) | GAT CTG TCA AAT CGC CTG CAG (SEQ ID NO: 713) |
| H44A(-08+17) | CAG ATC TGT CAA ATC GCC TGC AGG T (SEQ ID NO: 714) |
| H44A(-06+17) | CAG ATC TGT CAA ATC GCC TGC AG (SEQ ID NO: 715) |
| H50D(+04-18) | GGG ATC CAG TAT ACT TAC AGG C (SEQ ID NO: 716) |
| H50D(+07-18) | GGG ATC CAG TAT ACT TAC AGG CTC C (SEQ ID NO: 568) |
| H50D(+07-16) | GAT CCA GTA TAC TTA CAG GCT CC (SEQ ID NO: 717) |
| H50D(+07-17) | GGA TCC AGT ATA CTT ACA GGC TCC (SEQ ID NO: 718) |
| H50A(-19+07) | ACT TCC TCT TTA ACA GAA AAG CAT AC (SEQ ID NO: 719) |
| H50D(+07-15) | ATC AGT TAT ACT TAC AGG CTC C (SEQ ID NO: 720) |
| H50A(-02+23) | GAG CTC AGA TCT TCT AAC TTC CTC T (SEQ ID NO: 721) |
| H50D(+06-18) | GGG ATC CAG TAT ACT TAC AGG CTC (SEQ ID NO: 722) |
| H50D(+07-20) | ATG GGA TCC AGT ATA CTT ACA GGC TCC (SEQ ID NO: 723) |
| H52A(-01+24) | CTG TTC CAA ATC CTG CAT TGT TGC C (SEQ ID NO: 724) | wherein A is

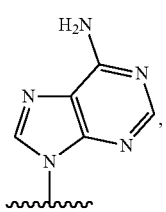

T is

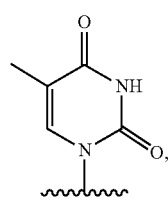

C is

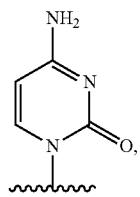 [SMILES: *n1ccc(N)nc1=O]

U is

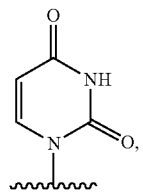

G is

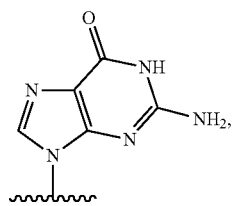 [SMILES: *n1cnc2c(=O)[nH]c(N)nc21]

Gm is methylated guanine, Am is methylated adenine, and m5C is

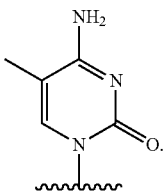 [SMILES: *n1cc(C)c(N)nc1=O]

In another aspect, the disclosure provides antisense oligomers of Formula (X):

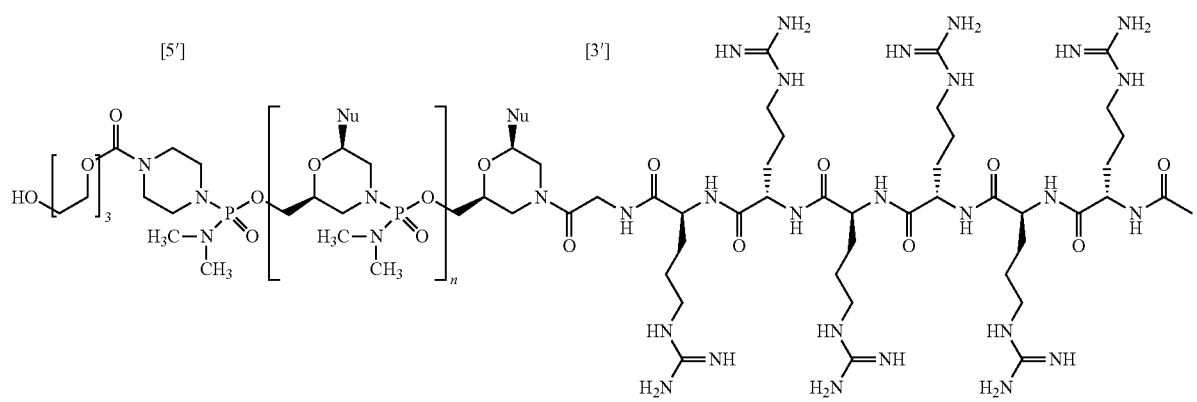

or a pharmaceutically acceptable salt thereof, where each Nu from 1 to (n+1) and 5' to 3' corresponds to the nucleobases in the following sequences:

| Annealing Site | Sequence [5' to 3'] |
| --- | --- |
| H51A(+61+90) | ACA TCA AGG AAG ATG GCA TTT CTA GTT TGG (SEQ ID NO: 725) |
| H51D(+16-07) | CTC ATA CCT TCT GCT TGA TGA TC (SEQ ID NO: 567) |
| H50D(+103+127) | GGG ATC AG TAT ACT TAC AGG CTC C (SEQ ID NO: 568) |
| H51A(+81+105) | GAG CAG GTA CCT CCA ACA TCA AGG AA (SEQ ID NO: 33) |
| H51A(+71+100) | GGT ACC TCC AAC ATC AAG GAA GAT GGC ATT (SEQ ID NO: 726) |
| H51A(+48+73) | ATT TCT AGT TTG GAG ATG GCA GTT TC (SEQ ID NO: 727) |
| H51A(+59+84) | GGA AGA TGG CAT TTC TAG TTT GGA G (SEQ ID NO: 728) |
| H51A(+64+88) | CAT CAA GGA AGA TGG CAT TTC TAG TT (SEQ ID NO: 729) |
| H51A(+89+113) | ATC TGC CAG AGC AGG TAC CTC CAA C (SEQ ID NO: 730) |
| H51A(+49+68) | TAG TTT GGA GAT GGC AGT TT (SEQ ID NO: 731) |
| H51A(+64+83) | GGA AGA TGG CAT TTC TAG TT (SEQ ID NO: 732) |
| H51A(+80+98) | TAC CTC CAA CAT CAA GGA AG (SEQ ID NO: 733) |
| H51A(+94+113) | ATC TGC CAG AGC AGG TAC CT (SEQ ID NO: 734) |
| H51A(+109+128) | CCA AGC CCG GTT GAA ATC TG (SEQ ID NO: 735) |
| H51A(+61+82) | GAA GAT GGC ATT TCT AGT TTG G (SEQ ID NO: 569) |
| H51A(+61+83) | GGA AGA TGG CAT TTC TAG TTT GG (SEQ ID NO: 570) |
| H51A(+61+89) | CAT CAA GGA AGA TGG CAT TTC TAG TTT GG (SEQ ID NO: 571) |

-continued

| Annealing Site | Sequence [5' to 3'] |
|---|---|
| H51A(+66+89) | CAT CAA GGA AGA TGG CAT TTC TAG (SEQ ID NO: 572) |
| H51A(+66+93) | CCA ACA TCA AGG AAG ATG GCA TTT CTA G (SEQ ID NO: 573) |
| H51A(+69+92) | CAA CAT CAA GGA AGA TGG CAT TTC (SEQ ID NO: 574) |
| H51A(+69+96) | CCT CCA ACA TCA AGG AAG ATG GCA TTT C (SEQ ID NO: 575) |
| H51A(+74+96) | CCT CCA ACA TCA AGG AAG ATG GC (SEQ ID NO: 576) |
| H51A(+74+99) | GTA CCT CCA ACA TCA AGG AAG ATG GC (SEQ ID NO: 577) |
| H51A(+74+100) | GGT ACC TCC AAC ATC AAG GAA GAT GGC (SEQ ID NO: 578) |
| H51A(+74+102) | CAG GTA CCT CCA ACA TCA AGG AAG ATG GC (SEQ ID NO: 579) |
| H51A(+74+103) | GCA GGT ACC TCC AAC ATC AAG GAA GAT GGC (SEQ ID NO: 580) |
| H51A(+75+96) | CCT CCA ACA TCA AGG AAG ATG G (SEQ ID NO: 581) |
| H51A(+75+99) | GTA CCT CCA ACA TCA AGG AAG ATG G (SEQ ID NO: 582) |
| H51A(+76+99) | GTA CCT CCA ACA TCA AGG AAG ATG (SEQ ID NO: 583) |
| H51A(+76+105) | GAG CAG GTA CCT CCA ACA TCA AGG AAG ATG (SEQ ID NO: 584) |
| H51A(+80+103) | GCA GGT ACC TCC AAC ATC AAG GAA G (SEQ ID NO: 585) |
| H51A(+80+105) | GAG CAG GTA CCT CCA ACA TCA AGG AAG (SEQ ID NO: 586) |
| H51A(+80+107) | CAG AGC AGG TAC CTC CAA CAT CAA GGA AG (SEQ ID NO: 587) |
| H51A(+80+108) | CCA GAG CAG GTA CCT CCA ACA TCA AGG AAG (SEQ ID NO: 588) |
| H51A(+83+103) | GCA GGT ACC TCC AAC ATC AAG G (SEQ ID NO: 589) |
| H51A(+83+105) | GAG CAG GTA CCT CCA ACA TCA AGG (SEQ ID NO: 590) |
| H51A(+83+107) | CAG AGC AGG TAC CTC CAA CAT CAA GG (SEQ ID NO: 591) |
| H51A(+83+109) | GCC AGA GCA GGT ACC TCC AAC ATC AAG G (SEQ ID NO: 592) |
| H51A(+84+107) | CAG AGC AGG TAC CTC CAA CAT CAA G (SEQ ID NO: 593) |
| H51A(+84+111) | CTG CCA GAG CAG GTA CCT CCA ACA TCA AG (SEQ ID NO: 594) |
| H51A(+84+105) | GAG CAG GTA CCT CCA ACA TCA AG (SEQ ID NO: 595) |
| H51A(+87+109) | GCC AGA GCA GGT ACC TCC AAC ATC (SEQ ID NO: 596) |
| H51A(+93+116) | GAA ATC TGC CAG AGC AGG TAC CTC (SEQ ID NO: 597) |
| H51A(+75+100) | GGT ACC TCC AAC ATC AAG GAA GAT GG (SEQ ID NO: 598) |
| H51A(+74+101) | AGG TAC CTC CAA CAT CAA GGA AGA TGG C (SEQ ID NO: 599) |
| H51A(+74+98) | TAC CTC CAA CAT CAA GGA AGA TGG C (SEQ ID NO: 600) |
| H51A(+74+97) | ACC TCC AAC ATC AAG GAA GAT GGC (SEQ ID NO: 601) |
| H51A(+74+94) | TCC AAC ATC AAG GAA GAT GGC (SEQ ID NO: 602) |
| H51A(+74+93) | CCA ACA TCA AGG AAG ATG GC (SEQ ID NO: 603) |
| H51A(+74+92) | CAA CAT CAA GGA AGA TGG C (SEQ ID NO: 604) |
| H51A(+69+99) | GTA CCT CCA ACA TCA AGG AAG ATG GCA TTT C (SEQ ID NO: 605) |
| H51A(+70+99) | GTA CCT CCA ACA TCA AGG AAG ATG GCA TTT (SEQ ID NO: 606) |
| H51A(+71+99) | GTA CCT CCA ACA TCA AGG AAG ATG GCA TT (SEQ ID NO: 607) |
| H51A(+72+99) | GTA CCT CCA ACA TCA AGG AAG ATG GCA T (SEQ ID NO: 608) |
| H51A(+73+99) | GTA CCT CCA ACA TCA AGG AAG ATG GCA (SEQ ID NO: 609) |
| H51A(+77+99) | GTA CCT CCA ACA TCA AGG AAG AT (SEQ ID NO: 610) |

-continued

| Annealing Site | Sequence [5' to 3'] |
|---|---|
| H51A(+78+99) | GTA CCT CCA ACA TCA AGG AAG A (SEQ ID NO: 611) |
| H51A(+79+99) | GTA CCT CCA ACA TCA AGG AAG |
| H51.SA.(-60-36) | GAA GAA AAA GAA AAA TTA GAA ACA C (SEQ ID NO: 613) |
| H51.SA.(-50-26) | AAG GAA AAA AGA AGA AAA AGA AAA A (SEQ ID NO: 614) |
| H51.SA.(-45-21) | GCA AAA AGG AAA AAA GAA GAA AAA G (SEQ ID NO: 615) |
| H51.SA.(-40-16) | TTT TTG CAA AAA GGA AAA AAG AAG A (SEQ ID NO: 616) |
| H51.SA.(-35-11) | TTG GGT TTT TGC AAA AAG GAA AAA A (SEQ ID NO: 617) |
| H51.SA.(-30-6) | ATA TTT TGG GTT TTT GCA AAA AGG A (SEQ ID NO: 618) |
| H51.SA.(-25-1) | CTA AAA TAT TTT GGG TTT TTG CAA A (SEQ ID NO: 619) |
| H51.SA.(-20+5) | AGG AGC TAA AAT ATT TTG GGT TTT T (SEQ ID NO: 620) |
| H51.SA.(-15+10) | TGA GTA GGA GCT AAA ATA TTT TGG G (SEQ ID NO: 621) |
| H51.SA.(-10+15) | CAG TCT GAG TAG GAG CTA AAA TAT T (SEQ ID NO: 622) |
| H51.SA.(-5+20) | AGT AAC AGT CTG AGT AGG AGC TAA A (SEQ ID NO: 623) |
| H51.SA.(-1+24) | CCA GAG TAA CAG TCT GAG TAG GAG C (SEQ ID NO: 624) |
| H51.SA.(-65-41) | AAA AGA AAA ATT AGA AAC ACA GCT (SEQ ID NO: 625) |
| H51.SA.(-70-46) | AAA AAT TAG AAA CAC AAG CTA AAG A (SEQ ID NO: 626) |
| H51.SA.(-75-51) | TTA GAA ACA CAA GCT AAA GAG CCA A (SEQ ID NO: 627) |
| H51.SA.(-80-56) | AAC ACA AGC TAA AGA GCC AAT TTC A (SEQ ID NO: 628) |
| H51.SA.(-85-61) | AAG CTA AAG AGC CAA TTT CAA TAA C (SEQ ID NO: 629) |
| H51.SA.(-90-66) | AAA GAG CCA ATT TCA ATA ACA ATA A (SEQ ID NO: 630) |
| H51.SA.(-95-71) | GCC AAT TTC AAT AAC AAT AAG TCA A (SEQ ID NO: 631) |
| H51.SA.(-100-76) | TTT CAA TAA CAA TAA GTC AAA TTT A (SEQ ID NO: 632) |
| H51A(+1+30) | GTG TCA CCA GAG TAA CAG TCT GAG TAG GAG (SEQ ID NO: 633) |
| H51A(+10+39) | CCA CAG GTT GTG TCA CCA GAG TAA CAG TCT (SEQ ID NO: 634) |
| H51A(+6+35) | AGG TTG TGT CAC CAG AGT AAC AGT CTG AGT (SEQ ID NO: 736) |
| H51A(+49+78) | ATG GCA TTT CTA GTT TGG AGA TGG CAG TTT (SEQ ID NO: 636) |
| H51A(+1+25) | ACC AGA GTA ACA GTC TGA GTA GGA G (SEQ ID NO: 637) |
| H51A(+4+28) | GTC ACC AGA GTA ACA GTC TGA GTA G (SEQ ID NO: 638) |
| H51A(+16+40) | ACC ACA GGT TGT GTC ACC AGA GTA A (SEQ ID NO: 639) |
| H51A(+21+45) | TAG TAA CCA CAG GTT GTG TCA CCA G (SEQ ID NO: 640) |
| H51A(+26+50) | TTC CTT AGT AAC CAC AGG TTG TGT C (SEQ ID NO: 641) |
| H51A(+31+55) | GCA GTT TCC TTA GTA ACC ACA GGT T (SEQ ID NO: 642) |
| H51A(+36+60) | AGA TGG CAG TTT CCT TAG TAA CCA C (SEQ ID NO: 643) |
| H51A(+41+65) | TTT GGA GAT GGC AGT TTC CTT AGT A (SEQ ID NO: 644) |
| H51A(+86+110) | TGC CAG AGC AGG TAC CTC CAA CAT C (SEQ ID NO: 645) |
| H51A(+91+115) | AAA TCT GCC AGA GCA GGT ACC TCC A (SEQ ID NO: 646) |
| H51A(+96+120) | GGT TGA AAT CTG CCA GAG CAG GTA C (SEQ ID NO: 647) |
| H51A(+101+125) | AGC CCG GTT GAA ATC TGC CAG AGC A (SEQ ID NO: 648) |

| Annealing Site | Sequence [5' to 3'] |
|---|---|
| H51A(+106+130) | GTC CAA GCC CGG TTG AAA TCT GCC A (SEQ ID NO: 649) |
| H51A(+111+135) | GTT CTG TCC AAG CCC GGT TGA AAT C (SEQ ID NO: 650) |
| H51A(+116+140) | GGT AAG TTC TGT CCA AGC CCG GTT G (SEQ ID NO: 651) |
| H51A(+121+145) | CAG TCG GTA AGT TCT GTC CAA GCC C (SEQ ID NO: 652) |
| H51A(+126+150) | AAA GCC AGT CGG TAA GTT CTG TCC A (SEQ ID NO: 653) |
| H51A(+131+155) | CAG AGA AAG CCA GTC GGTA AGT TCT (SEQ ID NO: 737) |
| H51A(+136+160) | TCA AGC AGA GAA AGC CAG TCG GTA A (SEQ ID NO: 655) |
| H51A(+141+165) | CTT GAT CAA GCA GAG AAA GCC AGT C (SEQ ID NO: 656) |
| H51A(+146+170) | TAT AAC TTGA TCA AGC AGA GAA AGC (SEQ ID NO: 738) |
| H51A(+151+175) | GAT TTT ATA ACT TGA TCA AGC AGA G (SEQ ID NO: 658) |
| H51A(+156+180) | TCT GTG ATT TTA TAA CTT GAT CAA G (SEQ ID NO: 659) |
| H51A(+161+185) | CAC CCT CTG TGA TTT TAT AAC TTG A (SEQ ID NO: 660) |
| H51A(+166+190) | ACC ATC ACC CTC TGT GAT TTT ATA A (SEQ ID NO: 661) |
| H51A(+171+195) | CAC CCA CCA TCA CCC TCT GTG ATT T (SEQ ID NO: 662) |
| H51A(+176+200) | AAG GTC ACC CAC CAT CAC CCT CTG T (SEQ ID NO: 663) |
| H51A(+181+205) | TCC TCA AGG TCA CCC ACC ATC ACC C (SEQ ID NO: 664) |
| H51A(+186+210) | TGA TAT CCT CAA GGT CAC CCA CCA T (SEQ ID NO: 665) |
| H51A(+191+215) | CTC GTT GAT ATC CTC AAG GTC ACC C (SEQ ID NO: 666) |
| H51A(+196+220) | ATC ATC TCG TTG ATA TCC TCA AGG T (SEQ ID NO: 667) |
| H51A(+201+225) | TGA TGA TCA TCT CGT TGA TAT CCT C (SEQ ID NO: 668) |
| H51A(+206+230) | CTG CTT GAT GAT CAT CTC GTT GAT A (SEQ ID NO: 669) |
| H51D(+211-02) | ACC TTC TGC TTG ATG ATC ATC TCG T (SEQ ID NO: 670) |
| H51D(+214-05) | CAT ACC TTC TGC TTG ATG ATC ATC T (SEQ ID NO: 671) |
| H51D(+217-08) | TCT CAT ACC TTC TGC TTG ATG ATC A (SEQ ID NO: 672) |
| H51D(+220-11) | TTT TCT CAT ACC TTC TGC TTG ATG A (SEQ ID NO: 673) |
| H51D(+223-14) | ATT TTT TCT CAT ACC TTC TGC TTG A (SEQ ID NO: 674) |
| H51D(+226-17) | ATC ATT TTT TCT CAT ACC TTC TGC T (SEQ ID NO: 675) |
| H51D(+229-20) | TTT ATC ATT TTT TCT CAT ACC TTC T (SEQ ID NO: 676) |
| H51D(+232-23) | ACT TTT ATC ATT TTT TCT CAT ACC T (SEQ ID NO: 677) |
| H51D(-02-26) | CCA ACT TTT ATC ATT TTT TCT CAT A (SEQ ID NO: 678) |
| H51A(+1+30) | GTG TCA CCA GAG TAA CAG TCT GAG TAG GAG (SEQ ID NO: 633) | wherein A is

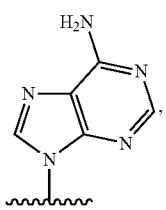 [SMILES: *n1cnc2c(N)ncnc21]

C is

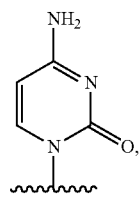 [SMILES: *n1ccc(N)nc1=O]

G is 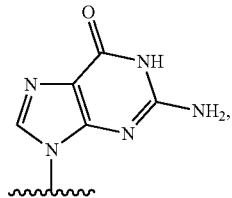 [SMILES: *n1cnc2c(=O)[nH]c(N)nc21] and T is 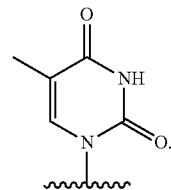 [SMILES: *n1cc(C)c(=O)[nH]c1=O]

In one aspect, the base sequence and annealing site are selected from one of the following:

| Annealing Site | Base Sequence [5' to 3'] |
|---|---|
| H51A(+66+95) | CTC CAA CAT CAA GGA AGA TGG CAT TTC TAG (SEQ ID NO: 679) |
| H51A(+74+97) | ACC TCC AAC ATC AAG GAA GAT GGC (SEQ ID NO: 601) |
| H51A(+70+99) | GTA CCT CCA ACA TCA AGG AAG ATG GCA TTT (SEQ ID NO: 606) |
| H51A(+72+99) | GTA CCT CCA ACA TCA AGG AAG ATG GCA T (SEQ ID NO: 608) |
| H51A(+68+87) | TCA AGG AAG ATG GCA TTT CT (SEQ ID NO: 680) |
| H51A(+68+87) | UCA AGG AmAGm AmUGm GmCA UUU CU (SEQ ID NO: 681) |
| H53A(+36+60) | GTT GCC TCC GGT TCT GAA GGT GTT C (SEQ ID NO: 682) |
| H53A(+36+60) | GTT G5mC5mC T5mC5mC GGT T5mC T GAA GGT GTT 5mC (SEQ ID NO: 683) |
| H53A(+36+56) | CCT CCG GTT CTG AAG GTG TTC (SEQ ID NO: 684) |
| H53A(+23+47) | CTG AAG GTG TTC TTG TAC TTC ATC C (SEQ ID NO: 34) |
| H53A(+32+56) | CCT CCG GTT CTG AAG GTG TTC TTG T (SEQ ID NO: 685) |
| H53A(+33+60) | GTT GCC TCC GGT TCT GAA GGT GTT CTT G (SEQ ID NO: 686) |
| H53A(+30+59) | TTG CCT CCG GTT CTG AAG GTG TTC TTG TAC (SEQ ID NO: 687) |
| H53A(+39+62) | CTG TTG CCT CCG GTT CTG AAG GTG (SEQ ID NO: 688) |
| H53A(+36+69) | CAT TCA ACT GTT GCC TCC GGT TCT GAA GGT G (SEQ ID NO: 689) |
| H53A(+45+62) | CTG TTG CCT CCG GTT CTG (SEQ ID NO: 690) |
| H45A(-03+19) | CAA TGC CAT CCT GGA GTT CCT G (SEQ ID NO: 691) |
| H45A(-09+25) | GCT GCC CAA TGC CAT CCT GGA GTT CCT GTA AGA T (SEQ ID NO: 692) |
| H45A(-03+25) | GCT GCC CAA TGC CAT CCT GGA GTT CCT G (SEQ ID NO: 693) |
| H45A(-06+25) | GCT GCC CAA TGC CAT CCT GGA GTT CCT GTA A (SEQ ID NO: 694) |
| H45A(-12+19) | CAA TGC CAT CCT GGA GTT CCT GTA AGA TAC C (SEQ ID NO: 695) |
| H45A(-09+19) | CAA TGC CAT CCT GGA GTT CCT GTA AGA T (SEQ ID NO: 696) |
| H45A(-12+16) | TGC CAT CCT GGA GTT CCT GT A AGA TAC C (SEQ ID NO: 697) |
| H45A(-14+25) | GCT GCC CAA TGC CAT CCT GGA GTT CCT GTA AGA TAC CAA (SEQ ID NO: 698) |
| H45A(-08+19) | CAA TGC CAT CCT GGA GTT CCT GTA AGA (SEQ ID NO: 699) |
| HM45A(-07+25) | GCT GCC CAA TGC CAT CCT GGA GTT CCT GTA AG (SEQ ID NO: 700) |
| H45A(-12+22) | GCC CAA TGC CAT CCT GGA GTT CCT GTA AGA TAC C (SEQ ID NO: 701) |
| H45A(-09+22) | GCC CAA TGC CAT CCT GGA GTT CCT GTA AGA T (SEQ ID NO: 702) |
| H45A(-09+30) | TTG CCG CTG CCC AAT GCC ATC CTG GAG TTC CTG TAA GAT (SEQ ID NO: 703) |

-continued

| Annealing Site | Base Sequence [5' to 3'] |
|---|---|
| H45A(-06+22) | GCC CAA TGC CAT CCT GGA GTT CCT GTA A (SEQ ID NO: 704) |
| H45A(-06+28) | GCC GCT GCC CAA TGC CAT CCT GGA GTT CCT GTA A (SEQ ID NO: 705) |
| H45A(-03+22) | GCC CAA TGC CAT CCT GGA GTT CCT G (SEQ ID NO: 706) |
| H45A(-03+28) | GCC GCT GCC CAA TGC CAT CCT GGA GTT CCT G (SEQ ID NO: 707) |
| H45A(+9+26) | m5C-G-m5C-T-G-C-m5C-m5C-A-A-T-G-m5C-m5C-A-U-m5C-m5C (SEQ ID NO: 708) |
| H44A(-10+15) | GAT CTG TCA AAT CGC CTG CAG GTA A (SEQ ID NO: 709) |
| H44A(-07+15) | GAT CTG TCA AAT CGC CTG CAG G (SEQ ID NO: 710) |
| H44M(-07+17) | CAG ATC TGT CAA ATC GCC TGC AGG (SEQ ID NO: 711) |
| H44A(-08+15) | GAT CTG TCA AAT CGC CTG CAG GT (SEQ ID NO: 712) |
| H44A(-06+15) | GAT CTG TCA AAT CGC CTG CAG (SEQ ID NO: 713) |
| H44A(-08+17) | CAG ATC TGT CAA ATC GCC TGC AGG T (SEQ ID NO: 714) |
| H44A(-06+17) | CAG ATC TGT CAA ATC GCC TGC AG (SEQ ID NO: 715) |
| H50D(+04-18) | GGG ATC CAG TAT ACT TAC AGG C (SEQ ID NO: 716) |
| H50D(+07-18) | GGG ATC CAG TAT ACT TAC AGG CTC C (SEQ ID NO: 568) |
| H50D(+07-16) | GAT CCA GTA TAC TTA CAG GCT CC (SEQ ID NO: 717) |
| H50D(+07-17) | GGA TCC AGT ATA CTT ACA GGC TCC (SEQ ID NO: 718) |
| H50A(-19+07) | ACT TCC TCT TTA ACA GAA AAG CAT AC (SEQ ID NO: 719) |
| H50D(+07-15) | ATC CAG TAT ACT TAC AGG CTC C (SEQ ID NO: 720) |
| H50A(-02+23) | GAG CTC AGA TCT TCT AAC TTC CTC T (SEQ ID NO: 721) |
| H50D(+06-18) | GGG ATC CAG TAT ACT TAC AGG CTC (SEQ ID NO: 722) |
| H50D(+07-20) | ATG GGA TCC AGT ATA CTT ACA GGC TCC (SEQ ID NO: 723) |
| H52A(-01+24) | CTG TTC CAA ATC CTG CAT TGT TGC C (SEQ ID NO: 724) | wherein A is

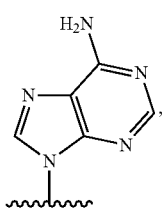

G is

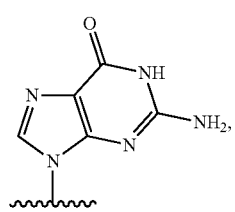

C is

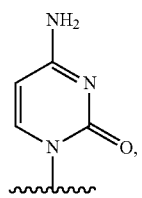 [SMILES: *n1ccc(N)nc1=O]

T is

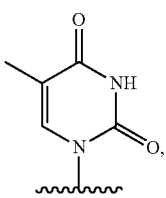

U is

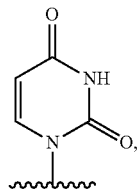 [SMILES: *n1ccc(=O)[nH]c1=O]

Gm is methylated guanine, Am is methylated adenine, and m5C is

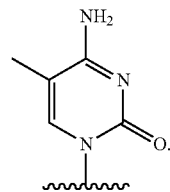 [SMILES: *n1cc(C)c(N)nc1=O]

In another aspect, the disclosure provides antisense oligomers of Formula (XA):

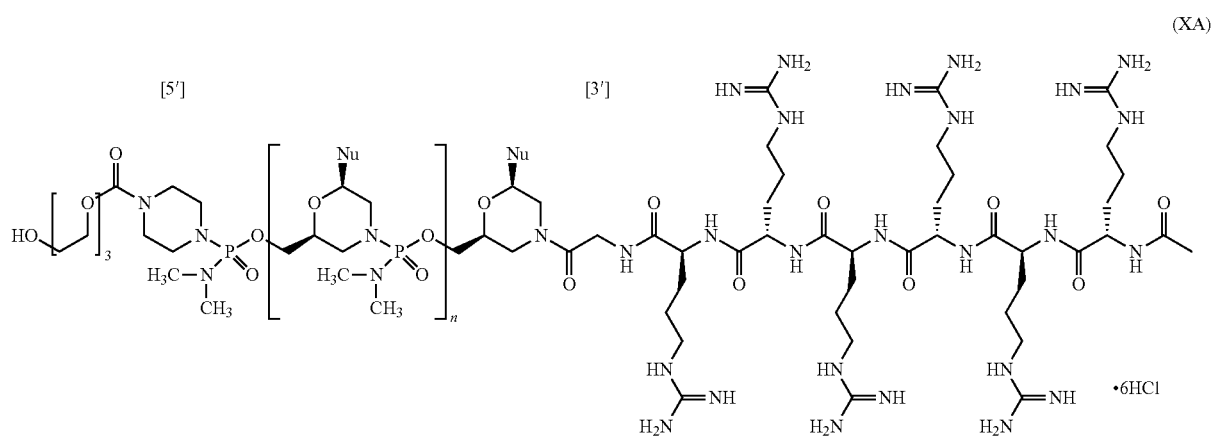

(XA)

where each Nu from 1 to (n+1) and 5' to 3' corresponds to the nucleobases in the following sequences:

| Annealing Site | Sequence [5' to 3'] |
|---|---|
| H51A(+61+90) | ACA TCA AGG AAG ATG GCA TTT CT A GTT TGG (SEQ ID NO: 725) |
| H51D(+16-07) | CTC ATA CCT TCT GCT TGA TGA TC (SEQ ID NO: 567) |
| H50D(+103+127) | GGG ATC AGT TAT ACT TAC AGG CTC C (SEQ ID NO: 568) |
| H51A(+81+105) | GAG CAG GTA CCT CCA ACA TCA AGG AA (SEQ ID NO: 33) |
| H51A(+71+100) | GGT ACC TCC AAC ATC AAG GAA GAT GGC ATT (SEQ ID NO: 726) |
| H51A(+48+73) | ATT TCT AGT TTG GAG ATG GCA GTT TC (SEQ ID NO: 727) |
| H51A(+59+84) | GGA AGA TGG CAT TTC TAG TTT GGA G (SEQ ID NO: 728) |
| H51A(+64+88) | CAT CAA GGA AGA TGG CAT TTC TAG TT (SEQ ID NO: 729) |
| H51A(+89+113) | ATC TGC CAG AGC AGG TAC CTC CAA C (SEQ ID NO: 730) |
| H51A(+49+68) | TAG TTT GGA GAT GGC AGT TT (SEQ ID NO: 731) |
| H51A(+64+83) | GGA AGA TGG CAT TTC TAG TT (SEQ ID NO: 732) |
| H51A(+80+98) | TAC CTC CAA CAT CAA GGA AG (SEQ ID NO: 733) |
| H51A(+94+113) | ATC TGC CAG AGC AGG TAC CT (SEQ ID NO: 734) |
| H51A(+109+128) | CCA AGC CCG GTT GAA ATC TG (SEQ ID NO: 735) |
| H51A(+61+82) | GAA GAT GGC ATT TCT AGT TTG G (SEQ ID NO: 569) |
| H51A(+61+83) | GGA AGA TGG CAT TTC TAG TTT GG (SEQ ID NO: 570) |
| H51A(+61+89) | CAT CAA GGA AGA TGG CAT TTC TAG TTT GG (SEQ ID NO: 571) |

-continued

| Annealing Site | Sequence [5' to 3'] |
| --- | --- |
| H51A(+66+89) | CAT CAA GGA AGA TGG CAT TTC TAG (SEQ ID NO: 572) |
| H51A(+66+93) | CCA ACA TCA AGG AAG ATG GCA TTT CTA G (SEQ ID NO: 573) |
| H51A(+69+92) | CAA CAT CAA GGA AGA TGG CAT TTC (SEQ ID NO: 574) |
| H51A(+69+96) | CCT CCA ACA TCA AGG AAG ATG GCA TTT C (SEQ ID NO: 575) |
| H51A(+74+96) | CCT CCA ACA TCA AGG AAG ATG GC (SEQ ID NO: 576) |
| H51A(+74+99) | GTA CCT CCA ACA TCA AGG AAG ATG GC (SEQ ID NO: 577) |
| H51A(+74+100) | GGT ACC TCC AAC ATC AAG GAA GAT GGC (SEQ ID NO: 578) |
| H51A(+74+102) | CAG GTA CCT CCA ACA TCA AGG AAG ATG GC (SEQ ID NO: 579) |
| H51A(+74+103) | GCA GGT ACC TCC AAC ATC AAG GAA GAT GGC (SEQ ID NO: 580) |
| H51A(+75+96) | CCT CCA ACA TCA AGG AAG ATG G (SEQ ID NO: 581) |
| H51A(+75+99) | GTA CCT CCA ACA TCA AGG AAG ATG G (SEQ ID NO: 582) |
| H51A(+76+99) | GTA CCT CCA ACA TCA AGG AAG ATG (SEQ ID NO: 583) |
| H51A(+76+105) | GAG CAG GTA CCT CCA ACA TCA AGG AAG ATG (SEQ ID NO: 584) |
| H51A(+80+103) | GCA GGT ACC TCC AAC ATC AAG GAA G (SEQ ID NO: 585) |
| H51A(+80+105) | GAG CAG GTA CCT CCA ACA TCA AGG AAG (SEQ ID NO: 586) |
| H51A(+80+107) | CAG AGC AGG TAC CTC CAA CAT CAA GGA AG (SEQ ID NO: 587) |
| H51A(+80+108) | CCA GAG CAG GTA CCT CCA ACA TCA AGG AAG (SEQ ID NO: 588) |
| H51A(+83+103) | GCA GGT ACC TCC AAC ATC AAG G (SEQ ID NO: 589) |
| H51A(+83+105) | GAG CAG GTA CCT CCA ACA TCA AGG (SEQ ID NO: 590) |
| H51A(+83+107) | CAG AGC AGG TAC CTC CAA CAT CAA GG (SEQ ID NO: 591) |
| H51A(+83+109) | GCC AGA GCA GGT ACC TCC AAC ATC AAG G (SEQ ID NO: 592) |
| H51A(+84+107) | CAG AGC AGG TAC CTC CAA CAT CAA G (SEQ ID NO: 593) |
| H51A(+84+111) | CTG CCA GAG CAG GTA CCT CCA ACA TCA AG (SEQ ID NO: 594) |
| H51A(+84+105) | GAG CAG GTA CCT CCA ACA TCA AG (SEQ ID NO: 595) |
| H51A(+87+109) | GCC AGA GCA GGT ACC TCC AAC ATC (SEQ ID NO: 596) |
| H51A(+93+116) | GAA ATC TGC CAG AGC AGG TAC CTC (SEQ ID NO: 597) |
| H51A(+75+100) | GGT ACC TCC AAC ATC AAG GAA GAT GG (SEQ ID NO: 598) |
| H51A(+74+101) | AGG TAC CTC CAA CAT CAA GGA AGA TGG C (SEQ ID NO: 599) |
| H51A(+74+98) | TAC CTC CAA CAT CAA GGA AGA TGG C (SEQ ID NO: 600) |
| H51A(+74+97) | ACC TCC AAC ATC AAG GAA GAT GGC (SEQ ID NO: 601) |
| H51A(+74+94) | TCC AAC ATC AAG GAA GAT GGC (SEQ ID NO: 602) |
| H51A(+74+93) | CCA ACA TCA AGG AAG ATG GC (SEQ ID NO: 603) |
| H51A(+74+92) | CAA CAT CAA GGA AGA TGG C (SEQ ID NO: 604) |
| H51A(+69+99) | GTA CCT CCA ACA TCA AGG AAG ATG GCA TTT C (SEQ ID NO: 605) |
| H51A(+70+99) | GTA CCT CCA ACA TCA AGG AAG ATG GCA TTT (SEQ ID NO: 606) |
| H51A(+71+99) | GTA CCT CCA ACA TCA AGG AAG ATG GCA TT (SEQ ID NO: 607) |
| H51A(+72+99) | GTA CCT CCA ACA TCA AGG AAG ATG GCA T (SEQ ID NO: 608) |
| H51A(+73+99) | GTA CCT CCA ACA TCA AGG AAG ATG GCA (SEQ ID NO: 609) |
| H51A(+77+99) | GTA CCT CCA ACA TCA AGG AAG AT (SEQ ID NO: 610) |

| Annealing Site | Sequence [5' to 3'] |
|---|---|
| H51A(+78+99) | GTA CCT CCA AC A TCA AGG AAG A (SEQ ID NO: 611) |
| H51A(+79+99) | GTA CCT CCA ACA TCA AGG AAG |
| H51.SA.(-60-36) | GAA GAA AAA GAA AAA TTA GAA ACA C (SEQ ID NO: 613) |
| H51.SA.(-50-26) | AAG GAA AAA AGA AGA AAA AGA AAA A (SEQ ID NO: 614) |
| H51.SA.(-45-21) | GCA AAA AGG AAA AAA GAA GAA AAA G (SEQ ID NO: 615) |
| H51.SA.(-40-16) | TTT TTG CAA AAA GGA AAA AAG AAG A (SEQ ID NO: 616) |
| H51.SA.(-35-11) | TTG GGT TTT TGC AAA AAG GAA AAA A (SEQ ID NO: 617) |
| H51.SA.(-30-6) | ATA TTT TGG GTT TTT GCA AAA AGG A (SEQ ID NO: 618) |
| H51.SA.(-25-1) | CTA AAA TAT TTT GGG TTT TTG CAA A (SEQ ID NO: 619) |
| H51.SA.(-20+5) | AGG AGC TAA AAT ATT TTG GGT TTT T (SEQ ID NO: 620) |
| H51.SA.(-15+10) | TGA GTA GGA GCT AAA ATA TTT TGG G (SEQ ID NO: 621) |
| H51.SA.(-10+15) | CAG TCT GAG TAG GAG CTA AAA TAT T (SEQ ID NO: 622) |
| H51.SA.(-5+20) | AGT AAC AGT CTG AGT AGG AGC TAA A (SEQ ID NO: 623) |
| H51.SA.(-1+24) | CCA GAG TAA CAG TCT GAG TAG GAG C (SEQ ID NO: 624) |
| H51.SA.(-65-41) | AAA AGA AAA ATT AGA AAC ACA GCA T (SEQ ID NO: 625) |
| H51.SA.(-70-46) | AAA AAT TAG AAA CAC AAG CTA AAG A (SEQ ID NO: 626) |
| H51.SA.(-75-51) | TTA GAA ACA CAA GCT AAA GAG CCA A (SEQ ID NO: 627) |
| H51.SA.(-80-56) | AAC ACA AGC TAA AGA GCC AAT TTC A (SEQ ID NO: 628) |
| H51.SA.(-85-61) | AAG CTA AAG AGC CAA TTT CAA TAA C (SEQ ID NO: 629) |
| H51.SA.(-90-66) | AAA GAG CCA ATT TCA ATA ACA ATA A (SEQ ID NO: 630) |
| H51.SA.(-95-71) | GCC AAT TTC AAT AAC AAT AAG TCA A (SEQ ID NO: 631) |
| H51.SA.(-100-76) | TTT CAA TAA CAA TAA GTC AAA TTT A (SEQ ID NO: 632) |
| H51A(+1+30) | GTG TCA CCA GAG TAA CAG TCT GAG TAG GAG (SEQ ID NO: 633) |
| H51A(+10+39) | CCA CAG GTT GTG TCA CCA GAG TAA CAG TCT (SEQ ID NO: 634) |
| H51A(+6+35) | AGG TTG TGT CAC CAG AGT AAC AGT CTG AGT (SEQ ID NO: 736) |
| H51A(+49+78) | ATG GCA TTT CTA GTT TGG AGA TGG CAG TTT (SEQ ID NO: 636) |
| H51A(+1+25) | ACC AGA GTA ACA GTC TGA GTA GGA G (SEQ ID NO: 637) |
| H51A(+4+28) | GTC ACC AGA GTA ACA GTC TGA GTA G (SEQ ID NO: 638) |
| H51A(+16+40) | ACC ACA GGT TGT GTC ACC AGA GTA A (SEQ ID NO: 639) |
| H51A(+21+45) | TAG TAA CCA CAG GTT GTG TCA CCA G (SEQ ID NO: 640) |
| H51A(+26+50) | TTC CTT AGT AAC CAC AGG TTG TGT C (SEQ ID NO: 641) |
| H51A(+31+55) | GCA GTT TCC TTA GTA ACC ACA GGT T (SEQ ID NO: 642) |
| H51A(+36+60) | AGA TGG CAG TTT CCT TAG TAA CCA C (SEQ ID NO: 643) |
| H51A(+41+65) | TTT GGA GAT GGC AGT TTC CTT AGT A (SEQ ID NO: 644) |
| H51A(+86+110) | TGC CAG AGC AGG TAC CTC CAA CAT C (SEQ ID NO: 645) |
| H51A(+91+115) | AAA TCT GCC AGA GCA GGT ACC TCC A (SEQ ID NO: 646) |
| H51A(+96+120) | GGT TGA AAT CTG CCA GAG CAG GTA C (SEQ ID NO: 647) |
| H51A(+101+125) | AGC CCG GTT GAA ATC TGC CAG AGC A (SEQ ID NO: 648) |

| Annealing Site | Sequence [5' to 3'] |
|---|---|
| H51A(+106+130) | GTC CAA GCC CGG TTG AAA TCT GCC A (SEQ ID NO: 649) |
| H51A(+111+135) | GTT CTG TCC AAG CCC GGT TGA AAT C (SEQ ID NO: 650) |
| H51A(+116+140) | GGT AAG TTC TGT CCA AGC CCG GTT G (SEQ ID NO: 651) |
| H51A(+121+145) | CAG TCG GTA AGT TCT GTC AAG CCC (SEQ ID NO: 652) |
| H51A(+126+150) | AAA GCC AGT CGG TAA GTT CTG TCC A (SEQ ID NO: 653) |
| H51A(+131+155) | CAG AGA AAG CCA GTC GGTA AGT TCT (SEQ ID NO: 737) |
| H51A(+136+160) | TCA AGC AGA GAA AGC CAG TCG GT A A (SEQ ID NO: 655) |
| H51A(+141+165) | CTT GAT CAA GCA GAG AAA GCC AGT C (SEQ ID NO: 656) |
| H51A(+146+170) | TAT AAC TTGA TCA AGC AGA GAA AGC (SEQ ID NO: 738) |
| H51A(+151+175) | GAT TTT ATA ACT TGA TCA AGC AGA G (SEQ ID NO: 658) |
| H51A(+156+180) | TCT GTG ATT TTA TAA CTT GAT CAA G (SEQ ID NO: 659) |
| H51A(+161+185) | CAC CCT CTG TGA TTT TAT AAC TTG A (SEQ ID NO: 660) |
| H51A(+166+190) | ACC ATC ACC CTC TGT GAT TTT ATA A (SEQ ID NO: 661) |
| H51A(+171+195) | CAC CCA CCA TCA CCC TCT GTG ATT T (SEQ ID NO: 662) |
| H51A(+176+200) | AAG GTC ACC CAC CAT CAC CCT CTG T (SEQ ID NO: 663) |
| H51A(+181+205) | TCC TCA AGG TCA CCC ACC ATC ACC C (SEQ ID NO: 664) |
| H51A(+186+210) | TGA TAT CCT CAA GGT CAC CCA CCA T (SEQ ID NO: 665) |
| H51A(+191+215) | CTC GTT GAT ATC CTC AAG GTC ACC C (SEQ ID NO: 666) |
| H51A(+196+220) | ATC ATC TCG TTG ATA TCC TCA AGG T (SEQ ID NO: 667) |
| H51A(+201+225) | TGA TGA TCA TCT CGT TGA TAT CCT C (SEQ ID NO: 668) |
| H51A(+206+230) | CTG CTT GAT GAT CAT CTC GTT GAT A (SEQ ID NO: 669) |
| H51D(+211-02) | ACC TTC TGC TTG ATG ATC ATC TCG T (SEQ ID NO: 670) |
| H51D(+214-05) | CAT ACC TTC TGC TTG ATG ATC ATC T (SEQ ID NO: 671) |
| H51D(+217-08) | TCT CAT ACC TTC TGC TTG ATG ATC A (SEQ ID NO: 672) |
| H51D(+220-11) | TTT TCT CAT ACC TTC TGC TTG ATG A (SEQ ID NO: 673) |
| H51D(+223-14) | ATT TTT TCT CAT ACC TTC TGC TTG A (SEQ ID NO: 674) |
| H51D(+226-17) | ATC ATT TTT TCT CAT ACC TTC TGC T (SEQ ID NO: 675) |
| H51D(+229-20) | TTT ATC ATT TTT TCT CAT ACC TTC T (SEQ ID NO: 676) |
| H51D(+232-23) | ACT TTT ATC ATT TTT TCT CAT ACC T (SEQ ID NO: 677) |
| H51D(-02-26) | CCA ACT TTT ATC ATT TTT TCT CAT A (SEQ ID NO: 678) |
| H51A(+1+30) | GTG TCA CCA GAG TAA CAG TCT GAG TAG GAG (SEQ ID NO: 633) | wherein A is

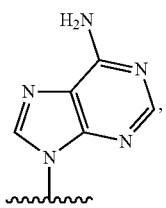 [SMILES: *n1cnc2c(N)ncnc21]

C is

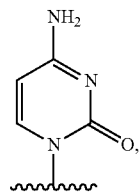 [SMILES: *n1ccc(N)nc1=O]

G is

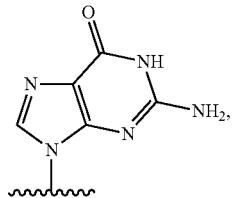 [SMILES: *n1cnc2c(=O)[nH]c(N)nc21]

and T is

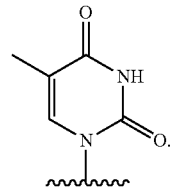 [SMILES: *n1cc(C)c(=O)[nH]c1=O]

In one aspect, the base sequence and annealing site are selected from one of the following:

| Annealing Site | Base Sequence [5' to 3'] |
|---|---|
| H51A(+66+95) | CTC AAC CAT CAA GGA AGA TGG CAT TTC TAG (SEQ ID NO: 679) |
| H51A(+74+97) | ACC TCC AAC ATC AAG GAA GAT GGC (SEQ ID NO: 601) |
| H51A(+70+99) | GTA CCT CCA ACA TCA AGG AAG ATG CA TTT (SEQ ID NO: 606) |
| H51A(+72+99) | GTA CCT CCA ACA TCA AGG AAG ATG CA T (SEQ ID NO: 608) |
| H51A(+68+87) | TCA AGG AAG ATG GCA TTT CT (SEQ ID NO: 680) |
| H51A(+68+87) | UCA AGG AmAGm AmUGm GmCA UUU CU (SEQ ID NO: 681) |
| H53A(+36+60) | GTT GCC TCC GGT TCT GAA GGT GTT C (SEQ ID NO: 682) |
| H53A(+36+60) | GTT G5mC5mC T5mC5mC GGT T5mC T GAA GGT GTT 5mC (SEQ ID NO: 683) |
| H53A(+36+56) | CCT CCG GTT CTG AAG GTG TTC (SEQ ID NO: 684) |
| H53A(+23+47) | CTG AAG GTG TTC TTG TAC TTC ATC C (SEQ ID NO: 34) |
| H53A(+32+56) | CCT CCG GTT CTG AAG GTG TTC TTG T (SEQ ID NO: 685) |
| H53A(+33+60) | GTT GCC TCC GGT TCT GAA GGT GTT CTT G (SEQ ID NO: 686) |
| H53A(+30+59) | TTG CCT CCG GTT CTG AAG GTG TTC TTG TAC (SEQ ID NO: 687) |
| H53A(+39+62) | CTG TTG CCT CCG GTT CTG AAG GTG (SEQ ID NO: 688) |
| H53A(+36+69) | CAT TCA ACT GTT GCC TCC GGT TCT GAA GGT G (SEQ ID NO: 689) |
| H53A(+45+62) | CTG TTG CCT CCG GTT CTG (SEQ ID NO: 690) |
| H45A(-03+19) | CAA TGC CAT CCT GGA GTT CCT G (SEQ ID NO: 691) |
| H45A(-09+25) | GCT GCC AAT GCC ATC CTG GAG TTC CTG TAG AGA T (SEQ ID NO: 692) |
| H45A(-03+25) | GCT GCC AAT GCC ATC CTG GAG TTC CTG G (SEQ ID NO: 693) |
| H45A(-06+25) | GCT GCC AAT GCC ATC CTG GAG TTC CTG TA A (SEQ ID NO: 694) |
| H45A(-12+19) | CAA TGC CAT CCT GGA GTT CCT GTA AGA TAC C (SEQ ID NO: 695) |
| H45A(-09+19) | CAA TGC CAT CCT GGA GTT CCT GTA AGA T (SEQ ID NO: 696) |
| H45A(-12+16) | TGC CAT CCT GGA GTT CCT GTA AGA TAC C (SEQ ID NO: 697) |
| H45A(-14+25) | GCT GCC AAT GCC ATC CTG GAG TTC CTG TAG AGA TAC CAA (SEQ ID NO: 698) |
| H45A(-08+19) | CAA TGC CAT CCT GGA GTT CCT GTA AGA (SEQ ID NO: 699) |
| HM45A(-07+25) | GCT GCC AAT GCC ATC CTG GAG TTC CTG TAG AG (SEQ ID NO: 700) |
| H45A(-12+22) | GCC AAT GCC ATC CTG GAG TTC CTG TAG AGA TAC C (SEQ ID NO: 701) |
| H45A(-09+22) | GCC AAT GCC ATC CTG GAG TTC CTG TAG AGA T (SEQ ID NO: 702) |
| H45A(-09+30) | TTG CCG CTG CCC AAT GCC ATC CTG GAG TTC CTG TAA GAT (SEQ ID NO: 703) |
| H45A(-06+22) | GCC AAT GCC ATC CTG GAG TTC CTG TA A (SEQ ID NO: 704) |

-continued

| Annealing Site | Base Sequence [5' to 3'] |
|---|---|
| H45A(-06+28) | GCC GCT GCC CAA TGC CAT CCT GGA GTT CCT GTA A (SEQ ID NO: 705) |
| H45A(-03+22) | GCC CAA TGC CAT CCT GGA GTT CCT G (SEQ ID NO: 706) |
| H45A(-03+28) | GCC GCT GCC CAA TGC CAT CCT GGA GTT CCT G (SEQ ID NO: 707) |
| H45A(+9+26) | m5C-G-m5C-T-G-C-m5C-m5C-A-A-T-G-m5C-m5C-A-U-m5C-m5C (SEQ ID NO: 708) |
| H44A(-10+15) | GAT CTG TCA AAT CGC CTG CAG GTA A (SEQ ID NO: 709) |
| H44A(-07+15) | GAT CTG TCA AAT CGC CTG CAG G (SEQ ID NO: 710) |
| H44M(-07+17) | CAG ATC TGT CAA ATC GCC TGC AGG (SEQ ID NO: 711) |
| H44A(-08+15) | GAT CTG TCA AAT CGC CTG CAG GT (SEQ ID NO: 712) |
| H44A(-06+15) | GAT CTG TCA AAT CGC CTG CAG (SEQ ID NO: 713) |
| H44A(-08+17) | CAG ATC TGT CAA ATC GCC TGC AGG T (SEQ ID NO: 714) |
| H44A(-06+17) | CAG ATC TGT CAA ATC GCC TGC AG (SEQ ID NO: 715) |
| H50D(+04-18) | GGG ATC CAG TAT ACT TAC AGG C (SEQ ID NO: 716) |
| H50D(+07-18) | GGG ATC CAG TAT ACT TAC AGG CTC C (SEQ ID NO: 568) |
| H50D(+07-16) | GAT CCA GTA TAC TTA CAG GCT CC (SEQ ID NO: 717) |
| H50D(+07-17) | GGA TCC AGT ATA CTT ACA GGC TCC (SEQ ID NO: 718) |
| H50A(-19+07) | ACT TCC TCT TTA ACA GAA AAG CAT AC (SEQ ID NO: 719) |
| H50D(+07-15) | ATC CAG TAT ACT TAC AGG CTC C (SEQ ID NO: 720) |
| H50A(-02+23) | GAG CTC AGA TCT TCT AAC TTC CTC T (SEQ ID NO: 721) |
| H50D(+06-18) | GGG ATC CAG TAT ACT TAC AGG CTC (SEQ ID NO: 722) |
| H50D(+07-20) | ATG GGA TCC AGT ATA CTT ACA GGC TCC (SEQ ID NO: 723) |
| H52A(-01+24) | CTG TTC CAA ATC CTG CAT TGT TGC C (SEQ ID NO: 724) | wherein A is

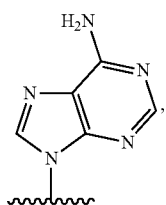 [SMILES: *n1cnc2c(N)ncnc21]

G is

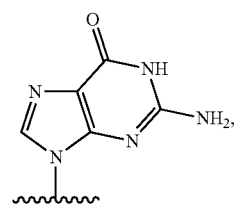

C is

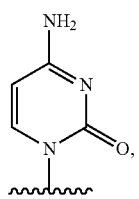 [SMILES: *n1ccc(N)nc1=O]

T is

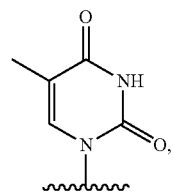

U is

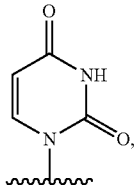 [SMILES: *n1ccc(=O)[nH]c1=O]

Gm is methylated guanine, Am is methylated adenine, and m5C is

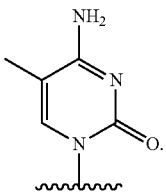 [SMILES: *n1cc(C)c(N)nc1=O]

Nucleobase Modifications and Substitutions

In certain embodiments, antisense oligomer conjugates of the disclosure are composed of RNA nucleobases and DNA nucleobases (often referred to in the art simply as "base"). RNA bases are commonly known as adenine (A), uracil (U), cytosine (C) and guanine (G). DNA bases are commonly known as adenine (A), thymine (T), cytosine (C) and guanine (G). In various embodiments, antisense oligomer conjugates of the disclosure are composed of cytosine (C), guanine (G), thymine (T), adenine (A), 5-methylcytosine (5mC), uracil (U), and hypoxanthine (I).

In certain embodiments, one or more RNA bases or DNA bases in an oligomer may be modified or substituted with a base other than a RNA base or DNA base. Oligomers containing a modified or substituted base include oligomers in which one or more purine or pyrimidine bases most commonly found in nucleic acids are replaced with less common or non-natural bases.

Purine bases comprise a pyrimidine ring fused to an imidazole ring, as described by the following general formula.

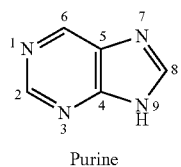

Purine

Adenine and guanine are the two purine nucleobases most commonly found in nucleic acids. Other naturally-occurring purines include, but are not limited to, $N^6$-methyladenine, $N^2$-methylguanine, hypoxanthine, and 7-methylguanine.

Pyrimidine bases comprise a six-membered pyrimidine ring as described by the following general formula.

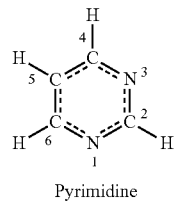

Pyrimidine

Cytosine, uracil, and thymine are the pyrimidine bases most commonly found in nucleic acids. Other naturally-occurring pyrimidines include, but not limited to, 5-methylcytosine, 5-hydroxymethylcytosine, pseudouracil, and 4-thiouracil. In one embodiment, the oligomers described herein contain thymine bases in place of uracil.

Other suitable bases include, but are not limited to: 2,6-diaminopurine, orotic acid, agmatidine, lysidine, 2-thiopyrimidines (e.g. 2-thiouracil, 2-thiothymine), G-clamp and its derivatives, 5-substituted pyrimidines (e.g. 5-halouracil, 5-propynyluracil, 5-propynylcytosine, 5-aminomethyluracil, 5-hydroxymethyluracil, 5-aminomethylcytosine, 5-hydroxymethylcytosine, Super T), 7-deazaguanine, 7-deazaadenine, 7-aza-2,6-diaminopurine, 8-aza-7-deazaguanine, 8-aza-7-deazaadenine, 8-aza-7-deaza-2,6-diaminopurine, Super G, Super A, and N4-ethylcytosine, or derivatives thereof; $N^2$-cyclopentylguanine (cPent-G), $N^2$-cyclopentyl-2-aminopurine (cPent-AP), and $N^2$-propyl aminopurine (Pr-AP), pseudouracil, or derivatives thereof; and degenerate or universal bases, like 2,6-difluorotoluene or absent bases like a basic sites (e.g. 1-deoxyribose, 1,2-dideoxyribose, 1-deoxy-2-O-methylribose; or pyrrolidine derivatives in which the ring oxygen has been replaced with nitrogen (azaribose)). Examples of derivatives of Super A, Super G, and Super T can be found in U.S. Pat. No. 6,683,173 (Epoch Biosciences), which is incorporated here entirely by reference. cPent-G, cPent-AP, and Pr-AP were shown to reduce immunostimulatory effects when incorporated in siRNA (Peacock H. et al. J. Am. Chem. Soc. 2011, 133, 9200). Pseudouracil is a naturally occurring isomerized version of uracil, with a C-glycoside rather than the regular N-glycoside as in uridine. Pseudouridine-containing synthetic mRNA may have an improved safety profile compared to uridine-containing mPvNA (WO 2009127230, incorporated here in its entirety by reference).

Certain nucleobases are particularly useful for increasing the binding affinity of the antisense oligomer conjugates of the disclosure. These include 5-substituted pyrimidines, 6-azapyrimidines, and N-2, N-6, and O-6 substituted purines, including 2-aminopropyladenine, 5-propynyluracil, and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications. Additional exemplary modified nucleobases include those wherein at least one hydrogen atom of the nucleobase is replaced with fluorine.

Pharmaceutically Acceptable Salts of Antisense Oligomer Conjugates

Certain embodiments of antisense oligomer conjugates described herein may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of antisense oligomer conjugates of the present disclosure. These salts can be prepared in situ in the administration vehicle or the dosage form manufacturing process, or by separately reacting a purified antisense oligomer conjugate of the disclosure in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, tosylate, citrate, maleate, fumarate, succinate, tartrate, naphthylate, mesylate, glucoheptonate, lactobionate, and laurylsulphonate salts and the like. (See, e.g., Berge et al. (1977) "Pharmaceutical Salts", J. Pharm. Sci. 66:1-19).

The pharmaceutically acceptable salts of the subject antisense oligomer conjugates include the conventional non-toxic salts or quaternary ammonium salts of the antisense oligomer conjugates, e.g., from non-toxic organic or inorganic acids. For example, such conventional nontoxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain embodiments, the antisense oligomer conjugates of the present disclosure may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of antisense oligomer conjugates of the present disclosure. These salts can likewise be prepared in situ in the administration vehicle or the dosage form manufacturing process, or by separately reacting the purified antisense oligomer conjugate in its free acid form with a suitable base, such as the hydroxide, carbonate, or bicarbonate of a pharmaceutically-acceptable metal cation, with ammonia, or with a pharmaceutically-acceptable organic primary, secondary, or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra).

Formulations and Modes of Administration

In certain embodiments, the present disclosure provides formulations or pharmaceutical compositions suitable for the therapeutic delivery of antisense oligomer conjugates, as described herein. Pharmaceutical formulations comprising antisense oligomers conjugated to cell-penetrating peptides (e.g., PPMOs) for DMD has been described in, e.g., U.S. Pat. No. 10,888,578, the disclosure of which is incorporated by reference herein. In certain embodiments, the present disclosure provides pharmaceutically acceptable compositions that comprise a therapeutically-effective amount of one or more of the antisense oligomer conjugates described herein, formulated together with one or more pharmaceutically acceptable carriers (additives) and/or diluents. While it is possible for an antisense oligomer conjugate of the present disclosure to be administered alone, it is preferable to administer the antisense oligomer conjugate as a pharmaceutical formulation (composition). In an embodiment, the antisense oligomer conjugate of the formulation is according to Formula (I).

In another aspect, the disclosure provides pharmaceutical compositions that include the antisense oligomers, or a pharmaceutically acceptable salt thereof, of the disclosure, and a pharmaceutically acceptable carrier. In some embodiments, the pharmaceutically acceptable carrier is a saline solution that includes a phosphate buffer.

The phrase "pharmaceutically acceptable" means the substance or composition must be compatible, chemically and/or toxicologically, with the other ingredients comprising a formulation, and/or the subject being treated therewith.

The phrase "pharmaceutically-acceptable carrier" as used herein means a non-toxic, inert solid, semi-solid or liquid filler, diluent, encapsulating material, or formulation auxiliary of any type. Some examples of materials which can serve as pharmaceutically acceptable carriers are: sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; non-toxic compatible lubricants such as sodium lauryl sulfate and magnesium stearate; coloring agents; releasing agents; coating agents; sweetening agents; flavoring agents; perfuming agents; preservatives; and antioxidants; according to the judgment of the formulator.

Methods for the delivery of nucleic acid molecules, which can be applicable to the antisense oligomer conjugates of the present disclosure, are described, for example, in: Akhtar et al., 1992, Trends Cell Bio., 2:139; Delivery Strategies for Antisense Oligonucleotide Therapeutics, ed. Akhtar, 1995, CRC Press; and Sullivan et al., PCT WO 94/02595. These and other protocols can be utilized for the delivery of virtually any nucleic acid molecule, including the antisense oligomer conjugates of the present disclosure.

The pharmaceutical compositions of the present disclosure may be specially formulated for administration in solid or liquid form, including those adapted for the following: (1) oral administration, for example, drenches (aqueous or non-aqueous solutions or suspensions), tablets (targeted for buccal, sublingual, or systemic absorption), boluses, powders, granules, pastes for application to the tongue; (2) parenteral administration, for example, by subcutaneous, intramuscular, intravenous, or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream, or foam; (5) sublingually; (6) ocularly; (7) transdermally; or (8) nasally.

Some examples of materials that can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates, and/or polyanhydrides; and (22) other non-toxic compatible substances employed in pharmaceutical formulations.

Additional non-limiting examples of agents suitable for formulation with the antisense oligomer conjugates of the instant disclosure include: PEG conjugated nucleic acids; phospholipid conjugated nucleic acids; nucleic acids containing lipophilic moieties; phosphorothioates; P-glycoprotein inhibitors (such as Pluronic P85) which can enhance entry of drugs into various tissues; biodegradable polymers, such as poly (D,L-lactide-coglycolide) microspheres for sustained release delivery after implantation (Emerich, D F et al., 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999).

The disclosure also features the use of the composition comprising surface-modified liposomes containing poly (ethylene glycol) ("PEG") lipids (PEG-modified, branched and unbranched or combinations thereof, or long-circulating liposomes or stealth liposomes). Oligomer conjugates of the disclosure can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

In a further embodiment, the present disclosure includes antisense oligomer conjugate pharmaceutical compositions prepared for delivery as described in U.S. Pat. Nos. 6,692, 911; 7,163,695; and 7,070,807. In this regard, in one embodiment, the present disclosure provides an antisense oligomer conjugate of the present disclosure in a composition comprising copolymers of lysine and histidine (HK) (as described in U.S. Pat. Nos. 7,163,695; 7,070,807; and 6,692, 911) either alone or in combination with PEG (e.g., branched or unbranched PEG or a mixture of both), in combination with PEG and a targeting moiety, or any of the foregoing in combination with a crosslinking agent. In certain embodiments, the present disclosure provides antisense oligomer conjugates in pharmaceutical compositions comprising gluconic-acid-modified polyhistidine or gluconylated-polyhistidine/transferrin-polylysine. One skilled in the art will also recognize that amino acids with properties similar to His and Lys may be substituted within the composition.

Wetting agents, emulsifiers and lubricants (such as sodium lauryl sulfate and magnesium stearate), coloring agents, release agents, coating agents, sweetening agents, flavoring agents, perfuming agents, preservatives, and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Methods of preparing these formulations or pharmaceutical compositions include the step of bringing into association an antisense oligomer conjugate of the present disclosure with the carrier and, optionally, one or more accessory ingredients. In general, the formulations are prepared by uniformly and intimately bringing into association an antisense oligomer conjugate of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an antisense oligomer conjugate of the present disclosure as an active ingredient. An antisense oligomer conjugate of the present disclosure may also be administered as a bolus, electuary, or paste.

Pharmaceutical compositions suitable for parenteral administration may comprise one or more oligomer conjugates of the disclosure in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In an embodiment, the antisense oligomer conjugate of the pharmaceutical composition is according to Formula (I).

These pharmaceutical compositions may also contain adjuvants such as preservatives, wetting agents, emulsifying agents, and dispersing agents. Prevention of the action of microorganisms upon the subject oligomer conjugates may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility, among other methods known in the art. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms may be made by forming microencapsule matrices of the subject oligomer conjugates in biodegradable polymers such as polylactide-polyglycolide. Depending on the ratio of oligomer to polymer, and the nature of the particular polymer employed, the rate of oligomer release can be controlled. Examples of other biodegradable polymers include poly(orthoesters) and poly(anhydrides). Depot injectable formulations may also be prepared by entrapping the drug in liposomes or microemulsions that are compatible with body tissues.

When the antisense oligomer conjugates of the present disclosure are administered as pharmaceuticals, to humans and animals, they can be given per se or as a pharmaceutical composition containing, for example, 0.1 to 99% (more preferably, 10 to 30%) of the antisense oligomer conjugate in combination with a pharmaceutically acceptable carrier.

In certain aspects, an antisense oligomer conjugate is administered in a liquid pharmaceutical formulation, wherein the concentration of the conjugate is about 50 mg/ml.

Regardless of the route of administration selected, the antisense oligomer conjugates of the present disclosure, which may be used in a suitable hydrated form, and/or the pharmaceutical compositions of the present disclosure, may be formulated into pharmaceutically-acceptable dosage forms by conventional methods known to those of skill in the art. Actual dosage levels of the active ingredients in the pharmaceutical compositions of this disclosure may be varied so as to obtain an amount of the active ingredient which is effective to achieve the desired therapeutic response for a particular patient, composition, and mode of administration, without being unacceptably toxic to the patient.

Methods of Use

Dosage regimens described in the present disclosure can be used to treat a patient with an antisense oligomer CPP conjugate in need of such treatment.

In one aspect, the disclosure provides a method for treating DMD in a subject in need thereof wherein the subject has a mutation of the dystrophin gene that is amenable to exon skipping, the method comprising administering to the subject an antisense oligomer CPP conjugate according to the dosing regimens described herein. In some aspects, the exon is exon 44, exon 45, exon 50, exon 51, exon 52, or exon 53 of the human dystrophin gene.

In another aspect, the disclosure provides a method of restoring an mRNA reading frame to induce dystrophin production in a subject having a mutation of the dystrophin gene that is amenable to exon skipping (for example, exon 44, exon 45, exon 50, exon 51, exon 52, exon 53 skipping), the method comprising administering to the subject an antisense oligomer CPP conjugate according to the dosing regimens described herein.

In another aspect, the disclosure provides a method of excluding an exon (for example, exon 44, exon 45, exon 50, exon 51, exon 52, exon 53) from dystrophin pre-mRNA during mRNA processing in a subject having a mutation of the dystrophin gene that is amenable to exon skipping, the method comprising administering to the subject an antisense oligomer CPP conjugate according to the dosing regimens described herein. In another aspect, the disclosure provides a method of binding exon (for example, exon 44, exon 45, exon 50, exon 51, exon 52, exon 53) of dystrophin pre-mRNA in a subject having a mutation of the dystrophin gene that is amenable to exon skipping (for example, exon 44, exon 45, exon 50, exon 51, exon 52, exon 53 skipping), the method comprising administering to the subject an antisense oligomer CPP conjugate according to the dosing regimens described herein.

In another aspect, the disclosure provides a method of targeting an exposure level of an antisense oligomer CPP conjugate in a patient with DMD who has a mutation that is amenable to exon skipping (for example, exon 44, exon 45, exon 50, exon 51, exon 52, exon 53 skipping), the method comprising administering to the subject an antisense oligomer CPP conjugate according to the dosing regimens described herein.

In another aspect, the disclosure provides a method of reducing the severity and/or frequency of hypomagnesemia in a patient who is being treated with an antisense oligomer CPP conjugate, the method comprising administering to the subject an antisense oligomer CPP conjugate according to the dosing regimens described herein and a magnesium supplement.

In another aspect, the disclosure provides a method for alleviating one or more symptoms of DMD in a human patient, comprising administering to the patient an antisense oligomer CPP conjugate according to the dosing regimens described herein, wherein the patient is receiving a steroid treatment. In some aspects, the conjugate is administered to induce exon (for example, exon 44, exon 45, exon 50, exon 51, exon 52, exon 53 of the human dystrophin gene) skipping. In some aspects, the administration of the conjugate according to the dosing regimens described herein and the steroid treatments are started at the same time. In other aspects, the patient was receiving the steroid treatment prior to the administration of the antisense oligomer CPP conjugate according to the dosing regimens described herein. In this aspect, it is preferred that said steroid is administered at least one day, more preferred at least one week, more preferred at least two weeks, more preferred at least three weeks prior to administering the antisense oligomer CPP conjugate according to the dosing regimens described herein. In one particular embodiment, the prior steroid treatment is for a period of at least three weeks prior to the administration of the antisense oligomer CPP conjugate according to the dosing regimens described herein.

In some aspects, the steroid is a glucocorticosteroid. The glucocorticosteroid can be chosen from, for example, prednisone, dexamethasone, prednisolone, or deflazacort. Dose ranges of a steroid (e.g., a glucocorticosteroid) to be used in the therapeutic applications as described herein are designed on the basis of rising dose studies in clinical trials for which rigorous protocol requirements exist. The usual doses are about 0.5-1.0 mg/kg/day, preferably about 0.75 mg/kg/day for prednisone and prednisolone, and about 0.4-1.4 mg/kg/day, preferably about 0.9 mg/kg/day for deflazacort.

The term "restoration" with respect to dystrophin synthesis or production refers generally to the production of a dystrophin protein including truncated forms of dystrophin in a patient with muscular dystrophy following treatment with an antisense oligomer conjugate described herein. In some embodiments, treatment results in an increase in novel dystrophin production in a patient by 1%, 5%, 10%, 20%, 30%, 40%, 50%, 60%, 70%, 80%, 90%, or 100% (including all integers in between). In some embodiments, treatment increases the number of dystrophin-positive fibers to at least about 20%, about 30%, about 40%, about 50%, about 60%, about 70%, about 80%, about 90%, or about 95% to 100% of normal in the subject. In other embodiments, treatment increases the number of dystrophin-positive fibers to about 20% to about 60%, or about 30% to about 50%, of normal in the subject. The percent of dystrophin-positive fibers in a patient following treatment can be determined by a muscle biopsy using known techniques. For example, a muscle biopsy may be taken from a suitable muscle, such as the biceps brachii muscle in a patient.

Analysis of the percentage of positive dystrophin fibers may be performed pre-treatment and/or post-treatment or at time points throughout the course of treatment. In some embodiments, a post-treatment biopsy is taken from the contralateral muscle from the pre-treatment biopsy. Pre- and post-treatment dystrophin expression analysis may be performed using any suitable assay for dystrophin. In some embodiments, immunohistochemical detection is performed on tissue sections from the muscle biopsy using an antibody that is a marker for dystrophin, such as a monoclonal or a polyclonal antibody. For example, the MANDYS106 antibody can be used which is a highly sensitive marker for dystrophin. Any suitable secondary antibody may be used.

In some embodiments, the percent dystrophin-positive fibers are calculated by dividing the number of positive fibers by the total fibers counted. Normal muscle samples have 100% dystrophin-positive fibers. Therefore, the percent dystrophin-positive fibers can be expressed as a percentage of normal. To control for the presence of trace levels of dystrophin in the pretreatment muscle, as well as revertant fibers, a baseline can be set using sections of pre-treatment muscles from a patient when counting dystrophin-positive fibers in post-treatment muscles. This may be used as a threshold for counting dystrophin-positive fibers in sections of post-treatment muscle in that patient. In other embodiments, antibody-stained tissue sections can also be used for dystrophin quantification using Bioquant image analysis software (Bioquant Image Analysis Corporation, Nashville, TN). The total dystrophin fluorescence signal intensity can be reported as a percentage of normal. In addition, Western blot analysis with monoclonal or polyclonal anti-dystrophin antibodies can be used to determine the percentage of dystrophin positive fibers. For example, the anti-dystrophin antibody NCL-Dys1 from Leica Biosystems may be used. The percentage of dystrophin-positive fibers can also be analyzed by determining the expression of the components of the sarcoglycan complex ($\beta,\gamma$) and/or neuronal NOS.

In some embodiments, treatment with an antisense oligomer conjugate of the disclosure slows or reduces the progressive respiratory muscle dysfunction and/or failure in patients with DMD that would be expected without treatment. In some embodiments, treatment with an antisense oligomer conjugate of the disclosure may reduce or eliminate the need for ventilation assistance that would be expected without treatment. In some embodiments, measurements of respiratory function for tracking the course of the disease, as well as the evaluation of potential therapeutic interventions include maximum inspiratory pressure (MIP), maximum expiratory pressure (MEP), and forced vital capacity (FVC). MIP and MEP measure the level of pressure a person can generate during inhalation and exhalation, respectively, and are sensitive measures of respiratory muscle strength. MIP is a measure of diaphragm muscle weakness.

In some embodiments, MEP may decline before changes in other pulmonary function tests, including MIP and FVC. In certain embodiments, MEP may be an early indicator of respiratory dysfunction. In certain embodiments, FVC may be used to measure the total volume of air expelled during forced exhalation after maximum inspiration. In patients with DMD, FVC increases concomitantly with physical growth until the early teens. However, as growth slows or is stunted by disease progression, and muscle weakness progresses, the vital capacity enters a descending phase and declines at an average rate of about 8 to 8.5 percent per year after 10 to 12 years of age. In certain embodiments, MIP percent predicted (MIP adjusted for weight), MEP percent predicted (MEP adjusted for age), and FVC percent predicted (FVC adjusted for age and height) are supportive analyses.

The terms "subject" and "patient" as used herein include any animal that exhibits a symptom, or is at risk for exhibiting a symptom, which can be treated with an antisense oligomer conjugate of the disclosure, such as a subject (or patient) that has or is at risk for having DMD or BMD, or any of the symptoms associated with these conditions (e.g., muscle fiber loss). Suitable subjects (or patients) include laboratory animals (such as mouse, rat, rabbit, or guinea pig), farm animals, and domestic animals or pets (such as a cat or dog). Non-human primates and, preferably, human patients (or subjects), are included. Also included are methods of producing dystrophin in a subject (or patient) having a mutation of the dystrophin gene that is amenable to exon skipping (for example, exon 44, exon 45, exon 50, exon 51, exon 52, exon 53 skipping).

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phase "targeting sequence" refers to a sequence of nucleobases of an oligomer that is complementary to a sequence of nucleotides in a target pre-mRNA. In some aspects of the disclosure, the sequence of nucleotides in the target pre-mRNA is an exon 51 annealing site in the dystrophin pre-mRNA designated as H51A(+66+95). In some aspect of the disclosure, the sequence of nucleotides in the target pre-mRNA is an exon 45 annealing site in the dystrophin pre-mRNA designated as H45A(−03+19). In some aspect, the sequence of nucleotides in the target pre-mRNA is an exon 53 annealing site in the dystrophin pre-mRNA designated as H53A(+36+60).

"Treatment" of a subject (e.g. a mammal, such as a human) is any type of intervention used in an attempt to alter the natural course of the subject. Treatment includes, but is not limited to, administration of an antisense oligomer conjugate or a pharmaceutical composition thereof, and may be performed either prophylactically or subsequent to the initiation of a pathologic event or contact with an etiologic agent. Treatment includes any desirable effect on the symptoms or pathology of a disease or condition associated with the dystrophin protein, as in certain forms of muscular dystrophy, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

In some embodiments, treatment with an antisense oligomer CPP conjugate of the disclosure increases novel dystrophin production, delays disease progression, slows or reduces the loss of ambulation, reduces muscle inflammation, reduces muscle damage, improves muscle function, reduces loss of pulmonary function, and/or enhances muscle regeneration that would be expected without treatment. In some embodiments, treatment maintains, delays, or slows disease progression. In some embodiments, treatment maintains ambulation or reduces the loss of ambulation. In some embodiments, treatment maintains pulmonary function or reduces loss of pulmonary function. In some embodiments, treatment maintains or increases a stable walking distance in a patient, as measured by, for example, the 6 Minute Walk Test (6MWT). In some embodiments, treatment maintains or reduces the time to walk/run 10 meters (i.e., the 10 meter walk/run test). In some embodiments, treatment maintains or reduces the time to stand from supine (i.e, time to stand test). In some embodiments, treatment maintains or reduces the time to climb four standard stairs (i.e., the four-stair climb test). In some embodiments, treatment maintains or reduces muscle inflammation in the patient, as measured by, for example, MRI (e.g., MRI of the leg muscles). In some embodiments, MM measures T2 and/or fat fraction to identify muscle degeneration. MM can identify changes in muscle structure and composition caused by inflammation, edema, muscle damage, and fat infiltration.

In some embodiments, treatment with an antisense oligomer conjugate of the disclosure increases novel dystrophin production and slows or reduces the loss of ambulation that would be expected without treatment. For example, treatment may stabilize, maintain, improve or increase walking ability (e.g., stabilization of ambulation) in the subject. In some embodiments, treatment maintains or increases a stable walking distance in a patient, as measured by, for example, the 6 Minute Walk Test (6MWT), described by McDonald, et al. (Muscle Nerve, 2010; 42:966-74, herein incorporated by reference). A change in the 6 Minute Walk Distance (6MWD) may be expressed as an absolute value, a percentage change or a change in the %-predicted value. In some embodiments, treatment maintains or improves a stable walking distance in a 6MWT from a 20% deficit in the subject relative to a healthy peer. The performance of a DMD patient in the 6MWT relative to the typical performance of a healthy peer can be determined by calculating a %-predicted value. For example, the %-predicted 6MWD may be calculated using the following equation for males: $196.72+(39.81\times age)-(1.36\times age^2)+(132.28\times height$ in meters). For females, the %-predicted 6MWD may be calculated using the following equation: $188.61+(51.50\times age)-(1.86\times age^2)+(86.10\times height$ in meters) (Henricson et al. PLoS Curr., 2012, version 2, herein incorporated by reference). In some embodiments, treatment with an antisense oligomer increases the stable walking distance in the patient from baseline to greater than 3, 5, 6, 7, 8, 9, 10, 15, 20, 25, 30, or 50 meters (including all integers in between).

Loss of muscle function in patients with DMD may occur against the background of normal childhood growth and development. Indeed, younger children with DMD may show an increase in distance walked during 6MWT over the course of about 1 year despite progressive muscular impairment. In some embodiments, the 6MWD from patients with DMD is compared to typically developing control subjects and to existing normative data from age and sex matched subjects. In some embodiments, normal growth and development can be accounted for using an age and height based equation fitted to normative data. Such an equation can be used to convert 6MWD to a percent-predicted (%-predicted) value in subjects with DMD. In certain embodiments, analysis of %-predicted 6MWD data represents a method to account for normal growth and development, and may show that gains in function at early ages (e.g., less than or equal to age 7) represent stable rather than improving abilities in patients with DMD (Henricson et al. PLoS Curr., 2012, version 2, herein incorporated by reference).

An antisense molecule nomenclature system was proposed and published to distinguish between the different antisense molecules (see Mann et al., (2002) J Gen Med 4, 644-654). This nomenclature became especially relevant when testing several slightly different antisense molecules, all directed at the same target region, as shown below:

H#A/D(x:y).

The first letter designates the species (e.g. H: human, M: murine, C: canine). "#" designates target dystrophin exon number. "A/D" indicates acceptor or donor splice site at the beginning and end of the exon, respectively. (x y) represents the annealing coordinates where "−" or "+" indicate intronic or exonic sequences respectively. For example, A(−6+18) would indicate the last 6 bases of the intron preceding the target exon and the first 18 bases of the target exon. The closest splice site would be the acceptor so these coordinates would be preceded with an "A". Describing annealing coordinates at the donor splice site could be D(+2-18) where the last 2 exonic bases and the first 18 intronic bases correspond to the annealing site of the antisense molecule. Entirely exonic annealing coordinates that would be represented by A(+65+85), that is the site between the 65th and 85th nucleotide from the start of that exon.

Restoration of the Dystrophin Reading Frame using Exon Skipping

A potential therapeutic approach to the treatment of DMD caused by out-of-frame mutations in the dystrophin gene is suggested by the milder form of dystrophinopathy known as BMD, which is caused by in-frame mutations. The ability to convert an out-of-frame mutation to an in-frame mutation would hypothetically preserve the mRNA reading frame and produce an internally shortened yet functional dystrophin protein. Antisense oligomer conjugates of the disclosure were designed to accomplish this.

Clinical outcomes for analyzing the effect of an antisense oligomer conjugate that is complementary to a target region of the human dystrophin pre-mRNA and induces exon skipping include percent dystrophin positive fibers (PDPF), six-minute walk test (6MWT), loss of ambulation (LOA), North Star Ambulatory Assessment (NSAA), pulmonary function tests (PFT), ability to rise (from a supine position) without external support, de novo dystrophin production, and other functional measures.

In some embodiments, the present disclosure provides methods for producing dystrophin in a subject having a mutation of the dystrophin gene that is amenable to exon skipping (e.g., exon 44, 45, 50, 51, 52, 53), the method comprising administering to the subject an antisense oligomer conjugate, or pharmaceutically acceptable salt thereof, as described herein. In certain embodiments, the present disclosure provides methods for restoring an mRNA reading frame to induce dystrophin protein production in a subject with Duchenne muscular dystrophy (DMD) who has a mutation of the dystrophin gene that is amenable to exon skipping (e.g., exon 44, 45, 50, 51, 52, 53). Protein production can be measured by reverse-transcription polymerase chain reaction (RT-PCR), western blot analysis, or immunohistochemistry (IHC).

In some embodiments, the present disclosure provides methods for treating DMD in a subject in need thereof, wherein the subject has a mutation of the dystrophin gene that is amenable to exon skipping (e.g., exon 44, 45, 50, 51, 52, 53), the method comprising administering to the subject an antisense oligomer conjugate, or pharmaceutically acceptable salt thereof, as described herein. In various embodiments, treatment of the subject is measured by delay of disease progression. In some embodiments, treatment of the subject is measured by maintenance of ambulation in the subject or reduction of loss of ambulation in the subject. In some embodiments, ambulation is measured using the 6 Minute Walk Test (6MWT). In certain embodiments, ambulation is measured using the North Start Ambulatory Assessment (NSAA).

In various embodiments, the present disclosure provides methods for maintaining pulmonary function or reducing loss of pulmonary function in a subject with DMD, wherein the subject has a mutation of the DMD gene that is amenable to exon skipping (e.g., exon 44, 45, 50, 51, 52, 53), the method comprising administering to the subject an antisense oligomer conjugate, or pharmaceutically acceptable salt thereof, as described herein. In some embodiments, pulmonary function is measured as Maximum Expiratory Pressure (MEP). In certain embodiments, pulmonary function is measured as Maximum Inspiratory Pressure (MIP). In some embodiments, pulmonary function is measured as Forced Vital Capacity (FVC).

In certain aspects, the methods of the present disclosure include administering to a subject with DMD a pharmaceutical formulation comprising an antisense oligomer conjugate, or pharmaceutically acceptable salt thereof, as described herein, wherein the concentration of the conjugate in the formulation is about 50 mg/ml.

In certain embodiments, there is described an antisense oligomer conjugate as described herein for use in therapy. In certain embodiments, there is described an antisense oligomer conjugate as described herein for use in the treatment of Duchenne muscular dystrophy. In certain embodiments, there is described an antisense oligomer conjugate as described herein for use in the manufacture of a medicament for use in therapy. In certain embodiments, there is described an antisense oligomer conjugate as described herein for use in the manufacture of a medicament for the treatment of Duchenne muscular dystrophy.

EXAMPLES

Although the foregoing disclosure has been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

Example 1. Toxicity and Toxikinetic Study of PPMO-1 in Non-Human Primates

Study 1. A 12-Week Intravenous Infusion (Once Every 4 Weeks) Toxicity and Toxicokinetic Study in Cynomolgus Monkeys with a 4 Week Recovery.

Non-human primates (NHPs) received three 1-hour IV infusions of vehicle control or PPMO-1 at dose levels of 30 or 60 mg/kg on Days 1, 29, and 57. PPMO-1 is an antisense oligo CPP conjugate with the following structure:

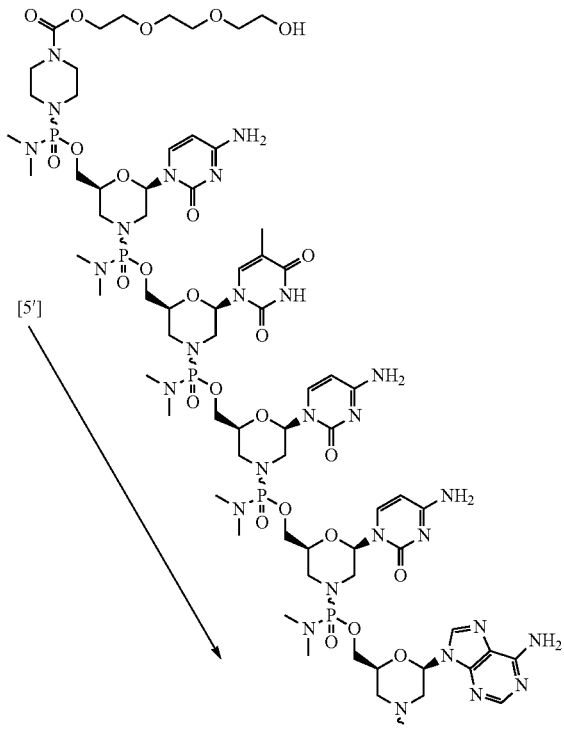

-continued
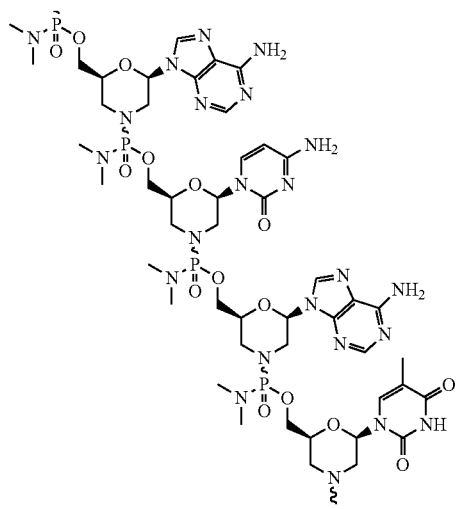
Break A
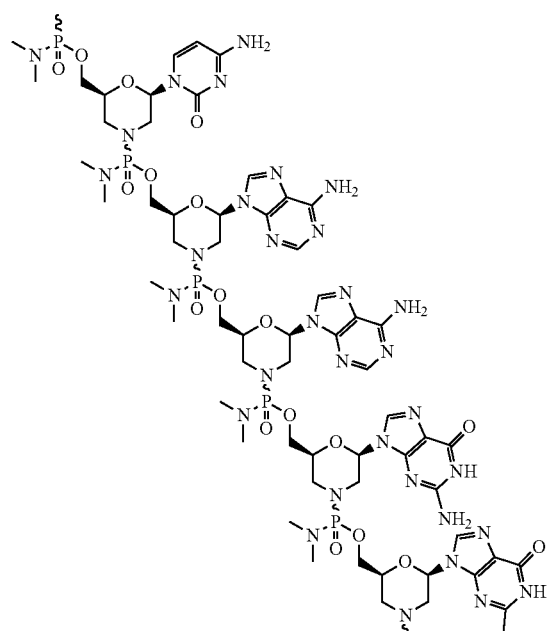
Break A

-continued
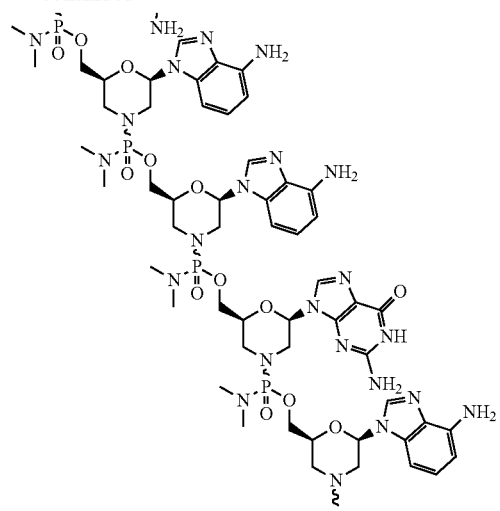
Break B
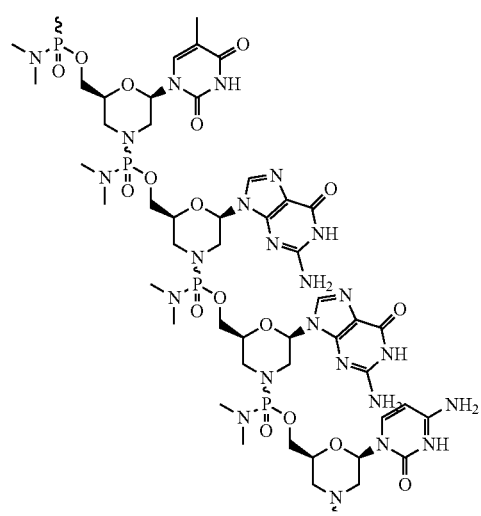

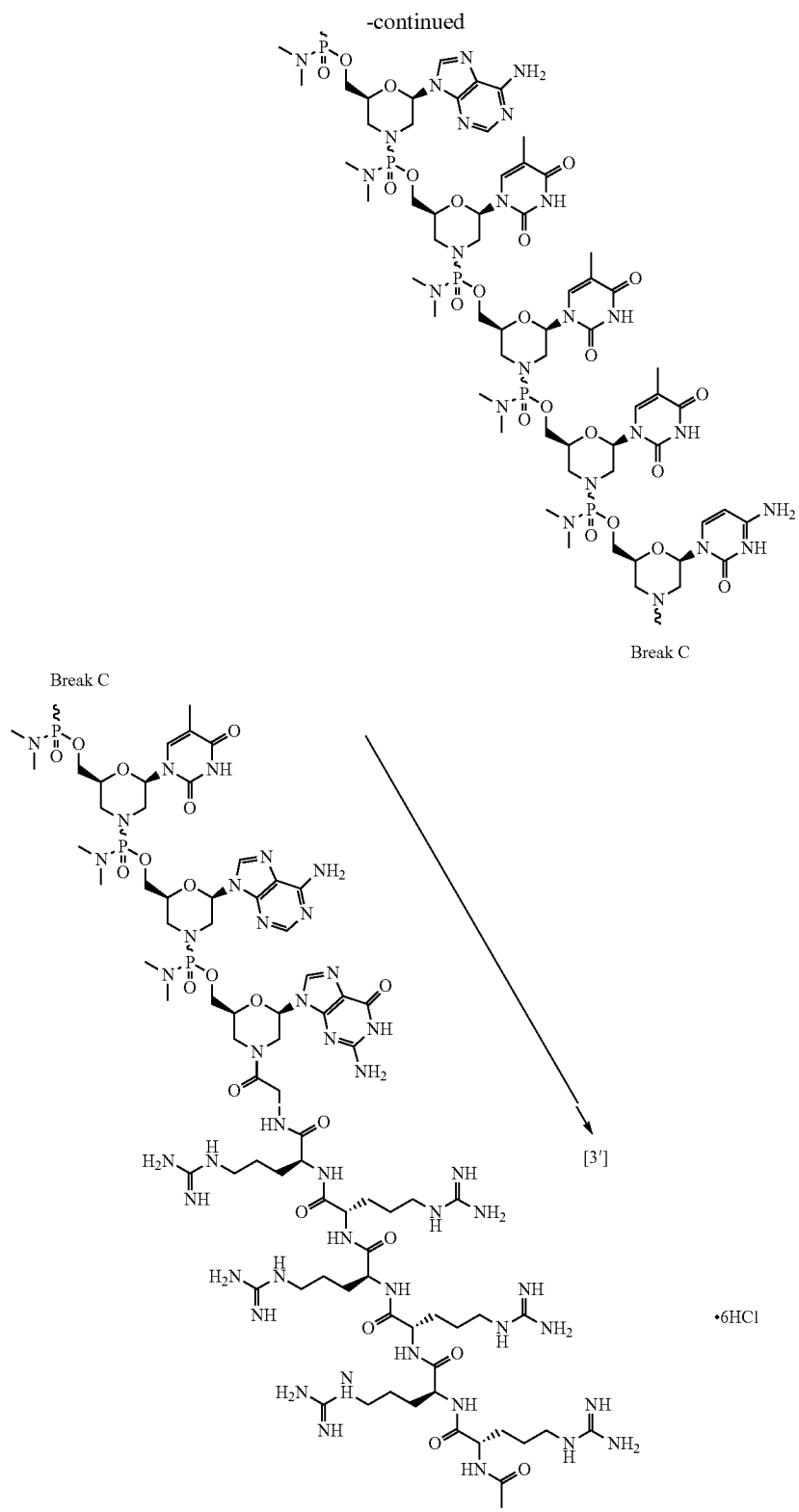

Blood samples were collected predose and at 1, 2, 4, 8, 12, 16, and 24 hours post-infusion for plasma PK analysis after the first and third doses. The mean body weights were 5.99±0.84 Kg (n=7), range 5.1-7.5 Kg on Day 1.

Study 2. Non-GLP (good laboratory practices) Pharmacokinetic (PK), Pharmacodynamic and Renal Safety Assessment of PPMO-1 After Four Once Every 4 Week (Q4W) Repeated Intravenous Dosing in Cynomolgus Monkeys.

NHPs received four 1-hour IV infusions of vehicle control or PPMO-1 at dose levels of 30 or 60 mg/kg on Days 1, 29, 57, and 85. Blood samples were collected predose and at 1, 2, 4, 8, 12, 16, and 24 hours post-infusion for plasma PK analysis after the first and fourth doses. the mean body weights were 2.25±0.1 Kg (n=8), range 2.1-2.4 Kg on Day 1.

As shown in FIG. 1, animals in Study 1 had higher initial body weight than animals in Study 2.

As shown in FIG. 2 animals in Study 1 had higher plasma AUC ($AUC_{last}$ (h*µg/mL) and $C_{max}$ (µg/kg) exposures at the same 60 mg/kg dose than animals in Study 1. First and last dose PK were used in the analysis.

Figure 3:
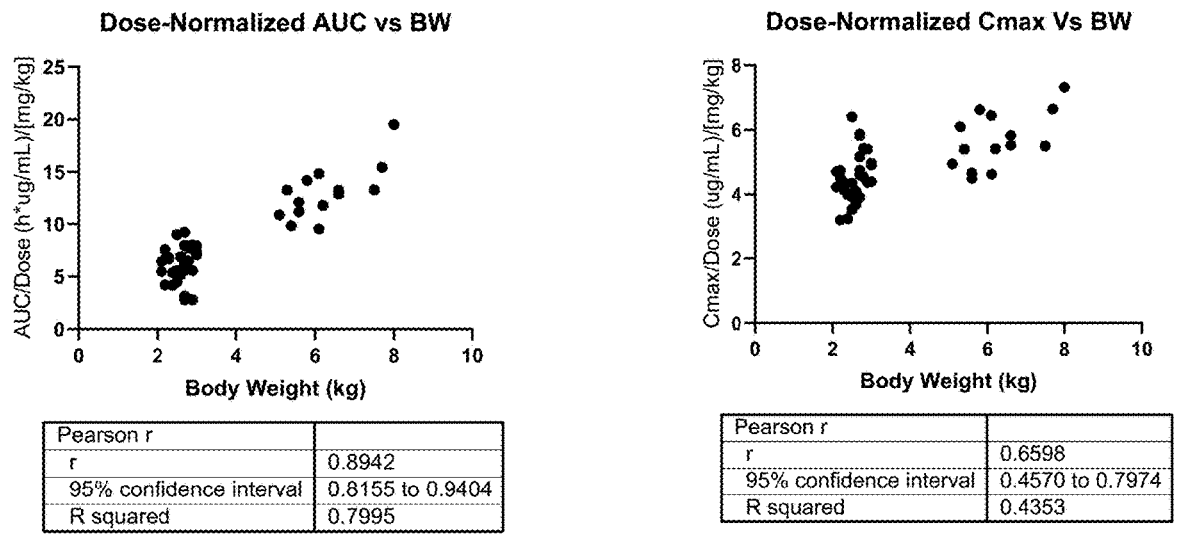
FIG. 3 depicts area under the curve (AUC) and plasma peak concentration ($C_{max}$) versus body weight in NHPs after administration of PPMO-1. Higher body weight is associated with higher AUC and $C_{max}$.

As shown in FIG. 3, there is an association of dose normalized PK to body weight. Higher body weight is associated with higher PK, both AUC and Cmax.

Figure 4:
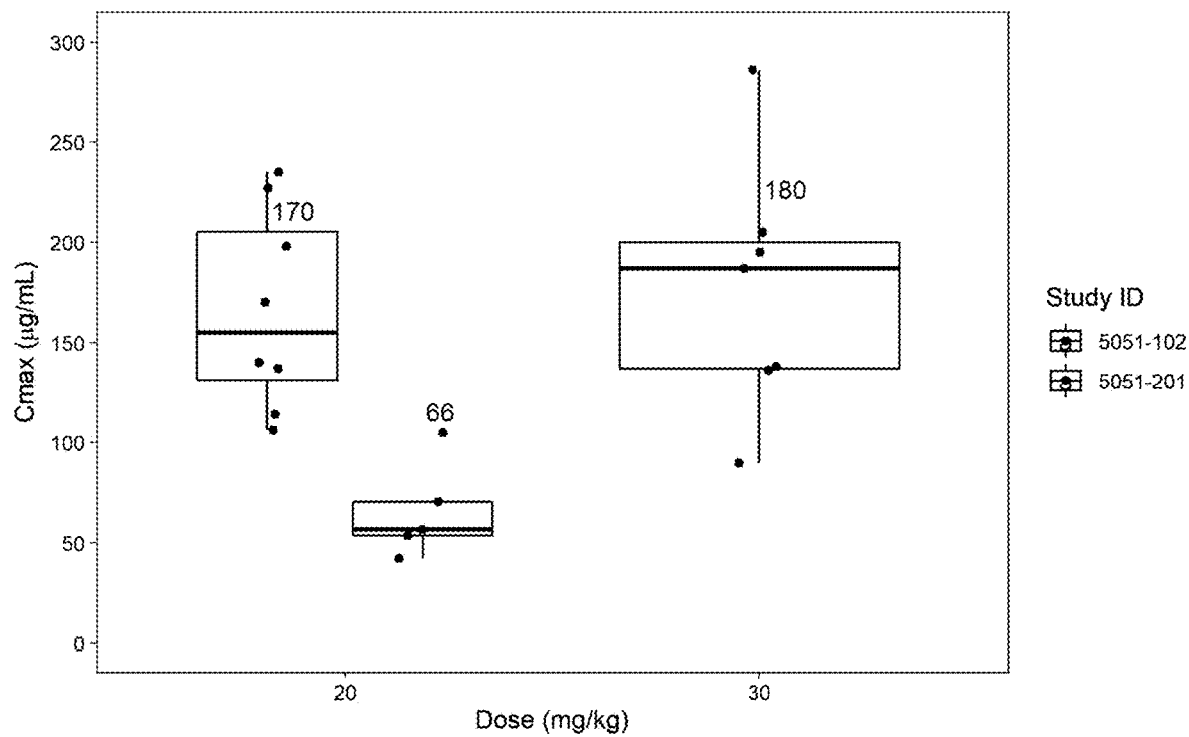
FIG. 4 is a graph depicting plasma peak concentration ($C_{max}$) of PPMO-1 at 20 and 30 mg/kg in human DMD patients.
Figure 5:
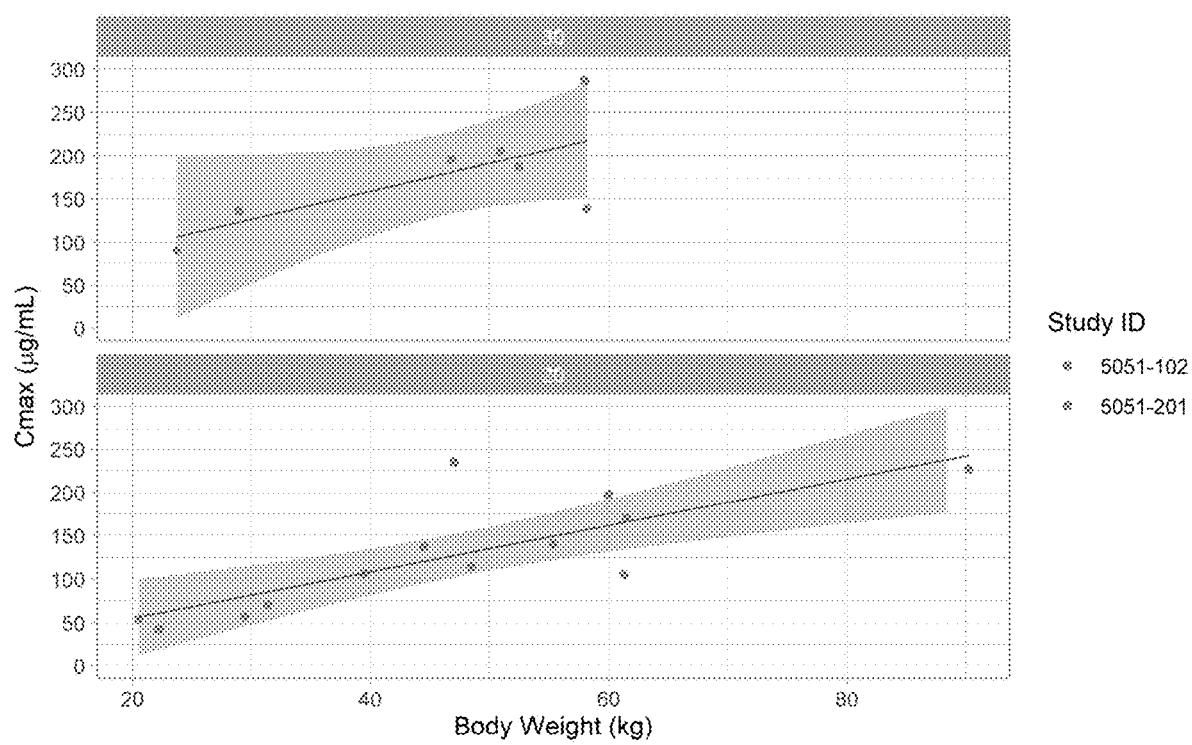
FIG. 5 depicts the correlation between plasma peak concentration ($C_{max}$) and body weight of DMD patients that were administered either 20 mg/kg PPMO-1 (bottom) or 30 mg/kg PPMO-1 (top).

Example 2. Developing a New Dose Paradigm to Achieve Target Drug Exposure in DMD Patients Correlation between body weight and plasma exposure of PPMO-1 was observed in the current ongoing clinical trial. As shown in FIG. 4, $C_{max}$ of PPMO-1 at 20 mg/kg in Study 5051-102 was 2.6×higher than that at 20 mg/kg in Study 5051-201. Notably, the observed $C_{max}$ difference was associated with pronounced body weight difference, 55.9±17.1 kg in 5051-102 vs. 33.0±16.5 kg (Mean±SD). Indeed, a good correlation was observed between $C_{max}$ and body weight at 20 and 30 mg/kg (FIG. 5). This suggests that a body-weight based, fixed mg/kg approach for a broad DMD patient population with body-weight range of about 10 to about 100 kg may cause evidently variable drug exposure and lead to heterogenous outcome of treatment effect on efficacy and safety. For example, for patients with lighter body weight, the drug exposure may fall below optimal target exposure range, leading to suboptimal efficacy or even no efficacy, whereas for patients with heavier body weight, the drug exposure may exceed optimal target exposure range, leading to potential safety issue.

Thus, a body-weight-band approach has been developed to bin the DMD patients into certain body weight band and different dose is chosen within each body weight band to achieve targeted drug exposure. Target exposure was defined based on clinical data on exposure vs. response relationship on efficacy and safety. A population pharmacokinetic model was developed based on the existing clinical data of SRP-5051, and the simulation was conducted to inform the body weight band and dose selection to achieve the target exposure across the DMD population. A similar methodology was described in Model-Based Approach for Optimization of Atazanir Dose Recommendations for HIV-Infected Pediatric Patients (Hong, Y. et al, *Antimicrobial Agents and Chemotherapy*, December 2011, p. 5746-5752).

Two target exposure of area under the plasma concentration vs. time curve (AUC) was selected: a lower one with median value of 150 µg/mL*h and range of 100-200 µg/mL*h and a higher one with median value of 300 µg/mL*h and range of 200-500 µg/mL*h. The body weight across the DMD population may be divided into different bands (1, 2, 3, or more) and a flat fixed mg dose may be selected within each body weight band. As demonstrated in Table 1B, for the higher target exposure:

If the number of body weight band=1, a flat dose of 1200 mg is anticipated to achieve target exposure across the body weight from 15 to 100 kg.

If the number of body weight band=2, 15-40 kg is selected as the first band with flat dose of 1100 mg and 40-100 kg is selected as the second band with flat dose of 1300 mg.

If the number of body weight band=3, 15-25 kg is selected as the first band with flat dose of 1100 mg, 25-50 kg as the second band with flat dose of 1200 mg and 15-25 kg as the third band with flat dose of 1400 mg.

The more body weight bands are chosen, the less variability of drug exposure is anticipated.

For those patients with the body weight less than 15 kg, a different dose may be selected based on their pharmacokinetic characteristics.

Overall, this demonstrates that the body weight band approach (with the band number ≥1 and flat dose within each band, e.g. 900-1800 mg) can adequately achieve the target higher exposure.

Similarly, Table 2A demonstrates the body weight band approach for lower target exposure.

In summary, this demonstrates that the body-weight-band approach (with the band number ≥1 and flat dose within each band) can adequately achieve the target lower and higher exposure.

TABLE 2

Body weight band dosing for PPMO-1 to achieve a lower (A) and higher (B) target exposure.

(A)

| Body weight range | # of BW Band | Proposed dose mg | Simulated AUC | | Simulated $C_{max}$ | |
|---|---|---|---|---|---|---|
| | | | Median | 95% CI | Median | 95% CI |
| 15 ≤ x ≤ 25 kg | 3 | 600 | 152 | [104, 222] | 95 | [69, 128] |
| 25 ≤ x ≤ 50 kg | | 650 | 150 | [102, 219] | 95 | [69, 128] |
| 50 ≤ x ≤ 100 kg | | 750 | 157 | [107, 228] | 98 | [72, 132] |
| 15 ≤ x ≤ 40 kg | 2 | 600 | 145 | [98, 212] | 91 | [66, 124] |
| 40 ≤ x ≤ 100 kg | | 700 | 147 | [100, 216] | 93 | [68, 125] |
| 15 ≤ x ≤ 25 kg | 1 | 700 | 180 | [119, 264] | 110 | [79, 151] |
| 25 ≤ x ≤ 50 kg | | | 163 | [112, 234] | 102 | [75, 138] |
| 50 ≤ x ≤ 100 kg | | | 145 | [99, 212] | 92 | [68, 124] |

| (B) | | | | | | |
|---|---|---|---|---|---|---|
| Body weight range | # of BW Band | Proposed dose mg | Simulated AUC Median | 95% CI | Simulated $C_{max}$ Median | 95% CI |
| 15 ≤ x ≤ 25 kg | 3 | 1100 | 293 | [199, 433] | 174 | [127, 236] |
| 25 ≤ x ≤ 50 kg | | 1200 | 292 | [197, 429] | 176 | [128, 237] |
| 50 ≤ x ≤ 100 kg | | 1400 | 308 | [208, 451] | 184 | [136, 247] |
| 15 ≤ x ≤ 40 kg | 2 | 1100 | 280 | [188, 412] | 168 | [121, 228] |
| 40 ≤ x ≤ 100 kg | | 1300 | 288 | [195, 426] | 173 | [127, 234] |
| 15 ≤ x ≤ 25 kg | 1 | 1200 | 321 | [213, 476] | 190 | [136, 260] |
| 25 ≤ x ≤ 50 kg | | | 292 | [200, 425] | 175 | [129, 238] |
| 50 ≤ x ≤ 100 kg | | | 260 | [177, 383] | 158 | [117, 213] |

Example 3. Clinical Dosing Rationale

Clinical and nonclinical findings suggest that higher drug exposure is associated with higher body weight. This was consistently observed among boys with DMD, between heavier adult healthy volunteers and DMD boys, and in nonclinical studies, and raised a challenge in achieving consistent and less variable drug exposure in a diverse and broad DMD pediatric population.

To avoid the possible overdose for heavier body weight patients and underdose for lighter body weight patients, a population PK model informed, body-weight-tiered, dose regimen is being implemented: the targeted DMD population in the study is binned into two body-weight tiers (18 to 50 kg, and >50 kg) and a flat dose is used within each tier to achieve target exposure.

Two target exposures for the study are selected by anchoring drug plasma exposure of those patients who previously underwent muscle biopsy at 20 and 30 mg/kg, respectively, as follows:

1. Lower target exposure with AUC of 180 μg·h/mL (range: 120 to 240 μg·h/mL). This is to bracket the exposure for the biopsied patients at 20 mg/kg (AUC geometric mean 128 μg·h/mL, N=2) and the lower part of the exposure for the biopsied patients at 30 mg/kg. Based on the relationship between dystrophin expression and AUC, an AUC of 180 μg·h/mL appears to be associated with about a 5% increase in dystrophin protein level from baseline.

2. Higher target exposure with AUC of 300 μg·h/mL (range: 200 to 500 μg·h/mL). This is to mimic the exposure for the biopsied patients at 30 mg/kg (AUC geometric mean 310 μg·h/mL, range 184 to 504 μg·h/mL, N=4). Based on the relationship between dystrophin expression and AUC, an AUC of 300 μg·h/mL appears to be associated with a ≥5% increase in dystrophin protein levels from baseline.

Thus, these two target exposures differ by ~1.7× with slightly overlapping AUCs (overlapped AUC from 200 to 240 μg·h/mL), which is a reasonable difference for exposure separation for assessing the optimal balance between benefit and risk. The proposed target exposure is supported by existing nonclinical safety data. The higher target AUC (300 μg·h/mL) is about 1.6×, 2.7×, and 1.3× lower than that at the NOAEL of 60 mg/kg in the SR-19-051 (NHP non-GLP), SR-20-027 (NHP GLP), and SR-20-028 (juvenile rat GLP) studies, respectively. Higher safety margins exist for the lower target AUC with about 2.7×, 4.6×, and 2.2× lower, respectively.

As shown in Table 3, to achieve a high target exposure of 300 μg·h/mL, less dose (total mg) is proposed for the lower body weight tier, with 1250 mg for ≥18 to <50 kg and 1350 mg for ≥50 kg. The anticipated 95% prediction interval of AUC falls well within the target range (200 to 500 μg·h/mL); the upper boundary, in particular, is up to 420 μg·h/mL (well below 500 μg·h/mL) and may offer additional cushion for safety while rendering adequate dystrophin expression. A similar scenario is proposed to target low target exposure.

In summary, the body-weight-tiered dose regimen targeting two exposures maximizes the opportunity of achieving an optimal benefit and risk ratio.

TABLE 3

Weight-tiered Dosing Regimen to Achieve Target Exposure Range Across 18 to 100 kg

| Target Exposure ($AUC_{0\text{-}24\,hr}$) median and range | Body Weight Tier* | SRP-5051 Dose | Simulated Exposure ($AUC_{0\text{-}24\,hr}$) median and 95% Prediction Interval |
|---|---|---|---|
| 180 μg · h/mL (120-240 μg · h/mL) | ≥18 but <50 kg | 750 mg | 171 μg · h/mL (126, 234) |
| | ≥50 kg | 850 mg | 178 μg · h/mL (130, 243) |
| 300 μg · h/mL (200-500 μg · h/mL) | ≥18 but <50 kg | 1250 mg | 296 μg · h/mL (218, 420) |
| | ≥50 kg | 1350 mg | 298 μg · h/mL (217, 406) |

AUC = area under the concentration-time curve
*For simulation purposes, the upper boundary of body weight is set as 100 kg.

In addition to the embodiments described above, the following embodiments are also contemplated by the present disclosure:

In one embodiment, the disclosure relates to a method of treating a patient with Duchenne muscular dystrophy (DMD) in need thereof who has a mutation that is amenable to exon skipping, comprising administering to the patient an antisense oligomer conjugate of Formula (IV), as described above, wherein the conjugate is administered in a dose effective to provide a mean area under the curve (AUC) of the conjugate, or the pharmaceutically acceptable salt thereof between about 100 and about 200 ug·h/mL, between about 120 and about 240 ug·h/mL, or is between about 200 and about 500 ug·h/mL.

In one embodiment, the disclosure relates to a method of treating a patient with Duchenne muscular dystrophy (DMD) in need thereof who has a mutation that is amenable to exon skipping, comprising administering to the patient an antisense oligomer conjugate of Formula (IV), as described above, wherein the conjugate, or a pharmaceutically acceptable salt thereof, is administered at a dose equivalent to about 300 mg to about 1500 mg of the 6HCl salt of the conjugate once every four weeks, to achieve a mean AUC of between about between about 100 and about 200 ug·h/mL, between about 120 and about 240 ug·h/mL, or between about 200 and about 500 ug·h/mL.

In one embodiment, the conjugate of formula (IV), or a pharmaceutically acceptable salt thereof, is administered at a dose effective to provide a mean AUC of between about 100 and about 200 ug·h/mL. In another embodiment, the conjugate of formula (IV), or a pharmaceutically acceptable salt thereof, is administered at a dose effective to provide a mean AUC of between about 120 and about 240 ug·h/mL. In another embodiment, the conjugate of formula (IV), or a pharmaceutically acceptable salt thereof, is administered at a dose effective to provide a mean AUC of between about 200 and about 500 ug·h/mL.

In certain embodiments, the conjugate of formula (IV), or a pharmaceutically acceptable salt thereof, is administered at a dose equivalent to about 300 mg, about 350 mg, about 400 mg, about 450 mg, about 500 mg, about 550 mg, about 600 mg, about 650 mg, about 700 mg, about 750 mg, about 800 mg, about 850 mg, or about 900 mg of the 6HCl salt of the conjugate. In certain other embodiments, the conjugate of formula (IV), or a pharmaceutically acceptable salt thereof, is administered at a dose equivalent to about 950 mg, about 1000 mg, about 1050 mg, about 1100 mg, about 1150 mg, about 1200 mg, about 1250 mg, about 1300 mg, about 1350 mg, about 1400 mg, about 1450 mg, or about 1500 mg of the 6HCl salt of the conjugate.

In one embodiment, the conjugate of formula (IV), or a pharmaceutically acceptable salt thereof, is administered at a dose equivalent to about 300 mg to about 700 mg of the 6HCl salt of the conjugate once every four weeks to a patient that weighs from about 10 kg to about 25 kg.

In one embodiment, the conjugate of formula (IV), or a pharmaceutically acceptable salt thereof, is administered at a dose equivalent to about 600 mg of the 6HCl salt of the conjugate once every four weeks to a patient that weighs from about 10 kg to about 25 kg.

In one embodiment, the conjugate of formula (IV), or a pharmaceutically acceptable salt thereof, is administered at a dose equivalent to about 900 mg to about 1200 mg of the 6HCl salt of the conjugate once every four weeks to a patient that weighs from about 10 kg to about 25 kg.

In one embodiment, the conjugate of formula (IV), or a pharmaceutically acceptable salt thereof, is administered at a dose equivalent to about 1100 mg of the 6HCl salt of the conjugate once every four weeks to a patient that weighs from about 10 kg to about 25 kg.

In one embodiment, the conjugate of formula (IV), or a pharmaceutically acceptable salt thereof is administered at a dose equivalent to about 750 mg to about 1250 mg of the 6HCl salt of the conjugate once every four weeks to a patient that weighs from about 18 kg to about 50 kg.

In one embodiment, the conjugate of formula (IV), or a pharmaceutically acceptable salt thereof is administered at a dose equivalent to about 600 mg to about 800 mg of the 6HCl salt of the conjugate once every four weeks to a patient that weighs from about 25 kg to about 50 kg.

In one embodiment, the conjugate of formula (IV), or a pharmaceutically acceptable salt thereof, is administered at a dose equivalent to about 650 mg of the 6HCl salt of the conjugate once every four weeks to a patient that weighs from about 25 kg to about 50 kg.

In one embodiment, the conjugate of formula (IV), or a pharmaceutically acceptable salt thereof, is administered at a dose equivalent to about 1000 mg of the 6HCl salt of the conjugate to about 1300 mg once every four weeks to a patient that weighs from about 25 kg to about 50 kg.

In one embodiment, the conjugate of formula (IV), or a pharmaceutically acceptable salt thereof, is administered at a dose equivalent to about 1200 mg of the 6HCl salt of the conjugate once every four weeks to a patient that weighs from about 25 kg to about 50 kg.

In one embodiment, the conjugate of formula (IV), or a pharmaceutically acceptable salt thereof, is administered at a dose equivalent to about 750 mg of the 6HCl salt of the conjugate once every four weeks to a patient that weighs from about 18 kg to about 50 kg.

In one embodiment, the conjugate of formula (IV), or a pharmaceutically acceptable salt thereof, is administered at a dose equivalent to about 1250 mg of the 6HCl salt of the conjugate once every four weeks to a patient that weighs from about 18 kg to about 50 kg.

In one embodiment, the conjugate of formula (IV), or a pharmaceutically acceptable salt thereof, is administered at a dose equivalent to about 700 mg to about 900 mg of the 6HCl salt of the conjugate once every four weeks to a patient that weighs from about 50 kg to about 100 kg.

In one embodiment, the conjugate of formula (IV), or a pharmaceutically acceptable salt thereof, is administered at a dose equivalent to about 750 mg of the 6HCl salt of the conjugate once every four weeks to a patient that weighs from about 50 kg to about 100 kg.

In one embodiment, the conjugate of formula (IV), or a pharmaceutically acceptable salt thereof, is administered at a dose equivalent to about 1200 mg to about 1500 mg of the 6HCl salt of the conjugate once every four weeks to a patient that weighs from about 50 kg to about 100 kg.

In one embodiment, the conjugate of formula (IV), or a pharmaceutically acceptable salt thereof, is administered at a dose equivalent to about 1400 mg of the 6HCl salt of the conjugate once every four weeks to a patient that weighs from about 50 kg to about 100 kg.

In one embodiment, the conjugate of formula (IV), or a pharmaceutically acceptable salt thereof, is administered at a dose equivalent to about 850 mg of the 6HCl salt of the conjugate once every four weeks to a patient that weighs greater than or equal to about 50 kg.

In another embodiment, the conjugate of formula (IV), or a pharmaceutically acceptable salt thereof, is administered at a dose equivalent to about 1350 mg of the 6HCl salt of the conjugate once every four weeks to a patient that weighs greater than or equal to about 50 kg.

In one embodiment, the disclosure relates to a method of treating a patient with Duchenne muscular dystrophy (DMD) in need thereof who has a mutation that is amenable to exon skipping, comprising administering to the patient an antisense oligomer conjugate of Formula (VI), as described above, wherein the conjugate is administered in a dose effective to provide a mean area under the curve (AUC) of the conjugate, or the pharmaceutically acceptable salt thereof between about 100 and about 200 ug·h/mL, 120 and about 240 ug·h/mL, or is between about 200 and about 500 ug·h/mL.

In one embodiment, the disclosure relates to a method of treating a patient with Duchenne muscular dystrophy (DMD) in need thereof who has a mutation that is amenable to exon skipping, comprising administering to the patient an antisense oligomer conjugate of Formula (VI), as described above, wherein the conjugate, or a pharmaceutically acceptable salt thereof, is administered at a dose equivalent to about 300 mg to about 1500 mg of the 6HCl salt of the conjugate once every four weeks, to achieve a mean AUC of between about between about 100 and about 200 ug·h/mL, between about 120 and about 240 ug·h/mL, or between about 200 and about 500 ug·h/mL.

In one embodiment, the conjugate of formula (VI), or a pharmaceutically acceptable salt thereof, is administered at a dose effective to provide a mean AUC of between about 100 and about 200 ug·h/mL. In another embodiment, the conjugate of formula (VI), or a pharmaceutically acceptable salt thereof, is administered at a dose effective to provide a mean AUC of between about 120 and about 240 ug·h/mL. In another embodiment, the conjugate of formula (VI), or a pharmaceutically acceptable salt thereof, is administered at a dose effective to provide a mean AUC of between about 200 and about 500 ug·h/mL.

In certain embodiments, the conjugate of formula (VI), or a pharmaceutically acceptable salt thereof, is administered at a dose equivalent to about 300 mg, about 350 mg, about 400 mg, about 450 mg, about 500 mg, about 550 mg, about 600 mg, about 650 mg, about 700 mg, about 750 mg, about 800 mg, about 850 mg, or about 900 mg of the 6HCl salt of the conjugate. In certain other embodiments, the conjugate of formula (VI), or a pharmaceutically acceptable salt thereof, is administered at a dose equivalent to about 950 mg, about 1000 mg, about 1050 mg, about 1100 mg, about 1150 mg, about 1200 mg, about 1250 mg, about 1300 mg, about 1350 mg, about 1400 mg, about 1450 mg, or about 1500 mg of the 6HCl salt of the conjugate.

In one embodiment, the conjugate of formula (VI), or a pharmaceutically acceptable salt thereof, is administered at a dose equivalent to about 300 mg to about 700 mg of the 6HCl salt of the conjugate once every four weeks to a patient that weighs from about 10 kg to about 25 kg.

In one embodiment, the conjugate of formula (VI), or a pharmaceutically acceptable salt thereof, is administered at a dose equivalent to about 600 mg of the 6HCl salt of the conjugate once every four weeks to a patient that weighs from about 10 kg to about 25 kg.

In one embodiment, the conjugate of formula (VI), or a pharmaceutically acceptable salt thereof, is administered at a dose equivalent to about 900 mg to about 1200 mg of the 6HCl salt of the conjugate once every four weeks to a patient that weighs from about 10 kg to about 25 kg.

In one embodiment, the conjugate of formula (VI), or a pharmaceutically acceptable salt thereof, is administered at a dose equivalent to about 1100 mg of the 6HCl salt of the conjugate once every four weeks to a patient that weighs from about 10 kg to about 25 kg.

In one embodiment, the conjugate of formula (VI), or a pharmaceutically acceptable salt thereof, is administered at a dose equivalent to about 750 mg of the 6HCl salt of the conjugate once every four weeks to a patient that weighs from about 18 kg to about 50 kg.

In one embodiment, the conjugate of formula (VI), or a pharmaceutically acceptable salt thereof, is administered at a dose equivalent to about 1250 mg of the 6HCl salt of the conjugate once every four weeks to a patient that weighs from about 18 kg to about 50 kg.

In one embodiment, the conjugate of formula (VI), or a pharmaceutically acceptable salt thereof is administered at a dose equivalent to about 600 mg to about 800 mg of the 6HCl salt of the conjugate once every four weeks to a patient that weighs from about 25 kg to about 50 kg.

In one embodiment, the conjugate of formula (VI), or a pharmaceutically acceptable salt thereof, is administered at a dose equivalent to about 650 mg of the 6HCl salt of the conjugate once every four weeks to a patient that weighs from about 25 kg to about 50 kg.

In one embodiment, the conjugate of formula (VI), or a pharmaceutically acceptable salt thereof, is administered at a dose equivalent to about 1000 mg of the 6HCl salt of the conjugate to about 1300 mg once every four weeks to a patient that weighs from about 25 kg to about 50 kg.

In one embodiment, the conjugate of formula (VI), or a pharmaceutically acceptable salt thereof, is administered at a dose equivalent to about 1200 mg of the 6HCl salt of the conjugate once every four weeks to a patient that weighs from about 25 kg to about 50 kg.

In one embodiment, the conjugate of formula (VI), or a pharmaceutically acceptable salt thereof, is administered at a dose equivalent to about 700 mg to about 900 mg of the 6HCl salt of the conjugate once every four weeks to a patient that weighs from about 50 kg to about 100 kg.

In one embodiment, the conjugate of formula (VI), or a pharmaceutically acceptable salt thereof, is administered at a dose equivalent to about 750 mg to about 950 mg of the 6HCl salt of the conjugate once every four weeks to a patient that weighs greater than or equal to about 50 kg.

In one embodiment, the conjugate of formula (VI), or a pharmaceutically acceptable salt thereof, is administered at a dose equivalent to about 1250 mg to about 1500 mg of the 6HCl salt of the conjugate once every four weeks to a patient that weighs from about 50 kg to about 100 kg.

In one embodiment, the conjugate of formula (VI), or a pharmaceutically acceptable salt thereof, is administered at a dose equivalent to about 750 mg of the 6HCl salt of the conjugate once every four weeks to a patient that weighs from about 50 kg to about 100 kg.

In one embodiment, the conjugate of formula (VI), or a pharmaceutically acceptable salt thereof, is administered at a dose equivalent to about 1200 mg to about 1500 mg of the 6HCl salt of the conjugate once every four weeks to a patient that weighs from about 50 kg to about 100 kg.

In one embodiment, the conjugate of formula (VI), or a pharmaceutically acceptable salt thereof, is administered at a dose equivalent to about 1400 mg of the 6HCl salt of the conjugate once every four weeks to a patient that weighs from about 50 kg to about 100 kg.

In one embodiment, the conjugate of formula (VI), or a pharmaceutically acceptable salt thereof, is administered at a dose equivalent to about 850 mg of the 6HCl salt of the conjugate once every four weeks to a patient that weighs greater than or equal to about 50 kg.

In one embodiment, the conjugate of formula (VI), or a pharmaceutically acceptable salt thereof, is administered at a dose equivalent to about 1350 mg of the 6HCl salt of the conjugate once every four weeks to a patient that weighs greater than or equal to about 50 kg.

In one embodiment, the disclosure relates to a method of treating a patient with Duchenne muscular dystrophy (DMD) in need thereof who has a mutation that is amenable to exon skipping, comprising administering to the patient an antisense oligomer conjugate of Formula (VIII), as described above, wherein the conjugate is administered in a dose effective to provide a mean area under the curve (AUC) of the conjugate, or the pharmaceutically acceptable salt thereof between about 100 and about 200 ug·h/mL, between about 120 and about 240 ug·h/mL, or is between about 200 and about 500 ug·h/mL.

In one embodiment, the disclosure relates to a method of treating a patient with Duchenne muscular dystrophy (DMD) in need thereof who has a mutation that is amenable to exon skipping, comprising administering to the patient an antisense oligomer conjugate of Formula (VIII), as described above, wherein the conjugate, or a pharmaceutically acceptable salt thereof, is administered at a dose equivalent to about 300 mg to about 1500 mg of the 6HCl salt of the conjugate once every four weeks, to achieve a mean AUC of between about between about 100 and about 200 ug·h/mL, between about 120 and about 240 ug·h/mL, or between about 200 and about 500 ug·h/mL.

In one embodiment, the conjugate of formula (VIII), or a pharmaceutically acceptable salt thereof, is administered at a dose effective to provide a mean AUC of between about 100 and about 200 ug·h/mL. In another embodiment, the conjugate of formula (VIII), or a pharmaceutically acceptable salt thereof, is administered at a dose effective to provide a mean AUC of between about 120 and about 240 ug·h/mL. In another embodiment, the conjugate of formula (VIII), or a pharmaceutically acceptable salt thereof, is administered at a dose effective to provide a mean AUC of between about 200 and about 500 ug·h/mL.

In certain embodiments, the conjugate of formula (VIII), or a pharmaceutically acceptable salt thereof, is administered at a dose equivalent to about 300 mg, about 350 mg, about 400 mg, about 450 mg, about 500 mg, about 550 mg, about 600 mg, about 650 mg, about 700 mg, about 750 mg, about 800 mg, about 850 mg, or about 900 mg of the 6HCl salt of the conjugate. In certain other embodiments, the conjugate of formula (VIII), or a pharmaceutically acceptable salt thereof, is administered at a dose equivalent to about 950 mg, about 1000 mg, about 1050 mg, about 1100 mg, about 1150 mg, about 1200 mg, about 1250 mg, about 1300 mg, about 1350 mg, about 1400 mg, about 1450 mg, or about 1500 mg of the 6HCl salt of the conjugate.

In one embodiment, the conjugate of formula (VIII), or a pharmaceutically acceptable salt thereof, is administered at a dose equivalent to about 300 mg to about 700 mg of the 6HCl salt of the conjugate once every four weeks to a patient that weighs from about 10 kg to about 25 kg.

In one embodiment, the conjugate of formula (VIII), or a pharmaceutically acceptable salt thereof, is administered at a dose equivalent to about 600 mg of the 6HCl salt of the conjugate once every four weeks to a patient that weighs from about 10 kg to about 25 kg.

In one embodiment, the conjugate of formula (VIII), or a pharmaceutically acceptable salt thereof, is administered at a dose equivalent to about 900 mg to about 1200 mg of the 6HCl salt of the conjugate once every four weeks to a patient that weighs from about 10 kg to about 25 kg.

In one embodiment, the conjugate of formula (VIII), or a pharmaceutically acceptable salt thereof, is administered at a dose equivalent to about 1100 mg of the 6HCl salt of the conjugate once every four weeks to a patient that weighs from about 10 kg to about 25 kg.

In one embodiment, the conjugate of formula (VIII), or a pharmaceutically acceptable salt thereof, is administered at a dose equivalent to about 750 mg of the 6HCl salt of the conjugate once every four weeks to a patient that weighs from about 18 kg to about 50 kg.

In one embodiment, the conjugate of formula (VIII), or a pharmaceutically acceptable salt thereof, is administered at a dose equivalent to about 1250 mg of the 6HCl salt of the conjugate once every four weeks to a patient that weighs from about 18 kg to about 50 kg.

In one embodiment, the conjugate of formula (VIII), or a pharmaceutically acceptable salt thereof is administered at a dose equivalent to about 600 mg to about 800 mg of the 6HCl salt of the conjugate once every four weeks to a patient that weighs from about 25 kg to about 50 kg.

In one embodiment, the conjugate of formula (VIII), or a pharmaceutically acceptable salt thereof, is administered at a dose equivalent to about 650 mg of the 6HCl salt of the conjugate once every four weeks to a patient that weighs from about 25 kg to about 50 kg.

In one embodiment, the conjugate of formula (VIII), or a pharmaceutically acceptable salt thereof, is administered at a dose equivalent to about 1000 mg of the 6HCl salt of the conjugate to about 1300 mg once every four weeks to a patient that weighs from about 25 kg to about 50 kg.

In one embodiment, the conjugate of formula (VIII), or a pharmaceutically acceptable salt thereof, is administered at a dose equivalent to about 1200 mg of the 6HCl salt of the conjugate once every four weeks to a patient that weighs from about 25 kg to about 50 kg.

In one embodiment, the conjugate of formula (VIII), or a pharmaceutically acceptable salt thereof, is administered at a dose equivalent to about 700 mg to about 900 mg of the 6HCl salt of the conjugate once every four weeks to a patient that weighs from about 50 kg to about 100 kg.

In one embodiment, the conjugate of formula (VIII), or a pharmaceutically acceptable salt thereof, is administered at a dose equivalent to about 750 mg of the 6HCl salt of the conjugate once every four weeks to a patient that weighs from about 50 kg to about 100 kg.

In one embodiment, the conjugate of formula (VIII), or a pharmaceutically acceptable salt thereof, is administered at a dose equivalent to about 1200 mg to about 1500 mg of the 6HCl salt of the conjugate once every four weeks to a patient that weighs from about 50 kg to about 100 kg.

In one embodiment, the conjugate of formula (VIII), or a pharmaceutically acceptable salt thereof, is administered at a dose equivalent to about 1400 mg of the 6HCl salt of the conjugate once every four weeks to a patient that weighs from about 50 kg to about 100 kg.

In one embodiment, the conjugate of formula (VIII), or a pharmaceutically acceptable salt thereof, is administered at a dose equivalent to about 850 mg of the 6HCl salt of the conjugate once every four weeks to a patient that weighs greater than about 50 kg.

In one embodiment, the conjugate of formula (VIII), or a pharmaceutically acceptable salt thereof, is administered at a dose equivalent to about 1350 mg of the 6HCl salt of the conjugate once every four weeks to a patient that weighs greater than about 50 kg.

One embodiment of the present disclosure relates to a method of targeting an exposure level of an antisense oligomer conjugate of Formula (IV), as described above, or a pharmaceutically acceptable salt thereof, in a patient with Duchenne muscular dystrophy (DMD) who has a mutation that is amenable to exon 51 skipping, comprising administering to the patient the conjugate, or a pharmaceutically acceptable salt thereof, at a dose equivalent to about 300 mg to about 900 mg of the ·6HCl salt of the conjugate once every four weeks to achieve the exposure level corresponding to an AUC of between about 100 and about 200 ug·h/mL.

One embodiment of the present disclosure relates to a method of targeting an exposure level of an antisense oligomer conjugate of Formula (IV), as described above, or a pharmaceutically acceptable salt thereof, in a patient with Duchenne muscular dystrophy (DMD) who has a mutation that is amenable to exon 51 skipping, comprising administering to the patient the conjugate, or a pharmaceutically acceptable salt thereof, at a dose equivalent to about 700 mg to about 900 mg of the ·6HCl salt of the conjugate once every four weeks to achieve the exposure level corresponding to an AUC of between about 120 and about 240 ug·h/mL.

One embodiment of the present disclosure relates to a method of targeting an exposure level of an antisense oligomer conjugate of Formula (IV), as described above, or a pharmaceutically acceptable salt thereof, in a patient with Duchenne muscular dystrophy (DMD) who has a mutation that is amenable to exon 51 skipping, comprising administering to the patient the conjugate, or a pharmaceutically acceptable salt thereof, at a dose equivalent to about 800 mg to about 1400 mg of the ·6HCl salt of the conjugate once every four weeks to achieve the exposure level corresponding to an AUC of between about 200 and about 500 ug·h/mL.

One embodiment of the present disclosure relates to a method of targeting an exposure level of an antisense oligomer conjugate of Formula (IV), as described above, or a pharmaceutically acceptable salt thereof, in a patient with Duchenne muscular dystrophy (DMD) who has a mutation that is amenable to exon 51 skipping, comprising administering to the patient the conjugate, or a pharmaceutically acceptable salt thereof, at a dose equivalent to about 950 mg to about 1500 mg of the ·6HCl salt of the conjugate once every four weeks to achieve the exposure level corresponding to an AUC of between about 200 and about 500 ug·h/mL.

One embodiment of the present disclosure relates to a method of targeting an exposure level of an antisense oligomer conjugate of Formula (IV), as described above, or a pharmaceutically acceptable salt thereof, in a patient with Duchenne muscular dystrophy (DMD) who has a mutation that is amenable to exon 51 skipping, comprising administering to the patient the conjugate, or a pharmaceutically acceptable salt thereof, at a dose equivalent to the dose of the ·6HCl salt of the conjugate according to the following schedule:
  i) about 300 mg to about 700 mg, or about 900 mg to about 1200 mg, once every four weeks for a patient that weighs from about 10 kg to about 25 kg;
  ii) about 600 mg to about 800 mg, or about 1000 mg to about 1300 mg, once every four weeks for a patient that weighs from about 25 kg to about 50 kg; or
  iii) about 700 mg to about 900 mg, or about 1200 mg to about 1500 mg, once every four weeks for a patient that weighs from about 50 kg to about 100 kg; to achieve the exposure level corresponding to an AUC of between about 100 and about 200 ug·h/mL, or is between about 200 and about 500 ug·h/mL.

One embodiment of the present disclosure relates to a method of treating DMD in a patient comprising administering to the patient an antisense oligomer conjugate of Formula (IV), as described above, or a pharmaceutically acceptable salt thereof, wherein the conjugate, or a pharmaceutically acceptable salt thereof, is administered at a dose equivalent to the dose of the ·6HCl salt of the conjugate according to the following schedule:
  i) about 500 mg to about 700 mg, or about 1000 mg to about 1200 mg, once every four weeks for a patient that weighs from about 15 kg to about 40 kg; or
  ii) about 600 mg to about 800 mg, or about 1100 mg to about 1400 mg, once every four weeks for a patient that weighs from about 40 kg to about 100 kg;
to achieve a mean AUC between about 100 and about 200 ug·h/mL, or is between about 200 and about 500 ug·h/mL.

One embodiment of the present disclosure relates to a method of treating DMD in a patient comprising administering to the patient an antisense oligomer conjugate of Formula (VI), as described above, or a pharmaceutically acceptable salt thereof, wherein the conjugate, or a pharmaceutically acceptable salt thereof, is administered at a dose equivalent to the dose of the ·6HCl salt of the conjugate according to the following schedule:
  i) about 500 mg to about 700 mg, or about 1000 mg to about 1200 mg, once every four weeks for a patient that weighs from about 15 kg to about 40 kg; or
  ii) about 600 mg to about 800 mg, or about 1100 mg to about 1400 mg, once every four weeks for a patient that weighs from about 40 kg to about 100 kg;
to achieve a mean AUC between about 100 and about 200 ug·h/mL, or is between about 200 and about 500 ug·h/mL.

One embodiment of the present disclosure relates to a method of treating DMD in a patient comprising administering to the patient an antisense oligomer conjugate of Formula (VIII), as described above, or a pharmaceutically acceptable salt thereof, wherein the conjugate, or a pharmaceutically acceptable salt thereof, is administered at a dose equivalent to the dose of the ·6HCl salt of the conjugate according to the following schedule:
  i) about 500 mg to about 700 mg, or about 1000 mg to about 1200 mg, once every four weeks for a patient that weighs from about 15 kg to about 40 kg; or
  ii) about 600 mg to about 800 mg, or about 1100 mg to about 1400 mg, once every four weeks for a patient that weighs from about 40 kg to about 100 kg; to achieve a mean AUC between about 100 and about 200 ug·h/mL, or is between about 200 and about 500 ug·h/mL.

One embodiment of the present disclosure relates to a method of treating DMD in a patient comprising administering to the patient an antisense oligomer conjugate of Formula (VIII), as described above, or a pharmaceutically acceptable salt thereof, wherein the conjugate, or a pharmaceutically acceptable salt thereof, is administered at a dose equivalent to the dose of the ·6HCl salt of the conjugate according to the following schedule:
  iii) about 700 mg to about 800 mg, or about 1200 mg to about 1250 mg, once every four weeks for a patient that weighs from about 18 kg to about 50 kg; or
  iv) about 800 mg to about 900 mg, or about 1300 mg to about 1400 mg, once every four weeks for a patient that weighs from about 40 kg to about 100 kg;
to achieve a mean AUC between about 120 and about 240 ug·h/mL, or is between about 200 and about 500 ug·h/mL.

One embodiment of the present disclosure relates to a method of treating a patient with Duchenne muscular dystrophy (DMD) with an antisense oligomer conjugate, comprising administering to the patient:
  i) an antisense oligomer conjugate of Formula (IV); and
  ii) a magnesium supplement,
wherein the conjugate, or a pharmaceutically acceptable salt thereof, is administered at a dose equivalent to about 20 mg/kg, about 30 mg/kg, or about 40 mg/kg of the 6HCl salt of the conjugate once every 4 weeks, and wherein the magnesium supplement is administered at a dose sufficient to normalize patient's serum magnesium level One embodiment of the present disclosure relates to a method of treating a patient with Duchenne muscular dystrophy (DMD) with an antisense oligomer conjugate, comprising administering to the patient:
  iii) an antisense oligomer conjugate of Formula (IV); and
  iv) a magnesium supplement.

In some embodiment, the conjugate of Formula (IV), or a pharmaceutically acceptable salt thereof, is administered at a dose equivalent to about 300 mg to about 1200 mg, about 300 mg to about 1000 mg, about 300 mg to about 750 mg, about 300 mg to about 500 mg, about 400 mg to about 1400 mg, about 400 mg to about 1100 mg, about 400 mg to about 900 mg, about 400 mg to about 600 mg, about 500 mg to about 1500 mg, about 500 mg to about 1300 mg, about 500 mg to about 1000 mg, about 500 mg to about 950 mg, about 500 mg to about 850 mg, about 500 mg to about 750 mg, about 500 mg to about 650 mg, about 600 mg to about 1400 mg, about 600 mg to about 1200 mg, about 600 mg to about 1200 mg, about 600 mg to about 1000, or about 600 mg to about 900 mg of the 6HCl salt of the conjugate; and the magnesium supplement is administered at a dose sufficient to normalize patient's serum magnesium level. In one embodiment, the conjugate is administered once every four weeks. In one embodiments, the magnesium supplement is administered at a dose equivalent to about 400 to about 2400 mg magnesium oxide per day.

In some embodiment, the conjugate of Formula (IV), or a pharmaceutically acceptable salt thereof, is administered at a dose equivalent to about 300 mg, about 350 mg, about 400 mg, about 450 mg, about 500 mg, about 550 mg, about 600 mg, about 650 mg, about 700 mg, about 750 mg, about 800 mg, about 850 mg, or about 900 mg of the 6HCl salt of the conjugate, and the magnesium supplement is administered at a dose sufficient to normalize patient's serum magnesium level. In one embodiment, the conjugate is administered once every four weeks. In one embodiment, the magnesium supplement is administered at a dose equivalent to about 400 to about 2400 mg magnesium oxide per day.

In some embodiment, the conjugate of Formula (IV), or a pharmaceutically acceptable salt thereof, is administered at a dose equivalent to about 950 mg, about 1000 mg, about 1050 mg, about 1100 mg, about 1150 mg, about 1200 mg, about 1250 mg, about 1300 mg, about 1350 mg, about 1400 mg, about 1450 mg, or about 1500 mg of the 6HCl salt of the conjugate, and the magnesium supplement is administered at a dose sufficient to normalize patient's serum magnesium level. In one embodiment, the conjugate is administered once every four weeks. In one embodiment, the magnesium supplement is administered at a dose equivalent to about 400 to about 2400 mg magnesium oxide per day.

In some embodiment, the conjugate of Formula (IV), or a pharmaceutically acceptable salt thereof, is administered at a dose equivalent to about 20 mg/kg, about 30 mg/kg, or about 40 mg/kg of the 6HCl salt of the conjugate once every 4 weeks, and the magnesium supplement is administered at a dose sufficient to normalize patient's serum magnesium level. In one embodiment, the conjugate is administered once every four weeks. In one embodiment, the magnesium supplement is administered at a dose equivalent to about 400 to about 2400 mg magnesium oxide per day.

One embodiment of the present disclosure relates to a method of treating a patient with Duchenne muscular dystrophy (DMD) with an antisense oligomer conjugate, comprising administering to the patient:
 v) an antisense oligomer conjugate of Formula (VI); and
 vi) a magnesium supplement.

In some embodiment, the conjugate of Formula (VI), or a pharmaceutically acceptable salt thereof, is administered at a dose equivalent to about 300 mg to about 1200 mg, about 300 mg to about 1000 mg, about 300 mg to about 750 mg, about 300 mg to about 500 mg, about 400 mg to about 1400 mg, about 400 mg to about 1100 mg, about 400 mg to about 900 mg, about 400 mg to about 600 mg, about 500 mg to about 1500 mg, about 500 mg to about 1300 mg, about 500 mg to about 1000 mg, about 500 mg to about 950 mg, about 500 mg to about 850 mg, about 500 mg to about 750 mg, about 500 mg to about 650 mg, about 600 mg to about 1400 mg, about 600 mg to about 1200 mg, about 600 mg to about 1200 mg, about 600 mg to about 1000, or about 600 mg to about 900 mg of the 6HCl salt of the conjugate; and the magnesium supplement is administered at a dose sufficient to normalize patient's serum magnesium level. In one embodiment, the conjugate is administered once every four weeks. In one embodiments, the magnesium supplement is administered at a dose equivalent to about 400 to about 2400 mg magnesium oxide per day.

In some embodiment, the conjugate of Formula (VI), or a pharmaceutically acceptable salt thereof, is administered at a dose equivalent to about 300 mg, about 350 mg, about 400 mg, about 450 mg, about 500 mg, about 550 mg, about 600 mg, about 650 mg, about 700 mg, about 750 mg, about 800 mg, about 850 mg, or about 900 mg of the 6HCl salt of the conjugate, and the magnesium supplement is administered at a dose sufficient to normalize patient's serum magnesium level. In one embodiment, the conjugate is administered once every four weeks. In one embodiment, the magnesium supplement is administered at a dose equivalent to about 400 to about 2400 mg magnesium oxide per day.

In some embodiment, the conjugate of Formula (VI), or a pharmaceutically acceptable salt thereof, is administered at a dose equivalent to about 950 mg, about 1000 mg, about 1050 mg, about 1100 mg, about 1150 mg, about 1200 mg, about 1250 mg, about 1300 mg, about 1350 mg, about 1400 mg, about 1450 mg, or about 1500 mg of the 6HCl salt of the conjugate, and the magnesium supplement is administered at a dose sufficient to normalize patient's serum magnesium level. In one embodiment, the conjugate is administered once every four weeks. In one embodiment, the magnesium supplement is administered at a dose equivalent to about 400 to about 2400 mg magnesium oxide per day.

In some embodiment, the conjugate of Formula (VI), or a pharmaceutically acceptable salt thereof, is administered at a dose equivalent to about 20 mg/kg, about 30 mg/kg, or about 40 mg/kg of the 6HCl salt of the conjugate once every 4 weeks, and the magnesium supplement is administered at a dose sufficient to normalize patient's serum magnesium level. In one embodiment, the conjugate is administered once every four weeks. In one embodiment, the magnesium supplement is administered at a dose equivalent to about 400 to about 2400 mg magnesium oxide per day.

One embodiment of the present disclosure relates to a method of treating a patient with Duchenne muscular dystrophy (DMD) with an antisense oligomer conjugate, comprising administering to the patient:
 vii) an antisense oligomer conjugate of Formula (VIII); and
 viii) a magnesium supplement.

In some embodiment, the conjugate of Formula (VIII), or a pharmaceutically acceptable salt thereof, is administered at a dose equivalent to about 300 mg to about 1200 mg, about 300 mg to about 1000 mg, about 300 mg to about 750 mg, about 300 mg to about 500 mg, about 400 mg to about 1400 mg, about 400 mg to about 1100 mg, about 400 mg to about 900 mg, about 400 mg to about 600 mg, about 500 mg to about 1500 mg, about 500 mg to about 1300 mg, about 500 mg to about 1000 mg, about 500 mg to about 950 mg, about 500 mg to about 850 mg, about 500 mg to about 750 mg, about 500 mg to about 650 mg, about 600 mg to about 1400 mg, about 600 mg to about 1200 mg, about 600 mg to about 1200 mg, about 600 mg to about 1000, or about 600 mg to about 900 mg of the 6HCl salt of the conjugate; and the magnesium supplement is administered at a dose sufficient to normalize patient's serum magnesium level. In one embodiment, the conjugate is administered once every four weeks. In one embodiments, the magnesium supplement is administered at a dose equivalent to about 400 to about 2400 mg magnesium oxide per day.

In some embodiment, the conjugate of Formula (VIII), or a pharmaceutically acceptable salt thereof, is administered at a dose equivalent to about 300 mg, about 350 mg, about 400 mg, about 450 mg, about 500 mg, about 550 mg, about 600 mg, about 650 mg, about 700 mg, about 750 mg, about 800 mg, about 850 mg, or about 900 mg of the 6HCl salt of the conjugate, and the magnesium supplement is administered at a dose sufficient to normalize patient's serum magnesium level. In one embodiment, the conjugate is administered once every four weeks. In one embodiment, the magnesium supplement is administered at a dose equivalent to about 400 to about 2400 mg magnesium oxide per day.

In some embodiment, the conjugate of Formula (VIII), or a pharmaceutically acceptable salt thereof, is administered at a dose equivalent to about 950 mg, about 1000 mg, about 1050 mg, about 1100 mg, about 1150 mg, about 1200 mg, about 1250 mg, about 1300 mg, about 1350 mg, about 1400 mg, about 1450 mg, or about 1500 mg of the 6HCl salt of the conjugate, and the magnesium supplement is administered at a dose sufficient to normalize patient's serum magnesium level. In one embodiment, the conjugate is administered once every four weeks. In one embodiment, the magnesium supplement is administered at a dose equivalent to about 400 to about 2400 mg magnesium oxide per day.

In some embodiment, the conjugate of Formula (VIII), or a pharmaceutically acceptable salt thereof, is administered at a dose equivalent to about 20 mg/kg, about 30 mg/kg, or about 40 mg/kg of the 6HCl salt of the conjugate once every 4 weeks, and the magnesium supplement is administered at a dose sufficient to normalize patient's serum magnesium level. In one embodiment, the magnesium supplement is administered at a dose equivalent to about 400 to about 2400 mg magnesium oxide per day.

What is claimed is:

1. A method of treating a patient with Duchenne muscular dystrophy (DMD) in need thereof who has a mutation that is amenable to exon skipping, comprising administering to the patient an antisense oligomer conjugate of Formula (I):

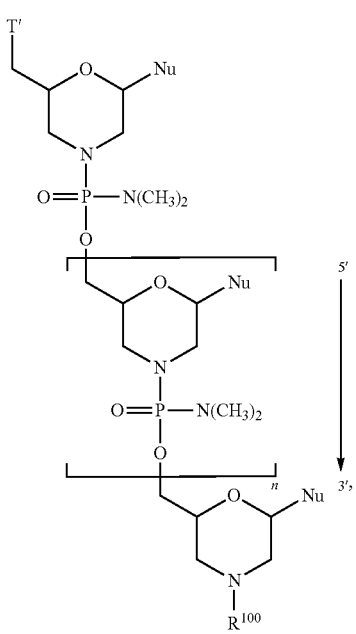

or a pharmaceutically acceptable salt thereof, wherein:

n is 1-40;

each Nu is a nucleobase, which, taken together, form a targeting sequence complementary to an exon annealing site in the dystrophin pre-mRNA;

T' is a moiety selected from:

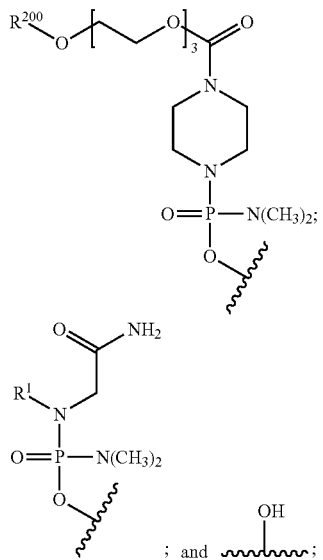

wherein $R^{100}$ a cell-penetrating peptide, $R^{200}$ is hydrogen, and $R^1$ is $C_1$-$C_6$ alkyl, at a dose equivalent to the dose of the 6HCl salt of the conjugate according to the following schedule:

i) about 300 mg to about 700 mg, or about 900 mg to about 1200 mg, once every four weeks for a patient that weighs from about 10 kg to about 25 kg;

ii) about 600 mg to about 800 mg, or about 1000 mg to about 1300 mg, once every four weeks for a patient that weighs from about 25 kg to about 50 kg; or iii) about 700 mg to about 900 mg, or about 1200 mg to about 1500 mg, once every four weeks for a patient that weighs from about 50 kg to about 100 kg;

to achieve a mean AUC about 100 and about 200 ug·h/mL, or is between about 200 and about 500 ug·h/mL, and wherein the method further comprises administering a magnesium supplement to the patient.

2. A method of treating a patient with Duchenne muscular dystrophy (DMD) in need thereof who has a mutation that is amenable to exon 51 skipping, comprising administering to the patient an antisense oligomer conjugate of Formula (I):

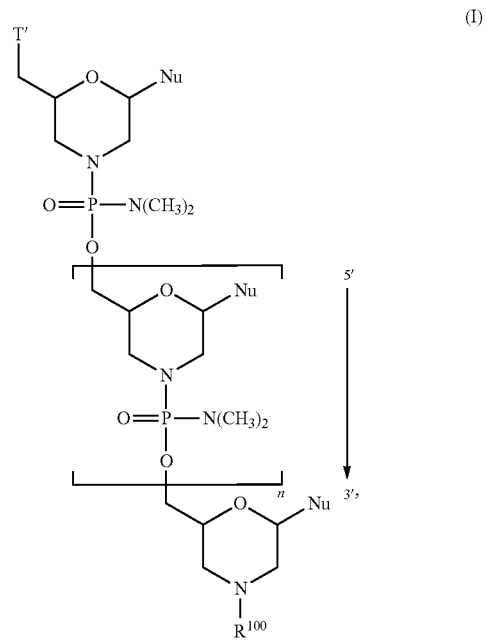

or a pharmaceutically acceptable salt thereof, wherein:

n is 1-40;

each Nu is a nucleobase, which, taken together, form a targeting sequence complementary to an exon annealing site in the dystrophin pre-mRNA;

T' is a moiety selected from:

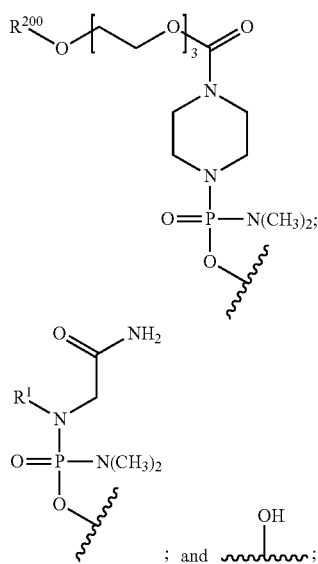

wherein
$R^{100}$ a cell-penetrating peptide, $R^{200}$ is hydrogen, and $R^1$ is $C_1$-$C_6$ alkyl,
at a dose equivalent to the dose of the 6HCl salt of the conjugate according to the following schedule:

i) about 300 mg to about 700 mg, or about 900 mg to about 1200 mg, once every four weeks for a patient that weighs from about 10 kg to about 25 kg;
ii) about 600 mg to about 800 mg, or about 1000 mg to about 1300 mg, once every four weeks for a patient that weighs from about 25 kg to about 50 kg; or
iii) about 700 mg to about 900 mg, or about 1200 mg to about 1500 mg, once every four weeks for a patient that weighs from about 50 kg to about 100 kg;
to achieve a mean AUC
about 100 and about 200 ug·h/mL, or between about 200 and about 500 ug·h/mL, and
wherein the method further comprises administering a magnesium supplement to the patient.

3. The method of claim 1, wherein the conjugate, or a pharmaceutically acceptable salt thereof, is administered at a dose effective to provide a mean AUC of between about 100 and about 200 ug·h/mL.

4. The method of claim 1, wherein the conjugate, or a pharmaceutically acceptable salt thereof, is administered at a dose effective to provide a mean AUC of between about 200 and about 500 ug·h/mL.

5. The method of claim 1, wherein the cell-penetrating peptide is chosen from RXRRXRRXRRXR (SEQ ID NO: 18), RFFRFFRFFR (SEQ ID NO: 19), RXRRXRRXRRXRXB (SEQ ID NO: 20), RFFRFFRFFRG (SEQ ID NO: 21), RRRRRRG (SEQ ID NO: 22), RRRRRR (SEQ ID NO: 23), RRRRRG (SEQ ID NO: 24), or RRRRR (SEQ ID NO: 25), wherein R is arginine, X is 6-aminohexanoic acid, B is β-alanine, F is phenylalanine, and G is glycine.

6. The method of claim 5, wherein the cell-penetrating peptide is chosen from RRRRRRG (SEQ ID NO: 22), RRRRRR (SEQ ID NO: 23), RRRRRG (SEQ ID NO: 24), or RRRRR (SEQ ID NO: 25), wherein R is arginine and G is glycine.

7. The method of claim 6, wherein the cell-penetrating peptide is RRRRRRG (SEQ ID NO: 22), wherein R is arginine and G is glycine.

8. The method of claim 1, wherein the antisense oligomer conjugate causes skipping of an exon in the human dystrophin gene.

9. The method of claim 8, wherein the exon is chosen from exon 44, 45, 50, 51, 52, or 53.

10. The method of claim 9, wherein the exon is chosen from exon 45, 51, or 53.

11. The method of claim 1, wherein the antisense oligomer conjugate has Formula (III):

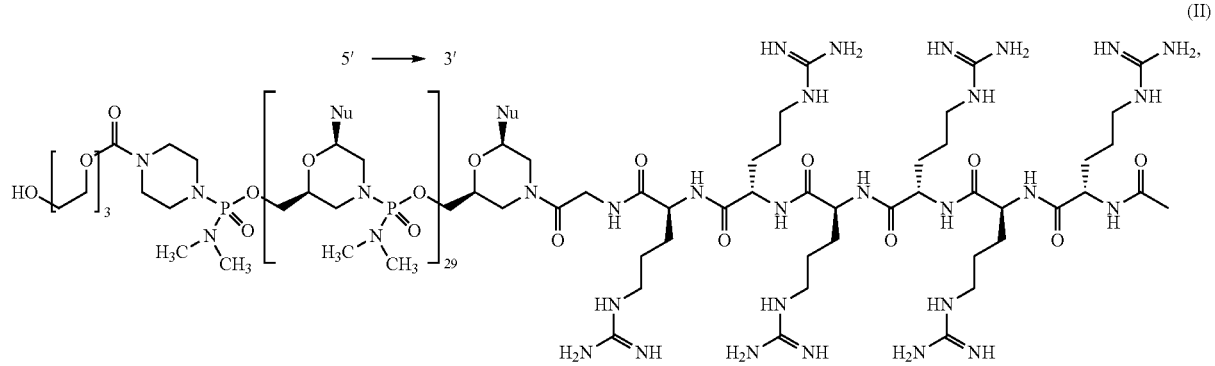

(II)

or a pharmaceutically acceptable salt thereof,
wherein each Nu is a nucleobase, which, taken together, form a targeting sequence that is complementary to an exon annealing site in the dystrophin pre-mRNA.

12. The method of claim 1 or claim 2, wherein the antisense oligomer conjugate, or a pharmaceutically acceptable salt thereof, is administered at a dose equivalent to about 600 mg, or about 1100 mg, of the 6HCl salt of the conjugate once every four weeks to a patient that weighs from about 10 kg to about 25 kg.

13. The method of claim 1 or claim 2, wherein the antisense oligomer conjugate, or a pharmaceutically acceptable salt thereof, is administered at a dose equivalent to about 650 mg, or about 1200 mg, of the 6HCl salt of the conjugate once every four weeks to a patient that weighs from about 25 kg to about 50 kg.

14. The method of claim 1 or claim 2, wherein the antisense oligomer conjugate, or a pharmaceutically acceptable salt thereof, is administered at a dose equivalent to about 750 mg, or about 1400 mg, of the 6HCl salt of the conjugate once every four weeks to a patient that weighs from about 50 kg to about 100 kg.

15. The method of claim 1 or claim 2, wherein the magnesium supplement is administered in an amount effective to provide a normal serum magnesium level.

16. The method of claim 1 or claim 2, wherein the magnesium supplement is administered at a dose equivalent to about 100 to about 2400 mg magnesium oxide per day.

17. The method of claim 1 or claim 2, wherein the magnesium supplement is administered at a dose equivalent to about 400 to about 2400 mg magnesium oxide per day.

18. The method of claim 1 or claim 2, further comprising measuring serum magnesium level of said patient at two or more weeks from said administration.

19. The method of claim 1 or claim 2, further comprising administering a second dose of magnesium supplement, at a dose based upon the measured serum magnesium level.

20. The method of claim 1 or claim 2, wherein the magnesium supplement is chosen from magnesium oxide, magnesium citrate, magnesium carbonate, magnesium hydrogen phosphate, magnesium glycerophosphate, magnesium trisilicate, magnesium hydroxide, magnesium hydroxide carbonate, magnesium acetate, magnesium citrate, magnesium lactate, magnesium gluconate, magnesium chloride, magnesium aspartate, magnesium caprilate, magnesium ascorbate; magnesium taurate, magnesium malate, and magnesium diglycinate, magnesium pidulate, or magnesium sulfate.

21. The method of claim 1 or claim 2, wherein the magnesium supplement is from magnesium oxide.

22. The method of claim 1 or claim 2, wherein the antisense oligomer conjugate, or a pharmaceutically acceptable salt thereof, is administered in a pharmaceutical formulation, wherein the concentration of the conjugate in the formulation is about 50 mg/ml.

* * * * *